US008889709B2

(12) United States Patent
Demuth et al.

(10) Patent No.: US 8,889,709 B2
(45) Date of Patent: Nov. 18, 2014

(54) USE OF ISOQC INHIBITORS IN THE TREATMENT AND PREVENTION OF INFLAMMATORY DISEASES OR CONDITIONS

(75) Inventors: Hans-Ulrich Demuth, Halle/Saale (DE); Stephan Schilling, Halle/Saale (DE); Michael Wermann, Halle/Saale (DE); Holger Cynis, Halle/Saale (DE); Astrid Kehlen, Halle/Saale (DE); Daniel Friedrich, Halle/Saale (DE); Torsten Hoffmann, Halle/Saale (DE); Kathrin Gans, Halle/Saale (DE); Jens-Ulrich Rahfeld, Lieskau (DE); Ulrich Heiser, Halle/Saale (DE); Michael Almstetter, Martinsried (DE); Robert Sommer, Halle/Saale (DE); Ulf-Torsten Gaertner, Halle/Saale (DE); Antje Hamann, Dieskau (DE); Michael Thormann, Martinsried (DE); Andreas Treml, Martinsried (DE)

(73) Assignee: Probiodrug AG, Halle/Saale (DE)

( * ) Notice: Subject to any disclaimer, the term of this patent is extended or adjusted under 35 U.S.C. 154(b) by 540 days.

(21) Appl. No.: 12/554,584

(22) Filed: Sep. 4, 2009

(65) Prior Publication Data
US 2010/0125086 A1 May 20, 2010

Related U.S. Application Data

(60) Continuation-in-part of application No. 12/497,082, filed on Jul. 2, 2009, now Pat. No. 8,129,160, which is a division of application No. 11/859,217, filed on Sep. 21, 2007, now abandoned.

(60) Provisional application No. 61/179,424, filed on May 19, 2009, provisional application No. 61/094,118, filed on Sep. 4, 2008, provisional application No. 60/947,780, filed on Jul. 3, 2007, provisional application No. 60/846,244, filed on Sep. 21, 2006.

(51) Int. Cl.
| | |
|---|---|
| *A01N 43/42* | (2006.01) |
| *C12N 9/00* | (2006.01) |
| *C12N 9/10* | (2006.01) |
| *C12N 1/20* | (2006.01) |
| *C12N 15/00* | (2006.01) |
| *C07H 21/04* | (2006.01) |
| *C07D 417/12* | (2006.01) |
| *C07D 405/12* | (2006.01) |
| *C07D 233/61* | (2006.01) |
| *C07D 409/12* | (2006.01) |
| *C07D 403/12* | (2006.01) |
| *C07D 413/12* | (2006.01) |
| *C07D 403/06* | (2006.01) |
| *C07D 401/12* | (2006.01) |
| *C07D 233/54* | (2006.01) |
| *C07D 235/06* | (2006.01) |

(52) U.S. Cl.
CPC ............ *C07D 233/54* (2013.01); *C07D 417/12* (2013.01); *C07D 405/12* (2013.01); *C07D 233/61* (2013.01); *C07D 409/12* (2013.01); *C12N 9/104* (2013.01); *C07D 403/12* (2013.01); *C07D 413/12* (2013.01); *C07D 403/06* (2013.01); *C07D 401/12* (2013.01); *C07D 235/06* (2013.01)
USPC ........ 514/300; 435/183; 435/193; 435/252.3; 435/320.1; 536/23.2

(58) Field of Classification Search
None
See application file for complete search history.

(56) References Cited

U.S. PATENT DOCUMENTS

| | | |
|---|---|---|
| 7,304,086 B2 | 12/2007 | Schilling |
| 7,371,871 B2 | 5/2008 | Schilling |
| 7,381,537 B2 | 6/2008 | Demuth |
| 7,462,599 B2 | 12/2008 | Schilling |
| 2004/0006011 A1 | 1/2004 | Gour et al. |
| 2004/0224875 A1 | 11/2004 | Schilling et al. |
| 2005/0137142 A1 | 6/2005 | Schulz |
| 2005/0171112 A1 | 8/2005 | Schulz |
| 2006/0100253 A1 | 5/2006 | Niestroj |
| 2007/0191366 A1 | 8/2007 | Hoffmann |
| 2008/0153892 A1 | 6/2008 | Schilling |
| 2008/0260688 A1 | 10/2008 | Buchholz et al. |

(Continued)

FOREIGN PATENT DOCUMENTS

| | | |
|---|---|---|
| DE | 293584 | 5/1991 |
| WO | 01/09090 | 2/2001 |

(Continued)

OTHER PUBLICATIONS

Gololobov et al. Biol Chem Hoppe Seyler. Jun. 1996;377(6):395-8 (Abstract).*

(Continued)

*Primary Examiner* — Christian Fronda
(74) *Attorney, Agent, or Firm* — Dentons US LLP

(57) ABSTRACT

The present invention relates in general to an inhibitor of a glutaminyl peptide cyclotransferase-like protein (QPCTL), and the use thereof for the treatment and/or prevention of an inflammatory disease or disorder selected from the group consisting of (a) chronic and acute inflammations, e.g. rheumatoid arthritis, atherosclerosis, restenosis, pancreatitis; (b) other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinating polyradiculoneuropathy and multiple sclerosis; (c) neuroinflammation; and (d) neurodegenerative diseases, e.g. mild cognitive impairment (MCI), Alzheimer's disease, neurodegeneration in Down Syndrome, Familial British Dementia, and Familial Danish Dementia, which may result from neuroinflammation.

37 Claims, 32 Drawing Sheets

(56) References Cited

U.S. PATENT DOCUMENTS

| | | |
|---|---|---|
| 2008/0286810 A1 | 11/2008 | Demuth |
| 2009/0018087 A1 | 1/2009 | Schilling |
| 2009/0068699 A1 | 3/2009 | Schilling |
| 2009/0149394 A1 | 6/2009 | Schilling |

FOREIGN PATENT DOCUMENTS

| | | |
|---|---|---|
| WO | 01/53331 | 7/2001 |
| WO | 2003/045321 | 6/2003 |
| WO | 2004/098591 | 11/2004 |
| WO | 2004/098625 | 11/2004 |
| WO | 2005/039548 | 5/2005 |
| WO | 2005/049025 | 6/2005 |
| WO | 2005/075436 | 8/2005 |
| WO | 2008/034891 | 3/2008 |
| WO | 2008/055947 | 5/2008 |

OTHER PUBLICATIONS

Gontsarova et al. Olin Chim Acta. Mar. 2008;389(1-2):152-9. Epub Dec. 17, 2007.*
Buchholz et al. J Med Chem. Nov. 26, 2009;52(22):7069-80.*
Buchholz et al., The First Potent Inhibitors for Human Glutaminyl Cyclase: Synthesis and Structure—Activity Relationship, J Medicinal Chemistry 2006, 49, 664-677.
Suzuki et al., Homo sapiens mRNA for glutaminyl-peptide cyclotransferase-like variant. clone: CBL03904., EMBL 2006.
Suzuki et al., Glutaminyl-peptide cyclotransferase-like variant (fragment), UniProt 2006.
Penn et al., Human Genome Derived Single Exon Probe, GENSEQ 2004.
Schilling et al., Identification of Human Glutaminyl Cyclase as a Metalloenzyme, Potent Inhibition by Imidazole Derivatives and Hetercyclic Chelators, The Journal of Biological Chemistry, vol. 278, No. 50, Dec. 12, 2003, pp. 49773-49779.
Ohsugi et al. Anti-platelet Aggregation and Anti-blood Coagulation Activities of Dipicolinic Acid, A Sporal Component of Bacillus Subtilis Natto, Chemical Abstracts Service 2005.
Chica et al., Semi-rational approaches to engineering enzyme activity: combining the benefits of directed evolution and rational design, Curr Opin Biotechnol 2005 16(4) pp. 378-384.
Sen et al, Developments in directed evolution for improving enzyme functions, Appl Biotechnol 2007 143(3) pp. 212-223.
Karim et al. Accession AAL61267 Sep. 22, 2003.
Jansen et al., Hydantoin-Substituted 4,6-Dichloroindole-2-carboxylic Acids as Ligands with High Affinity for the Glycine Binding Site of the NMDA receptor, J Med Chem, 2003, 46:64-73.
Werbel and Elslager, Antischistosomal Effects of 5-(2,4,5-Trichlorophenyl)hydantoin and Related Compounds, J Med Chem, 1977, 20:1569-72.

* cited by examiner

Figure 9
(a)
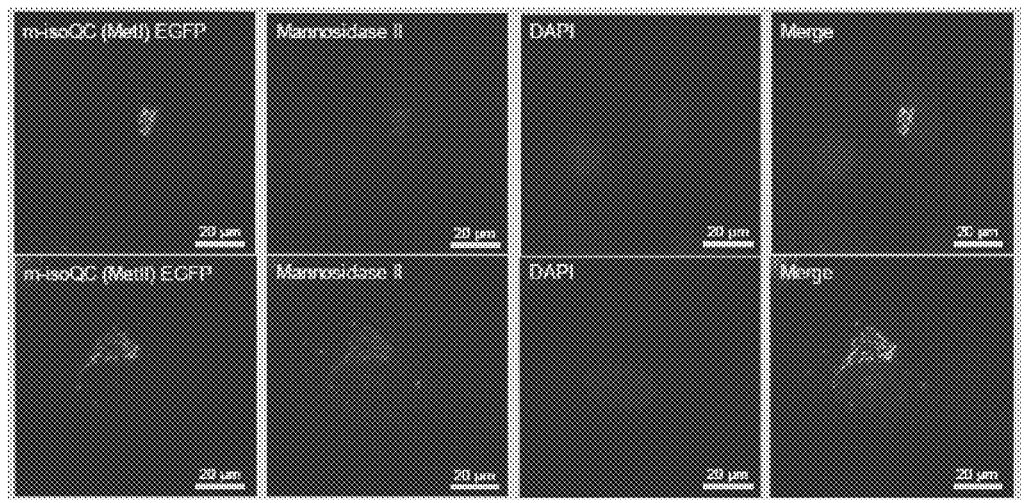
(b)
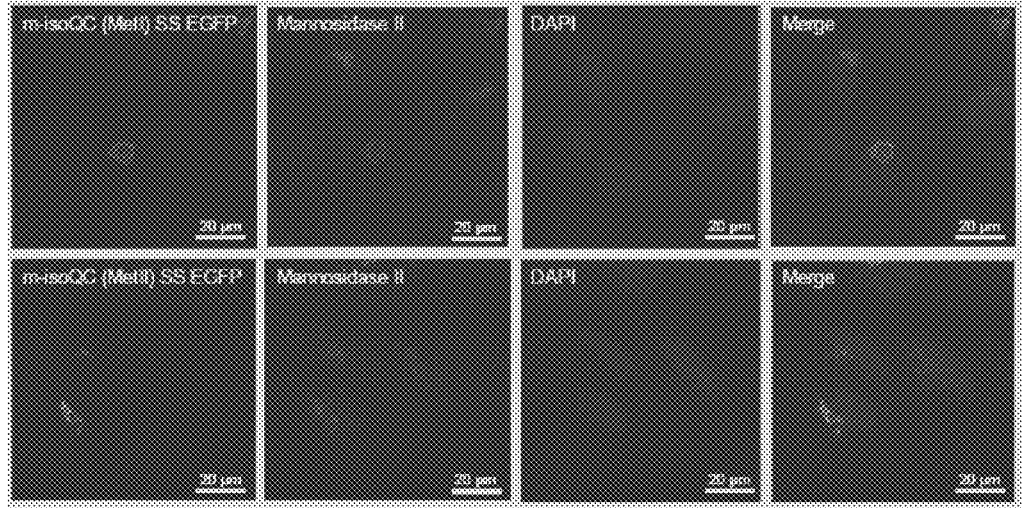

Figure 10
(a)
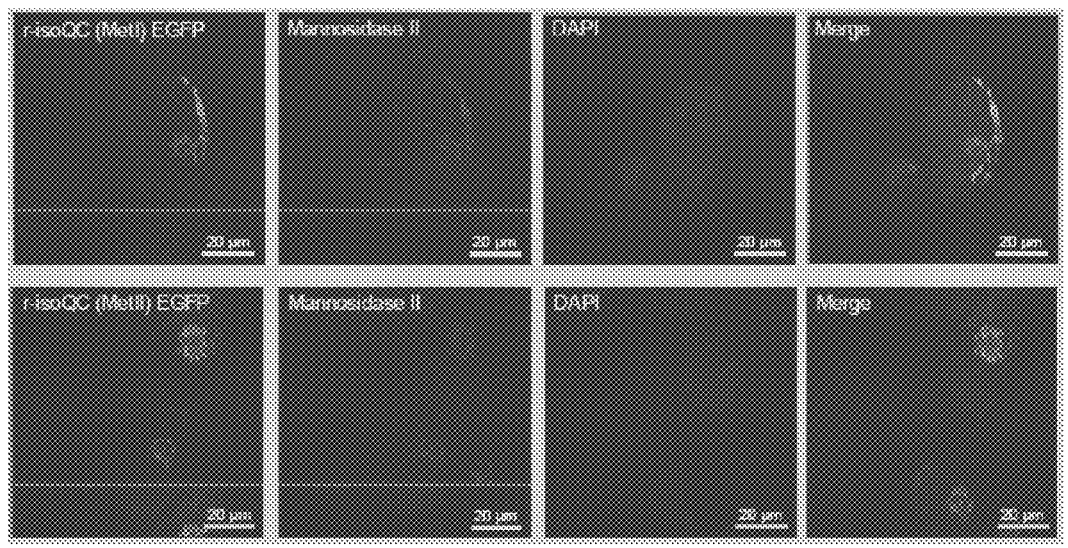
(b)
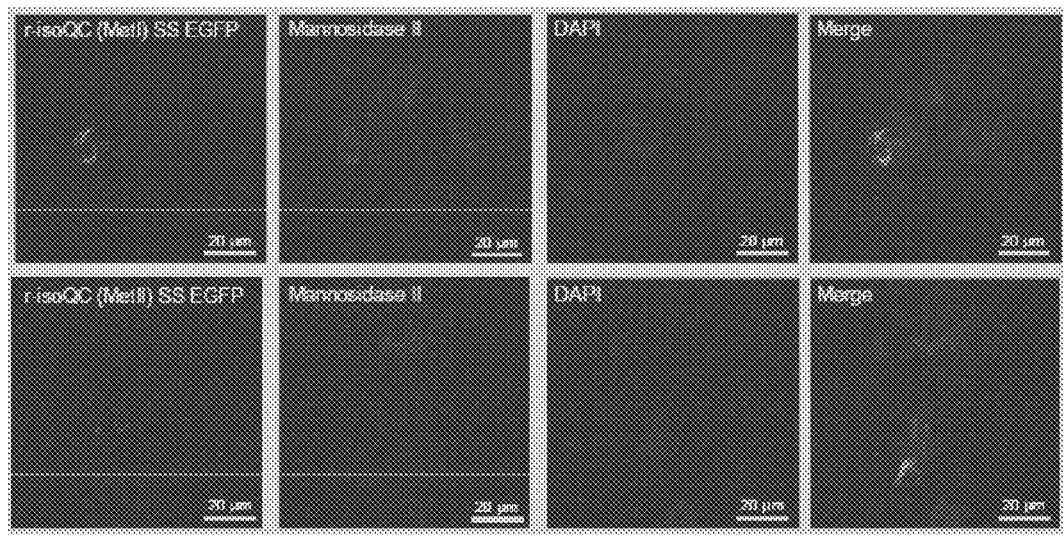

Figure 11
(a)
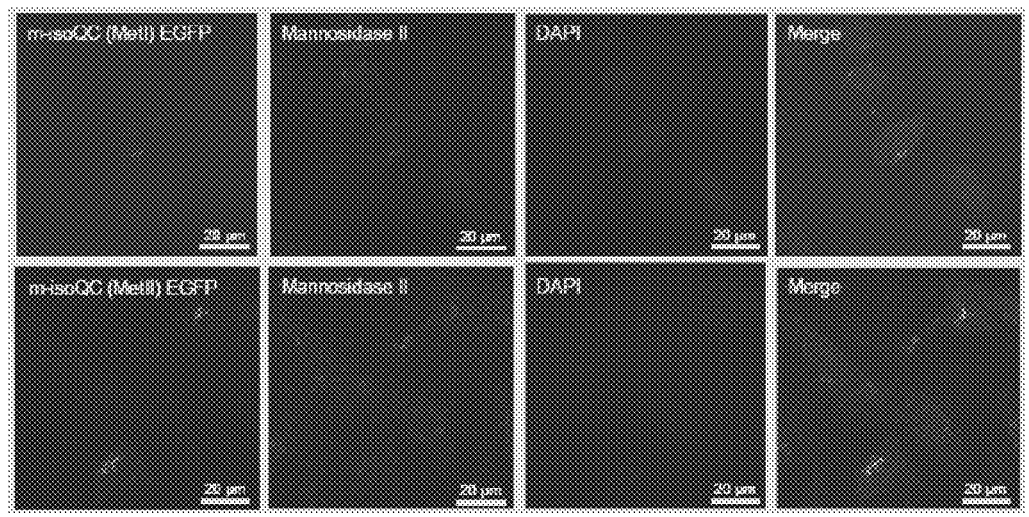
(b)
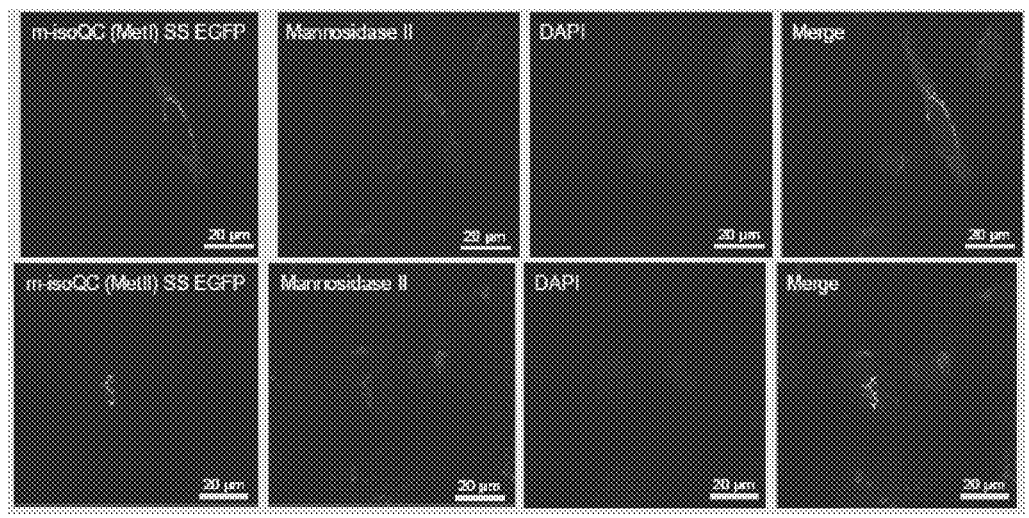

Figure 12
(a)
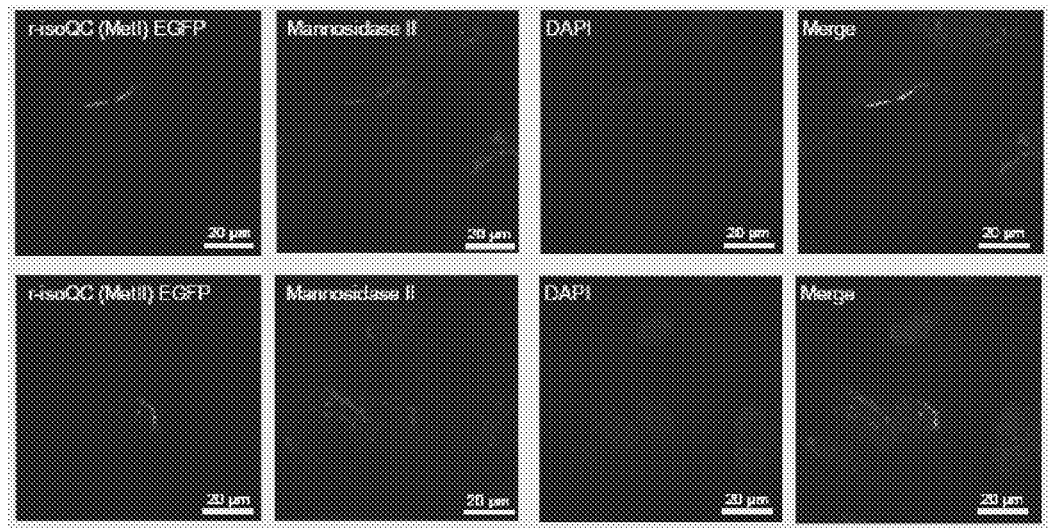
(b)
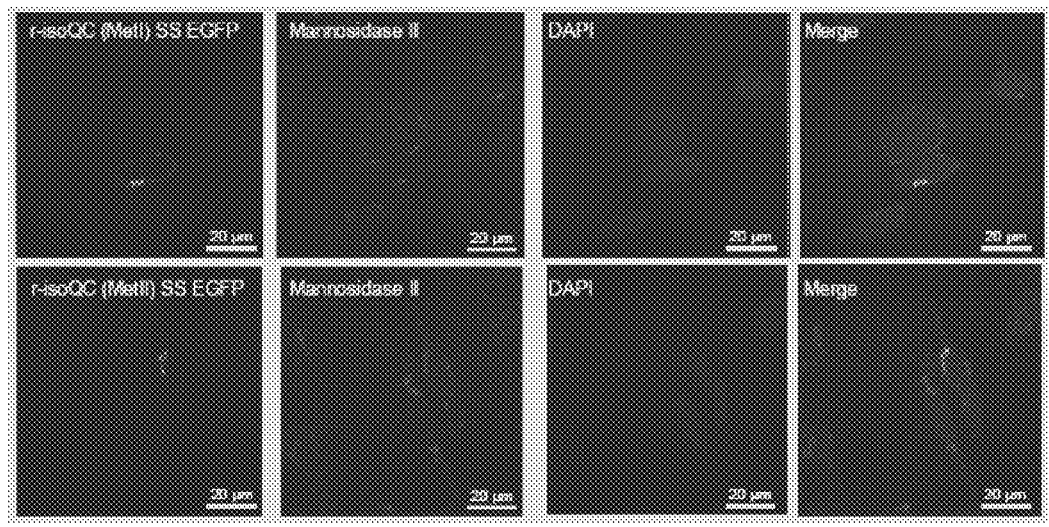

(a)

Figure 14
hQPCT in THP1 Cells
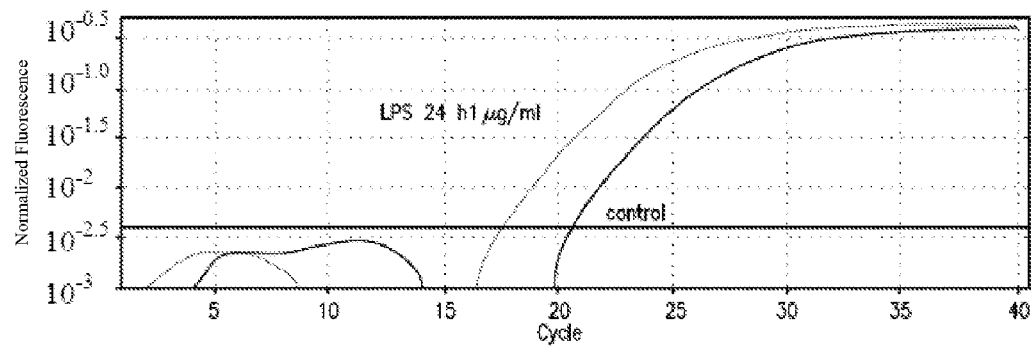
hQPCT in THP1 Cells
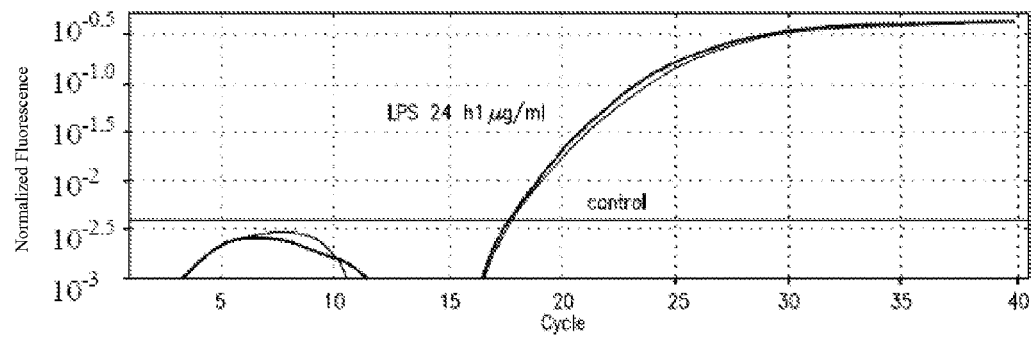

Figure 15

```
hisoQC  MRSGGRGRPRLRLGERGLMEPLLPPKRRLLPRVRLLP-LLLALAVGSAFYTIWSGWHRRT
misoQC  MSPGSRGRPRQRLEDRGLMKPPSLSKRRLLPRVQFLPLLLLALAMGLAFYIVWNSWHPGV
risoQC  MSPASRGRSRQRLGDRGLMKPPSLSKRRLLPRVQLLPLLLLALALGLAFYIVWNSWHPGV
        *  ...***.* ** :****:*     .********::** ******:* *** :*...**  .

hisoQC  EELPLGRELRVPLIGSLPEARLRRVVGQLDPQRLWSTYLRPLLVVRTPGSPGNLQVRKFL
misoQC  EEMSRSRDLRVPLIGSLSEAKLRLVVGQLDPQRLWGTFLRPLLIVRPPGSSGNLQVRKFL
risoQC  EEVSRSRDLRVPLIGSLSEAKLRLVVGQLDPQRLWGTFLRPLLIVRPPGSPGNLQVRKFL
        **:.  .*:******.: *********.*:***:.*.******* hisoQC  EATLRSLTAGWHVELDPFTASTPLGPVDFGNVVATLDPRAARHLTLACHYDSKLFPPGST
misoQC  EATLQSLSAGWHVELDPFTASTPLGPLDFGNVVATLDPGAARHLTLACHYDSKFFPPGLP
risoQC  EATLQSLSAGWHVELDPFTASTPLGPLDFGNVVATLDPGAARHLTLACHYDSKFFPPGLP
        ****:**:*****************:*********** *****:*****.****  .

hisoQC  PFVGATDSAVPCALLLELAQALDLELSRAKKQAAPVTLQLLFLDGEEALKEWGPKDSLYG
misoQC  PFVGATDSAVPCALLLELVQALDAMLSRIKQQAAPVTLQLLFLG-EEALKEWGPKDSLYG
risoQC  PFVGATDSAVPCALLLELVQALDVMLSRIKQQAAPVTLQLLFLDGEEALKEWGPKDSLYG
        ****************.   * *:*********. ************* hisoQC  SRHLAQLMESIPHSPGPTRIQAIELFMLLDLLGAPNPTFYSHFPRTVRWFHRLRSIEKRL
misoQC  SRHLAQIMESIPHSPGPTRIQAIELFVLLDLLGASSPIFFSHFPRTARWFQRLRSIEKRL
risoQC  SRHLAQIMESIPHSPGPTRIQAIELFVLLDLLGAPSPIFFSHFPRTARWFQRLRSIEKRL
        ****:**************:*****  .* *:****.*:********* hisoQC  HRLNLLQSHPQEVMYFQPGEPSGSVEDDHIPFLRRGVPVLHLISTPFPAVWHTPADTEVN
misoQC  HRLNLLQSHPQEVMYFQPGEPPGPVEDDHIPFLRRGVPVLHLATPFPAVLHTPADTEAN
risoQC  HRLNLLQSHPQEVMYFQPGEPPGPVEDDHIPFLRRGVPVLHIAMPFPAVWHTPADTEAN
        ********************.*.****************: * *****.* hisoQC  LHPPTVHNLCRILAVFLAEYLGL
misoQC  LHPPTVHNLSRILAVFLAEYLGL
risoQC  LHPPTVHNLSRILAVFLAEYLGL
        *********.*************
```

Figure 25
(a)
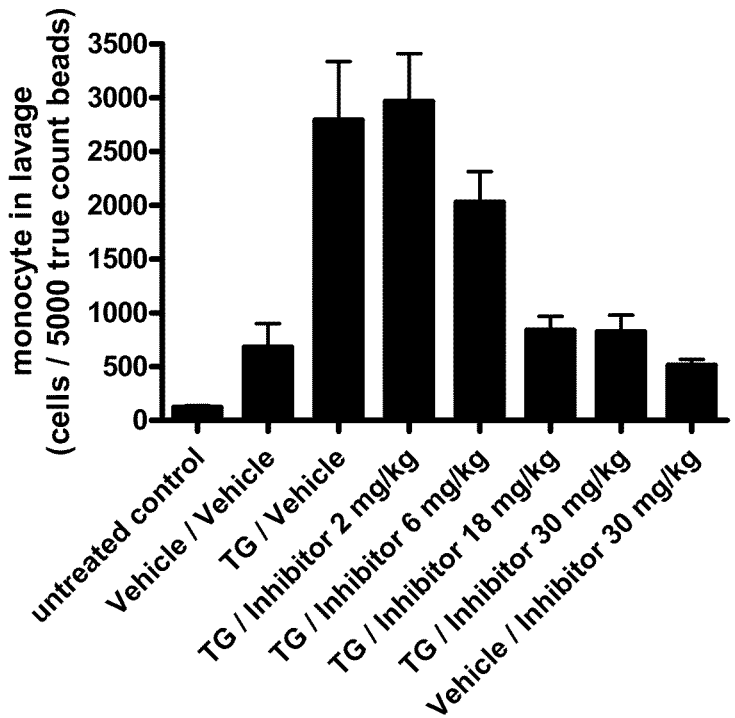
(b)
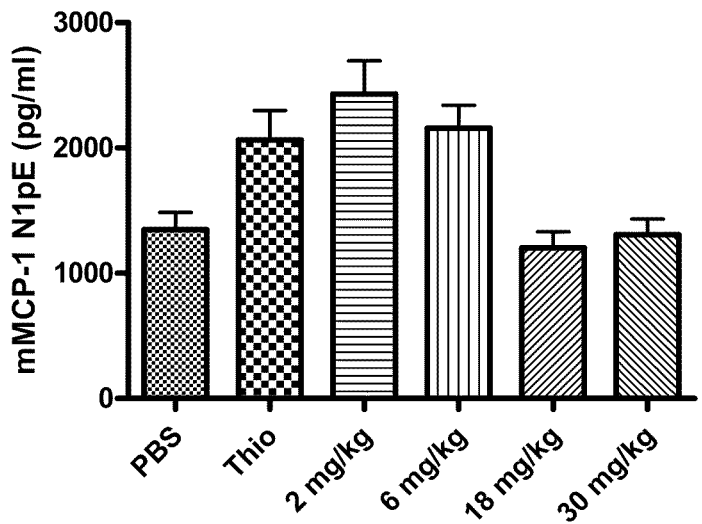

Figure 26
(a)
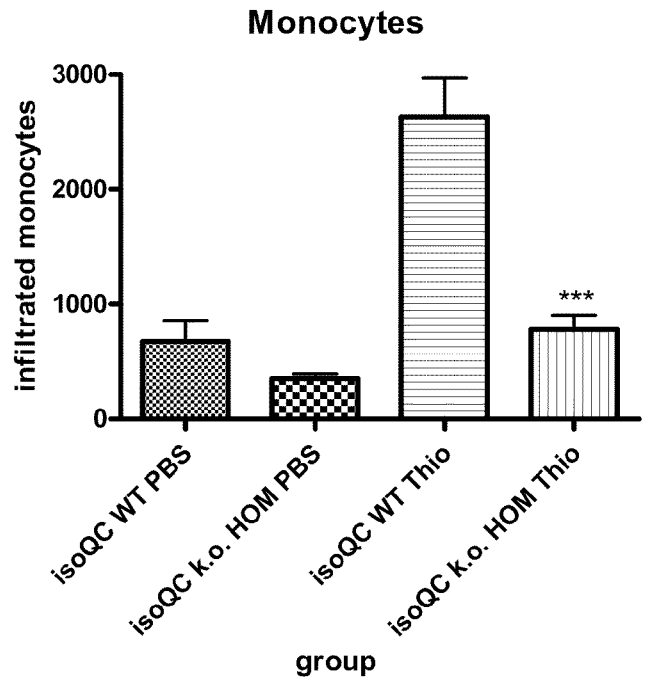
(b)
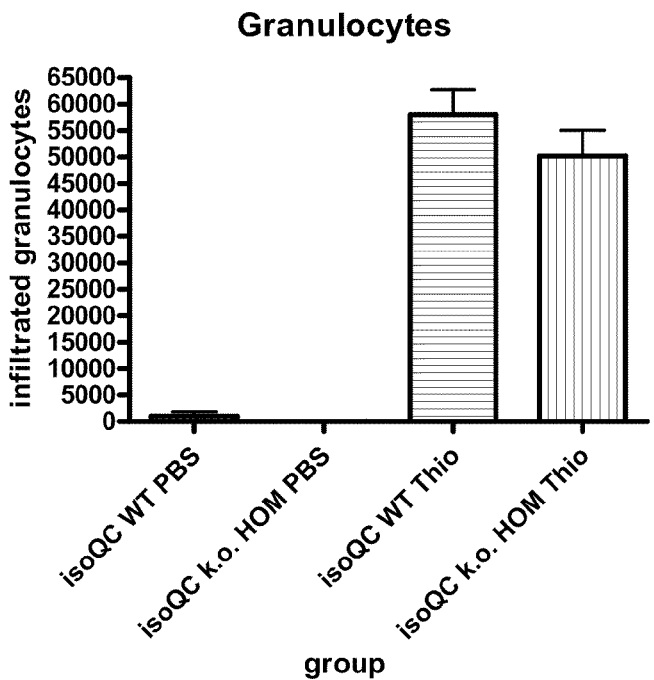

Figure 28
(a)
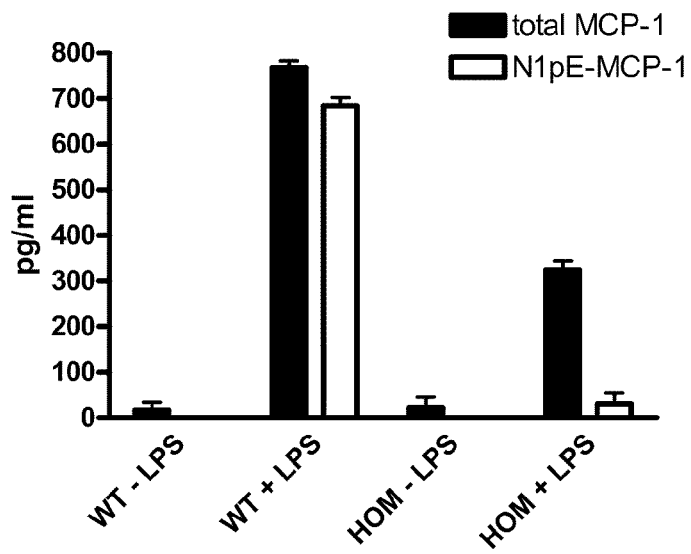
(b)
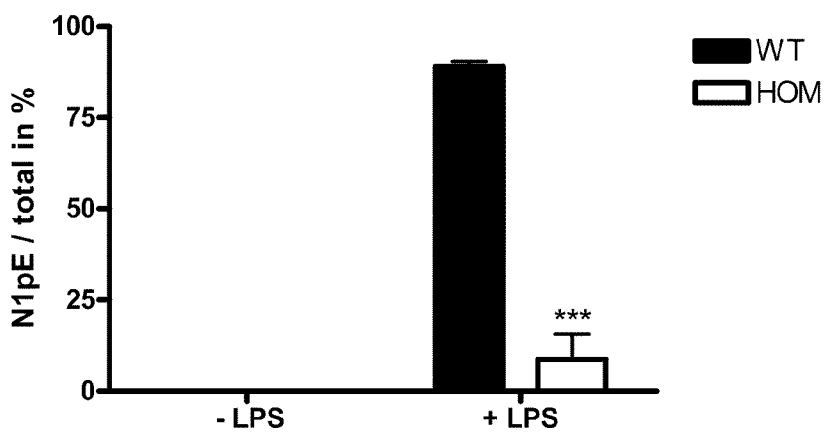

Figure 29
(a)
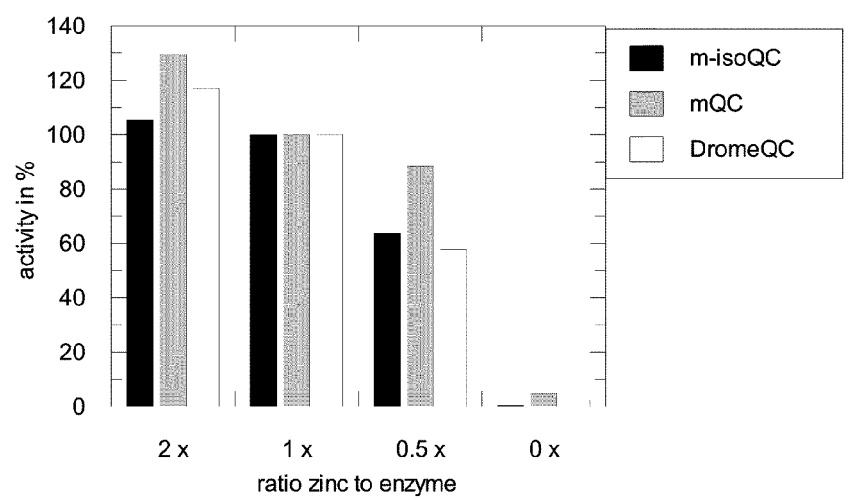
(b)
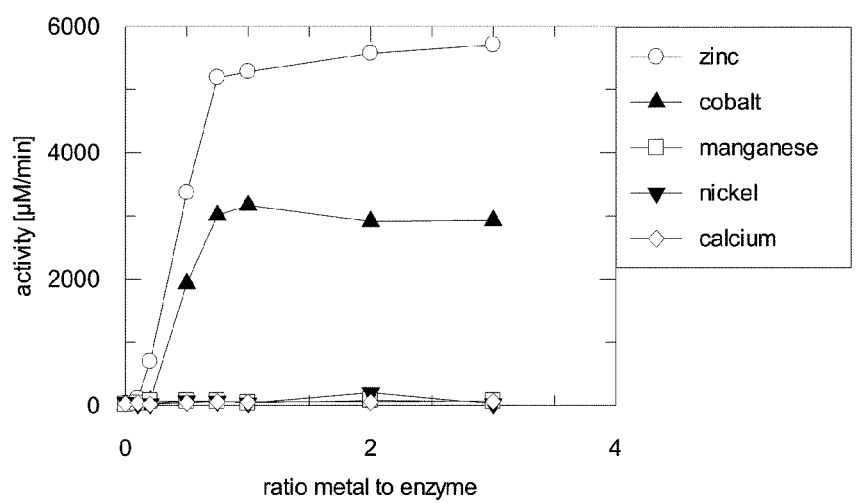

USE OF ISOQC INHIBITORS IN THE TREATMENT AND PREVENTION OF INFLAMMATORY DISEASES OR CONDITIONS

CROSS-REFERENCE TO RELATED APPLICATIONS

This application is a Continuation-in-Part application of U.S. application Ser. No. 12/497,082 filed on Jul. 2, 2009, which in turn was a Divisional application from U.S. application Ser. No. 11/859,217 filed on Sep. 21, 2007, which in turn claims priority from U.S. Provisional Application Ser. No. 60/846,244 filed Sep. 21, 2007, and U.S. Provisional Application Ser. No. 60/947,780 filed Jul. 3, 2007, each of which is incorporated herein by reference in their entirety to the extent permitted by law. The present application also claims priority from U.S. Provisional Application Ser. No. 61/094,118 filed on Sep. 4, 2008, and U.S. Provisional Application Ser. No. 61/179,424 filed on May 19, 2009, each of which is incorporated herein by reference in their entirety to the extent permitted by law.

INCORPORATION-BY-REFERENCE OF SEQUENCE LISTING

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present invention relates in general to an inhibitor of a glutaminyl peptide cyclotransferase-like protein (QPCTL), and the use thereof for the treatment and/or prevention of an inflammatory disease or disorder.

Further, the present invention pertains to diagnostic kits and methods based on the use of a said inhibitor.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant Carica papaya in 1963 (Messer, M. (1963) Nature 4874, 1299). 24 years later, a corresponding enzymatic activity was discovered in animal pituitary (Busby, W. H. J. et al. (1987) J Biol. Chem. 262, 8532-8536; Fischer, W. H. and Spiess, J. (1987) Proc. Natl. Acad. Sci. U.S.A. 84, 3628-3632). For the mammalian QC, the conversion of Gln into pGlu by QC could be shown for the precursors of TRH and GnRH (Busby, W. H. J. et al. (1987) J Biol. Chem. 262, 8532-8536; Fischer, W. H. and Spiess, J. (1987) Proc. Natl. Acad. Sci. U.S.A. 84, 3628-3632). In addition, initial localization experiments of QC revealed a co-localization with its putative products of catalysis in bovine pituitary, further improving the suggested function in peptide hormone synthesis (Bockers, T. M. et al. (1995) J Neuroendocrinol 7, 445-453). In contrast, the physiological function of the plant QC is less clear. In the case of the enzyme from C. papaya, a role in the plant defense against pathogenic microorganisms was suggested (El Moussaoui, A. et al. (2001) Cell Mol Life Sci 58, 556-570). Putative QCs from other plants were identified by sequence comparisons recently (Dahl, S. W. et al. (2000) Protein Expr. Purif. 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. (1991) Proc. Natl. Acad. Sci U.S.A. 88, 10059-10063; Consalvo, A. P. et al. (1988) Anal. Biochem. 175, 131-138; Gololobov, M. Y. et al. (1996) Biol. Chem. Hoppe Seyler 377, 395-398). A comparison of the primary structures of the QCs from C. papaya and that of the highly conserved QC from mammals, however, did not reveal any sequence homology (Dahl, S. W. et al. (2000) Protein Expr. Purif. 20, 27-36). Whereas the plant QCs appear to belong to a new enzyme family (Dahl, S. W. et al. (2000) Protein Expr. Purif. 20, 27-36), the mammalian QCs were found to have a pronounced sequence homology to bacterial aminopeptidases (Bateman, R. C. et al. (2001) Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed Glu1-conversion is favored around pH 6.0 while Gln1-conversion to pGlu-derivatives occurs with a pH-optimum of around 8.0 (Schilling et al. (2004), FEBS-Letters 563 (1-3) 191-196). Since the formation of pGlu-Aβ-related peptides can be suppressed by inhibition of recombinant human QC and QC-activity from pig pituitary extracts, the enzyme QC is a target in drug development for treatment of Alzheimer's disease (Schilling et al. (2008), Nature Medicine 14, 1106-1111).

Moreover, it was shown recently in WO 2008/034891 that isoenzymes of QC exist, designated as "isoQC" or "QPCTL".

Chemotactic cytokines (chemokines) are proteins that attract and activate leukocytes and are thought to play a fundamental role in inflammation. Chemokines are divided into four groups categorized by the appearance of N-terminal cysteine residues ("C"-; "CC"-; "CXC"- and "CX3C"-chemokines). "CXC"-chemokines preferentially act on neutrophils. In contrast, "CC"-chemokines attract preferentially monocytes to sites of inflammation. Monocyte infiltration is considered to be a key event in a number of disease conditions (Gerard, C. and Rollins, B. J. (2001) Nat. Immunol. 2, 108-115; Bhatia, M., et al. (2005) Pancreatology. 5, 132-144; Kitamoto, S., Egashira, K., and Takeshita, A. (2003) J Pharmacol. Sci. 91, 192-196). The MCP family, as one family of chemokines, consists of four members (MCP-1 to 4), displaying a preference for attracting monocytes but showing differences in their potential (Luini, W., et al. (1994) Cytokine 6, 28-31; Uguccioni, M., et al. (1995) Eur. J Immunol. 25, 64-68).

A number of studies have underlined in particular the crucial role of MCP-1 for the development of atherosclerosis (Gu, L., et al. (1998) Mol. Cell 2, 275-281; Gosling, J., et al. (1999) J Clin. Invest. 103, 773-778); rheumatoid arthritis (Gong, J. H., et al. (1997) J Exp. Med. 186, 131-137; Ogata, H., et al. (1997) J Pathol. 182, 106-114); pancreatitis (Bhatia, M., et al. (2005) Am. J Physiol. Gastrointest. Liver Physiol 288, G1259-G1265); Alzheimer's disease (Yamamoto, M., et al. (2005) Am. J Pathol. 166, 1475-1485); lung fibrosis (Inoshima, I., et al. (2004) Am. J Physiol Lung Cell Mol. Physiol 286, L1038-L1044); renal fibrosis (Wada, T., et al. (2004) J Am. Soc. Nephrol. 15, 940-948), and graft rejection (Saiura, A., et al. (2004) Arterioscler. Thromb. Vasc. Biol. 24, 1886-1890). Furthermore, MCP-1 might also play a role in gestosis (Katabuchi, H., et al. (2003) Med. Electron Microsc.

36, 253-262), as a paracrine factor in tumor development (Ohta, M., et al. (2003) Int. J Oncol. 22, 773-778; Li, S., et al. (2005) J Exp. Med 202, 617-624), neuropathic pain (White, F. A., et al. (2005) Proc. Natl. Acad. Sci. U.S.A) and AIDS (Park, I. W., Wang, J. F., and Groopman, J. E. (2001) Blood 97, 352-358; Coll, B., et al. (2006) Cytokine 34, 51-55).

The mature form of human and rodent MCP-1 is posttranslationally modified by Glutaminyl Cyclase (QC) to possess an N-terminal pyroglutamyl (pGlu) residue. The N-terminal pGlu modification makes the protein resistant against N-terminal degradation by aminopeptidases, which is of importance, since chemotactic potency of MCP-1 is mediated by its N-terminus (Van Damme, J., et al. (1999) Chem. Immunol. 72, 42-56). Artificial elongation or degradation leads to a loss of function although MCP-1 still binds to its receptor (CCR2) (Proost, P., et al. (1998), J Immunol. 160, 4034-4041; Zhang, Y. J., et al. 1994, J Biol. Chem. 269, 15918-15924; Masure, S., et al. 1995, J Interferon Cytokine Res. 15, 955-963; Hemmerich, S., et al. (1999) Biochemistry 38, 13013-13025).

Due to the major role of MCP-1 in a number of disease conditions, an anti-MCP-1 strategy is required. Therefore, small orally available compounds inhibiting the action of MCP-1 are promising candidates for a drug development. Such compounds are, for instance, inhibitors of QC as shown in WO 2008/104580.

Atherosclerotic lesions, which limit or obstruct coronary blood flow, are the major cause of ischemic heart disease related mortality, resulting in 500,000-600,000 deaths annually. Percutaneous transluminal coronary angioplasty (PTCA) to open the obstructed artery was performed in over 550,000 patients in the U.S. and 945,000+ patients worldwide in 1996 (Lemaitre et al. 1996). A major limitation of this technique is the problem of post-PTCA closure of the vessel, both immediately after PTCA (acute occlusion) and in the long term (restenosis): 30% of patients with subtotal lesions and 50% of patients with chronic total lesions will progress to restenosis after angioplasty. Additionally, restenosis is a significant problem in patients undergoing saphenous vein bypass graft. The mechanism of acute occlusion appears to involve several factors and may result from vascular recoil with resultant closure of the artery and/or deposition of blood platelets along the damaged length of the newly opened blood vessel followed by formation of a fibrin/red blood cell thrombus.

Restenosis after angioplasty is a more gradual process and involves initial formation of a subcritical thrombosis with release from adherent platelets of cell derived growth factors with subsequent proliferation of intimal smooth muscle cells and local infiltration of inflammatory cells contributing to vascular hyperplasia. It is important to note that multiple processes, among which thrombosis, cell proliferation, cell migration and inflammation each seem to contribute to the restenotic process.

In the U.S.A., a 30-50% restenosis rate translates to 120,000-200,000 U.S. patients at risk from restenosis. If only 80% of such patients elect repeated angioplasty (with the remaining 20% electing coronary artery bypass graft) and this is added to the costs of coronary artery bypass graft for the remaining 20%, the total costs for restenosis tretment easily amounts to billions of dollars in the U.S. Thus, successful prevention of restenosis could result not only in significant therapeutic benefit but also in significant health care savings.

As outlined above, monocyte chemoattractant protein 1 (MCP-1, CCL2) belongs to a family of potent chemotactic cytokines (CC chemokines), that regulate the trafficking of leukocytes, especially monocytes, macrophages and T-cells, to sites of inflammation (Charo, I. F. and Taubman, M. B. (2004) Circ. Res. 95, 858-866). Besides its role in, e.g. vascular diseases, compelling evidence points to a role of MCP-1 in Alzheimer's disease (AD) (Xia, M. Q. and Hyman, B. T. (1999) J Neurovirol. 5, 32-41). The presence of MCP-1 in senile plaques and in reactive microglia, the residential macrophages of the CNS have been observed in brains of patients suffering from AD (Ishizuka, K., et al. (1997) Psychiatry Clin. Neurosci. 51, 135-138). Stimulation of monocytes and microglia with Amyloid-β protein (Aβ) induces chemokine secretion in vitro (Meda, L., et al. (1996) J Immunol. 157, 1213-1218; Szczepanik, A. M., et al. (2001) J Neuroimmunol. 113, 49-62) and intracerebroventricular infusion of $A\beta_{(1-42)}$ into murine hippocampus significantly increases MCP-1 in vivo. Moreover, Aβ deposits attract and activate microglial cells and force them to produce inflammatory mediators such as MCP-1, which in turn leads to a feed back to induce further chemotaxis, activation and tissue damage. At the site of Aβ deposition, activated microglia also phagocytose Aβ peptides leading to an amplified activation (Rogers, J. and Lue, L. F. (2001) Neurochem. Int. 39, 333-340).

Examination of chemokine expression in a 3×Tg mouse model for AD revealed that neuronal inflammation precedes plaque formation and MCP-1 is upregulated by a factor of 11. Furthermore, the upregulation of MCP-1 seems to correlate with the occurrence of first intracellular Aβ deposits (Janelsins, M. C., et al. (2005) J Neuroinflammation. 2, 23). Crossbreeding of the Tg2576 mouse model for AD with a MCP-1 overexpressing mouse model has shown an increased microglia accumulation around Aβ deposits and that this accumulation was accompanied by increased amount of diffuse plaques compared to single-transgenic Tg2576 littermates (Yamamoto, M., et al. (2005) Am. J Pathol. 166, 1475-1485).

MCP-1 levels are increased in CSF of AD patients and patients showing mild cognitive impairment (MCI) (Galimberti, D., et al. (2006) Arch. Neurol. 63, 538-543). Furthermore, MCP-1 shows an increased level in serum of patients with MCI and early AD (Clerici, F., et al. (2006) Neurobiol. Aging 27, 1763-1768).

Osteoporosis is a disease of bone loss, typically as a result of estrogen depletion. The process of osteoclastogenesis plays a central role in osteoporosis. Osteoclastogenesis is a multistep event involving not only the proliferation of preosteoclasts from the monocyte and macrophage linage but also their differentiation into osteoclasts. Enhanced osteoclast activity is the main reason for bone loss mediated by estrogen deficiency. Binder et al. have shown that the chemokine recepter CCR2 is involved in the pathomechanisms leading to postmenopausal osteoporosis. $Ccr2^{-/-}$ mice were protected from estrogen deficiency-mediated bone loss, and this effect was mediated via osteoclasts (Binder et al., (2009) Nat Med. April; 15(4), 417-24). Moreover, estrogen was also shown to downregulate MCP-1, and studies comparing pre- and postmenopausal women showed that there is increased expression of MCP-1 in the latter group. Binder et al. further found that MCP-1 deficient mice show only an intermediate bone phenotype, i.e. that MCP-1 is not the only ligand for CCR2 playing a role in osteoporosis. They showed that MCP-3, which is also a ligand of CCR2, has similar pro-osteoclastogenic effects in presence of CCR2 and can substitute for MCP-1 (Binder et al., (2009) Nat Med. April; 15(4), 417-24).

SUMMARY OF THE INVENTION

At least one object of the present invention is to provide novel possibilities for a treatment of inflammatory diseases. In particular, it is desired to provide an improved approach to affect the MCP family of chemokines, which consists of four members (MCP-1, MCP-2, MCP-3, MCP-3 and MCP-4). More particularly, it is an object of the present invention to provide an improved approach to affect the chemokine MCP-1.

The present invention relates to inhibitors of an isoglutaminyl peptide cyclotransferase (isoQC) and the use thereof for the treatment and/or prevention of a disease or disorder selected from the group consisting of inflammatory diseases selected from:

(a) chronic and acute inflammations, e.g. rheumatoid arthritis, atherosclerosis, restenosis, pancreatitis, osteoporosis;

(b) other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis;

(c) neuroinflammation; and (d) neurodegenerative diseases, e.g. mild cognitive impairment (MCI), Alzheimer's disease, neurodegeneration in Down Syndrome, Familial British Dementia, and Familial Danish Dementia, which may result from neuroinflammation.

Inhibitors of isoQC are small orally available compounds, which prevent the important step of pGlu-formation at the N-terminus of peptide hormones and chemokines, e.g. the chemokines MCP-1, MCP-2, MCP-3 and/or MCP-4. In consequence, caused by isoQC-inhibition, the N-terminus of MCP-1, MCP-2, MCP-3 and/or MCP-4 is not protected by a pGlu-residue. Instead, the N-terminus possesses a glutamine-proline motif, which is prone to cleavage by aminopeptidases, e.g. dipeptidylpeptidases like dipeptidylpeptidase 4, other aminopeptidases, like aminopeptidase P or aminopeptidase N, and fibroblast activating protein (FAP, Seprase), which are abundant on the endothelium and within the blood circulation. This cleavage results in the formation of N-terminal truncated MCP-1, MCP-2, MCP-3 and/or MCP-4. These molecules unfold, in turn, an antagonistic action at the CCR2 receptor and therefore, monocyte-related disease conditions are inhibited efficiently. Particularly preferred in this regard is the inhibition of the pGlu-formation at the N-terminus of MCP-1.

BRIEF DESCRIPTION OF THE DRAWINGS

Those of skill in the art will understand that the drawings, described below, are for illustrative purposes only. The drawings are not intended to limit the scope of the present teachings in any way.

TABLE 1

| | |
|---|---|
| —▽— | 0 µM |
| —▲— | 0.3125 µM |
| —△— | 0.625 µM |
| —■— | 1.25 µM |
| —□— | 2.5 µM |
| —●— | 5 µM |

The determined Ki-value was 240+/−8 nM.

Figure 2:
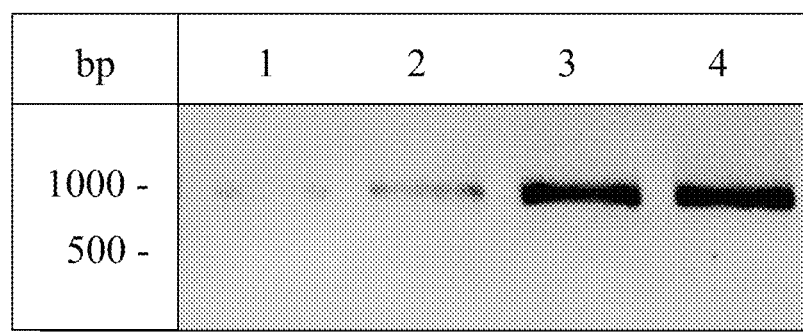

FIG. 2 shows the analysis of isoQC expression by RT-PCR. Detection in SH-SY5Y, LN405, HaCaT and Hep-G2. Lanes: bp, DNA standard; 1, amplified PCR product of human isoQC from SH-SY5Y; 2, amplified PCR product of human isoQC from LN405; 3, amplified PCR product of human isoQC from HaCaT; 4, amplified PCR product of human isoQC from Hep-G2.

Figure 3:
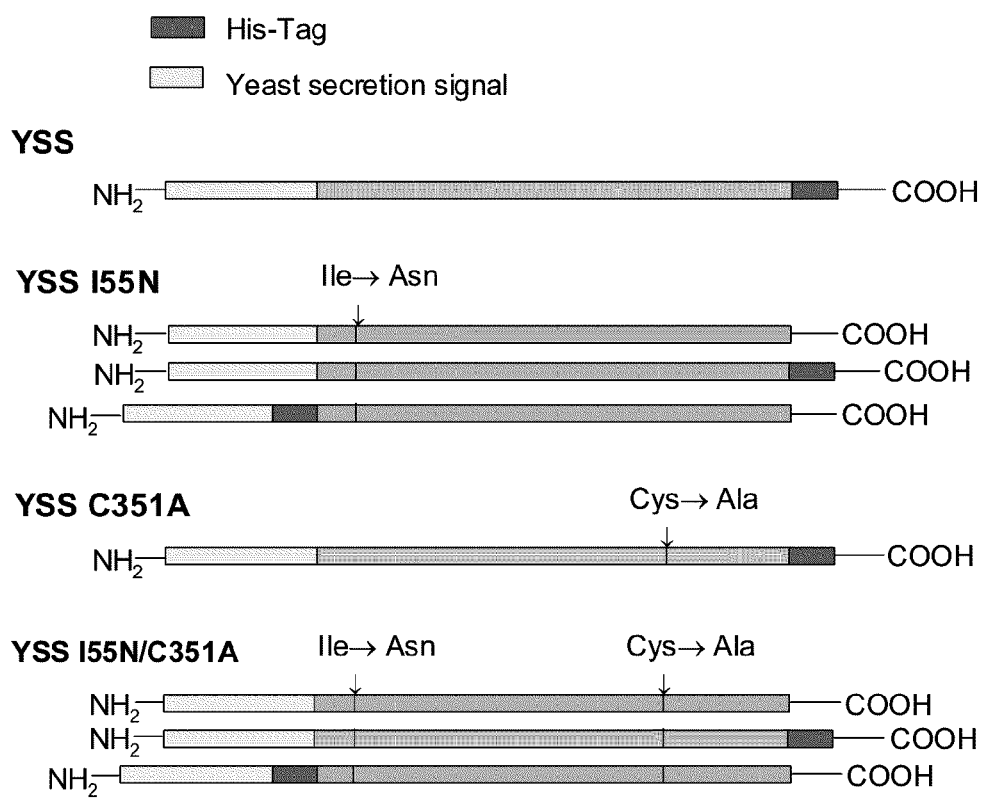

FIG. 3 provides a schematic representation of the human isoQC protein constructs that were expressed hetereologously in the yeast P. pastoris. Two mutations were introduced in some proteins, leading to a glycosylation site at position 55 (I55N) and a mutated cystein residue at position 351 (C351A). For expression, the N-terminus including the transmembrane domain was replaced by a secretion signal of yeast (YSS). The constructs containing the N-terminal secretion signal should be efficiently secreted into the medium.

Figure 4:
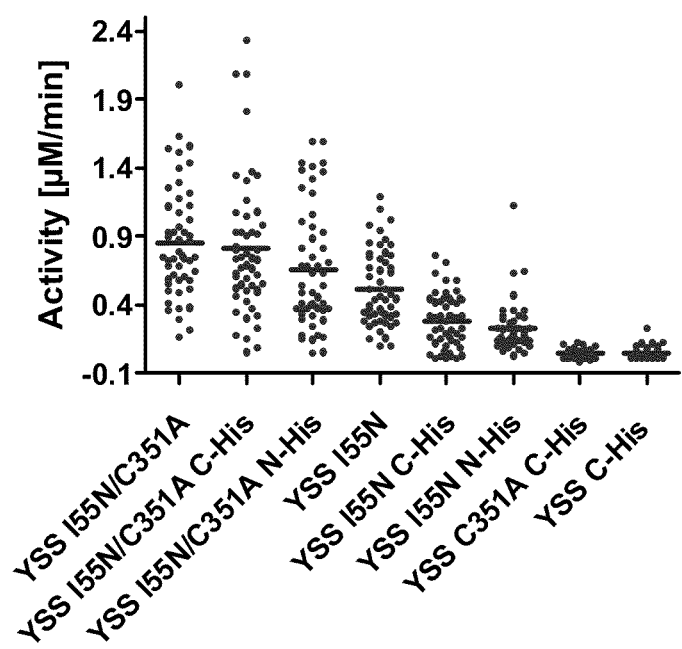

FIG. 4 shows the isoQC activity, which was determined in the medium of expressing yeast cells. Due to the transmembrane domain, the native constructs were not secreted into the medium (not implemented). Caused by glycosylation (I55N), proteins are most efficiently secreted. The mutation C351A resulted also in higher isoQC activity detected in the medium.

Figure 5:
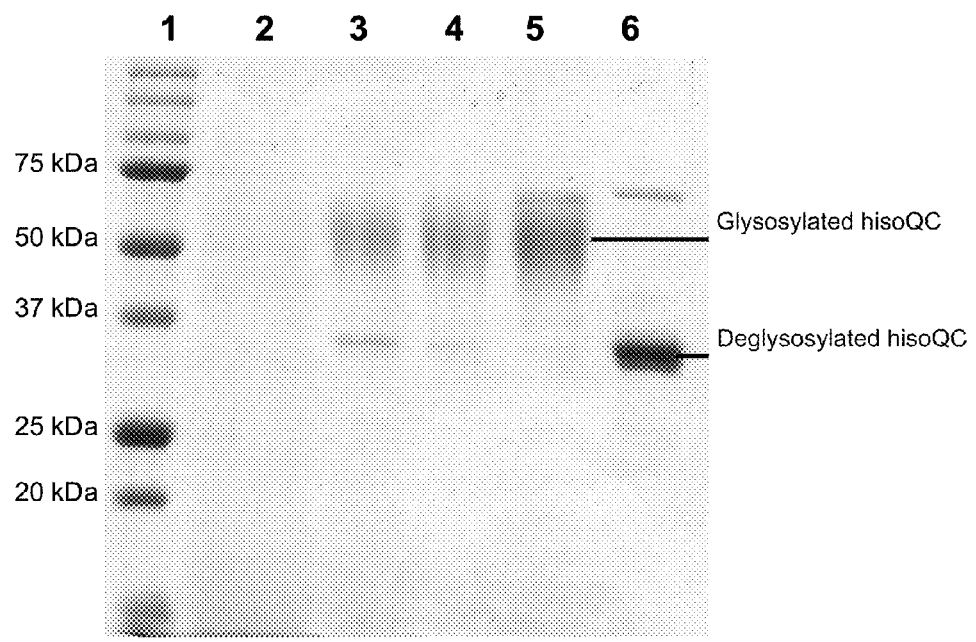

FIG. 5 shows the purification of the human isoQC, based on construct YSShisoQCI55NC351A C-His, from the medium of a transgenic P. pastoris strain. The isoQC was purified by a combination of IMAC (immobilized metal affinity chromatography, lane 3), HIC (hydrophobic interaction chromatography, lane 4) and desalting (lane 5). The glycosylation of the enzyme was evidence by enzymatic deglycosalytion, which results in a shift in migration of the protein (lane 6). Lane 1, protein standard: Lane 2, medium prior to purification.

Figure 6:
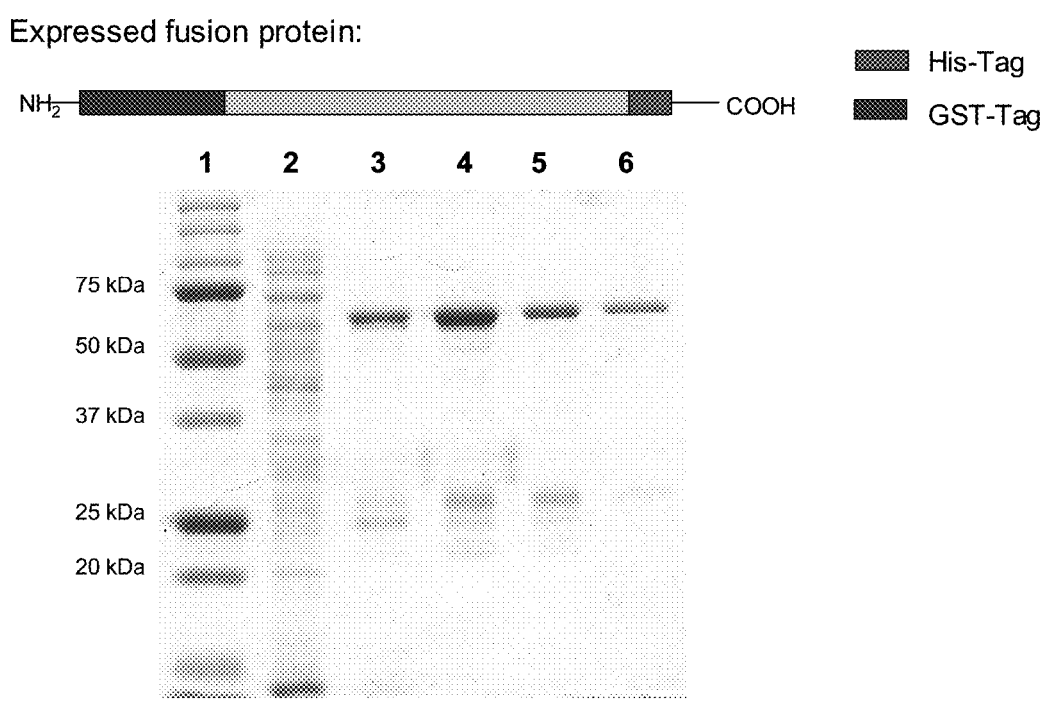

FIG. 6 shows the purification of the human isoQC, based on construct GST-hisoQC C-His, from the cell homogenate of transformed E. coli. The isoQC was purified by a combination of IMAC (immobilized metal affinity chromatography, lane 3), GST-affinity (lane 4), desalting (lane 5) and ion exchange chromatography (lane 6). Lane 1, protein standard: Lane 2, cell homogenate prior to purification. The difference in the molecular mass between the hisoQC which was expressed in yeast and E. coli is caused by the N-terminal GST-tag fusion. The expressed construct is provided schematically in the upper part of the figure.

Figure 7:
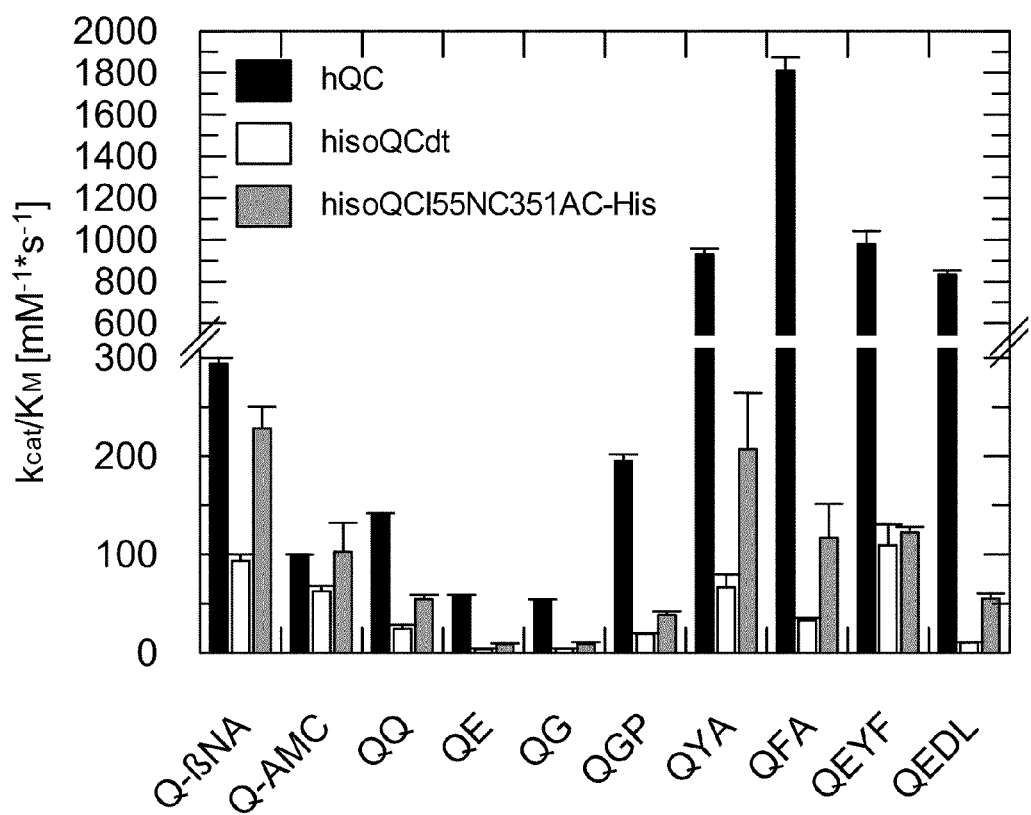

FIG. 7 shows the specificity constants for conversion of dipeptide-surrogates, dipeptides and oligopeptides by human isoQC (YSShisoQCI55NC351A C-His), GST-hisoQC and human QC. The specificity of GST-hisoQC was the lowest, followed by YSShisoQCI55NC351A C-His. The highest specificity displayed human QC, indicating a higher overall enzymatic activity.

Figure 8:
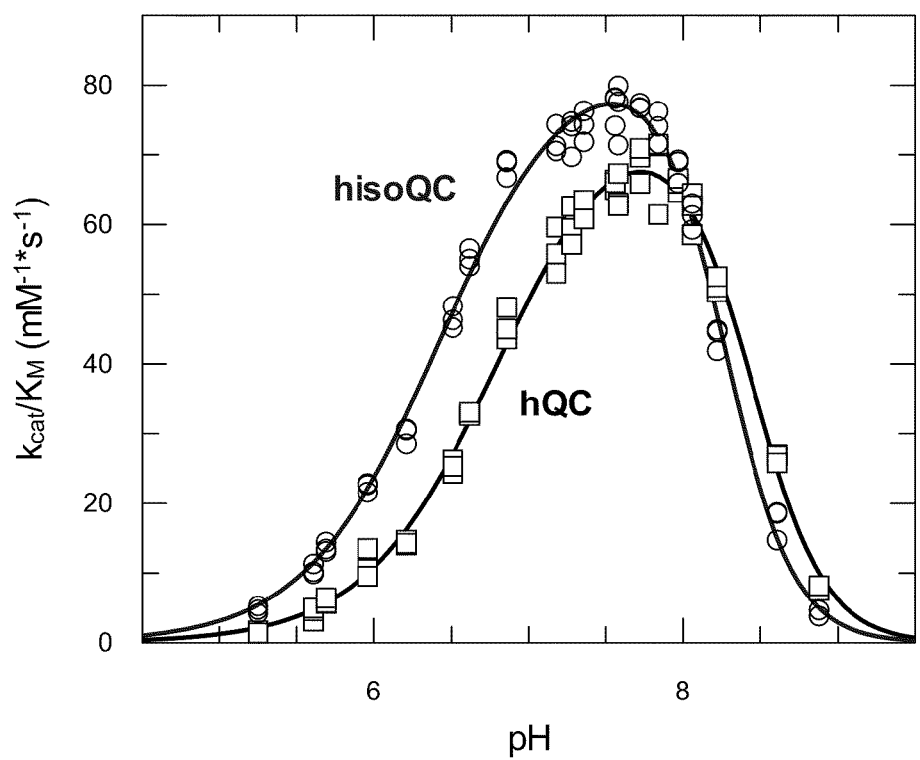

FIG. 8 shows the pH-dependency of catalysis, investigated with human isoQC (hisoQC), which was expressed in yeast, and human QC (hQC). Both proteins display a pH-optimum between pH 7 and 8. The fitted curve is based on three dissociating groups that influence catalysis, one at acidic pH, two at basic pH.

FIG. 9 shows the subcellular localization of mouse-isoQC (m-isoQC) in LN405 cells: (a) localization of m-isoQC-EGFP fusion proteins starting with one of the alternative start methionines MetI or MetII, and (b) localization of a fusion protein consisting of the N-terminal sequences of m-isoQC starting with MetI or MetII and ending at Ser 55 (numbering is based on MetI representing the N-terminal amino acid position 1, compare to FIG. 15), and a C-terminal EGFP fusion. The Golgi complex was stained using anti-mannosidase II antibody. Co-localization is shown by superimposition of EGFP fluorescence and Cy3 fluorescence (Merge).

FIG. 10 shows the subcellular localization of rat-isoQC (r-isoQC) in LN405 cells: (a) localization of r-isoQC-EGFP fusion proteins starting with one of the alternative start methioniens MetI or with MetII and of (b) localization of a fusion protein consisting of the N-terminal sequences of r-isoQC starting with MetI or MetII and ending at Ser 55 (numbering is based on MetI representing the N-terminal amino acid position 1, compare to FIG. 15), and a C-terminal EGFP fusion. The Golgi complex was stained using anti-mannosidase II antibody. Co-localization is shown by superimposition of EGFP fluorescence and Cy3 fluorescence (Merge).

FIG. 11 shows the subcellular localization of mouse-isoQC (m-isoQC) in SH-SY5Y cells: (a) localization of m-isoQC-EGFP fusion proteins starting with one of the alternative start methionines MetI or MetII, and (b) localization of a fusion protein consisting of the N-terminal sequences of m-isoQC starting with MetI or MetII and ending at Ser 55 (numbering is based on MetI representing the N-terminal amino acid position 1, compare to FIG. 15), and a C-terminal EGFP fusion. The Golgi complex was stained using anti-mannosidase II antibody. Co-localization is shown by superimposition of EGFP fluorescence and Cy3 fluorescence (Merge).

FIG. 12 shows the subcellular localization of rat-isoQC (r-isoQC) in SH-SYS5 cells: (a) localization of r-isoQC-EGFP fusion proteins starting with one of the alternative start methioniens MetI or with MetII and of (b) localization of a fusion protein consisting of the N-terminal sequences of r-isoQC starting with MetI or MetII and ending at Ser 55 (numbering is based on MetI representing the N-terminal amino acid position 1, compare to FIG. 15), and a C-terminal EGFP fusion. The Golgi complex was stained using anti-mannosidase II antibody. Co-localization is shown by superimposition of EGFP fluorescence and Cy3 fluorescence (Merge).

Figure 13:
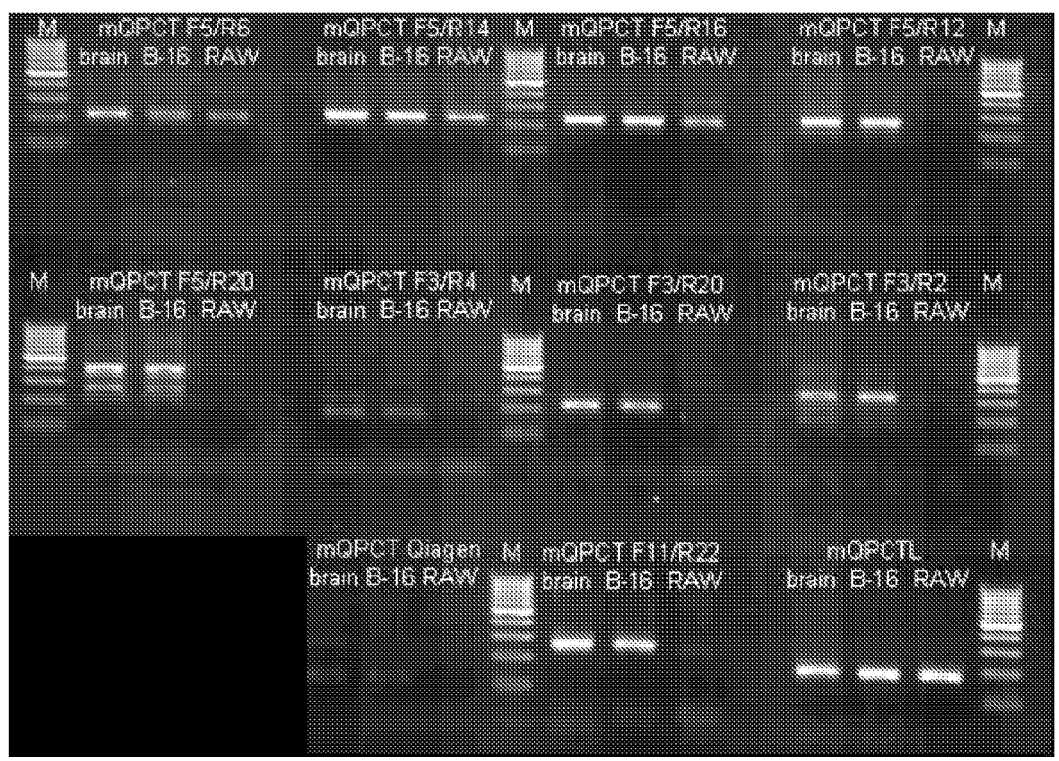
Figure 13:
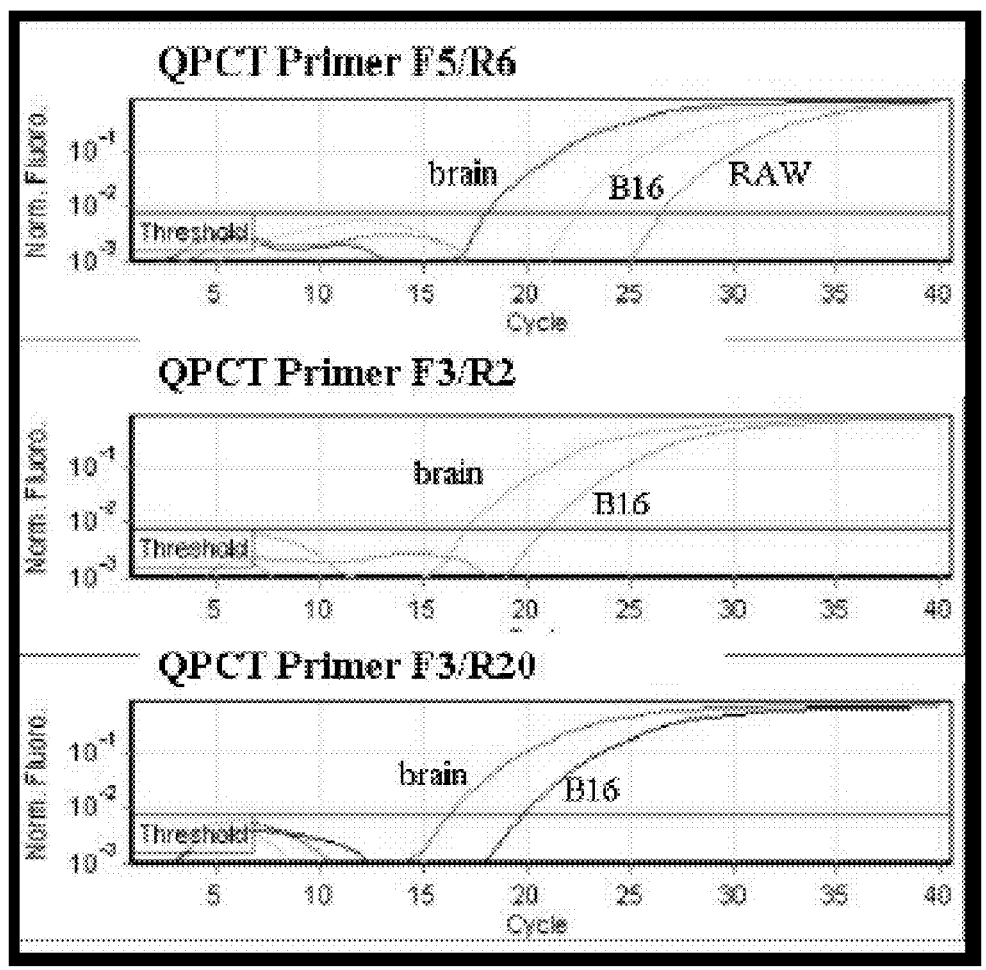

FIG. 13 shows the results of the quantitative PCR for characterization of mouse QC (mQPCT) and mouse-isoQC (mQPCTL) expression in RAW cells. (a) Analysis of PCR amplification products using agarose gel electrophoresis. M-100 bp ladder (Peqlab, Erlangen, Germany), Brain: products of RNA isolated from brain tissues, B16: products of RNA isolated from B16 melanoma cells, RAW: products of RNA isolated from RAW264.7 cells. (b) Amplification curves using primer pairs QPCT F5/R6, F3/R2 and F3/R20.

FIG. 14 shows quantitative PCR results for human QC (hQPCT) and human isoQC (hQPCTL) gene expression in THP1 cells after treatment with LPS (1 µg/ml) for 24 h.

FIG. 15 shows a sequence alignment of human, mouse and rat isoQC. The proteins share a sequence identity of 83%. The two different, potential start methionines are highlighted in bold.

Figure 16:
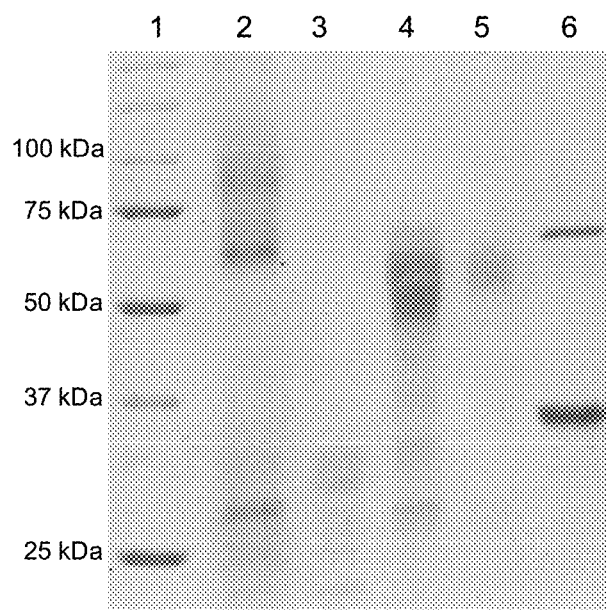

FIG. 16 shows the SDS-PAGE analysis illustrating the purification of mouse-isoQC after fermentation. Proteins were visualized by Coomassie staining. Lane 1, molecular mass standards (kilodaltons) (Dual Color, Bio-Rad); lane 2, supernatant after expression; lane 3, mouse-isoQC containing fractions after initial hydrophobic interaction chromatography in expanded bed modus; lane 4, mouse-isoQC after hydrophobic interaction chromatography; lane 5, mouse-isoQC after UnoQ column. lane 6 mouse-isoQC after gelfiltration and treatment with deglycosylation enzyme EndoHF. The isoQC protein corresponds to a protein between 50 kDa and 70 kDa. The deglycosylated protein corresponds to a protein band at 37 kDa. The mouse-isoQC was purified to homogeneity.

Figure 17:
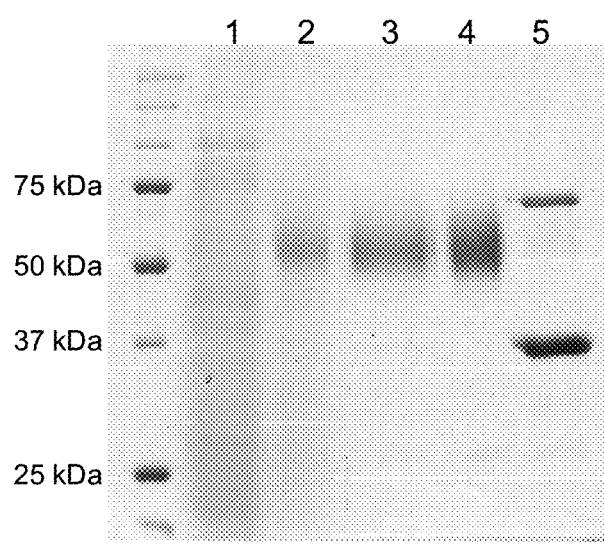

FIG. 17 illustrates the purification of rat-isoQC as analysed by SDS-PAGE. Lanes represent: lane 1; supernatant after rat-isoQC fermentation; lane 2 rat-isoQC containing fractions after metal affinity chromatography; lane 3 rat-isoQC protein after hydrophobic interaction chromatography, lane 4 purified rat-isoQC after desalting column; The isoQC protein corresponds to a protein between 50 kDa and 70 kDa. The homogenous deglycosylated rat-isoQC corresponds to a protein band at 37 kDa (lane 5) and the deglycosylation enzyme EndoHF migrates at 75 kDa. Proteins were visualized by Coomassie staining. The rat-isoQC was purified to homogeneity.

Figure 18:
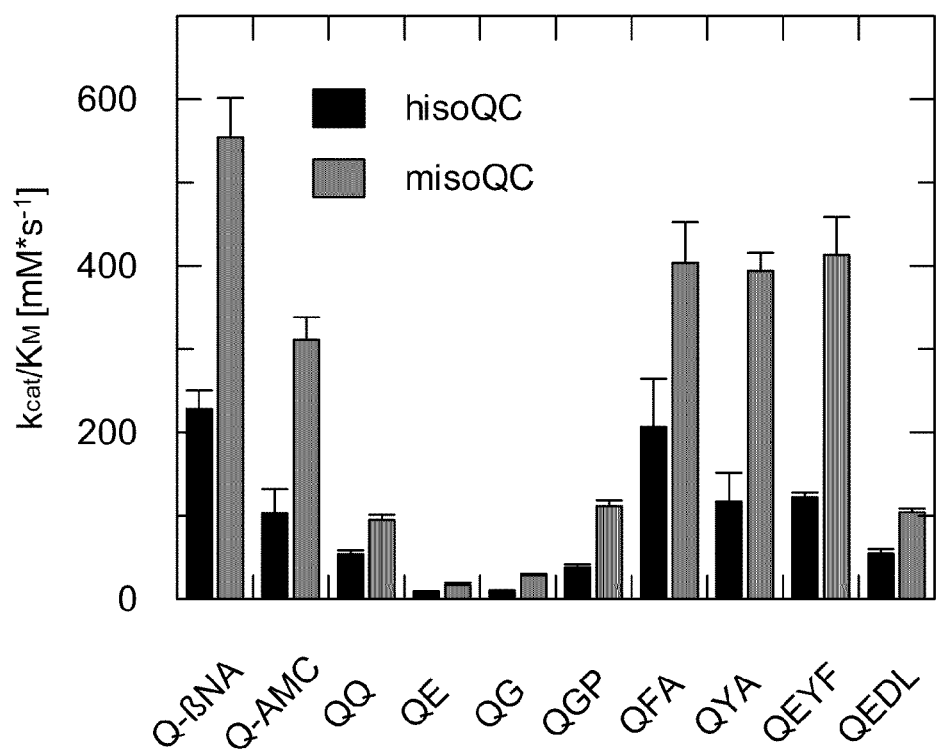

FIG. 18 shows the specificity constants for conversion of dipeptide-surrogates, dipeptides and oligopeptides by mouse-isoQC and human isoQC. The highest specificity was displayed by mouse-isoQC, indicating a higher overall enzymatic activity.

Figure 19:
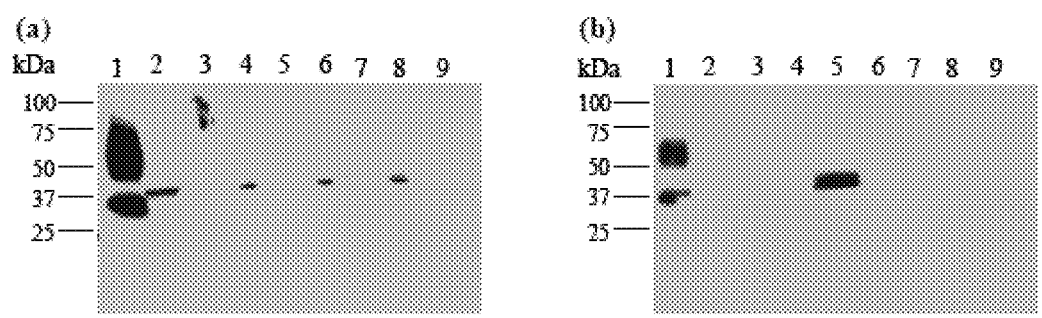

FIG. 19 shows the western blot analysis for the determination of human isoQC antibody pAb 3284 after transfection of HEK293 cells with different QC and isoQC constructs (per transfected construct, 32 µl disrupted cells and 32 µl 1:10 concentrated media were loaded on a SDS-Gel). (a) lane 1, purified human isoQC (500 ng); lane 2, cells transfected with human isoQC; lane 3, Media after human isoQC expression; lane 4, cells after transfection with human QC; lane 5, media after human QC expression; lane 6, cells after rat-isoQC expression; lane 7, media after rat-isoQC expression; lane 8, cells after rat QC expression; lane 9, media after rat QC expression. Protein detection using the specific human isoQC antibody pAb 3284. (b) Development of the western blot after washing with Restore™ Western Blot Stripping Buffer (Thermo Scientific) with specific human QC antibody (pAb 8695)

Figure 20:
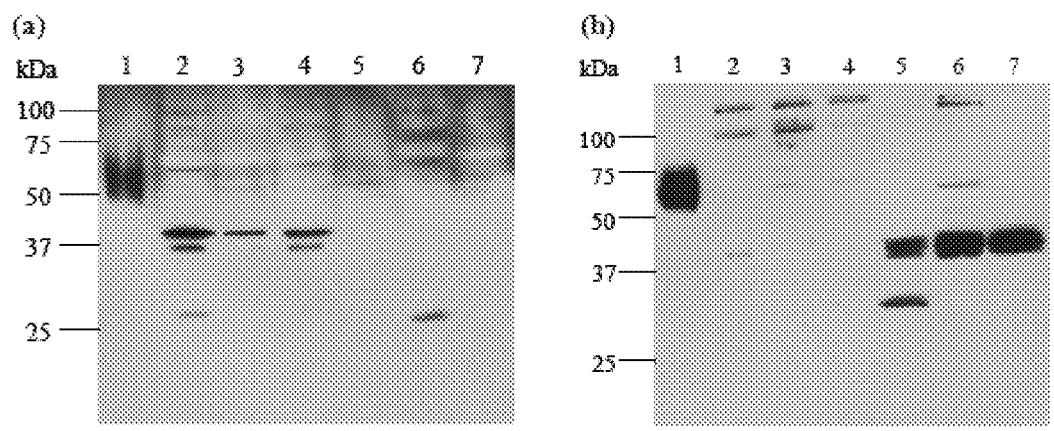

FIG. 20 shows the determination of basal expression levels of isoQC in cells from different mammalian species by western blot analysis. 120 µg protein from the disrupted cells was loaded to the SDS-Gel lane 1, purified human isoQC (10 ng); lane 2, HEK293 (human); lane 3, SH-SY5Y (human); lane 4, U343 (human); lane 5, RAW (mouse); lane 6, N2a (mouse); lane 7, PC12 (rat). (a) Detection of the protein with human isoQC antibody pAb 3284. (b) Detection of the proteins with rat-isoQC antibody pAb 3286

Figure 21:
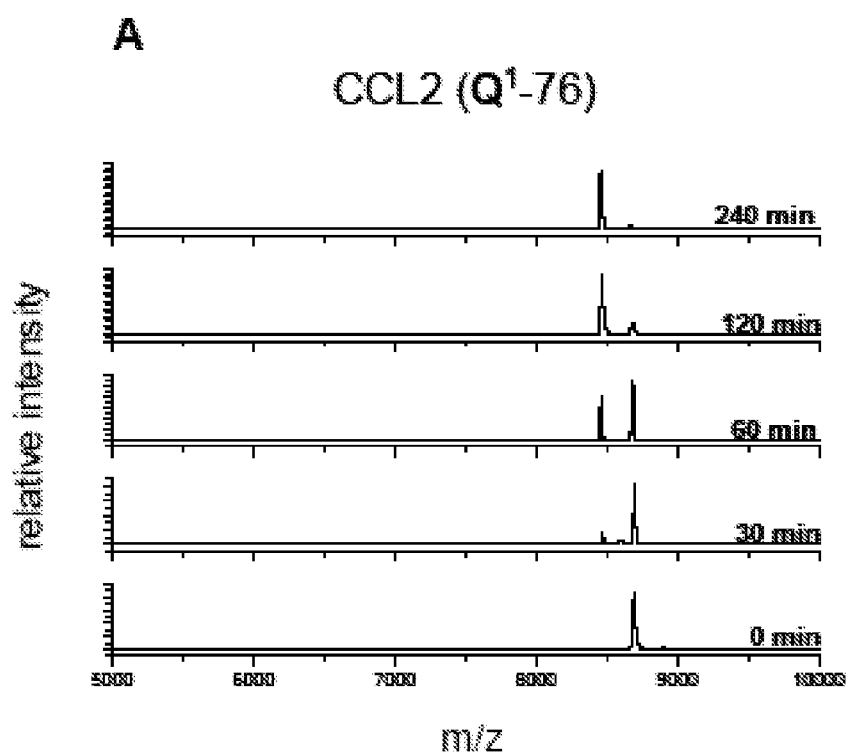
Figure 21:
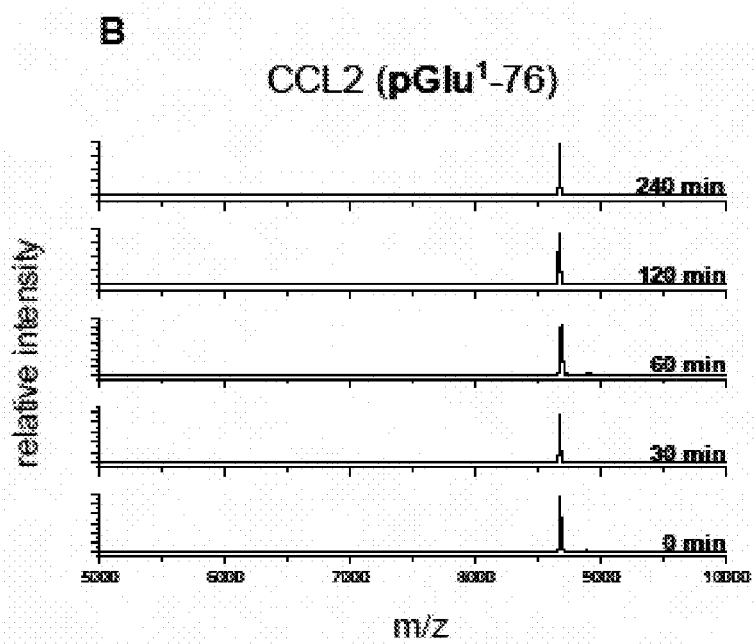

FIG. 21 shows the incubation of human CCL2 (MCP-1) with recombinant human DP4. (a) Cleavage of CCL2 (Q1-76) (20 µg/ml) by recombinant human DP4 (1:200). (b) Incubation of human CCL2 with recombinant human isoQC (1:1000) (CCL2 (pGlu1-76)) followed by incubation with DP4 (1:200). Cleavage was monitored for the indicated time points up to 4 h and products were analyzed using Maldi-TOF MS.

Figure 22:
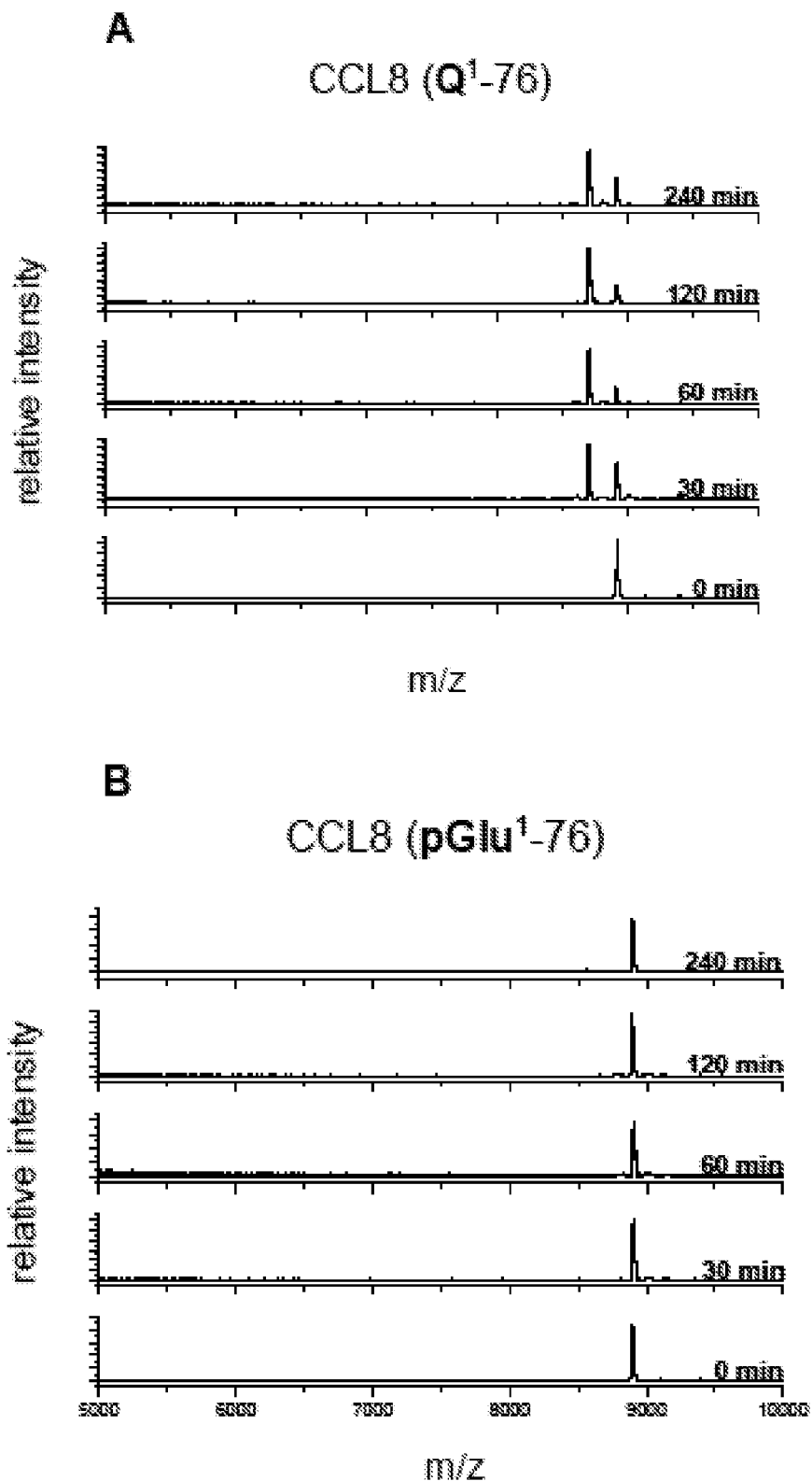

FIG. 22 shows the incubation of human CCL8 (MCP-2) with recombinant human DP4. (a) Cleavage of CCL8 (Q1-76) (10 µg/ml) by recombinant human DP4 (1:100). (b) Incubation of human CCL8 with recombinant human isoQC (1:1000) (CCL8 (pGlu1-76)) followed by incubation with DP4 (1:200). Cleavage was monitored for the indicated time points up to 4 h and products were analyzed using Maldi-TOF MS.

Figure 23:
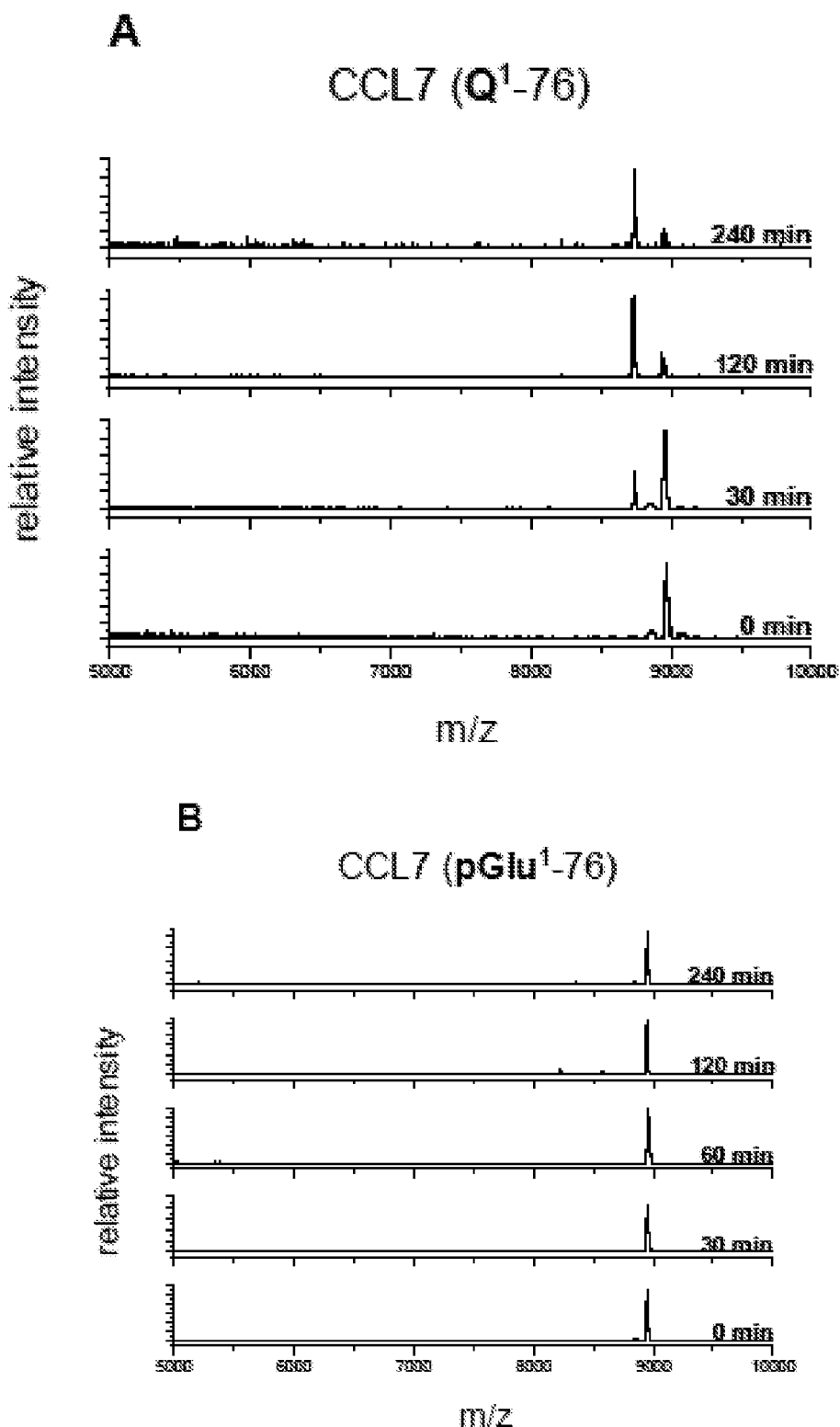

FIG. 23 shows the incubation of human CCL7 (MCP-3) with recombinant human DP4. (a) Cleavage of CCL7 (Q1-76) (10 µg/ml) by recombinant human DP4 (1:2000). (b) Incubation of human CCL7 with human recombinant isoQC (1:1000) (CCL7 (pGlu1-76)) followed by incubation with DP4 (1:200). Cleavage was monitored for the indicated time points up to 4 h and products were analyzed using Maldi-TOF MS.

Figure 24:
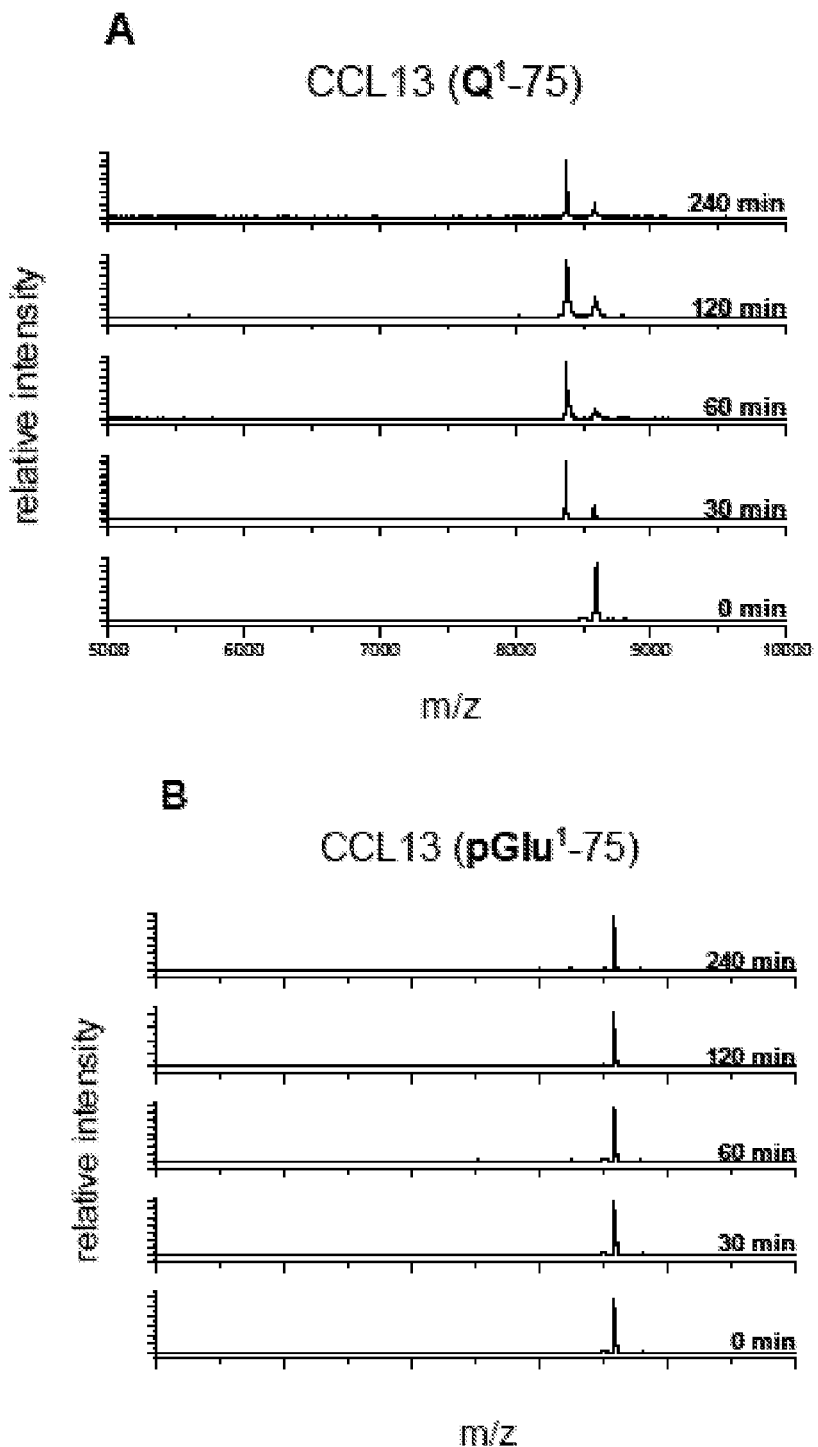

FIG. 24 shows the incubation of human CCL13 (MCP-4) with recombinant human DP4. (a) Cleavage of CCL13 (Q1-76) (10 µg/ml) by recombinant human DP4 (1:2000). (b) Incubation of human CCL13 with human recombinant isoQC (1:1000) (CCL13 (pGlu1-76)) followed by incubation with DP4 (1:200). Cleavage was monitored for the indicated time points up to 4 h and products were analyzed using Maldi-TOF MS.

FIG. 25 (a) shows the effect of the QC/isoQC inhibitor isoQC-I on monocyte infiltration in thioglycollate-induced peritonitis (mean SEM, n>5 per group). Thioglycollate (TG) and inhibitor were applied by ip injection. Cells positive for surface marker 7/4 (7/4(high)) and possessing only a weak immunoreactivity for marker Ly6G (Ly6G(low)) represent the infiltrated monocyte population. The positive cell population was counted by cytofluorometry using true count beads (BD). (b) shows the determination of the MCP-1 N1pE concentration in the lavage fluid of the mice injected with thioglycollate and treated with different doses of isoQC-I compared to control animals and animals injected with thioglycollate alone.

FIG. 26 shows the infiltration of monocytes (a) and granulocytes (b) in mixed male/female homozygous (HOM) QPCTL knock out animals in comparison to mixed male/female wild type littermates (WT). Animals were injected with thioglycollate (Thio) or saline (PBS). (***, P<0.001; ANOVA followed by Tuckey post-hoc analysis).

Figure 27:
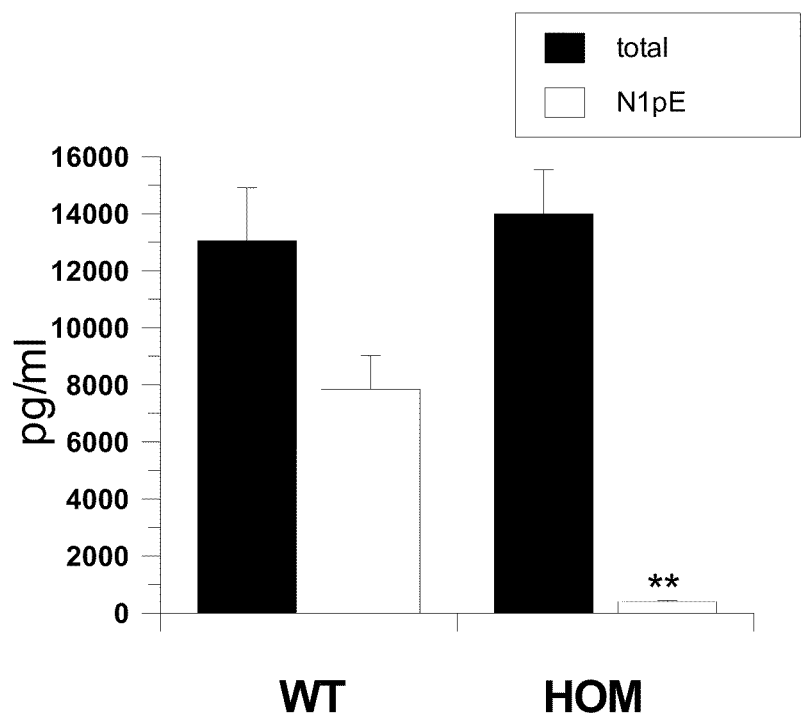

FIG. 27 shows the analysis of total MCP-1 (black bars) and pGlu-MCP-1 (open bars) using specific ELISAs in thioglycollate-injected mixed male/female homozygous (HOM) QPCTL k.o. animals compared to mixed male/female wild type littermates (WT). (**, P<0.01, Student's t-test).

FIG. 28 (a) shows the analysis of total MCP-1 (black bars) and pGlu-MCP-1 (open bars) using specific ELISAs in LPS-stimulated PBMC (+LPS) compared to unstimulated PBMCs (−LPS) isolated from QPCTL k.o. animals (HOM) and wild type littermates (WT). (b) shows the ratio of pGlu-MCP-1 and total MCP-1 in % from QPCTL k.o. animals (open bars) and wild type littermates (black bars) in absence (−LPS) or presence (+LPS) of LPS-stimulus (***, P<0.001; 2-way ANOVA, followed by Bonferroni's post-hoc test).

FIG. 29 (a) shows the reactivation of mouse-isoQC, mouse QC and QC from *Drosophila melanogaster* (DromeQC) with different ratios of zinc to enzyme. Prior to reactivation, enzymes were inactivated with 1,10-phenantroline in 50 mM BisTris, pH 6.8 containing 500 mM NaCl to a residual activity under 1%. Subsequently, the enzyme was subjected to dialysis against 50 mM BisTris, pH 6.8 containing 500 mM NaCl and 50 g/l Chelex. Reactivation was carried out by addition of different concentrations of ZnSO4 to the inactivated proteins. (b) Reactivation of mouse-isoQC with zinc ions, the protein to zinc content was increasing in order to determine the zinc necessary to full reactivate the enzyme. Inactivation was carried out with 1,10-phenantroline in 50 mM BisTris, pH 6.8 containing 500 mM NaCl.

Figure 30:
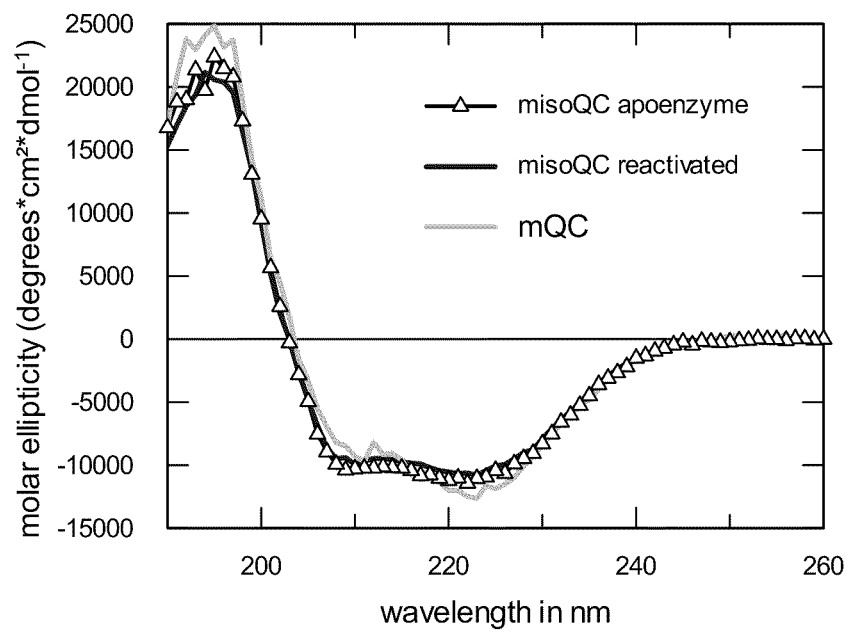

FIG. 30 shows a CD-spectroscopic analysis of the secondary structure of inactivated and reactivated mouse isoQC. The protein was dissolved in 10 mM potassium phosphate buffer, pH 6.8. An estimation of the secondary structure revealed 50% α-helix and 26% β-turn for both enzymes. The zinc ion does not exert an influence on the secondary structure.

DEFINITIONS

Enzyme Inhibitors

Reversible enzyme inhibitors comprise competitive inhibitors, non-competitive reversible inhibitors, slow-binding or tight-binding inhibitors, transition state analogs and multisubstrate analogs.

Competitive Inhibitors Show
i) non-covalent interactions with the enzyme,
ii) compete with substrate for the enzyme active site, The principal mechanism of action of a reversible enzyme inhibitor and the definition of the dissociation constant can be visualized as follows:

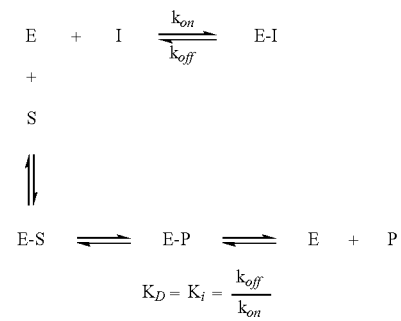

The formation of the enzyme-inhibitor [E–I] complex prevents binding of substrates, therefore the reaction cannot proceed to the normal physiological product, P. A larger inhibitor concentration [I] leads to larger [E–I], leaving less free enzyme to which the substrate can bind.

Non-Competitive Reversible Inhibitors
i) bind at a site other than active site (allosteric binding site)
ii) cause a conformational change in the enzyme which decreases or stops catalytic activity.

Slow-Binding or Tight-Binding Inhibitors
i) are competitive inhibitors where the equilibrium between inhibitor and enzyme is reached slowly,
ii) ($k_{on}$ is slow), possibly due to conformational changes that must occur in the enzyme or inhibitor
a) are often transition state analogs
b) are effective at concentrations similar to the enzyme conc. (subnanomolar KD values)
c) due to $k_{off}$ values being so low these types of inhibitors are "almost" irreversible.

Transition State Analogs
are competitive inhibitors which mimic the transition state of an enzyme catalyzed reaction. Enzyme catalysis occurs due to a lowering of the energy of the transition state, therefore, transition state binding is favored over substrate binding.

Multisubstrate Analogs
For a reaction involving two or more substrates, a competitive inhibitor or transition state analog can be designed which contains structural characteristics resembling two or more of the substrates.

Irreversible enzyme inhibitors: drive the equilibrium between the unbound enzyme and inhibitor and enzyme inhibitor complex (E+I⇌E−I) all the way to the right with a covalent bond (~100 kcal/mole), making the inhibition irreversible.

Affinity Labeling Agents
Active-site directed irreversible inhibitors (competitive irreversible inhibitors) are recognized by the enzyme (reversible, specific binding) followed by covalent bond formation, and
i) are structurally similar to substrate, transition state or product allowing for specific interaction between drug and target enzyme,
ii) contain reactive functional group (e.g. a nucleophile, —COCH$_2$Br) allowing for covalent bond formation.

The reaction scheme below describes an active-site directed reagent with its target enzyme where $K_D$ is the dissociation constant and kinactivation is the rate of covalent bond formation.

Mechanism-based enzyme inactivators (also called suicide inhibitors) are active-site directed reagents (unreactive) which binds to the enzyme active site where it is transformed to a reactive form (activated) by the enzyme's catalytic capabilities. Once activated, a covalent bond between the inhibitor and the enzyme is formed.

The reaction scheme below shows the mechanism of action of a mechanism based enzyme inactivator, where $K_D$ is the dissociation complex, $k_2$ is the rate of activation of the inhibitor once bound to the enzyme, $k_3$ is the rate of dissociation of the activated inhibitor, P, from the enzyme (product can still be reactive) from the enzyme and $k_4$ is the rate of covalent bond formation between the activated inhibitor and the enzyme.

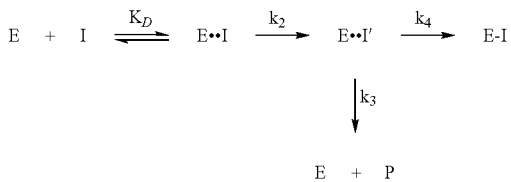

Inactivation (covalent bond formation, $k_4$) must occur prior to dissociation ($k_3$) otherwise the now reactive inhibitor is released into the environment. Partition ratio, $k_3/k_4$: ratio of released product to inactivation should be minimized for efficient inactivation of the system and minimal undesirable side reactions.

A large partition ratio (favors dissocation) leads to nonspecific reactions.

Uncompetitive enzyme inhibitors: From the definition of uncompetitive inhibitor (an inhibitor which binds only to ES complexes) the following equilibria can be written:

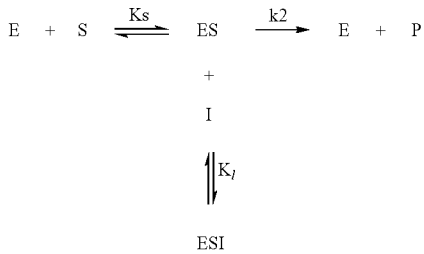

The ES complex dissociates the substrate with a dissociation constant equal to $K_S$, whereas the ESI complex does not dissociate it (i.e has a $K_S$ value equal to zero). The Km's of Michaelis-Menten type enzymes are expected to be reduced. Increasing substrate concentration leads to increasing ESI concentration (a complex incapable of progressing to reaction products), therefore the inhibition cannot be removed.

Preferred according to the present invention are reversible enzyme inhibitors.

Most preferred according to the present invention are competitive enzyme inhibitors.

The terms "$k_i$" or "$K_I$" and "$K_D$" are binding constants, which describe the binding of an inhibitor to and the subsequent release from an enzyme. Another measure is the "IC50" value, which reflects the inhibitor concentration, which at a given substrate concentration results in 50% enzyme activity.

Pharmaceutically Acceptable Salts

In view of the close relationship between the free compounds and the compounds in the form of their salts or solvates, whenever a compound or inhibitor, respectively, is referred to in this context, a corresponding salt or solvate is also intended, provided such is possible or appropriate under the circumstances.

Salts and solvates of the inhibitors of the present invention and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulphuric, nitric, citric, tartaric, phosphoric, lactic, pyruvic, acetic, trifluoroacetic, triphenylacetic, sulphamic, sulphanilic, succinic, oxalic, fumaric, maleic, malic, mandelic, glutamic, aspartic, oxaloacetic, methanesulphonic, ethanesulphonic, arylsulphonic (for example p-toluenesulphonic, benzenesulphonic, naphthalenesulphonic or naphthalene-disulphonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4 methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glutamine.

All pharmaceutically acceptable acid addition salt forms of the inhibitors of the present invention are intended to be embraced by the scope of this invention.

Examples of solvates include hydrates.

Polymorph Crystal Forms

Furthermore, some of the crystalline forms of the inhibitors may exist as polymorphs and as such are intended to be included in the present invention. In addition, some of the compounds may form solvates with water (i.e. hydrates) or common organic solvents, and such solvates are also intended to be encompassed within the scope of this invention. The inhibitors, including their salts, can also be obtained in the form of their hydrates, or include other solvents used for their crystallization.

Prodrugs

The present invention further includes within its scope prodrugs of the inhibitors of this invention. In general, such prodrugs will be functional derivatives of the inhibitors, which are readily convertible in vivo into the desired therapeutically active inhibitors. Thus, in these cases, the methods of treatment of the present invention, the term "administering" shall encompass the treatment of the various disorders described with prodrug versions of one or more of the itemed inhibitors, but which convert to the above specified inhibitors in vivo after administration to the subject. Conventional procedures for the selection and preparation of suitable prodrug derivatives are described, for example, in "Design of Prodrugs", ed. H. Bundgaard, Elsevier, 1985 and the patent applications DE 198 28 113, DE 198 28 114, WO 99/67228 and WO 99/67279 which are fully incorporated herein by reference.

Protective Groups

During any of the processes for preparation of the inhibitors of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

As used herein, the term "composition" is intended to encompass a product comprising the compounds in question in the therapeutically effective amounts, as well as any product, which results, directly or indirectly, from combinations of the itemed compounds.

Chemical Definitions

Throughout the description and the claims the expression "alkyl", unless specifically limited, denotes a $C_{1-12}$ alkyl group, suitably a $C_{1-8}$ alkyl group, e.g. $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary thioalkyl groups include methylthio-. Exemplary haloalkyl groups include fluoroalkyl e.g. $CF_3$.

The expression "alkenyl", unless specifically limited, denotes a $C_{2-12}$ alkenyl group, suitably a $C_{2-6}$ alkenyl group, e.g. a $C_{2-4}$ alkenyl group, which contains at least one double bond at any desired location and which does not contain any triple bonds. Alkenyl groups may be straight chain or branched. Exemplary alkenyl groups including one double bond include propenyl and butenyl. Exemplary alkenyl groups including two double bonds include pentadienyl, e.g. (1E,3E)-pentadienyl.

The expression "alkynyl", unless specifically limited, denotes a $C_{2-12}$ alkynyl group, suitably a $C_{2-6}$ alkynyl group, e.g. a $C_{2-4}$ alkynyl group, which contains at least one triple bond at any desired location and may or may not also contain one or more double bonds. Alkynyl groups may be straight chain or branched. Exemplary alkynyl groups include propynyl and butynyl.

The expression "alkylene" denotes a chain of formula $-(CH_2)_n-$ wherein n is an integer e.g. 2-5, unless specifically limited.

The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "cycloalkenyl", unless specifically limited, denotes a $C_{5-10}$ cycloalkenyl group (i.e. 5 to 10 ring carbon atoms), more suitably a $C_{5-8}$ cycloalkenyl group e.g. a $C_{5-6}$ cycloalkenyl group. Exemplary cycloalkenyl groups include cyclopropenyl, cyclohexenyl, cycloheptenyl and cyclooctenyl. A most suitable number of ring carbon atoms is five to six.

The expression "carbocyclyl", unless specifically limited, denotes any ring system in which all the ring atoms are carbon and which contains between three and twelve ring carbon atoms, suitably between three and ten carbon atoms and more suitably between three and eight carbon atoms. Carbocyclyl groups may be saturated or partially unsaturated, but do not include aromatic rings. Examples of carbocyclyl groups include monocyclic, bicyclic, and tricyclic ring systems, in particular monocyclic and bicyclic ring systems. Other carbocylcyl groups include bridged ring systems (e.g. bicyclo[2.2.1]heptenyl). A specific example of a carbocyclyl group is a cycloalkyl group. A further example of a carbocyclyl group is a cycloalkenyl group.

The expression "heterocyclyl", unless specifically limited, refers to a carbocyclyl group wherein one or more (e.g. 1, 2 or 3) ring atoms are replaced by heteroatoms selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-).

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings). An example of a typical aryl group with one aromatic ring is phenyl. An example of a typical aryl group with two aromatic rings is naphthyl.

The expression "heteroaryl", unless specifically limited, denotes an aryl residue, wherein one or more (e.g. 1, 2, 3, or 4, suitably 1, 2 or 3) ring atoms are replaced by heteroatoms selected from N, S and O, or else a 5-membered aromatic ring containing one or more (e.g. 1, 2, 3, or 4, suitably 1, 2 or 3) ring atoms selected from N, S and O. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl imidazol-4-yl); six membered rings (e.g. pyridazine, pyrimidine, pyrazine). Exemplary monocyclic heteroaryl groups having three heteroatoms include: 1,2,3-triazole and 1,2,4-triazole. Exemplary monocyclic heteroaryl groups having four heteroatoms include tetrazole. Exemplary bicyclic heteroaryl groups include: indole (e.g. indol-6-yl), benzofuran, benzthiophene, quinoline, isoquinoline, indazole, benzimidazole, benzthiazole, quinazoline and purine.

The expression "-alkylaryl", unless specifically limited, denotes an aryl residue which is connected via an alkylene moiety e.g. a $C_{1-4}$alkylene moiety.

The expression "-alkylheteroaryl", unless specifically limited, denotes a heteroaryl residue which is connected via an alkylene moiety e.g. a $C_{1-4}$alkylene moiety.

The term "halogen" or "halo" comprises fluorine (F), chlorine (Cl) and bromine (Br).

The term "amino" refers to the group —$NH_2$.

The term "phenyl substituted by phenyl" refers to biphenyl.

The term "∿∿∿" denotes a single bond where the stereochemistry is not defined.

When benzimidazolyl is shown as benzimidazol-5-yl, which is represented as:

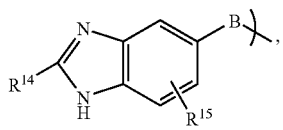

the person skilled in the art will appreciate that benzimidazol-6-yl, which is represented as:

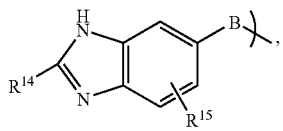

is an equivalent structure. As employed herein, the two forms of benzimidazolyl are covered by the term "benzimidazol-5-yl".

This applies mutatis mutandis to all similar situations.

Carriers and Additives for Galenic Formulations

For liquid oral preparations, such as for example, suspensions, elixirs and solutions, suitable carriers and additives may advantageously include water, glycols, oils, alcohols, flavouring agents, preservatives, colouring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavours, sweeteners, preservatives, coatings, disintegrating agents, dyes and colouring agents.

Soluble polymers as suitable drug carriers can include polyvinylpyrrolidone, pyran copolymer, polyhydroxypropylmeth-acrylamidephenol, polyhydroxyethylaspartamidephenol, or polyethyleneoxidepolyllysine substituted with palmitoyl residue(s). Furthermore, the inhibitors of the present invention may be coupled to a class of biodegradable polymers useful in achieving controlled/sustained release of a drug, for example, poly actic acid, poly-epsilon caprolactone, polyhydroxy butyric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like.

Disintegrating agents include, without limitation, starch, methyl cellulose, agar, bentonite, xanthan gum and the like.

Antagonist

The term "antagonist", as it is used herein, refers to an inhibitor molecule which, when bound to QPCTL, decreases the amount or the duration of the effect of the biological or immunological activity of QPCTL, e.g. decreasing the enzymatic activity of the peptidase to cyclise Glu- or Gln-residues at the N-termini of the QPCTL substrates. Antagonists may include proteins, nucleic acids, carbohydrates, antibodies, or any other molecules which decrease the effect of QPCTL; for example, they may include small molecules and organic compounds that bind to and inactivate QPCTLs by a competitive or non-competitive type mechanism. Preferred are small molecule inhibitors of QPCTL. Most preferred are competitive small molecule inhibitors of QPCTL.

QC

The term "QC" as used herein comprises glutaminyl cyclase (QC), which is synonymous to glutaminyl-peptide cyclotransferase (QPCT); while isoQC refers to QC-like enzymes, which are synonymous to glutaminyl-peptide cyclotransferase-like proteins (QPCTLs). QC and QC-like enzymes have similar enzymatic activity, further defined as "QC activity" or "isoQC activity". However, QC-like enzymes can fundamentally differ in their molecular structure from QC.

The term "glutaminyl cyclase (QC)" according to this embodiment and throughout the description of the present invention comprises glutaminyl cyclase enzymes from various species, e.g. mammalian, insect or plant QC. Preferably, the gluaminyl cyclase (QC) according to this embodiment througouth the description of the present invention is a mammalian QC, more preferably a rodent QC, e.g. from mouse or rat, but most preferably human QC.

Similarly, the term "iso-glutaminyl cyclase (isoQC, QPCTL)" according to this embodiment throughout the description of the present invention comprises iso-glutaminyl cylase enzymes from various species, e.g. mammalian, insect or plant isoQC. Preferably, the iso-gluaminyl cyclase (isoQC) according to this embodiment and througouth the description of the present invention is a mammalian isoQC, more preferably a rodent isoQC, e.g. from mouse or rat, but most preferably human isoQC. Iso-glutaminyl cyclase enzymes differ from glutaminyl cyclase enzmyes in their nucleic acid and amino acid sequences.

QC Activity

"QC activity" is defined as the catalytic activity of glutaminyl cyclase (QC, QPCT) and QC-like enzymes (QPCTLs). These enzymes are found in various tissues of the body of a mammal including kidney, liver, intestine, brain and body fluids such as CSF, where they cyclize glutamine or glutamate at the N-terminus of biologically active peptides with a high specificity.

In particular, the terms "QC activity" or "isoQC activity" as used herein is defined as intramolecular cyclization of N-terminal glutamine residues into pyroglutamic acid (pGlu*) or of N-terminal L-homoglutamine or L-α-homoglutamine to a cyclic pyro-homoglutamine derivative under liberation of ammonia. See therefore schemes 1 and 2.

Scheme 1: Cyclization of glutamine by (iso)QC

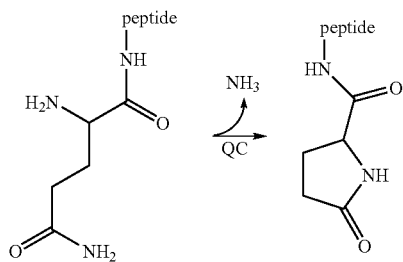

Scheme 2: Cyclization of L-homoglutamine by (iso)QC

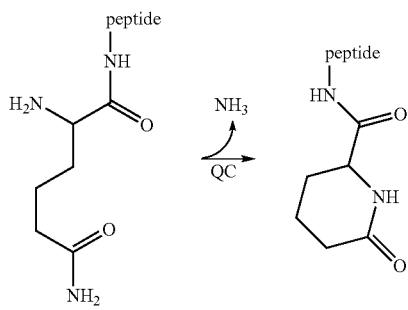

EC

The term "EC" as used herein comprises the activity of glutaminyl cyclase (QC, QPCT) and QC-like enzymes (QPCTLs) as glutamate cyclase (EC), further defined as EC activity.

EC Activity

The term "EC activity" as used herein is defined as intramolecular cyclization of N-terminal glutamate residues into pyroglutamic acid (pGlu*) by glutaminyl cyclase (QC, QPCT) and QC-like enzymes (QPCTLs). See scheme 3 in that regard.

Selective isoQC-Inhibitor

The term "selective isoQC-inhibitor" as defined herein means enzyme inhibitors, which inhibit the catalytic activity of iso-glutaminyl cyclase (isoQC, QPCTL) but do not or with a lower potency inhibit the catalytic activity of glutaminyl cyclase (QC, QPCT). Preferred are selective isoQC-inhibitors, which inhibit a iso-glutaminyl cyclase (isoQC) with an $K_i$-value, which is 10% lower than its $K_i$-value for the inhibition of glutaminyl cyclase (QC). More preferably, the $K_i$-value of said selective isoQC-inhibitor for the inhibition of iso-glutaminyl cyclase (isoQC, QPCTL) is 50% lower than its $K_i$-value for the inhibition of glutaminyl cyclase (QC). Even more preferred are selective isoQC-inhibitors, which inhibit iso-glutaminyl cyclase (isoQC) with an $K_i$-value, which is one order of magnitude lower than its $K_i$-value for the inhibition of gluaminyl cyclase (QC). More preferably, the $K_i$-value of said selective isoQC-inhibitor for the inhibition of iso-glutaminyl cyclase (isoQC, QPCTL) is two orders of magnitude lower than its $K_i$-value for the inhibition of gluaminyl cyclase (QC). Even more preferred are selective isoQC-inhibitors, wherein their $K_i$-value for the inhibition of iso-glutaminyl cyclase (isoQC, QPCTL) is three orders of magnitude lower than their $K_i$-value for the inhibition of gluaminyl cyclase (QC). Most preferred are selective isoQC-inhibitors, which do not inhibit glutaminyl cyclase (QC).

Potency of isoQC Inhibition

In light of the correlation with isoQC inhibition, in preferred embodiments, the subject method and medical use utilize an inhibitor with a $K_i$ for isoQC inhibition of 10 μM or less, more preferably of 1 μM or less, even more preferably of 0.1 μM or less or 0.01 μM or less, or most preferably 0.001 μM or less. Indeed, inhibitors with $K_i$ values in the lower micromolar, preferably the nanomolar and even more preferably the picomolar range are contemplated. Thus, while the active agents are described herein, for convenience, as "isoQC inhibitors", it will be understood that such nomenclature is not intending to limit the subject of the invention to a particular mechanism of action.

Molecular Weight of isoQC Inhibitors

In general, the isoQC inhibitors of the subject method or medical use will be small molecules, e.g., with molecular Scheme 3: N-terminal cyclization of uncharged glutamyl peptides by QC (EC) and isoQC

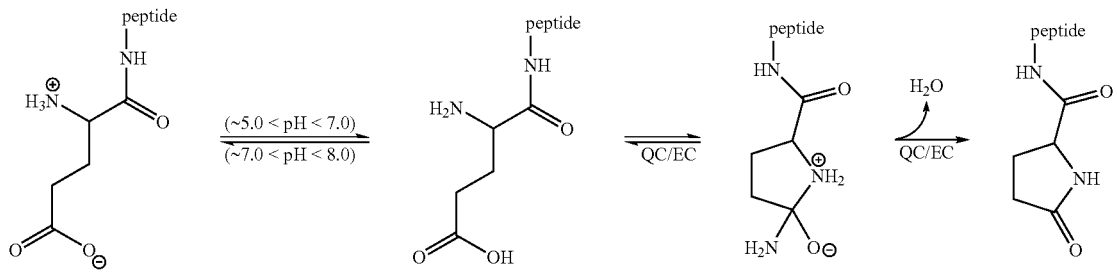

(iso)QC-Inhibitor

The term "(iso)QC-inhibitor" or "(iso)glutaminyl cyclase inhibitor" is generally known to a person skilled in the art and means enzyme inhibitors, which inhibit the catalytic activity of glutaminyl cyclase (QPCT) or of the iso-glutaminyl cyclase enzymes (QPCTLs) or their glutamyl cyclase (EC) activity, preferably by direct interaction of the inhibitor with the respective enzyme.

weights of 1000 g/mole or less, 500 g/mole or less, preferably of 400 g/mole or less, and even more preferably of 350 g/mole or less and even of 300 g/mole or less.

Subject

The term "subject" as used herein, refers to an animal, preferably a mammal, most preferably a human, who has been the object of treatment, observation or experiment.

Therapeutically Effective Amount

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

Pharmaceutically Acceptable

As used herein, the term "pharmaceutically acceptable" embraces both human and veterinary use: for example the term "pharmaceutically acceptable" embraces a veterinarily acceptable compound or a compound acceptable in human medicine and health care.

DETAILED DESCRIPTION OF THE PRESENTLY PREFERRED EMBODIMENTS

In particular the present invention pertains to the following items:

1. An isoQC inhibitor for the treatment and/or prevention of an inflammatory disease or condition, selected from the group consisting of
   (a) chronic and acute inflammations, e.g. rheumatoid arthritis, atherosclerosis, restenosis, pancreatitis, osteoporosis,
   (b) other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis,
   (c) neuroinflammation, and
   (d) neurodegenerative diseases, e.g. mild cognitive impairment (MCI), Alzheimer's disease, neurodegeneration in Down Syndrome, Familial British Dementia, and Familial Danish Dementia, which may result from neuroinflammation.

2. Use of an isoQC inhibitor for the treatment and/or prevention of an inflammatory disease or condition, selected from the group consisting of
   (a) chronic and acute inflammations, e.g. rheumatoid arthritis, atherosclerosis, restenosis, pancreatitis, osteoporosis,
   (b) other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis,
   (c) neuroinflammation, and
   (d) neurodegenerative diseases, e.g. mild cognitive impairment (MCI), Alzheimer's disease, neurodegeneration in Down Syndrome, Familial British Dementia, and Familial Danish Dementia, which may result from neuroinflammation.

3. Use of an isoQC inhibitor for the preparation of a medicament for treating and/or preventing an inflammatory disease or condition, selected from the group consisting of
   (a) chronic and acute inflammations, e.g. rheumatoid arthritis, atherosclerosis, restenosis, pancreatitis, osteoporosis,
   (b) other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis,
   (c) neuroinflammation, and
   (d) neurodegenerative diseases, e.g. mild cognitive impairment (MCI), Alzheimer's disease, neurodegeneration in Down Syndrome, Familial British Dementia, Familial Danish Dementia, which may result from neuroinflammation.

4. A method of treatment and/or prevention of an inflammatory disease or condition, selected from the group consisting of
   (a) chronic and acute inflammations, e.g. rheumatoid arthritis, atherosclerosis, restenosis, pancreatitis, osteoporosis,
   (b) other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis,
   (c) neuroinflammation, and
   (d) neurodegenerative diseases, e.g. mild cognitive impairment (MCI), Alzheimer's disease, neurodegeneration in Down Syndrome, Familial British Dementia, and Familial Danish Dementia, which may result from neuroinflammation,
wherein a therapeutically effective amount of an isoQC inhibitor is administered to a subject in need thereof.

5. The isoQC inhibitor, use or method according to any of items 1 to 4, wherein the inflammatory disease is a chronic and acute inflammation, selected from rheumatoid arthritis, atherosclerosis, restenosis, pancreatitis and osteoporosis.

6. The isoQC inhibitor, use or method according to any of items 1 to 4, wherein the inflammatory disease is selected from neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis.

7. The isoQC inhibitor, use or method according to any of items 1 to 4, wherein the inflammatory disease is neuroinflammation.

8. The isoQC inhibitor, use or method according to any of items 1 to 4, wherein the inflammatory disease is a neurodegenerative disease, which may result from neuroinflammation.

9. The isoQC inhibitor, use or method according to item 8, wherein the neurodegenerative disease is selected from mild cognitive impairment (MCI), Alzheimer's disease, neurodegeneration in Down Syndrome, Familial British Dementia and Familial Danish Dementia.

10. The isoQC inhibitor, use or method according to any of items 1 to 9, wherein the isoQC inhibitor is administered in combination with a further agent, selected from the group consisting of anti-inflammatory agents, nootropic agents, neuroptrotectants, antiparkinsonian drugs, amyloid protein deposition inhibitors, beta amyloid synthesis inhibitors, antidepressants, anxiolytic drugs, antipsychotic drugs and anti-multiple sclerosis drugs, inhibitors of the angiotensin converting enzyme (ACE), angiotensin II receptor blockers, diuretics; calcium channel blockers (CCB), beta-blockers, platelet aggregation inhibitors, cholesterol absorption modulators, HMG-Co-A reductase inhibitors, high density lipoprotein (HDL) increasing compounds, renin inhibitors, IL-6 inhibitors, antiinflammatory corticosteroids, antiproliferative agents, nitric oxide donors, inhibitors of extracellular matrix synthesis, growth factor or cytokine signal transduction inhibitors, MCP-1 antagonists and tyrosine kinase inhibitors.

11. The isoQC inhibitor, use or method of any of items 1 to 10, wherein the disease and/or condition afflicts a human being.

12. A pharmaceutical composition comprising an isoQC inhibitor according any of items 1 to 9 or a combination according to item 10.

13. The isoQC inhibitor, use, method or pharmaceutical composition according to any one of items 1 to 12, wherein said isoQC inhibitor is a compound of formula (I)

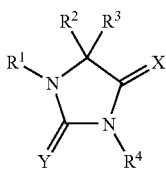
(I)

or a pharmaceutically acceptable salt, solvate or polymorph thereof, including all tautomers and stereoisomers thereof wherein:

$R^1$ represents —$C_{3-8}$carbocyclyl-heteroaryl, —$C_{2-6}$alkenylheteroaryl, —$C_{1-6}$alkylheteroaryl, or $(CH_2)_aCR^5R^6(CH_2)_b$heteroaryl wherein a and b independently represent integers 0-5 provided that a+b=0-5 and $R^5$ and $R^6$ are alkylene which, together with the carbon to which they are attached, form a $C_3$-$C_5$ cycloalkyl group, or a bicyclic heteroaryl group;

in which any of aforesaid heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-5}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —$NH_2$, —NH$C_{1-4}$ alkyl, —N($C_{1-4}$alkyl)($C_{1-4}$alkyl), —C(O)N($C_{1-4}$alkyl)($C_{1-4}$ alkyl), —C(O)$NH_2$, —C(O)NH($C_{1-4}$alkyl) and —C(O)NH($C_{3-10}$cycloalkyl);

and in which any of aforesaid carbocyclyl groups may optionally be substituted by one or more groups selected from $C_{1-4}$alkyl, oxo, halogen and $C_{1-4}$alkoxy;

$R^2$ represents $C_{1-8}$alkyl, aryl, heteroaryl, carbocyclyl, heterocyclyl, —$C_{1-4}$alkylaryl, —$C_{1-4}$alkylheteroaryl, —$C_{1-4}$alkylcarbocyclyl or —$C_{1-4}$alkylheterocyclyl;

in which any of aforesaid aryl and heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —$NH_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)$NH_2$, —C(O)NH($C_{1-4}$alkyl) and —C(O)NH($C_{3-10}$cycloalkyl);

and in which any of aforesaid carbocyclyl and heterocyclyl groups may optionally be substituted by one or more groups selected from $C_{1-4}$alkyl, oxo, halogen and $C_{1-4}$alkoxy;

or $R^2$ represents phenyl substituted by phenyl, phenyl substituted by a monocyclic heteroaryl group, phenyl substituted by benzyloxy, phenyl fused to carbocyclyl, phenyl fused to heterocyclyl, —$C_{1-4}$alkyl(phenyl substituted by phenyl), —$C_{1-4}$alkyl(phenyl substituted by a monocyclic heteroaryl group), —$C_{1-4}$alkyl(phenyl substituted by benzyloxy), —$C_{1-4}$ alkyl(optionally substituted phenyl fused to optionally substituted carbocyclyl or —$C_{1-4}$alkyl(optionally substituted phenyl fused to optionally substituted heterocyclyl);

in which any of aforesaid phenyl, benzyloxy and heteroaryl groups may optionally be substituted by one or more groups selected from $C_{1-4}$alkyl, halogen and $C_{1-4}$alkoxy, and in which any of aforesaid carbocyclyl and heterocyclyl groups may optionally be substituted by one or more groups selected from $C_{1-4}$alkyl, oxo, halogen and $C_{1-4}$alkoxy;

$R^3$ represents H, —$C_{1-4}$alkyl or aryl;

in which aforesaid aryl may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —$NH_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)$NH_2$, —C(O)NH($C_{1-4}$alkyl) and, —C(O)NH($C_{3-10}$cycloalkyl);

or $R^2$ and $R^3$ are joined to form a carbocyclyl ring which is optionally substituted by one or more $C_{1-2}$alkyl groups;

or $R^2$ and $R^3$ are joined to form a carbocyclyl ring which is fused to phenyl, wherein aforesaid carbocyclyl and/or phenyl may optionally be substituted by one or more groups selected from $C_{1-4}$alkyl, halogen and $C_{1-4}$alkoxy;

or $R^2$ and $R^3$ are joined to form a carbocyclyl ring which is fused to monocyclic heteroaryl, wherein aforesaid carbocyclyl and/or heteroaryl may optionally be substituted by one or more groups selected from $C_{1-4}$alkyl, halogen and $C_{1-4}$alkoxy;

$R^4$ represents H, —$C_{1-8}$alkyl, —C(O)$C_{1-6}$alkyl or —$NH_2$;

X represents O or S; and

Y represents O or S.

14. The isoQC inhibitor, use, method or pharmaceutical composition according to item 13, wherein $R^1$ represents a bicyclic heteroaryl group.

15. The isoQC inhibitor, use, method or pharmaceutical composition according to item 14, wherein $R^1$ represents a benzene or pyridine ring fused to a 5-membered ring containing one or two nitrogen atoms.

16. The isoQC inhibitor, use, method or pharmaceutical composition according to item 15, wherein the point of attachment is through the benzene or pyridine ring.

17. The isoQC inhibitor, use, method or pharmaceutical composition according to item 16, wherein $R^1$ is:

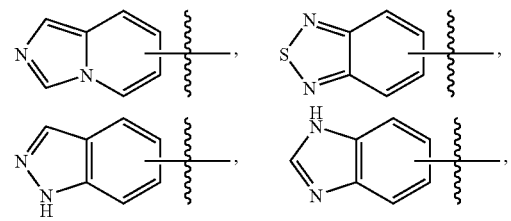

imidazo[1,2-a]pyridine or benzo[c][1,25]thiadiazolyl.

18. The isoQC inhibitor, use, method or pharmaceutical composition according to item 17, wherein $R^1$ represents

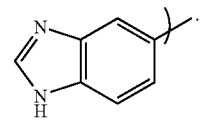

19. The isoQC inhibitor, use, method or pharmaceutical composition according to item 18, wherein $R^1$ represents —$C_{1-6}$alkylheteroaryl.

20. The isoQC inhibitor, use, method or pharmaceutical composition according to item 19, wherein the heteroaryl group of $R^1$ is a 5-membered ring containing 1 to 3 nitrogen atoms optionally substituted by one or more substituents selected from $C_{1-4}$ alkyl, $C_{1-4}$ alkoxy- and halogen.

21. The isoQC inhibitor, use, method or pharmaceutical composition according to item 20, wherein the heteroaryl group is:

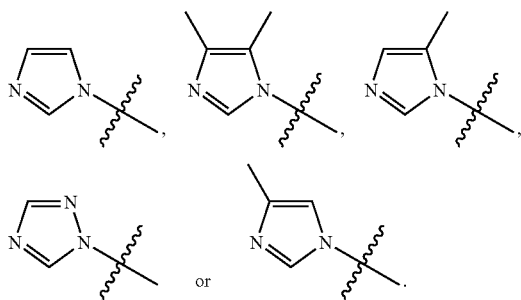

or

22. The isoQC inhibitor, use, method or pharmaceutical composition according to item 13, wherein $R^1$ represents:

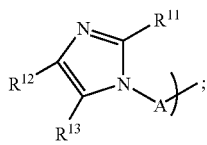

wherein A represents an unbranched or branched $C_{1-6}$ alkylene chain or A represents a branched $C_{1-6}$ alkylene chain or A represents $(CH_2)_a CR^5R^6(CH_2)_b$ and $R^{11}$, $R^{12}$ and $R^{13}$ independently represent H or $C_{1-2}$ alkyl.

23. The isoQC inhibitor, use, method or pharmaceutical composition according to item 14 or 19, wherein $R^1$ represents

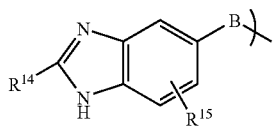

wherein B represents a bond, —$CH_2$—, —$CH_2$—$CH_2$—, —CH(Me)-, —CH(Me)-$CH_2$— or —$CH_2$—CH(Me)- and $R^{14}$ and $R^{15}$ independently represent H or $C_{1-2}$ alkyl.

24. The isoQC inhibitor, use, method or pharmaceutical composition according to any one of items 13 to 23 represented by the formula:

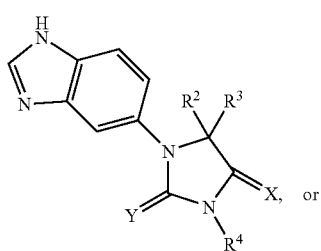

-continued

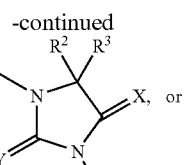

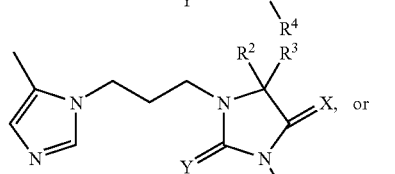

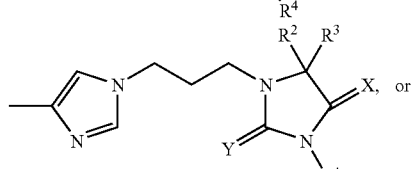

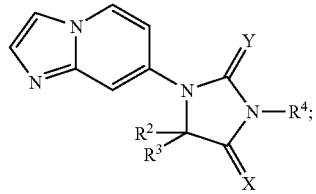

wherein $R^2$, $R^3$, $R^4$, X and Y are as defined in item 13.

25. The isoQC inhibitor, use, method or pharmaceutical composition according to any one of items 13 to 24, wherein $R^2$ represents aryl, heteroaryl, phenyl substituted by phenyl, phenyl fused to heterocyclyl or $R^2$ and $R^3$ are joined to form a carbocyclyl ring which is fused to phenyl; the aforesaid aryl, heteroaryl, phenyl, heterocyclyl and carbocyclyl optionally being substituted.

26. The isoQC inhibitor, use, method or pharmaceutical composition according to item 25, wherein $R^2$ represents phenyl substituted by phenyl, the aforesaid phenyl groups optionally being substituted by one or more substituents which may be the same or different and are chosen from halo, OH, $C_{1-3}$ alkyl, $C_{1-3}$ haloalkyl, $C_{1-3}$ alkoxy, $C_{1-3}$ haloalkoxy.

27. The isoQC inhibitor, use, method or pharmaceutical composition according to item 26, wherein $R^2$ is -biphenyl-4-yl.

28. The isoQC inhibitor, use, method or pharmaceutical composition according to item 25, wherein $R^2$ represents phenyl optionally substituted by one, two or three substituents, which may be the same or different and are chosen from halo, OH, $C_{1-3}$ alkyl, $C_{1-3}$ haloalkyl, $C_{1-3}$ alkoxy, $C_{1-3}$ haloalkoxy.

29. The isoQC inhibitor, use, method or pharmaceutical composition according to item 28, wherein $R^2$ is phenyl substituted by n-propyloxy.

30. The isoQC inhibitor, use, method or pharmaceutical composition according to any one of items 13 to 29, wherein $R^3$ represents H.

31. The isoQC inhibitor, use, method or pharmaceutical composition according to any one of items 13 to 25, wherein $R^2$ and $R^3$ are joined to form a carbocyclyl ring which is fused to phenyl.

32. The isoQC inhibitor, use, method or pharmaceutical composition according to any one of items 13 to 31, wherein $R^4$ represents H.

33. The isoQC inhibitor, use, method or pharmaceutical composition according to any one of items 13 to 32, wherein X represents O.

34. The isoQC inhibitor, use, method or pharmaceutical composition according to any one of items 13 to 33, wherein Y represents O.

35. The isoQC inhibitor, use, method or pharmaceutical composition according to any one of items 13 to 34, wherein the compound of formula (I) is represented by

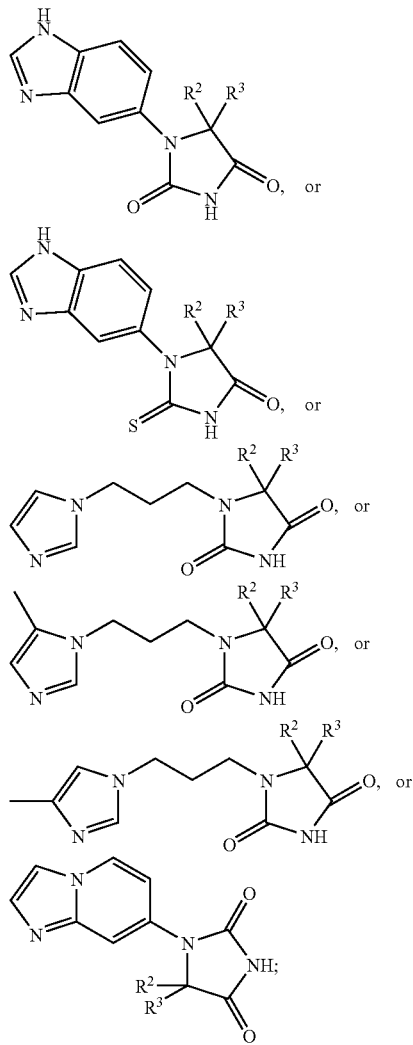

wherein R² and R³ are as defined in item 13.

36. The isoQC inhibitor, use, method or pharmaceutical composition according to any one of items 13 to 35, wherein the compound of formula (I) is selected from
5-(benzo[c][1,2,5]thiadiazol-6-yl)-1-(1H-benzo[d]imidazol-5-yl)imidazolidine-2,4-dione;
1-(1H-benzo[d]imidazol-5-yl)-5-phenylimidazolidine-2,4-dione;
1-(1H-benzo[d]imidazol-5-yl)-5-(2-hydroxy-5-methylphenyl)imidazolidine-2,4-dione;
1-(1H-benzo[d]imidazol-5-yl)-5-(2-fluoro-5-trifluoromethyl)phenyl)imidazolidine-2,4-dione;
1-(1H-benzo[d]imidazol-5-yl)-5-(2-bromo-5-fluorophenyl)imidazolidine-2,4-dione;
1-(1H-benzo[d]imidazol-5-yl)-5-(4-propoxyphenyl)imidazolidine-2,4-dione;
1-(1H-benzo[d]imidazol-5-yl)-5-(4-chloro-3-trifluoromethyl)phenyl)imidazolidine-2,4-dione;
1-(1H-benzo[d]imidazol-5-yl)-5-(3-fluoro-4(trifluoromethyl)phenyl)imidazolidine-2,4-dione;
1-(1H-benzo[d]imidazol-5-yl)-5-(3-hydroxy-4-methoxyphenyl)imidazolidine-2,4-dione;
1-(1H-benzo[d]imidazol-5-yl)-5-(2-hydroxy-3-methoxyphenyl)imidazolidine-2,4-dione;
1-(1H-benzimidazol-5-yl)-5-(1,1'-biphenyl-4-yl)imidazolidine-2,4-dione;
1-(1H-benzo[d]imidazol-5-yl)-5-(3-chlorophenyl)imidazolidine-2,4-dione;
1-(1H-benzo[d]imidazol-5-yl)-5-(4-chlorophenyl)imidazolidine-2,4-dione;
1-(1H-benzo[d]imidazol-5-yl)-5-(2-chlorophenyl)imidazolidine-2,4-dione;
1-(1H-benzo[d]imidazol-5-yl)-5-(4-fluorophenyl)imidazolidine-2,4-dione;
1-(1H-benzo[d]imidazol-5-yl)-5-(2,3-dihydrobenzo[b][1,4]dioxin-7-yl)imidazolidine-2,4-dione;
1-(3-(1H-imidazol-1-yl)propyl)-5-phenylimidazolidine-2,4-dione;
1-(3-(1H-imidazol-1-yl)propyl)-5-(2-bromo-4-fluorophenyl)imidazolidine-2,4-dione;
1-(3-(1H-imidazol-1-yl)propyl)-5-(4-propoxyphenyl)imidazolidine-2,4-dione;
1-(3-(1H-imidazol-1-yl)propyl)-5-(3-fluoro-4-(trifluoromethyl)phenyl)imidazolidine-2,4-dione;
1-[3-(1H-imidazol-1-yl)propyl]-5-(4-biphenyl)imidazolidine-2,4-dione;
1-(3-(1H-imidazol-1-yl)propyl)-5-(3-chlorophenyl)imidazolidine-2,4-dione;
1-(3-(1H-imidazol-1-yl)propyl)-5-(2-chlorophenyl)imidazolidine-2,4-dione;
1-(3-(5-methyl-1H-imidazol-1-yl)propyl)-5-phenylimidazolidine-2,4-dione;
5-(2-bromo-5-fluorophenyl)-1-(3-(5-methyl-1H-imidazol-1-yl)propyl)imidazolidine-2,4-dione;
1-(3-(5-methyl-1H-imidazol-1-yl)propyl)-5-(4-propoxyphenyl)imidazolidine-2,4-dione;
1-[3-(5-methyl-1H-imidazol-1-yl)propyl]-5-(4-phenylphenyl)imidazolidine-2,4-dione;
5-(3-chlorophenyl)-1-(3-(5-methyl-1H-imidazol-1-yl)propyl)imidazolidine-2,4-dione;
1-(3-(4-methyl-1H-imidazol-1-yl)propyl)-5-phenylimidazolidine-2,4-dione;
1-[3-(4-methyl-1H-imidazol-1-yl)propyl]-5-(4-biphenyl)imidazolidine-2,4-dione;
5-(3-chlorophenyl)-1-(3-(4-methyl-1H-imidazol-1-yl)propyl)imidazolidine-2,4-dione;
3-(1H-benzimidazol-5-yl)-1',3'-dihydro-2H,5H-spiro[imidazolidine-4,2'-indene]-2,5-dione;
5-(benzo[c][1,2,5]thiadiazol-6-yl)-1-(1H-benzo[d]imidazol-5-yl)-2-thioxoimidazolidin-4-one;
1-(1H-benzo[d]imidazol-5-yl)-5-phenyl-2-thioxoimidazolidin-4-one;
1-(1H-benzimidazol-5-yl)-5-(1,1'-biphenyl-4-yl)-2-thioxoimidazolidin-4-one;
1-(1H-benzo[d]imidazol-5-yl)-5-(3-hydroxy-4-methoxyphenyl)-2-thioxoimidazolidin-4-one;
1-(1H-benzo[d]imidazol-5-yl)-5-phenyl-4-thioxoimidazolidin-2-one;
1-(1H-benzimidazol-5-yl)-5-(1,1'-biphenyl-4-yl)-4-thioxoimidazolidin-2-one;
3-(1H-benzimidazol-5-yl)-5-thioxo-1',3'-dihydro-2H-spiro[imidazolidine-4,2'-inden]-2-one;
1-(1H-benzo[d]imidazol-5-yl)-5-(4-chlorophenyl)-4-thioxoimidazolidin-2-one;

1-(1H-benzo[d]imidazol-5-yl)-5-(2,3,4-trifluorophenyl)-4-thioxoimidazolidin-2-one;

1-(1H-benzo[d]imidazol-6-yl)-5-(4-bromo-2-fluorophenyl)-4-thioxoimidazolidin-2-one;

1-(1H-benzo[d]imidazol-5-yl)-5-(2,3-difluoro-4-methylphenyl)-4-thioxoimidazolidin-2-one;

1-(1H-benzo[d]imidazol-5-yl)-5-(4-chloro-3-methylphenyl)-4-thioxoimidazolidin-2-one;

1-(1H-benzo[d]imidazol-5-yl)-3-methyl-5-phenylimida4zolidine-2,4-dione;

1-(H-imidazo[1,2-a]pyridin-7-yl)-5-phenylimidazolidine-2,4-dione;

or a pharmaceutically acceptable salt, solvate or polymorph thereof, including all tautomers and stereoisomers thereof.

37. The isoQC inhibitor, use, method or pharmaceutical composition according to any one of items 1 to 36, wherein the isoQC inhibitor is 1-(1H-benzo[d]imidazol-5-yl)-5-(4-propoxyphenyl)imidazolidine-2,4-dione, which has the structure:

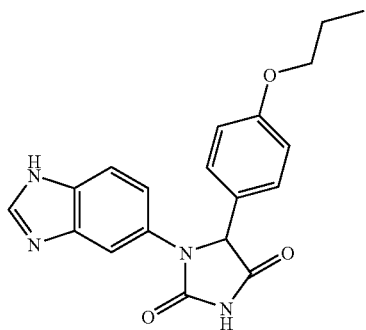 [SMILES: CCCOc1ccc(C2C(=O)NC(=O)N2c2ccc3[nH]cnc3c2)cc1]

or a pharmaceutically acceptable salt, solvate or polymorph thereof, including all tautomers and stereoisomers thereof.

38. Diagnostic assay, comprising an isoQC inhibitor.

39. Diagnostic assay according to item 38, wherein said isoQC inhibitor is a compound including pharmaceutically acceptable salts, solvates and stereoisomers thereof, as defined in any of items 13 to 37.

40. Diagnostic assay according to any of items 38 or 39, wherein said isoQC inhibitor is (1-(1H-benzo[d]imidazol-5-yl)-5-(4-propoxyphenyl)imidazolidine-2,4-dione.

41. A method of diagnosing any one of the diseases and/or conditions as defined in any of items 1 to 9, comprising the steps of collecting a sample from a subject who is suspected to be afflicted with said disease and/or condition, contacting said sample with an isoQC inhibitor, and determining whether or not said subject is afflicted by said disease and/or condition.

42. The method according to item 41, wherein said subject is a human being.

43. The method according to item 41 or 42, wherein said isoQC inhibitor is a compound including pharmaceutically acceptable salts, solvates and stereoisomers thereof, as defined in any of items 13 to 31.

44. The method according to any of items 41 to 43, wherein said isoQC inhibitor is (1-(1H-benzo[d]imidazol-5-yl)-5-(4-propoxyphenyl)imidazolidine-2,4-dione.

45. The method according to any of items 41 to 44, wherein said sample is a blood sample, a serum sample, a sample of cerebrospinal liquor or a urine sample.

46. Diagnostic kit for carrying out the method according to any of items 41 to 45 comprising as detection means the diagnostic assay of any of items 38 to 40 and a determination means.

47. The isoQC inhibitor, use, method, kit or pharmaceutical composition according to any one of the preceding items, wherein the isoQC inhibitor inhibits any one of the polypeptides selected from the group of polypeptides that comprise any of SEQ ID NO: 11, 12, 13, 14, 15, 16, 17, 18, 57, 58, 59 or 60 or that are encoded by a nucleic acid comprising any of SEQ ID NO: 2, 3, 4, 5, 6, 7, 8, 9, 53, 54, 55 or 56.

48. The isoQC inhibitor, use, method, kit or pharmaceutical composition according to any one of the preceding items, wherein the isoQC inhibitor inhibits any one of the polypeptides selected from the group of polypeptides that comprise any of SEQ ID NO's: 11 or 12 or that are encoded by a nucleic acid comprising any of SEQ ID NO's: 2 or 3.

49. The isoQC inhibitor, use, method, kit or pharmaceutical composition according to any one of the preceding items, wherein the isoQC inhibitor inhibits the polypeptide that comprises SEQ ID NO: 11 or that is encoded by the nucleic acid comprising SEQ ID NO: 2.

50. The isoQC inhibitor, use, method, kit or pharmaceutical composition according to any one of the preceding items, wherein the isoQC inhibitor inhibits the polypeptide that comprises SEQ ID NO: 12 or that is encoded by the nucleic acid comprising SEQ ID NO: 3.

Very surprisingly, it was shown with the present invention that in particular inhibitors of isoQC are well suited for a selective inhibition, are high binding and are particularly well suited for use in the treatment of inflammatory diseases. This particular relationship between isoQC inhibition and inflammatory diseases was surprising and provides clear advantages in the treatment of inflammatory conditions.

The effect of an isoQC inhibitor for treating a chronic or acute inflammation, selected from (a) chronic and acute inflammations, e.g. rheumatoid arthritis, atherosclerosis, restenosis, pancreatitis, osteoporosis, (b) other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinizing polyradiculoneuropathy and multiple sclerosis, (c) neuroinflammation, and (d) neurodegenerative diseases, e.g. mild cognitive impairment (MCI), Alzheimer's disease, neurodegeneration in Down Syndrome, Familial British Dementia, and Familial Danish Dementia, which may result from neuroinflammation, can be tested using the in vivo assays described in examples 12, 15 and 17 of the present invention.

Even preferred according to the present invention is the use of an isoQC inhibitor in methods of treating atherosclerosis or multiple sclerosis.

Additionally, the inventors also provide a genetic proof of concept for the efficacy of the inactivation of isoQC on inflammatory chemokines in QPCTL knock-out mice, i.e. isolated peripheral blood mononuclear cells from QPCTL knock out mice generate after LPS stimulation only scarce amounts of the N-terminally pGlu-modified MCP-1 as shown in Example 17, and, the application of thioglycollate in QPCTL knock out animals does not stimulate monocyte infiltration to the peritoneum. However, in QPCTL wild type littermates an infiltration of monocytes was detected (Example 16 and FIG. 26*a*), since the activity of isoQC is present there, resulting in proper maturation of MCPs. These results clearly proof the responsibility of isoQC for the maturation of inflammatory cytokines like MCP-1, MCP-2, MCP-3 and MCP-4 and, in the reverse case, the efficacy of isoQC inhibition in preventing the maturation of these chemokines and thereby in preventing and treating inflammatory diseases.

QPCTLs are proteins with glutaminyl cyclase activities that constitute novel members of a family of proteins related to glutaminyl cyclase, including the full-length proteins, alternative splice forms, subunits, and mutants, as well as nucleotide sequences encoding the same.

These QPCTL proteins having significant sequence similarity to glutaminyl cyclase (nucleic acid sequence of SEQ ID NO: 1, protein sequence of SEQ ID NO 10) are proteins (QPCTLs) from human (further named as human isoQC) (GenBank accession no. NM_017659), mouse (GenBank accession no. NM_027455), *Macaca fascicularis* (GenBank accession no. AB168255), *Macaca mulatta* (GenBank accession no. XM_001110995), cat (GenBank accession no. XM_541552), rat (GenBank accession no. XM_001066591), cow (GenBank accession no. BT026254) or an analogue thereof having at least 50%/75% sequence identity/similarity, preferably 70%/85% sequence identity/similarity, most preferably 90%/95% sequence identity/similarity.

The respective protein sequences are given in SEQ. ID NOS: 11 to 18. Further disclosed are nucleic acid sequences coding for these proteins (SEQ. ID NOS: 2 to 9).

TABLE 2

List of Sequences

| SEQ ID NO. | Description |
|---|---|
| 1 | human QC, nucleic acid |
| 2 | human isoQC Met I, nucleic acid |
| 3 | human isoQC Met II, nucleic acid |
| 4 | *Macaca fascicularis* QPCTL, nucleic acid |
| 5 | *Macaca mulatta* QPCTL, nucleic acid |
| 6 | *Canis familiaris* QPCTL, nucleic acid |
| 7 | rat QPCTL, nucleic acid |
| 8 | mouse QPCTL, nucleic acid |
| 9 | bovine QPCTL, nucleic acid |
| 10 | human QC, protein |
| 11 | human isoQC Met I, protein |
| 12 | human isoQC Met II, protein |
| 13 | *Macaca fascicularis* QPCTL, protein |
| 14 | *Macaca mulatta* QPCTL, protein |
| 15 | *Canis familiaris* QPCTL, protein |
| 16 | rat QPCTL, protein |
| 17 | mouse QPCTL, protein |
| 18 | bovine QPCTL, protein |
| 19 | Human isoQC forward primer used for cell line screening |
| 20 | human isoQC reverse primer used for cell line screening |
| 21 | forward primer used for isolation of human isoQC |
| 22 | reverse primer used for isolation of human isoQC |
| 23 | forward primer used for cloning of human isoQC (isoform Met I) into vector pEGFP-N3 |
| 24 | forward primer used for cloning of human isoQC (isoform Met II) into vector pEGFP-N3 |
| 25 | reverse primer used for cloning of human isoQC (isoforms Met I and Met II) into vector pEGFP-N3 |
| 26 | forward primer used for cloning of human isoQC into vector pET41a |
| 27 | reverse primer used for cloning of human isoQC into vector pET41a |
| 28 | forward primer for cloning human isoQC into vector pPICZαA with a C-terminal histidine tag |
| 29 | forward primer for cloning human isoQC into vector pPICZαA with a N-terminal histidine tag |
| 30 | reverse primer for cloning human isoQC into vector pPICZαA with a N-terminal histidine tag |
| 31 | forward primer for real-time PCR analysis of isoQC |
| 32 | reverse primer for cloning human isoQC into vector pPICZαA with a C-terminal histidine tag |
| 33 | reverse primer for real-time PCR analysis of isoQC |
| 34 | Forward primer for cloning of murine isoQC cDNA |
| 35 | Reverse primer for cloning of murine isoQC cDNA |
| 36 | Forward primer for cloning of murine isoQC cDNA |
| 37 | forward primer for real-time PCR analysis of murine QC |
| 38 | reverse primer for real-time PCR analysis of murine QC |
| 39 | forward primer for real-time PCR analysis of murine QC |
| 40 | reverse primer for real-time PCR analysis of murine QC |
| 41 | forward primer for site-directed mutagenesis hisoQC I55N |
| 42 | reverse primer for site-directed mutagenesis hisoQC I55N |
| 43 | forward primer for site-directed mutagenesis hisoQC C351A |
| 44 | reverse primer for site-directed mutagenesis hisoQC C351A |
| 45 | forward primer for insertion of native hQC into pcDNA 3.1 |
| 46 | reverse primer for insertion of native hQC into pcDNA 3.1 |
| 47 | reverse primer for amplification of hisoQC including the stop codon for insertion into pcDNA 3.1 |
| 48 | forward primer for amplification EGFP |
| 49 | reverse primer for amplification EGFP |

TABLE 2-continued

List of Sequences

| SEQ ID NO. | Description |
|---|---|
| 50 | Reverse primer for amplification of hisoQC N-terminal sequence for fusion with EGFP |
| 51 | Reverse primer for amplification hQC C-FLAG for insertion into pcDNA 3.1 |
| 52 | Reverse primer for amplification hisoQC C-FLAG for insertion into pcDNA 3.1 |
| 53 | mouse-isoQC cDNA starting at MetI |
| 54 | mouse-isoQC cDNA starting at MetII |
| 55 | rat-isoQC cDNA starting at MetI |
| 56 | rat-isoQC cDNA starting at MetII |
| 57 | mouse-isoQC protein starting at MetI |
| 58 | mouse-isoQC protein starting at MetI |
| 59 | rat-isoQC protein starting at MetI |
| 60 | rat-isoQC protein starting at MetII |
| 61 | sense primer used for cloning of mouse and rat isoQC into vector pcDNA 3.1 |
| 62 | antisense primer used for cloning of mouse and rat isoQC into vector pcDNA 3.1 |
| 63 | sense primer used for amplification of mouse isoQC (isoform Met I) |
| 64 | antisense primer used for amplification of mouse isoQC (isoforms Met I and Met II) |
| 65 | sense primer used for amplification of mouse and rat isoQC (isoform Met II) |
| 66 | sense primer used for amplification of rat isoQC (isoform Met I) |
| 67 | antisense primer used for amplification of rat isoQC (isoforms Met I and Met II) |
| 68 | antisense primer for amplification of the mouse isoQC N-terminal sequence |
| 69 | antisense primer for amplification of the rat isoQC N-terminal sequence |
| 70 | forward primer for the amplification of murine QPCT |
| 71 | forward primer for the amplification of murine QPCT |
| 72 | forward primer for the amplification of murine QPCT |
| 73 | reverse primer for the amplification of murine QPCT |
| 74 | reverse primer for the amplification of murine QPCT |
| 75 | reverse primer for the amplification of murine QPCT |
| 76 | reverse primer for the amplification of murine QPCT |
| 77 | reverse primer for the amplification of murine QPCT |
| 78 | reverse primer for the amplification of murine QPCT |
| 79 | reverse primer for the amplification of murine QPCT |
| 80 | reverse primer for the amplification of murine QPCT |
| 81 | forward primer for the amplification of murine QPCTL |
| 82 | reverse primer for the amplification of murine QPCTL |
| 83 | Sense primer for amplification of murine isoQC starting with Glu 43 |
| 84 | antisense primer for amplification of murine isoQC for insertion into pPICZαA vector |
| 85 | sense primer for introduction of a Ile 56 to Asn mutation in murine isoQC |
| 86 | antisense primer for introduction of a Ile 56 to Asn mutation in murine isoQC |
| 87 | sense primer used for cloning and mutation of rat isoQC |
| 88 | antisense primer used for cloning and mutation of rat isoQC |
| 89 | sense primer for introduction of a Ile 56 to Asn mutation in rat isoQC |
| 90 | antisense primer for introduction of a Ile 56 to Asn mutation in rat isoQC |
| 91 | Amyloid beta peptide 3-40 |
| 92 | Amyloid beta peptide 3-42 |
| 93 | Amyloid beta peptide 11-40 |
| 94 | Amyloid beta peptide 11-42 |
| 95 | ABri |
| 96 | ADan |
| 97 | Gastrin 17 |
| 98 | Neurotensin |
| 99 | FPP |
| 100 | CCL2 |
| 101 | CCL7 |
| 102 | CCL8 |
| 103 | CCL13 |
| 104 | CCL16 |
| 105 | CCL18 |
| 106 | Fractalkine |
| 107 | Orexin A |
| 108 | Substance P |
| 109 | QYNAD |
| 110 | Primer for isolation of human MCP-1 |
| 111 | Primer for isolation of human MCP-1 |
| 112 | Primer for site-directed muatgenesis ΔQ1 |
| 113 | Primer for site-directed muatgenesis ΔQ1 |
| 114 | Primer for site-directed mutagenesis ΔQ1P2 |
| 115 | Primer for site-directed mutagenesis ΔQ1P2 |

IsoQC Inhibitors

Specific examples of QPCTL enzyme activity inhibitors are described below. Inhibitors can be, for example, inhibitors of the QPCTL cyclase activity, or alternatively inhibitors of the binding activity of the QPCTL to proteins with which they interact. Specific examples of such inhibitors can include, for example, anti-QPCTL antibodies, peptides, protein fragments, or small peptidyl protease inhibitors, or small non-peptide, organic molecule inhibitors which are formulated in a medium that allows introduction into the desired cell type. Alternatively, such inhibitors can be attached to targeting ligands for introduction by cell-mediated endocytosis and other receptor mediated events. Such methods are described further below and can be practiced by those skilled in the art given the QPCTL nucleotide and amino acid sequences described herein.

Useful inhibitors of QC, which also could be useful as inhibitors of QPCTLs, are described in WO 2004/098591, WO 2005/075436, WO 2008/055945, WO 2008/055947, WO 2008/055950, WO 2008/065141, WO 2008/110523, WO 2008/128981, WO 2008/128982, WO 2008/128983, WO 2008/128984, WO 2008/128985, WO 2008/128986 and WO 2008/128987, which are incorporated herein in their entirety, especially with regard to the structure of the inhibitors and their production.

Potential QPCTL-inhibitors, which are suitable for uses and methods according to the present invention, are compounds of formula (I),

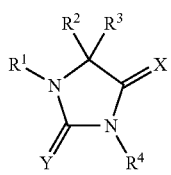

(I)

as described under item 13 above.

When carbocyclyl and heterocyclyl are substituted, they are typically substituted by 1 or 2 substituents (e.g. 1 substituent). Typically the substituent is methyl. More typically carbocyclyl and heterocyclyl groups are unsubstituted.

When aryl and heteroaryl are substituted, they are typically substituted by 1, 2 or 3 (e.g. 1 or 2) substituents. Substituents for aryl and heteroaryl are selected from $C_{1-6}$alkyl (e.g. methyl), $C_{2-6}$alkenyl (e.g. buten-3-yl), $C_{2-6}$alkynyl (e.g. butyn-3-yl), $C_{1-6}$haloalkyl (e.g. fluoromethyl, trifluoromethyl), —$C_{1-6}$thioalkyl (e.g. —S-methyl), —$SOC_{1-4}$alkyl (e.g. —SOmethyl), —$SO_2C_{1-4}$alkyl (e.g. —$SO_2$methyl), $C_{1-6}$alkoxy- (e.g. methoxy, ethoxy), —O—$C_{3-8}$cycloalkyl (e.g. —O-cyclopentyl), $C_{3-8}$cycloalkyl (e.g. cyclopropyl, cyclohexyl), —$SO_2C_{3-8}$cycloalkyl (e.g. —$SO_2$cyclohexyl), —$SOC_{3-6}$cycloalkyl (e.g. —SOcyclopropyl), $C_{3-6}$alkenyloxy- (e.g. —O-buten-2-yl), $C_{3-6}$alkynyloxy- (e.g. —O-buten-2-yl), —C(O)$C_{1-6}$alkyl (e.g. —C(O)ethyl), —C(O)O$C_{1-6}$alkyl (e.g. —C(O)O-methyl), $C_{1-6}$alkoxy-$C_{1-6}$alkyl- (e.g. methoxy-ethyl-), nitro, halogen (e.g. fluoro, chloro, bromo), cyano, hydroxyl, —C(O)OH, —$NH_2$, —NH$C_{1-4}$alkyl (e.g. —NHmethyl), —N($C_{1-4}$alkyl)($C_{1-4}$alkyl) (e.g. —N(methyl)$_2$), —C(O)N($C_{1-4}$alkyl)($C_{1-4}$alkyl) (e.g. —C(O)N(methyl)$_2$), —C(O)$NH_2$, —C(O)NH($C_{1-4}$alkyl) (e.g. —C(O)NHmethyl), —C(O)NH($C_{3-10}$cycloalkyl) (e.g. —C(O)NHcyclopropyl). More typically, substituents will be selected from $C_{1-6}$alkyl (e.g. methyl), $C_{1-6}$haloalkyl (e.g. $C_{1-6}$fluoroalkyl, e.g. $CF_3$), $C_{1-6}$alkoxy (e.g. OMe), halogen and hydroxy.

In one embodiment of the invention, $R^1$ represents a bicyclic heteroaryl group. Suitable bicyclic heteroaryl groups include, for example 9 or 10 membered, but particularly 9 membered heteroaryl groups. Suitably, these groups contain nitrogen atoms, for example. 1 or 2 nitrogen atoms. Particularly suitable bicyclic heteroaryl rings include a 9-membered heteroaryl ring containing 1 or 2 nitrogen atoms. In some cases, the heteroaryl group may optionally contain an additional heteroatom selected from N, O or S, but particularly S. Suitably, the 9-membered heteroaryl ring comprises a benzene or pyridine ring fused to a 5-membered ring containing one or two nitrogen atoms. More suitably, it comprises a benzene ring fused to a 5-membered ring containing one or two nitrogen atoms. In some cases, the 5-membered ring may also contain an additional heteroatom selected from N, O or S, but particularly S although in more suitable compounds, the heteroaryl group does not contain S atoms. In these fused heteroaryl systems, the point of attachment is most suitably through the benzene or pyridine ring.

The aforementioned heteroaryl groups will usually be unsubstituted but may suitably be substituted by one or more substituents, suitably 1 or 2 substituents, selected from alkyl (e.g. $C_{1-4}$ alkyl such as Me), alkoxy- (e.g. $C_{1-4}$ alkoxy- such as OMe) and halogen (e.g. F).

Specific examples of bicyclic heteroaryl groups comprising a phenyl group fused to a 5-membered ring which may be present in the compounds of general formula (I) include, for example:

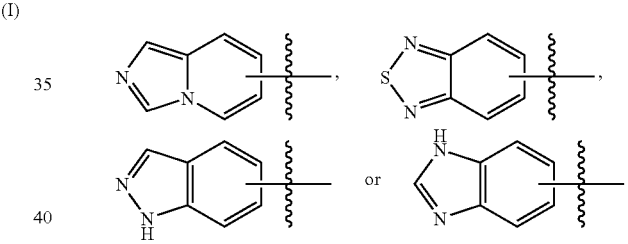

These groups may be substituted as described above.

Examples of particularly suitable bicyclic heteroaryl groups include 1H-benzimidazolyl, imidazo[1,2-a]pyridine and benzo[c][1,25]thiadiazolyl. 1H-benzoimidazol-5-yl is especially suitable.

In an alternative embodiment, $R^1$ represents —$C_{3-8}$carbocyclyl-heteroaryl, —$C_{2-6}$alkenylheteroaryl, —$C_{1-6}$alkyl-heteroaryl, or $(CH_2)_aCR^5R^6(CH_2)_b$heteroaryl. Compounds in which $R^1$ is —$C_{1-6}$alkylheteroaryl are particularly suitable.

In this embodiment, the heteroaryl group of $R^1$ may be bicyclic, for example one of the groups described above. However, more suitable heteroaryl groups are monocyclic, especially 5 or 6 membered rings and more particularly 5 membered rings. Typically they are nitrogen-containing heterocyclic groups and more typically contain 1 to 3 nitrogen atoms. Suitably, the heteroaryl group does not contain S atoms. Aforementioned heteroaryl groups may either be unsubstituted or may suitably be substituted by one or more substituents, suitably 1 or 2 substituents selected from alkyl (e.g. $C_{1-4}$ alkyl such as Me), alkoxy- (e.g. $C_{1-4}$ alkoxy- such as OMe) and halogen (e.g. F).

Particular examples of suitable monocyclic heteroaryl groups include a 5-membered ring containing 2 or 3 nitrogen atoms, which ring may optionally be substituted (e.g. in particular by one or two groups, such as methyl, for example:

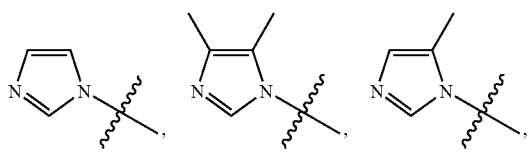

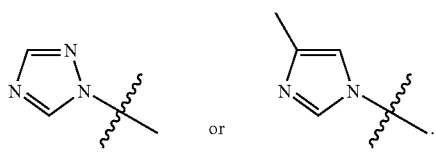

A particularly suitable heteroaryl group is imidazol-1-yl, which may optionally be substituted as set out above, although methyl is a particularly suitable substituent.

When $R^1$ represents —$C_{3-8}$carbocyclyl-heteroaryl, examples of carbocycyl include cycloalkyl (e.g. cyclohexyl) and cycloalkenyl (e.g. cyclohexenyl). An exemplary —$C_{3-8}$carbocyclyl-heteroaryl group is 3-imidazol-1-yl-cyclohexyl-.

When $R^1$ represents —$C_{2-6}$alkenyheteroaryl, examples of $C_{2-6}$ alkenyl include $C_{2-4}$ alkenyl, in particular propenyl. An exemplary -alkenylheteroaryl group is 3-imidazol-1-yl-prop-2-enyl-.

When $R^1$ represents $(CH_2)_aCR^5R^6(CH_2)_b$heteroaryl wherein a and b independently represent integers 0-5 provided that a+b=0-5 and $R^5$ and $R^6$ are alkylene which together with the carbon to which they are attached form a $C_3$-$C_5$ cycloalkyl group, examples include:

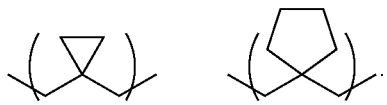

Particularly suitable compounds of this embodiment are those in which $R^1$ represents —$C_{1-6}$alkylheteroaryl. In such compounds, examples of $C_{1-6}$ alkyl include $C_{1-5}$alkyl or $C_{1-4}$alkyl, especially $C_{2-5}$alkyl or $C_{2-4}$ alkyl. The alkyl group may be straight or branched and examples where the alkyl group is branched include

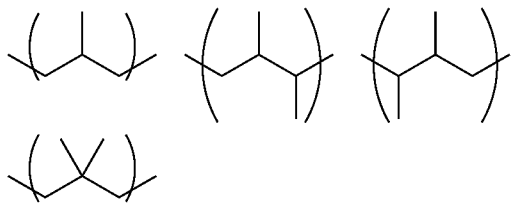

Most suitably, the alkyl group is —$CH_2$—, —$(CH_2)_2$ or —$(CH_2)_3$—, with —$(CH_2)_3$— being particularly suitable. A particularly suitable -alkylheteroaryl group is 3-imidazol-1-yl-propyl-.

In one embodiment $R^1$ represents

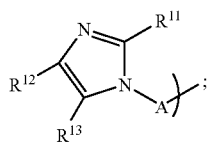

wherein A represents an unbranched $C_{1-6}$alkylene chain (e.g. an unbranched $C_{1-5}$alkylene chain, e.g. an unbranched $C_{1-4}$alkylene chain, e.g. an unbranched $C_{1-3}$alkylene chain) or A represents a branched $C_{1-6}$alkylene chain (e.g. wherein the one or more (e.g. one or two) branches consist of one or more (e.g. one or two) methyl groups at the same or different positions) or A represents $(CH_2)_aCR^5R^6(CH_2)_b$ and $R^{11}$, $R^{12}$ and $R^{13}$ independently represent H or $C_{1-2}$alkyl.

In a further embodiment, $R^1$ represents

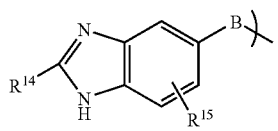

wherein B represents a bond, —$CH_2$—, —$CH_2$—$CH_2$—, —CH(Me)-, —CH(Me)-$CH_2$— or —$CH_2$—CH(Me)- and $R^{14}$ and $R^{15}$ independently represent H or $C_{1-2}$alkyl.

In a yet another embodiment, $R^1$ represents

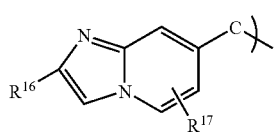

wherein C represents a bond, —$CH_2$—, —$CH_2$—$CH_2$—, —CH(Me)-, —CH(Me)-$CH_2$— or —$CH_2$—CH(Me)- and $R^{16}$ and $R^{17}$ independently represent H or $C_{1-2}$alkyl.

In another embodiment, $R^1$ represents

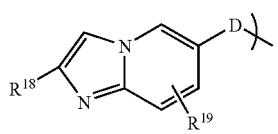

wherein D represents a bond, —$CH_2$—, —$CH_2$—$CH_2$—, —CH(Me)-, —CH(Me)-$CH_2$— or —$CH_2$—CH(Me)- and $R^{18}$ and $R^{19}$ independently represent H or $C_{1-2}$alkyl;

In particularly suitable compounds $R^1$ represents

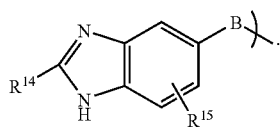

In one embodiment $R^{14}$ represents H and $R^{15}$ represents H. In another embodiment $R^{14}$ represents H and $R^{15}$ represents $C_{1-2}$alkyl. In a third embodiment $R^{14}$ represents $C_{1-2}$alkyl and $R^{15}$ represents H.

In such compounds B represents a bond, —$CH_2$— or —$CH_2CH_2$—. In a particularly suitable embodiment, B represents a bond. In another embodiment, B represents —CH$_2$—. In a third embodiment, B represents —CH$_2$CH$_2$—.

Alternatively R$^1$ represents

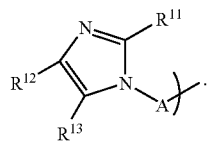

R$^{11}$ suitably represents H,
R$^{12}$ suitably represents H or methyl.
R$^{13}$ suitably represents H or methyl.

In one embodiment of the invention, R$^{12}$ represents H and R$^{13}$ represents methyl. In another embodiment, R$^{12}$ represents methyl and R$^{13}$ represents H. In a third embodiment, R$^{12}$ represents H and R$^{13}$ represents H.

Suitably A represents an unbranched C$_{2-5}$ alkylene chain. In one embodiment, A represents —(CH$_2$)$_2$—. In another embodiment, A represents —(CH$_2$)$_3$—. In a third embodiment, A represents —(CH$_2$)$_4$—. In further embodiment, A represents —(CH$_2$)$_5$—. More suitably A represents —(CH$_2$)$_2$—, —(CH$_2$)$_4$— or —(CH$_2$)$_5$—. In one embodiment, A represents —(CH$_2$)$_3$—. In another embodiment, A represents —(CH$_2$)$_4$—.

Alternatively A represents a branched C$_{2-5}$ alkylene chain. In one embodiment A does not represent —(CH$_2$)$_3$—.

When A represents a C$_{2-5}$ alkylene chain, which is substituted by two alkylene substituents at the same position wherein the two alkylene substituents are joined to each other to form a C$_{3-5}$spiro-cycloalkyl group, the spiro-cycloalkyl group is suitably C$_3$spiro-cycloalkyl.

Alternatively R$^1$ represents

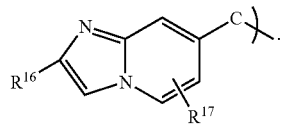

In one embodiment R$^{16}$ represents H and R$^{17}$ represents H. In another embodiment R$^{16}$ represents H and R$^{17}$ represents C$_{1-2}$alkyl. In a third embodiment R$^{16}$ represents C$_{1-2}$alkyl and R$^{17}$ represents H.

Suitably C represents a bond, —CH$_2$— or —CH$_2$CH$_2$—. In one embodiment C represents a bond. In another embodiment, C represents —CH$_2$—. In a third embodiment, C represents —CH$_2$CH$_2$—.

Alternatively R$^1$ represents

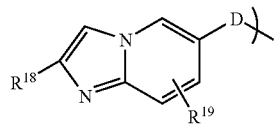

In one embodiment R$^{18}$ represents H and R$^{19}$ represents H. In another embodiment R$^{18}$ represents H and R$^{19}$ represents C$_{1-2}$alkyl. In a third embodiment R$^{18}$ represents C$_{1-2}$alkyl and R$^{19}$ represents H.

Suitably D represents a bond, —CH$_2$— or —CH$_2$CH$_2$—. In one embodiment D represents a bond. In another embodiment, D represents —CH$_2$—. In a third embodiment, D represents —CH$_2$CH$_2$—.

More suitably R$^1$ represents

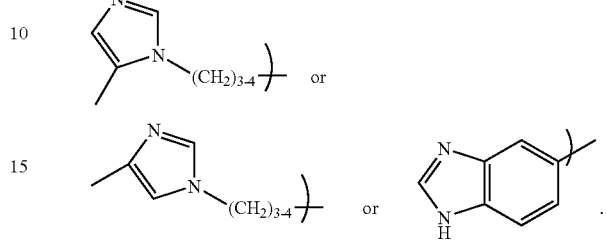

Most suitably R$^1$ represents

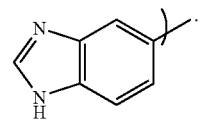

In a particularly suitable embodiment, the compound of formula (I) is represented by

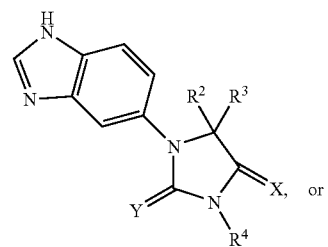

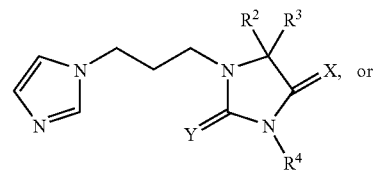

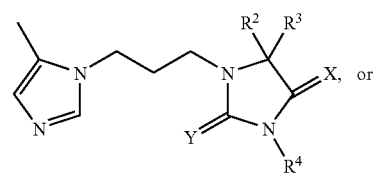

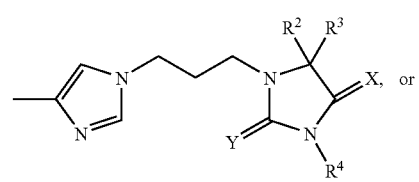

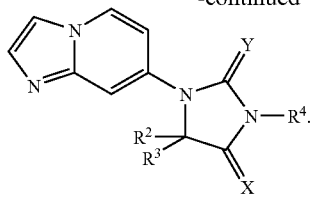

Most suitably, the compound of formula (I) is represented by

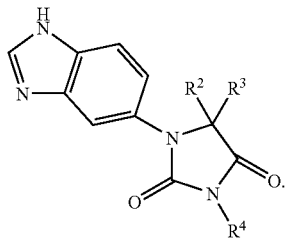

When $R^2$ represents —$C_{1-8}$alkyl, examples include methyl, ethyl, propyl (e.g. n-propyl, isopropyl), butyl (e.g. n-butyl-sec-butyl, isobutyl and tert-butyl), pentyl (e.g. n-pentyl, 3,3,-dimethylpropyl), hexyl, heptyl and octyl.

When $R^2$ represents optionally substituted aryl, aryl may typically represent phenyl. Exemplary substituted phenyl groups include 2,4-dichlorophenyl-, 2,4-difluororophenyl-, 2,4-dimethoxyphenyl-, 2,4-dimethylphenyl-, 2,4-bis(trifluoromethyl)phenyl-, 2,4,6-trifluorophenyl-, 2,4,6-trimethylphenyl-, 2,6-dichlorophenyl-, 2,6-difluorophenyl-, 2,6-dimethoxyphenyl-, 2-isopropyl-6-methylphenyl-, 3-(cyclopentyloxy)-4-methoxyphenyl-, 3,4,5-trimethoxyphenyl-, 3,4-dimethoxyphenyl-, 3,4-dichlorophenyl-, 3,4-dimethylphenyl-, 3,4,5-trifluorophenyl-, 3,5-bis(trifluororomethyl)phenyl-, 3,5-dimethoxyphenyl-, 3-methoxyphenyl-, 4-(trifluoromethyl)phenyl-, 4-bromo-2-(trifluoromethyl)phenyl-, 4-bromophenyl-, 4-chloro-3-(trifluoromethyl)phenyl-, 4-chlorophenyl-, 4-cyanophenyl-, 4-ethoxyphenyl-, 4-ethylphenyl-, 4-fluorophenyl-, 4-isopropylphenyl-, 4-methoxyphenyl-. Alternatively, $R^2$ may represent unsubstituted phenyl-. Further exemplary substituted phenyl groups include 2,3,4-trifluorophenyl, 2,3-difluoro-4-methylphenyl, 2-bromo-4-fluorophenyl-, 2-bromo-5-fluorophenyl-, 2-chlorophenyl-, 2-fluoro-5-(trifluoromethyl)phenyl-, 2-hydroxy-3-methoxyphenyl-, 2-hydroxy-5-methylphenyl-, 3-chlorophenyl-, 3-fluoro-4-(trifluoromethyl)phenyl-, 3-hydroxy-4-methoxyphenyl-, 4-bromo-2-fluorophenyl, 4-chloro-3-(trifluoromethyl)phenyl-, 4-chloro-3-methylphenyl, 4-chlorophenyl-, 4-fluorophenyl- and 4-propoxyphenyl-.

When $R^2$ represents optionally substituted aryl and aryl represents naphthyl, examples include unsubstituted naphthyl (e.g. naphthalen-1-yl, naphthalen-2-yl, naphthalen-3-yl) as well as substituted naphthyl (e.g. 4-methyl-naphthalen-2-yl-, 5-methyl-naphthalen-3-yl-, 7-methyl-naphthalen-3-y- and 4-fluoro-naphthalen-2-yl-).

When $R^2$ represents optionally substituted heteroaryl, examples include monocyclic rings (e.g. 5 or 6 membered rings) and bicyclic rings (e.g. 9 or 10 membered rings) which may optionally be substituted. Example 5 membered rings include pyrrolyl (e.g. pyrrol-2-yl) and imidazolyl (e.g. 1H-imidazol-2-yl or 1H-imidazol-4-yl), pyrazolyl (e.g. 1H-pyrazol-3-yl), furanyl (e.g. furan-2-yl), thiazolyl (e.g. thiazol-2-yl), thiophenyl (e.g. thiophen-2-yl, thiophen-3-yl). Example 6 membered rings include pyridinyl (e.g. pyridin-2-yl and pyridin-4-yl). Specific substituents that may be mentioned are one or more e.g. 1, 2 or 3 groups selected from halogen, hydroxyl, alkyl (e.g. methyl) and alkoxy- (e.g. methoxy-). Example substituted 5 membered rings include 4,5-dimethyl-furan-2-yl-, 5-hydroxymethyl-furan-2-yl-, 5-methyl-furan-2-yl- and 6-methyl-pyridin-2-yl-. An example substituted 6-membered ring is 1-oxy-pyridin-4-yl-. Example 9 membered rings include 1H-indolyl (e.g. 1H-indol-3-yl, 1H-indol-5-yl), benzothiophenyl (e.g. benzo[b]thiophen-3-yl, particularly 2-benzo[b]thiophen-3-yl), benzo[1,2,5]-oxadiazolyl (e.g. benzo[1,2,5]-oxadiazol-5-yl), benzo[1,2,5]-thiadiazolyl (e.g. benzo[1,2,5]-thiadiazol-5-yl, benzo[1,2,5]thiadiazol-6-yl). Example 10 membered rings include quinolinyl (e.g. quinolin-3-yl, quinolin-4-yl, quinolin-8-yl). Specific substituents that may be mentioned are one or more e.g. 1, 2 or 3 groups selected from halogen, hydroxyl, alkyl (e.g. methyl) and alkoxy- (e.g. methoxy-). Example substituted 9-membered rings include 1-methyl-1H-indol-3-yl, 2-methyl-1H-indol-3-yl, 6-methyl-1H-indol-3-yl. Example substituted 10 membered rings include 2-chloro-quinolin-3-yl, 8-hydroxy-quinolin-2-yl, oxo-chromenyl (e.g. 4-oxo-4H-chromen-3-yl) and 6-methyl-4-oxo-4H-chromen-3-yl.

When $R^2$ represents carbocyclyl, examples include cycloalkyl and cycloalkenyl. Examples of cycloalkyl include cyclopropyl, cyclobutyl, cyclopentyl, cyclohexyl and cycloheptyl. Examples of cycloalkenyl include cyclohexenyl (e.g. cyclohex-2-enyl, cyclohex-3-enyl). Examples of substituted carbocyclyl include 2-methyl-cyclohexyl-, 3-methyl-cyclohexyl-, 4-methyl-cyclohexyl-, 2-methyl-cyclohex-2-enyl, 2-methyl-cyclohex-3-enyl, 3-methyl-cyclohex-3-enyl, 3-methyl-cyclohex-3-enyl.

When $R^2$ represents heterocyclyl (which may optionally be substituted), examples include tetrahydrofuranyl, morpholinyl, piperdinyl, 3,4-dihydro-2H-pyranyl, pyrrolidinyl, methyltetrahydrofuranyl- (e.g. 5-methyltetrahydrofuran-2-yl-).

When $R^2$ represents —$C_{1-4}$alkylaryl, examples include -alkyl(substituted phenyl) e.g. in which phenyl is substituted by one or more groups selected from alkyl, fluoroalkyl, halogen and alkoxy (e.g. methyl, trifluoromethyl, tert-butyl, chloro, fluoro and methoxy) and, for example, alkyl is $C_{1-4}$ alkyl. Another specific group is -alkyl(bicyclic aryl) e.g. wherein bicyclic aryl is optionally substituted naphthyl. A further specific group is benzyl.

When $R^2$ represents —$C_{1-4}$alkylheteroaryl in which heteroaryl is optionally substituted, examples include methylheteroaryl and -ethylheteroaryl (e.g. 1-heteroarylethyl- and 2-heteroarylethyl-), -propylheteroaryl and -butylheteroaryl in which heteroaryl is optionally substituted. Specific examples of -alkylheteroaryl groups include pyridinylmethyl-, N-methyl-pyrrol-2-methyl-N-methyl-pyrrol-2-ethyl-, N-methyl-pyrrol-3-methyl-, N-methyl-pyrrol-3-ethyl-, 2-methyl-pyrrol-1-methyl-, 2-methyl-pyrrol-1-ethyl-, 3-methyl-pyrrol-1-methyl-, 3-methyl-pyrrol-1-ethyl-, 4-pyridinomethyl-, 4-pyridino-ethyl-, 2-(thiazol-2-yl)-ethyl-, 2-ethyl-indol-1-methyl-, 2-ethyl-indol-1-ethyl-, 3-ethyl-indol-1-methyl-, 3-ethyl-indol-1-ethyl-, 4-methyl-pyridin-2-methyl-, 4-methyl-pyridin-2-yl-ethyl-, 4-methyl-pyridin-3-methyl-, 4-methyl-pyridin-3-ethyl-.

When $R^2$ represents —$C_{1-4}$alkyl-carbocyclyl (which may optionally be substituted), examples include -methyl-cyclopentyl, -methyl-cyclohexyl, -ethyl-cyclohexyl, -propyl-cyclohexyl, -methyl-cyclohexenyl, -ethyl-cyclohexenyl, -methyl(4-methylcyclohexyl) and -propyl(3-methylcyclyohexyl).

When $R^2$ represents —$C_{1-4}$alkylheterocyclyl (which may optionally be substituted); examples include -methyl-tetrahydrofuranyl (e.g. -methyl-tetrahydrofuran-2-yl, -methyl-tetrahydrofuran-3-yl), -ethyl-tetrahydrofuranyl, -methyl-piperidinyl.

When $R^2$ represents phenyl substituted by phenyl or phenyl substituted by a monocyclic heteroaryl group, in which any of aforesaid phenyl and heteroaryl groups may optionally be substituted, typically the phenyl ring connected directly to the nitrogen atom is unsubstituted and the terminal phenyl ring or the monocyclic heteroaryl ring is optionally substituted by one, two or three substitutents (e.g. one or two, e.g. one). Typically the terminal phenyl or monocyclic heteroaryl group is unsubstituted. Typically the terminal phenyl or monocyclic heteroaryl group substitutes the other phenyl group at the 4-position.

When $R^2$ represents phenyl substituted by phenyl in which any of aforesaid phenyl groups may optionally be substituted, examples include -biphenyl-4-yl.

When $R^2$ represents phenyl substituted by a monocyclic heteroaryl group, in which any of aforesaid phenyl and heteroaryl groups may optionally be substituted, examples include 4-(oxazol-5-yl)phenyl-.

When $R^2$ represents phenyl substituted by benzyloxy in which any of aforesaid phenyl and benzyloxy groups may optionally be substituted, examples include 4-benzyloxyphenyl-, 4-(3-methylbenzyloxy)phenyl- and 4-(4-methylbenzyloxy)phenyl-.

When $R^2$ represents optionally substituted phenyl fused to optionally substituted carbocyclyl, examples include indanyl (e.g. indan-4-yl-, 2-methyl-indan-4-yl-), indenyl and tetralinyl.

When $R^2$ represents optionally substituted phenyl fused to optionally substituted heterocyclyl, examples include benzo[1,3]dioxo-4-yl- and 2,3-dihydro-benzo[1,4]dioxin-4-yl-.

When $R^2$ represents —$C_{1-4}$alkyl(phenyl substituted by phenyl), examples include biphenyl-4-yl-methyl-.

When R2 represents —C1-4alkyl(phenyl substituted by a monocyclic heteroaryl group), examples include 4-(oxazol-5-yl)phenyl-methyl-.

When R2 represents —C1-4alkyl(phenyl substituted by benzyloxy) in which any of aforesaid phenyl and benzyloxy groups may optionally be substituted, examples include 4-benzyloxy-phenyl-methyl-, 4-(3-methylbenzyloxy)phenyl-methyl- and 4-(4-methylbenzyloxy)phenyl-methyl-.

When R2 represents —C1-4alkyl(optionally substituted phenyl fused to optionally substituted carbocyclyl), examples include indanyl-methyl- (e.g. indan-4-yl-methyl-, 2-methyl-indan-4-yl-methyl-), indenyl-methyl- and tetralinyl-methyl-.

When R2 represents —C1-4alkyl(optionally substituted phenyl fused to optionally substituted heterocyclyl); examples include benzo[1,3]dioxo-4-yl-methyl- and 2,3-dihydro-benzo[1,4]dioxin-4-yl-methyl-.

Suitably R2 represents aryl, heteroaryl, phenyl substituted by phenyl, phenyl fused to heterocyclyl or R2 and R3 are joined to form a carbocyclyl ring which is fused to phenyl, the aforesaid aryl, heteroaryl, phenyl, heterocyclyl and carbocyclyl groups optionally being substituted.

More suitably, R2 represents aryl, heteroaryl, phenyl substituted by phenyl or phenyl fused to heterocyclyl, the aforesaid aryl, heteroaryl, phenyl and heterocyclyl groups optionally being substituted.

In one embodiment, R2 represents optionally substituted heteroaryl. When R2 represents optionally substituted heteroaryl, R2 suitably represents benzo[c][1,2,5]thiadiazol-6-yl.

In one embodiment, R2 represents phenyl substituted by phenyl, the aforesaid phenyl groups optionally being substituted, for example by one or more substitutents which may be the same or different and are chosen from halo, OH, C1-3alkyl, C1-3 haloalkyl, C1-3 alkoxy, C1-3 haloalkoxy. When R2 represents phenyl substituted by phenyl, R2 suitably represents -biphenyl-4-yl.

In one embodiment, R2 represents optionally substituted phenyl fused to optionally substituted heterocyclyl. When R2 represents optionally substituted phenyl fused to optionally substituted heterocyclyl, R2 suitably represents 2,3-dihydrobenzo[1,4]dioxin-4-yl-.

In a further embodiment, R2 represents optionally substituted aryl especially optionally substituted phenyl. In suitable compounds of this type, R2 represents phenyl optionally substituted by one or more substitutents. In general, when R2 is optionally substituted phenyl, it is unsubstituted or has one, two or three substituents, which may be the same or different and are chosen from halo, OH, C1-3alkyl, C1-3 haloalkyl, C1-3 alkoxy, C1-3 haloalkoxy. Specific examples of these substituents include F, Cl, Br, OH, methyl, trifluoromethyl, ethyl, n-propyl, methoxy, ethoxy and n-propoxy.

A particularly suitable R2 group is phenyl substituted by n-propyloxy, particularly 4-n-propoxyphenyl.

When R3 represents —C1-4alkyl, examples include methyl, ethyl, propyl (e.g. n-propyl, isopropyl) and butyl (e.g. n-butyl-sec-butyl, isobutyl and tert-butyl).

When R3 represents optionally substituted aryl, aryl may typically represent phenyl. Exemplary substituted phenyl groups include 2,4-dichlorophenyl-, 2,4-difluororophenyl-, 2,4-dimethoxyphenyl-, 2,4-dimethylphenyl-, 2,4-bis(trifluoromethyl)phenyl-, 2,4,6-trifluorophenyl-, 2,4,6-trimethylphenyl-, 2,6-dichlorophenyl-, 2,6-difluorophenyl-, 2,6-dimethoxyphenyl-, 2-isopropyl-6-methylphenyl-, 3-(cyclopentyloxy)-4-methoxyphenyl-, 3,4,5-trimethoxyphenyl-, 3,4-dimethoxyphenyl-, 3,4-dichlorophenyl-, 3,4-dimethylphenyl-, 3,4,5-trifluorophenyl-, 3,5-bis(trifluororomethyl)phenyl-, 3,5-dimethoxyphenyl-, 3-methoxyphenyl-, 4-(trifluoromethyl)phenyl-, 4-bromo-2-(trifluoromethyl)phenyl-, 4-bromophenyl-, 4-chloro-3-(trifluoromethyl)phenyl-, 4-chlorophenyl-, 4-cyanophenyl-, 4-ethoxyphenyl-, 4-ethylphenyl-, 4-fluorophenyl-, 4-isopropylphenyl-, 4-methoxyphenyl-. Alternatively, R3 may represents unsubstituted phenyl-. Further exemplary substituted phenyl groups include 2-bromo-4-fluorophenyl-, 2-bromo-5-fluorophenyl-, 2-chlorophenyl-, 2-fluoro-5-(trifluoromethyl)phenyl-, 2-hydroxy-3-methoxyphenyl-, 2-hydroxy-5-methylphenyl-, 3-chlorophenyl-, 3-fluoro-4-(trifluoromethyl)phenyl-, 3-hydroxy-4-methoxyphenyl-, 4-chloro-3-(trifluoromethyl)phenyl-, 4-chlorophenyl-, 4-fluorophenyl- and 4-propoxyphenyl-.

When R2 and R3 are joined to form a carbocyclyl ring, which is optionally substituted by one or more C1-2alkyl groups, examples include cycloalkyl (e.g. cyclopropyl, cyclopentyl and cyclohexyl) and cycloalkenyl (e.g. cyclohexenyl).

When R2 and R3 are joined to form a carbocyclyl ring which is fused to phenyl; examples include indanyl (e.g. indan-2-yl) and tetralinyl.

When R2 and R3 are joined to form a carbocyclyl ring which is fused to monocyclic heteroaryl; examples include 5-membered carbocyclyl fused to 6-membered heteroaryl, 6-membered carbocyclyl fused to 6-membered heteroaryl, 5-membered carbocyclyl fused to 5-membered heteroaryl and 6-membered carbocyclyl fused to 5-membered heteroaryl. The monocyclic heteroaryl to which carbocyclyl is fused contains at least one heteroatom (e.g. one, two or three heteroatoms, e.g. one or two, e.g. one heteroatom).

Suitably R3 represents H or R2 and R3 are joined to form a carbocyclyl ring which is fused to phenyl. Most suitably R3 represents H.

When R4 represents —C1-8alkyl examples include methyl, ethyl, propyl (e.g. n-propyl, isopropyl), butyl (e.g. n-butyl-sec-butyl, isobutyl and tert-butyl), pentyl (e.g. n-pentyl, 3,3,-dimethylpropyl), hexyl, heptyl and octyl.

When R4 represents —C(O)C1-6alkyl; examples include —C(O)C1-4alkyl such as —C(O)methyl, —C(O)ethyl, —C(O)propyl and —C(O)butyl.

Suitably R4 represents H, —C1-8alkyl or —C(O)C1-6alkyl. More suitably R4 represents H or —C1-8alkyl, e.g. H or methyl. Most suitably R4 represents H.

In one embodiment X represents O. In an alternative embodiment X represents S.

In one embodiment Y represents O. In an alternative embodiment Y represents S.

In one embodiment X represents O and Y represents S. In an alternative embodiment X represents S and Y represents O. Suitably X and Y both represent O.

Most particularly, the compound of formula (I) is represented by

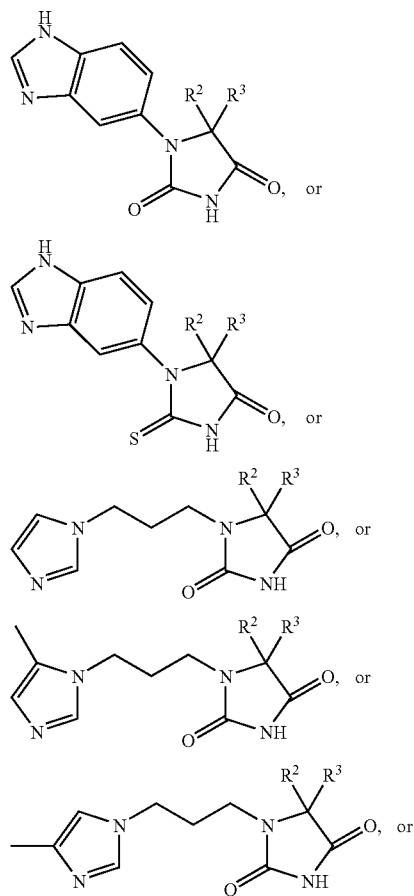

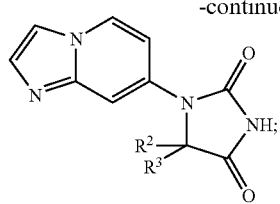

wherein R2 and R3 are as defined above.

Most suitably, the compound of formula (I) is represented by

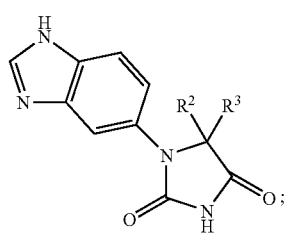

wherein R2 and R3 are as defined above.

The compounds of the present invention have several advantages, which make them especially useful for the treatment of QC related disases in the CNS, i.e. the compounds of the present invention are potent QC inhibitors and have a favourable logBB as well as reach a high concentration in brain.

Particularly suitable compounds of general formula (I) are selected from:
1. 5-(benzo[c][1,2,5]thiadiazol-6-yl)-1-(1H-benzo[d]imidazol-5-yl)imidazolidine-2,4-dione
2. 1-(1H-benzo[d]imidazol-5-yl)-5-phenylimidazolidine-2,4-dione
3. 1-(1H-benzo[d]imidazol-5-yl)-5-(2-hydroxy-5-methylphenyl)imidazolidine-2,4-dione
4. 1-(1H-benzo[d]imidazol-5-yl)-5-(2-fluoro-5-trifluoromethyl)phenyl)imidazolidine-2,4-dione
5. 1-(1H-benzo[d]imidazol-5-yl)-5-(2-bromo-5-fluorophenyl)imidazolidine-2,4-dione
6. 1-(1H-benzo[d]imidazol-5-yl)-5-(4-propoxyphenyl)imidazolidine-2,4-dione
7. 1-(1H-benzo[d]imidazol-5-yl)-5-(4-chloro-3-trifluoromethyl)phenyl)imidazolidine-2,4-dione
8. 1-(1H-benzo[d]imidazol-5-yl)-5-(3-fluoro-4(trifluoromethyl)phenyl)imidazolidine-2,4-dione
9. 1-(1H-benzo[d]imidazol-5-yl)-5-(3-hydroxy-4-methoxyphenyl)imidazolidine-2,4-dione
10. 1-(1H-benzo[d]imidazol-5-yl)-5-(2-hydroxy-3-methoxyphenyl)imidazolidine-2,4-dione
11. 1-(1H-benzimidazol-5-yl)-5-(1,1'-biphenyl-4-yl)imidazolidine-2,4-dione
12. 1-(1H-benzo[d]imidazol-5-yl)-5-(3-chlorophenyl)imidazolidine-2,4-dione
13. 1-(1H-benzo[d]imidazol-5-yl)-5-(4-chlorophenyl)imidazolidine-2,4-dione
14. 1-(1H-benzo[d]imidazol-5-yl)-5-(2-chlorophenyl)imidazolidine-2,4-dione
15. 1-(1H-benzo[d]imidazol-5-yl)-5-(4-fluorophenyl)imidazolidine-2,4-dione
16. 1-(1H-benzo[d]imidazol-5-yl)-5-(2,3-dihydrobenzo[b][1,4]dioxin-7-yl)imidazolidine-2,4-dione 17. 1-(3-(1H-imidazol-1-yl)propyl)-5-phenylimidazolidine-2,4-dione
18. 1-(3-(1H-imidazol-1-yl)propyl)-5-(2-bromo-4-fluorophenyl)imidazolidine-2,4-dione
19. 1-(3-(1H-imidazol-1-yl)propyl)-5-(4-propoxyphenyl) imidazolidine-2,4-dione
20. 1-(3-(1H-imidazol-1-yl)propyl)-5-(3-fluoro-4-(trifluoromethyl)phenyl) imidazolidine-2,4-dione
21. 1-[3-(1H-imidazol-1-yl)propyl]-5-(4-biphenyl)imidazolidine-2,4-dione
22. 1-(3-(1H-imidazol-1-yl)propyl)-5-(3-chlorophenyl)imidazolidine-2,4-dione
23. 1-(3-(1H-imidazol-1-yl)propyl)-5-(2-chlorophenyl)imidazolidine-2,4-dione
24. 1-(3-(5-methyl-1H-imidazol-1-yl)propyl)-5-phenylimidazolidine-2,4-dione
25. 5-(2-bromo-5-fluorophenyl)-1-(3-(5-methyl-1H-imidazol-1-yl)propyl)imidazolidine-2,4-dione
26. 1-(3-(5-methyl-1H-imidazol-1-yl)propyl)-5-(4-propoxyphenyl)imidazolidine-2,4-dione
27. 1-[3-(5-methyl-1H-imidazol-1-yl)propyl]-5-(4-phenylphenyl)imidazolidine-2,4-dione
28. 5-(3-chlorophenyl)-1-(3-(5-methyl-1H-imidazol-1-yl)propyl)imidazolidine-2,4-dione
29. 1-(3-(4-methyl-1H-imidazol-1-yl)propyl)-5-phenylimidazolidine-2,4-dione
30. 1-[3-(4-methyl-1H-imidazol-1-yl)propyl]-5-(4-biphenyl)imidazolidine-2,4-dione
31. 5-(3-chlorophenyl)-1-(3-(4-methyl-1H-imidazol-1-yl)propyl)imidazolidine-2,4-dione
32. 3-(1H-benzimidazol-5-yl)-1',3'-dihydro-2H,5H-spiro[imidazolidine-4,2'-indene]-2,5-dione
33. 5-(benzo[c][1,2,5]thiadiazol-6-yl)-1-(1H-benzo[d]imidazol-5-yl)-2-thioxoimidazolidin-4-one
34. 1-(1H-benzo[d]imidazol-5-yl)-5-phenyl-2-thioxoimidazolidin-4-one
35. 1-(1H-benzimidazol-5-yl)-5-(1,1'-biphenyl-4-yl)-2-thioxoimidazolidin-4-one
36. 1-(1H-benzo[d]imidazol-5-yl)-5-(3-hydroxy-4-methoxyphenyl)-2-thioxoimidazolidin-4-one
37. 1-(1H-benzo[d]imidazol-5-yl)-5-phenyl-4-thioxoimidazolidin-2-one
38. 1-(1H-benzimidazol-5-yl)-5-(1,1'-biphenyl-4-yl)-4-thioxoimidazolidin-2-one
39. 3-(1H-benzimidazol-5-yl)-5-thioxo-1,3'-dihydro-2H-spiro[imidazolidine-4,2'-inden]-2-one
40. 1-(1H-benzo[d]imidazol-5-yl)-5-(4-chlorophenyl)-4-thioxoimidazolidin-2-one
41. 1-(1H-benzo[d]imidazol-5-yl)-5-(2,3,4-trifluorophenyl)-4-thioxoimidazolidin-2-one
42. 1-(1H-benzo[d]imidazol-6-yl)-5-(4-bromo-2-fluorophenyl)-4-thioxoimidazolidin-2-one
43. 1-(1H-benzo[d]imidazol-5-yl)-5-(2,3-difluoro-4-methylphenyl)-4-thioxoimidazolidin-2-one
44. 1-(1H-benzo[d]imidazol-5-yl)-5-(4-chloro-3-methylphenyl)-4-thioxoimidazolidin-2-one
45. 1-(1H-benzo[d]imidazol-5-yl)-3-methyl-5-phenylimida4zolidine-2,4-dione
46. 1-(H-imidazo[1,2-a]pyridin-7-yl)-5-phenylimidazolidine-2,4-dione;

or a pharmaceutically acceptable salt, solvate or polymorph thereof, including all tautomers and stereoisomers thereof.

A particularly suitable compound of formula (I) in this regard is the compound of Example 6, 1-(1H-benzo[d]imidazol-5-yl)-5-(4-propoxyphenyl)imidazolidine-2,4-dione, which has the structure:

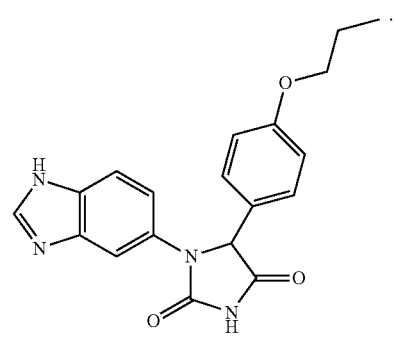 [SMILES: CCCOc1ccc(C2C(=O)NC(=O)N2c2ccc3[nH]cnc3c2)cc1]

The compounds of formula (I) have a chiral centre at the carbon atom to which R2 and R3 are attached and the inventors have succeeded in isolating each of the enantiomers in compounds of formula (I). For example in the case of the compound of Example 6, the inventors have isolated both, (R)-1-(1H-benzo[d]imidazol-5-yl)-5-(4-propoxyphenyl)imidazolidine-2,4-dione and (S)-1-(1H-benzo[d]imidazol-5-yl)-5-(4-propoxyphenyl)imidazolidine-2,4-dione.

Therapeutic Uses

Physiological substrates of isoQC (QPCTL) in mammals are, e.g. amyloid beta-peptides (3-40) (SEQ ID NO. 91), (3-42) (SEQ ID NO. 92), (11-40) (SEQ ID NO. 93) and (11-42) (SEQ ID NO. 94), Abri (SEQ ID NO. 95), Adan (SEQ ID NO. 96), Gastrin (SEQ ID NO. 97), Neurotensin (SEQ ID NO. 98), FPP (SEQ ID NO. 99), CCL2 (SEQ ID NO. 100), CCL7 (SEQ ID NO. 101), CCL8 (SEQ ID NO. 102), CCL13 (SEQ ID NO. 103), CCL16 (SEQ ID NO. 104), CCL18 (SEQ ID NO. 105), Fractalkine (SEQ ID NO. 106), Orexin A (SEQ ID NO. 107), [Gln5]-substance P(5-11) (SEQ ID NO. 108) and the peptide QYNAD (SEQ ID NO. 109). The isoQC inhibitors and/or combinations according to the present invention and pharmaceutical compositions comprising at least one inhibitor of isoQC are useful for the treatment of conditions that can be treated by modulation of QC activity.

Glutamate is found in positions 3, 11 and 22 of the amyloid β-peptide (Aβ). Among them the mutation from glutamic acid (E) to glutamine (Q) in position 22 (corresponding to amyloid precursor protein APP 693, Swissprot P05067) has been described as the so called Dutch type cerebroarterial amyloidosis mutation.

The β-amyloid peptides with a pyroglutamic acid residue in position 3, 11 and/or 22 have been described to be more cytotoxic and hydrophobic than the amyloid β-peptides 1-40/42 (Saido T. C. 2000 Medical Hypotheses 54(3): 427-429).

The multiple N-terminal variations, e.g. Aβ(3-40), Aβ(3-42), Aβ(11-40) and Aβ(11-42) can be generated by the β-secretase enzyme β-site amyloid precursor protein-cleaving enzyme (BACE) at different sites (Huse J. T. et al. 2002 J. Biol. Chem. 277 (18): 16278-16284), and/or by aminopeptidase or dipeptidylaminopeptidase processing from the full length peptides Aβ(1-40) and Aβ(1-42). In all cases, cyclization of the then N-terminal occuring glutamic acid residue to pyroglutamate can by catalyzed by isoQC.

CCL2 (MCP-1), CCL7 (MCP-3), CCL8 (MCP-2), CCL13 (MCP-4), CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, vasculitis, humoral and cell-mediated immunity responses, leukocyte adhesion and migration processes at the endothelium, inflammatory bowel disease, restenosis, pulmonary fibrosis, pulmonary hypertension, liver fibrosis, liver cirrhosis, nephrosclerosis, ventricular remodeling, heart failure, arteriopathy after organ transplantations and failure of vein grafts. The N-terminus of each of these peptides starts with an glutaminyl residue and the cyclization of the then N-terminal occuring glutaminyl residue to pyroglutamate can by catalyzed by isoQC.

Recently, increased levels of the pentapeptide QYNAD were identified in the cerebrospinal fluid (CSF) of patients suffering from multiple sclerosis or Guillain-Barré syndrome compared to healthy individuals (Brinkmeier H. et al. 2000, Nature Medicine 6, 808-811). There is a big controversy in the literature about the mechanism of action of the pentapeptide Gln-Tyr-Asn-Ala-Asp (QYNAD), especially its efficacy to interact with and block sodium channels resulting in the promotion of axonal dysfunction, which are involved in inflammatory autoimmune diseases of the central nervous system. But recently, it could be demonstrated that not QYNAD, but its cyclized, pyroglutamated form, pEYNAD, is the active form, which blocks sodium channels resulting in the promotion of axonal dysfunction. Sodium channels are expressed at high density in myelinated axons and play an obligatory role in conducting action potentials along axons within the mammalian brain and spinal cord. Therefore, it is speculated that they are involved in several aspects of the pathophysiology of inflammatory autoimmune diseases, especially multiple sclerosis, the Guillain-Barré syndrome and chronic inflammatory demyelinizing polyradiculoneuropathy.

Furthermore, QYNAD is a substrate of isoQC, which is also present in the brain of mammals, especially in human brain. IsoQC catalyzes effectively the formation of pEYNAD from its precursor QYNAD.

Accordingly, the present invention provides the use of isoQC inhibitors for the prevention or treatment of a disease selected from the group consisting of (a) chronic and acute inflammations, e.g. rheumatoid arthritis, atherosclerosis, restenosis, pancreatitis, osteoporosis, (b) other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis, (c) neuroinflammation, and (d) neurodegenerative diseases, e.g. mild cognitive impairment (MCI), Alzheimer's disease, neurodegeneration in Down Syndrome, Familial British Dementia, and Familial Danish Dementia, which may result from neuroinflammation.

Preferred according to the present invention is the use of isoQC inhibitors for the treatment of chronic and acute inflammations, e.g. rheumatoid arthritis, atherosclerosis, restenosis, pancreatitis and osteoporosis.

Especially preferred is the use of isoQC inhibitors for the treatment of rheumatiod arthritis and/or atherosclerosis.

Even preferred is the use of isoQC inhibitors for the treatment of multiple sclerosis.

Most preferred is the use of isoQC inhibitors for the treatment of neuroinflammation.

In particular preferred is the use of isoQC inhibitors for the treatment of mild cognitive impairment (MCI), Alzheimer's disease, neurodegeneration in Down Syndrome, Familial British Dementia, and Familial Danish Dementia, which may result from neuroinflammation.

In a further embodiment the present invention provides a method for preventing or treating a disease or condition as aforementioned, comprising administering to a subject in need thereof a pharmaceutically effective amount of an isoQC-inhibitor or a pharmaceutically acceptable salt thereof.

Additionally, the present invention provides the use of an isoQC-inhibitor or a pharmaceutically acceptable salt thereof for the preparation of a medicament for the prevention or treatment of any of the aforementioned diseases or conditions.

Any isoQC inhibitor may be employed for use in said method of treatment or pharmaceutical use. Preferred are the isoQC inhibitors of formula (I). More preferred are the isoQC inhibitors of examples 1 to 46 as listed in the table below. Most preferred for the use in said method of treatment or pharmaceutical use is example 6 (1-(1H-benzo[d]imidazol-5-yl)-5-(4-propoxyphenyl)imidazolidine-2,4-dione) of the formula

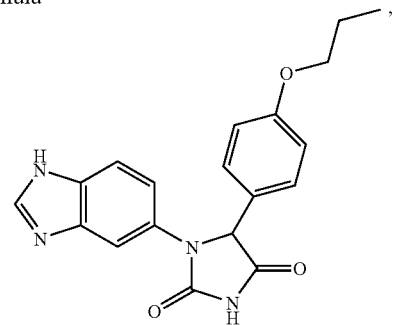

furtheron referred to herein as isoQC-I.

TABLE 3

Examples of isoQC inhibitors of formula (I)

| Example | Structure | Formula | Mol Weight |
|---------|-----------|---------|------------|
| 1 | 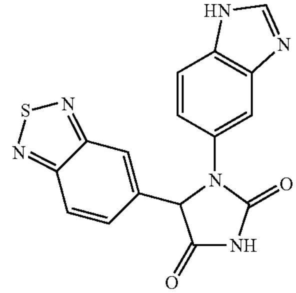 [SMILES: O=C1NC(=O)N(c2ccc3[nH]cnc3c2)C1c1ccc2nsnc2c1] | $C_{16}H_{10}N_6O_2S$ | 350.355 |

TABLE 3-continued
Examples of isoQC inhibitors of formula (I)
| Example | Structure | Formula | Mol Weight |
|---|---|---|---|
| 2 | 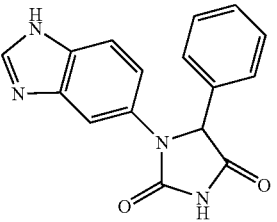 [SMILES: O=C1NC(=O)N(c2ccc3[nH]cnc3c2)C1c1ccccc1] | $C_{16}H_{12}N_4O_2$ | 292.292 |
| 3 | 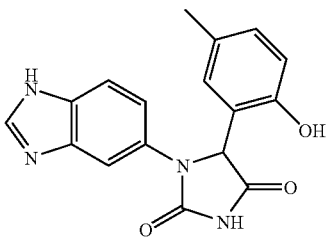 [SMILES: Cc1ccc(O)c(C2C(=O)NC(=O)N2c2ccc3[nH]cnc3c2)c1] | $C_{17}H_{14}N_4O_3$ | 322.318 |
| 4 | 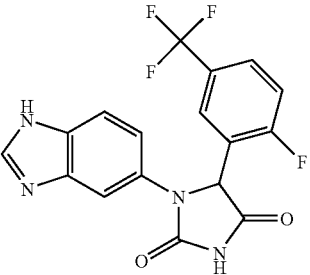 [SMILES: O=C1NC(=O)N(c2ccc3[nH]cnc3c2)C1c1cc(C(F)(F)F)ccc1F] | $C_{17}H_{10}F_4N_4O_2$ | 378.281 |
| 5 | 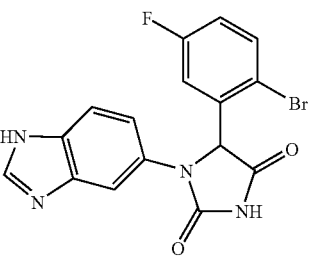 [SMILES: O=C1NC(=O)N(c2ccc3[nH]cnc3c2)C1c1cc(F)ccc1Br] | $C_{16}H_{10}BrFN_4O_2$ | 389.179 |
| 6 | 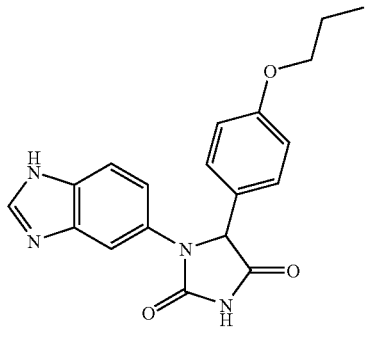 [SMILES: CCCOc1ccc(C2C(=O)NC(=O)N2c2ccc3[nH]cnc3c2)cc1] | $C_{19}H_{18}N_4O_3$ | 350.371 |

TABLE 3-continued

Examples of isoQC inhibitors of formula (I)

| Example | Structure | Formula | Mol Weight |
|---|---|---|---|
| 7 | 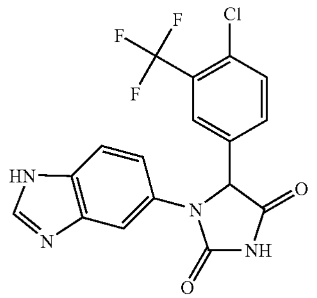 [SMILES: O=C1NC(=O)N(c2ccc3[nH]cnc3c2)C1c1ccc(Cl)c(C(F)(F)F)c1] | $C_{17}H_{10}ClF_3N_4O_2$ | 394.735 |
| 8 | 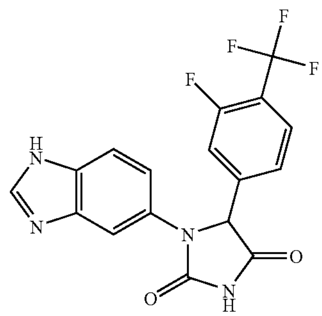 [SMILES: O=C1NC(=O)N(c2ccc3[nH]cnc3c2)C1c1ccc(C(F)(F)F)c(F)c1] | $C_{17}H_{10}F_4N_4O_2$ | 378.281 |
| 9 | 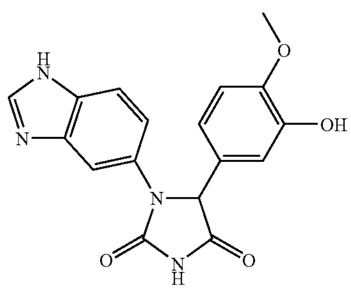 [SMILES: COc1ccc(C2C(=O)NC(=O)N2c2ccc3[nH]cnc3c2)cc1O] | $C_{17}H_{14}N_4O_4$ | 338.317 |
| 10 | 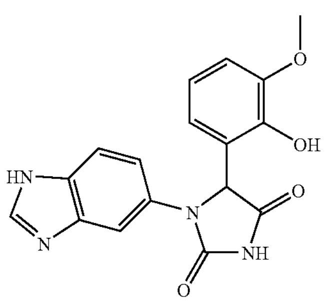 [SMILES: COc1cccc(C2C(=O)NC(=O)N2c2ccc3[nH]cnc3c2)c1O] | $C_{17}H_{14}N_4O_4$ | 338.317 |
| 11 | 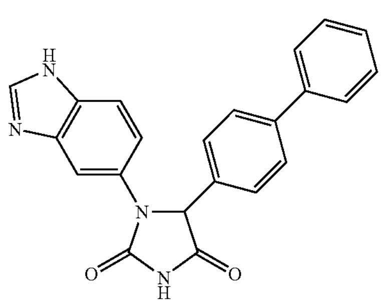 [SMILES: O=C1NC(=O)N(c2ccc3[nH]cnc3c2)C1c1ccc(-c2ccccc2)cc1] | $C_{22}H_{16}N_4O_2$ | 368.388 |

TABLE 3-continued

Examples of isoQC inhibitors of formula (I)

| Example | Structure | Formula | Mol Weight |
|---------|-----------|---------|------------|
| 12 | 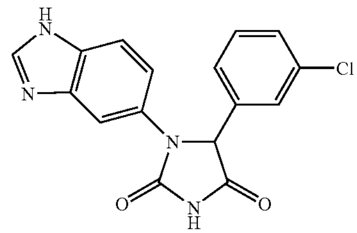 [SMILES: O=C1NC(=O)N(c2ccc3[nH]cnc3c2)C1c1cccc(Cl)c1] | $C_{16}H_{11}ClN_4O_2$ | 326.737 |
| 13 | 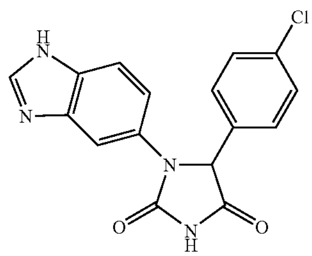 [SMILES: O=C1NC(=O)N(c2ccc3[nH]cnc3c2)C1c1ccc(Cl)cc1] | $C_{16}H_{11}ClN_4O_2$ | 326.737 |
| 14 | 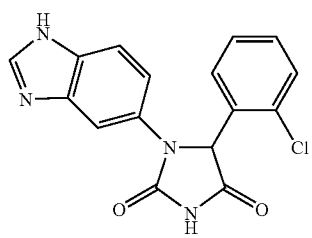 [SMILES: O=C1NC(=O)N(c2ccc3[nH]cnc3c2)C1c1ccccc1Cl] | $C_{16}H_{11}ClN_4O_2$ | 326.737 |
| 15 | 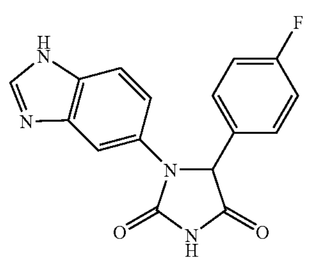 [SMILES: O=C1NC(=O)N(c2ccc3[nH]cnc3c2)C1c1ccc(F)cc1] | $C_{16}H_{11}FN_4O_2$ | 310.283 |
| 16 | 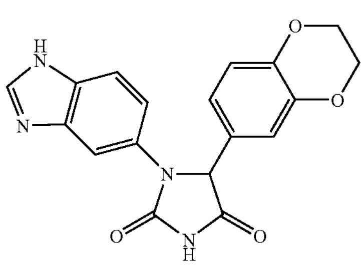 [SMILES: O=C1NC(=O)N(c2ccc3[nH]cnc3c2)C1c1ccc2c(c1)OCCO2] | $C_{18}H_{14}N_4O_4$ | 350.328 |
| 17 | 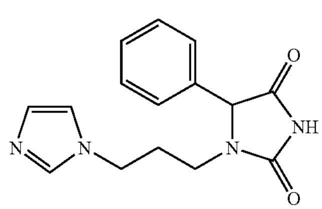 [SMILES: O=C1NC(=O)N(CCCn2ccnc2)C1c1ccccc1] | $C_{15}H_{16}N_4O_2$ | 284.313 |

TABLE 3-continued

Examples of isoQC inhibitors of formula (I)

| Example | Structure | Formula | Mol Weight |
|---|---|---|---|
| 18 | 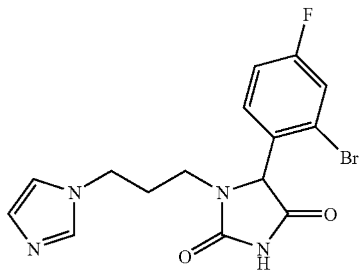 [SMILES: O=C1NC(=O)N(CCCn2ccnc2)C1c1ccc(F)cc1Br] | $C_{15}H_{14}BrFN_4O_2$ | 381.2 |
| 19 | 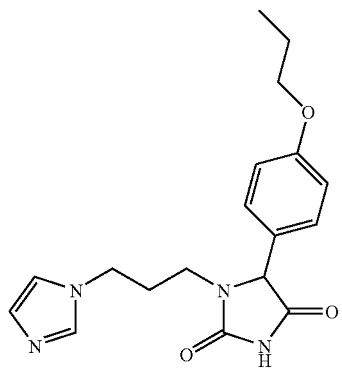 [SMILES: CCCOc1ccc(C2C(=O)NC(=O)N2CCCn2ccnc2)cc1] | $C_{18}H_{22}N_4O_3$ | 342.392 |
| 20 | 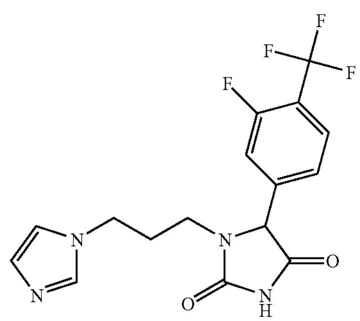 [SMILES: O=C1NC(=O)N(CCCn2ccnc2)C1c1ccc(C(F)(F)F)c(F)c1] | $C_{16}H_{14}F_4N_4O_2$ | 370.302 |
| 21 | 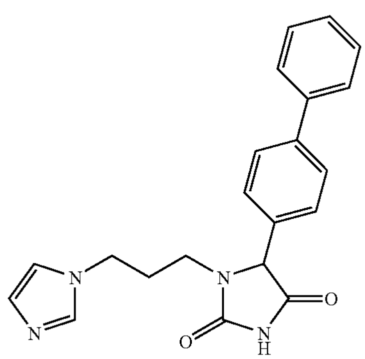 [SMILES: O=C1NC(=O)N(CCCn2ccnc2)C1c1ccc(-c2ccccc2)cc1] | $C_{21}H_{20}N_4O_2$ | 360.409 |
| 22 | 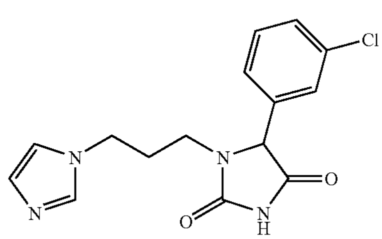 [SMILES: O=C1NC(=O)N(CCCn2ccnc2)C1c1cccc(Cl)c1] | $C_{15}H_{15}ClN4O_2$ | 318.758 |

TABLE 3-continued

Examples of isoQC inhibitors of formula (I)

| Example | Structure | Formula | Mol Weight |
|---------|-----------|---------|------------|
| 23 | 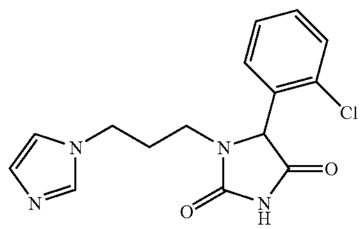 [SMILES: O=C1NC(=O)N(CCCn2ccnc2)C1c1ccccc1Cl] | $C_{15}H_{15}ClN_4O_2$ | 318.758 |
| 24 | 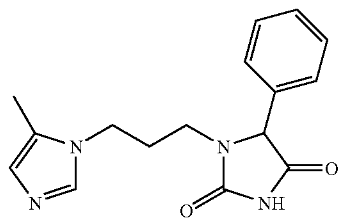 [SMILES: Cc1cncn1CCCN1C(=O)NC(=O)C1c1ccccc1] | $C_{16}H_{18}N_4O_2$ | 298.34 |
| 25 | 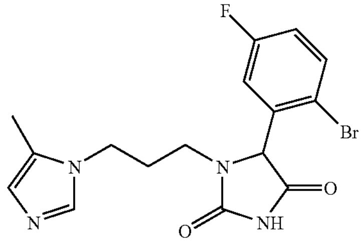 [SMILES: Cc1cncn1CCCN1C(=O)NC(=O)C1c1cc(F)ccc1Br] | $C_{16}H_{16}BrFN_4O_2$ | 395.226 |
| 26 | 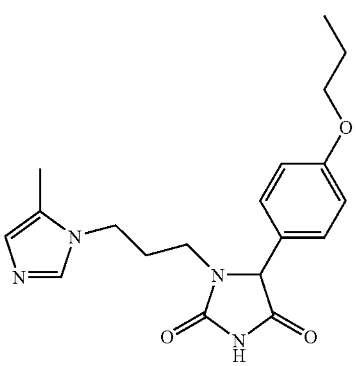 [SMILES: CCCOc1ccc(C2C(=O)NC(=O)N2CCCn2cncc2C)cc1] | $C_{19}H_{24}N_4O_3$ | 356.419 |
| 27 | 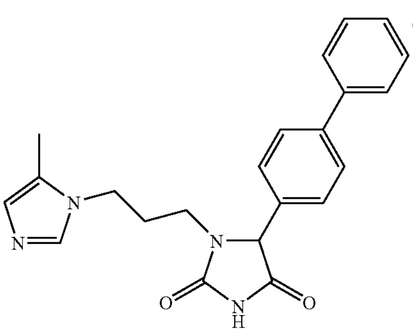 [SMILES: Cc1cncn1CCCN1C(=O)NC(=O)C1c1ccc(-c2ccccc2)cc1] | $C_{22}H_{22}N_4O_2$ | 374.436 |

TABLE 3-continued

Examples of isoQC inhibitors of formula (I)

| Example | Structure | Formula | Mol Weight |
|---------|-----------|---------|------------|
| 28 | 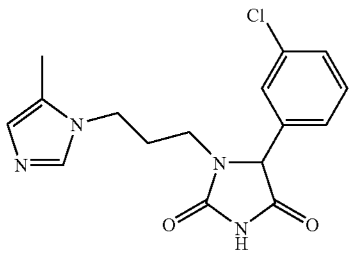 [SMILES: Cc1cncn1CCCN1C(=O)NC(=O)C1c1cccc(Cl)c1] | $C_{16}H_{17}ClN_4O_2$ | 332.785 |
| 29 | 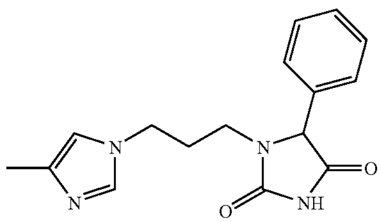 [SMILES: Cc1cn(CCCN2C(=O)NC(=O)C2c2ccccc2)cn1] | $C_{16}H_{18}N_4O_2$ | 298.34 |
| 30 | 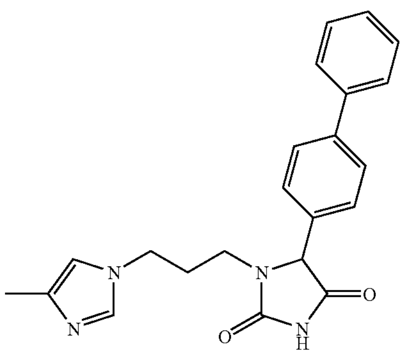 [SMILES: Cc1cn(CCCN2C(=O)NC(=O)C2c2ccc(-c3ccccc3)cc2)cn1] | $C_{22}H_{22}N_4O_2$ | 374.436 |
| 31 | 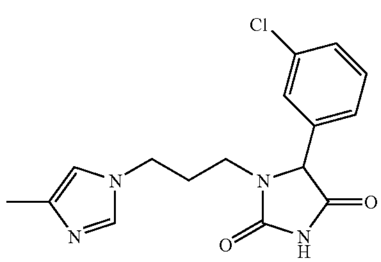 [SMILES: Cc1cn(CCCN2C(=O)NC(=O)C2c2cccc(Cl)c2)cn1] | $C_{16}H_{17}ClN_4O_2$ | 332.785 |
| 32 | 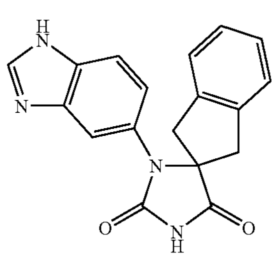 [SMILES: O=C1NC(=O)C2(Cc3ccccc3C2)N1c1ccc2[nH]cnc2c1] | $C_{18}H_{14}N_4O_2$ | 318.329 |

TABLE 3-continued

Examples of isoQC inhibitors of formula (I)

| Example | Structure | Formula | Mol Weight |
|---------|-----------|---------|------------|
| 33 | 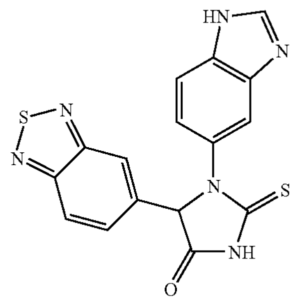 [SMILES: O=C1NC(=S)N(c2ccc3[nH]cnc3c2)C1c1ccc2nsnc2c1] | $C_{16}H_{10}N_6OS_2$ | 366.42 |
| 34 | 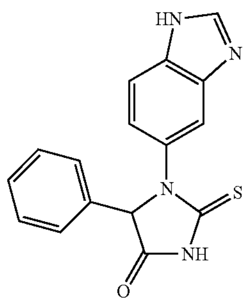 [SMILES: O=C1NC(=S)N(c2ccc3[nH]cnc3c2)C1c1ccccc1] | $C_{16}H_{12}N_4OS$ | 308.358 |
| 35 | 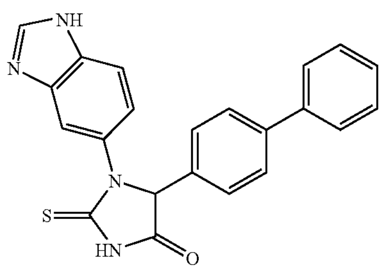 [SMILES: O=C1NC(=S)N(c2ccc3[nH]cnc3c2)C1c1ccc(-c2ccccc2)cc1] | $C_{22}H_{16}N_4OS$ | 384.454 |
| 36 | 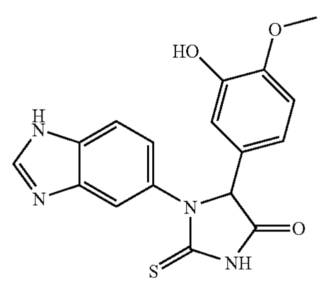 [SMILES: COc1ccc(C2C(=O)NC(=S)N2c2ccc3[nH]cnc3c2)cc1O] | $C_{17}H_{14}N_4O_3S$ | 354.383 |
| 37 | 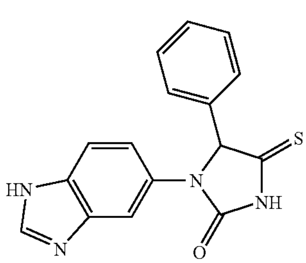 [SMILES: O=C1NC(=S)C(c2ccccc2)N1c1ccc2[nH]cnc2c1] | $C_{16}H_{12}N_4OS$ | 308.358 |

TABLE 3-continued

Examples of isoQC inhibitors of formula (I)

| Example | Structure | Formula | Mol Weight |
|---------|-----------|---------|------------|
| 38 | 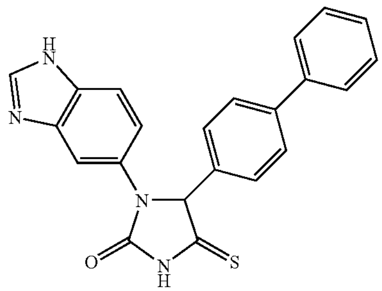 | $C_{22}H_{16}N_4OS$ | 384.454 |
| 39 | 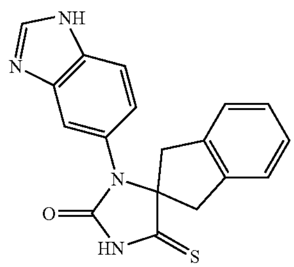 [SMILES: O=C1NC(=S)C2(Cc3ccccc3C2)N1c1ccc2[nH]cnc2c1] | $C_{18}H_{14}N_4OS$ | 334.395 |
| 40 | 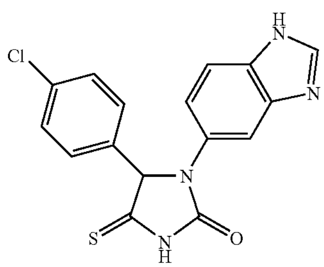 [SMILES: O=C1NC(=S)C(c2ccc(Cl)cc2)N1c1ccc2[nH]cnc2c1] | $C_{16}H_{11}ClN_4OS$ | 342.80 |
| 41 | 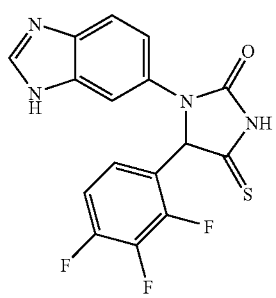 [SMILES: O=C1NC(=S)C(c2ccc(F)c(F)c2F)N1c1ccc2nc[nH]c2c1] | $C_{16}H_9F_3N_4OS$ | 362.32 |
| 42 | 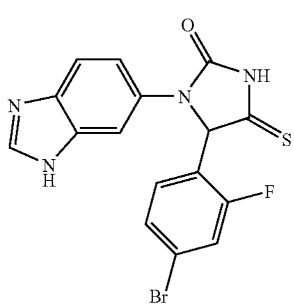 [SMILES: O=C1NC(=S)C(c2ccc(Br)cc2F)N1c1ccc2nc[nH]c2c1] | $C_{16}H_{10}BrFN_4OS$ | 405.24 |

TABLE 3-continued
Examples of isoQC inhibitors of formula (I)
| Example | Structure | Formula | Mol Weight |
|---|---|---|---|
| 43 | 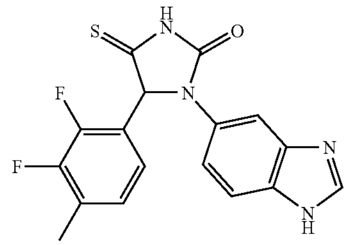 [SMILES: Cc1ccc(C2C(=S)NC(=O)N2c2ccc3[nH]cnc3c2)c(F)c1F] | $C_{17}H_{12}F_2N_4OS$ | 358.36 |
| 44 | 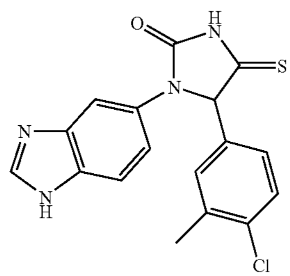 [SMILES: Cc1cc(C2C(=S)NC(=O)N2c2ccc3[nH]cnc3c2)ccc1Cl] | $C_{17}H_{13}ClN_4OS$ | 356.82 |
| 45 | 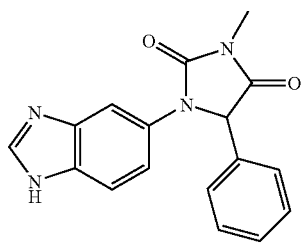 [SMILES: CN1C(=O)C(c2ccccc2)N(c2ccc3[nH]cnc3c2)C1=O] | $C_{17}H_{14}N_4O_2$ | 306.319 |
| 46 | 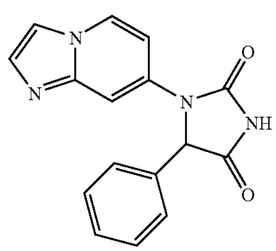 [SMILES: O=C1NC(=O)N(c2ccn3ccnc3c2)C1c1ccccc1] | $C_{16}H_{12}N_4O_2$ | 292.292 |
GENERAL SYNTHESIS DESCRIPTION
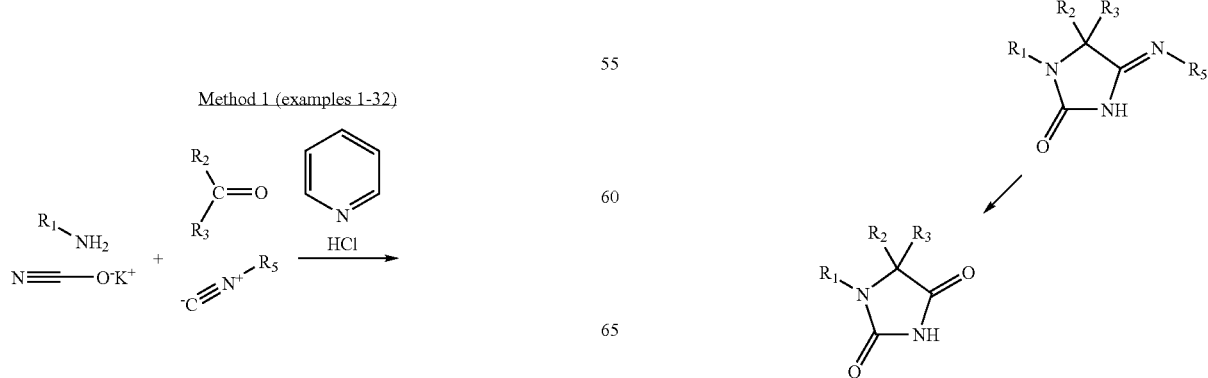

The corresponding amine (1 eq) was dissolved in abs. EtOH (25 ml in case of 0.01 mol starting material). The aldehyde (1 eq) or ketone was added and the mixture was stirred overnight at 25-30° C. (reaction control for completeness of the Schiff-base formation by TLC, eluent: 10% v/v methanole in CHCl$_3$, on Alugram® SIL G Silica-Gel 60, R$_f$ 0.2 mm).

Ethylene glycole (25 ml in case of 0.01 mol starting material) was added and the solution was cooled down to 0-5° C., then the corresponding isonitrile (1 eq), KOCN (1 eq), and pyridiniumchloride (1 eq) were added. The mixture was stirred for 2.5 h at 0-5° C., then overnight at r.t.

After that an aqueous solution of TFA (10% (v/v, 150 ml in case of 0.01 mol starting material) was added and the mixture was stirred overnight at 50-60° C. After that the EtOH and TFA were evaporated and the remaining aqueous solution was subjected to semi-preparative HPLC.

The free base of the product was suspended in water and 1 equivalent of NaOH (aqueous solution) was added. The solution was frozen and subjected to lyophylisation.

Method 3 (Example 37-44)

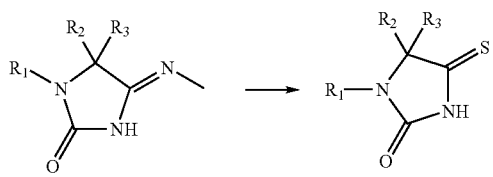

The 4-methylimino-imdazoldine-2-one resulted form the reaction of amine, aldehyde, methyl isonitrile and KOCN as described in Method 1.

1 eq. of the corresponding 4-methylimino-imdazoldine-2-one is dissolved in 1.25 M HCl in methanol (dry, 1 ml for a 0.25 mmol starting material) and 1.5 eq. sodiumsulfide containing solution is added into a sealed microwave vessel. The reaction mixture is heated in a microwave for 20 min at 140° C.

After evaporation of the solvent the crude reaction product is extracted with H$_2$O/EtOAc. The organic phase is dried with Method 2 (Examples 33-36)

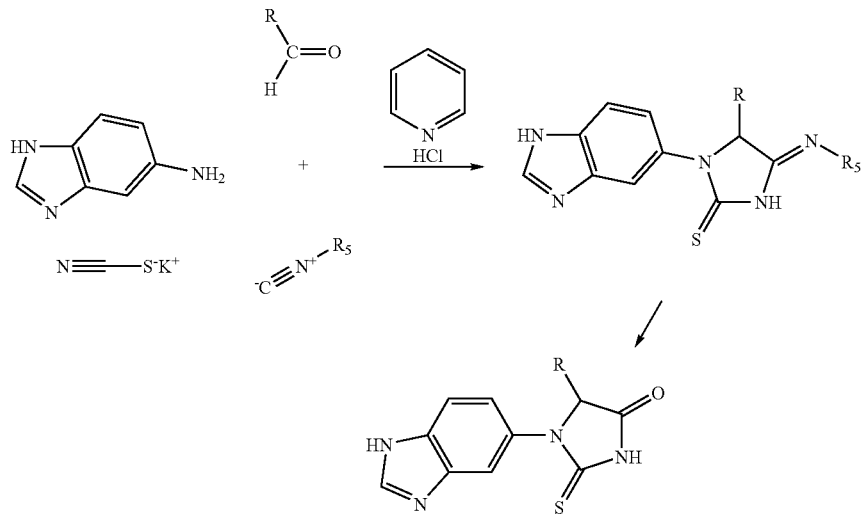

5-Aminobenzimidazole (1 eq) was dissolved in abs. EtOH (25 ml in case of 0.01 mol starting material). The aldehyde (1 eq) was added and the mixture was stirred overnight at 25-30° C. (reaction control for completeness of the Schiff-base formation by TLC, eluent: 10% v/v methanole in CHCl$_3$, on Alugram® SIL G Silica-Gel 60, R$_f$ 0.2 mm).

Ethylene glycole (25 ml in case of 0.01 mol starting material) was added and the solution was cooled down to 0-5° C., then the corresponding isonitrile (1 eq), KSCN (1 eq), and pryridinium-chloride (1 eq) were added. The mixture was stirred for 2.5 h at 0-5° C., then overnight at r.t.

After that an aqueous solution of TFA (10% (v/v), 150 ml in case of 0.01 mol starting material) was added and the mixture was stirred overnight at 50-60° C. After that the EtOH and TFA were evaporated and the remaining aqueous solution was subjected to preparative HPLC.

Na$_2$SO$_4$, filtered and removed. The resulting reaction product is purified by means of semi-preparative HPLC.

Method 4 (Example 45, 46)

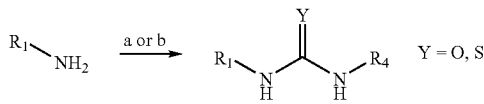

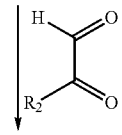

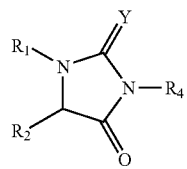

The amine (1 eq) was dissolved in $CH_2Cl_2$ and di-(1H-imidazol-1-yl)methanone (1 eq) was added at 0° C. The mixture was stirred for 4 hours at room temperature. After that 1 eq of the corresponding amine was added (if the hydrochlorides were applied 1 eq of TEA was added additionally). The mixture was then stirred for additional 12 h at r.t. The solvent was removed and the resulting urea was subjected to chromatography.

The urea or thiourea was dissolved in a mixture of HCl/AcOH (1/40 v/v) and the corresponding glyoxal was added. The amount of glyoxal was 1 eq corresponding of the amount of the urea. The mixture was kept under reflux for 4 h. After that the solvent was removed and the resulting product was purified by means of preparative HPLC.

Method 5

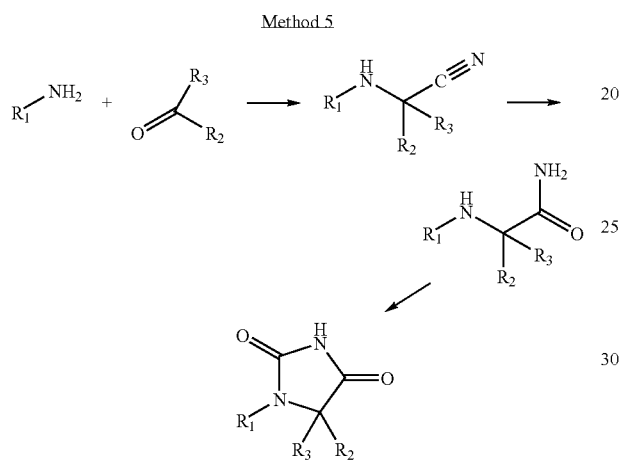

1 equivalent of the aldehyde was dissolved in AcOH (5 ml in case of 4 mmol starting material) and 1.1 equivalents of the amine were added. Into that mixture 1 equivalent of trimethylsilylcyanide (TMSCN) were added. The mixture was stirred for 1.5 h at r.t.

After that, the mixture was poured on ice/ammonia (containing 12 ml of a 25% $NH_3$ solution in case of 4 mmol starting material). The aqueous layer was extracted 3 times by means of $CH_2Cl_2$ the organic phases were combined, dried, filtrated and the solvent was removed. The remains were re-dissolved in concentrated HCl and kept at 40° C. overnight. Water was added and the solution was neutralized by adding NaOH. The aqueous phase was extracted three times by means of $CH_2Cl_2$ whereupon the organic phases were combined and dried.

The solvent was removed and the remaining oil was subjected to either of the following alternative methods:

a) The product was taken up in dry $CHCl_3$ and EtO(CO)Cl and triethylamine were added. The mixture was kept under reflux for 12 h. After that the solvent was removed and the remaining oil was dissolved in dry EtOH, and NaOEt, was added. The solution was kept under reflux for 10 h, or b) The product was dissolved in toluene and carbonyldiimidazole and triethylamine were added. The solution was kept under reflux for 18 h, or c) The product was taken up in formamide and kept at 200° C. for 2 h.

Semi-Preparative HPLC-Method

The system consisted of a Merck-Hitachi device (model LaChrom) equipped with a SP250/21 Luna® 100-7 C18 semi-preparative column (Phenomenex length: 250 mm, diameter: 21 mm). The compounds were purified using a gradient at a flow rate of 6 ml/min; whereby eluent (A) was acetonitrile, eluent (B) was water, both containing 0.1% (v/v) trifluoroacetic acid applying the following gradient: 0 min-40 min. 40-95% (A).

SYNTHESIS OF THE EXAMPLES

Example 1

5-(benzo[c][1,2,5]thiadiazol-6-yl)-1-(1H-benzo[d]imidazol-5-yl)imidazolidine-2,4-dione The compound was synthesized starting from 5-aminobenzimidazole 5.32 g (40 mmol), benzo[c][1,2,5]thiadiazol-6-yl-carbaldehyde 6.56 g (40 mmol), n-butyl isonitrile 4.24 ml (40 mmol) and KOCN 3.28 g (40 mmol) as described in method 1.

Yield: 2.7 g (14.5%); MS m/z 351.1 $(M+H)^+$; $^1$H NMR (DMSO-$D_6$, 400 MHz) δ: 6.19 (s, 1H), 7.67-7.75 (m, 3H), 8.00-8.02 (d, 1H, J=9.13 Hz) 8.08-8.13 (m, 2H), 9.09 (s, 1H), HPLC (λ=214 nm, [A]): rt 8.87 min (96%).

Example 2

1-(1H-benzo[d]imidazol-5-yl)-5-phenylimidazolidine-2,4-dione

The compound was synthesized starting from 5-aminobenzimidazole 1.331 g (10 mmol), benzaldehyde 1.02 ml (10 mmol), benzyl isonitrile 1.22 ml (10 mmol) and KOCN 0.84 g (10 mmol) as described in method 1.

Yield: 1.01 g (34.4%); MS m/z 293.0 $(M+H)^+$; $^1$H NMR: (500 MHz, DMSO-$D_6$) δ: 6.04 (s, 1H), 7.24-7.45 (m, 5H), 7.51 (dd, $^3$J=8.7 Hz, $^4$J=2.1 Hz, 1H), 7.63 (d, $^3$J=8.8 Hz, 1H), 7.87 (d, $^4$J=2.0 Hz, 1H), 8.14 (br. s, 1H), 8.95 (s, 1H), 11.45 (s, 1H), HPLC (λ=214 nm, [A]): rt 8.34 min (100%).

Example 3

1-(1H-benzo[d]imidazol-5-yl)-5-(2-hydroxy-5-methylphenyl)imidazolidine-2,4-dione The compound was synthesized starting from 5-aminobenzimidazole 0.4 g (3.0 mmol), 2-hydroxy-5-methylphenyl carbaldehyde 0.409 g (3.0 mmol), n-butyl isonitrile 0.316 ml (3.0 mmol) and KOCN 0.244 g (0.2 mmol) as described in method 1.

Yield: 0.188 g (19%); MS m/z 323.2 $(M+H)^+$; ($^1$H NMR: DMSO-$D_6$, 400 MHz) δ: 2.06-2.11 (s, 3H), 5.89-6.01 (s, 1H), 6.56-6.67 (d, 1H, $^3$J=7.88 Hz), 6.83-6.90 (m, 1H), 7.01-7.10 (s, 1H), 7.49-7.54 (d, 1H, $^3$J=8.71 Hz), 7.64-7.68 (d, 1H, $^3$J=8.71 Hz), 7.82-7.85 (s, 1H), 9.09-9.13 (s, 1H), 9.68-9.73, (s, 1H), 11.27-11.31, (s, 1H); HPLC (λ=214 nm, [A]): rt 8.23 min (98%).

Example 4

1-(1H-benzo[d]imidazol-5-yl)-5-(2-fluoro-5-(trifluoromethyl)phenyl)imidazolidine-2,4-dione The compound was synthesized starting from 5-aminobenzimidazole 0.213 g (1.6 mmol), 2-fluoro-5-(trifluoromethyl) phenyl carbaldehyde 0.362 ml (1.6 mmol), n-butyl isonitrile 0.169 ml (1.6 mmol), pyridiniumchloride 0.185 g (1.6 mmol) and KOCN 0.13 g (1.6 mmol) as described in method 1.

Yield: 0.172 g (28%); MS m/z 379.3 (M+H)+; 1H NMR: (400 MHz, CD3OD) δ: 6.23 (s, 1H, CH—N), 7.33-7.36 (m, 1H), 7.63-7.65 (m, 1H), 7.67-7.72 (m, 1H), 7.73-7.76 (m, 1H), 7.81-7.84 (m, 1H), 7.95-7.96 (m, 1H), 9.16 (s, 1H), HPLC (λ=214 nm, [A]): rt 10.24 min (100%).

Example 5

1-(1H-benzo[d]imidazol-5-yl)-5-(2-bromo-5-fluorophenyl)imidazolidine-2,4-dione

The compound was synthesized starting from 5-aminobenzimidazole 0.213 g (1.6 mmol), 2-bromo-5-fluorophenyl carbaldehyde 0.325 (1.6 mmol), n-butyl isonitrile 0.169 ml (1.6 mmol), pyridiniumchloride 0.185 g (1.6 mmol) and KOCN 0.13 g (1.6 mmol) as described in method 1.

Yield: 0.047 g (7.5%); MS m/z 391.1 (M+H)+ 389.1 (M+H isotope)+; 1H NMR: (DMSO D6, 400 MHz) δ: 6.21-6.35 (s, 0.3H), 6.35-6.44 (s, 0.7H), 7.10-7.17 (m, 1H), 7.36-7.67 (m, 2H), 7.67-7.76 (m, 2H), 7.80-7.85 (s, 1H), 9.10-9.15 (s, 1H), 11.54-11.63 (s, 0.7H, amide), 11.65-11.82 (s, 0.3H, amide) HPLC (λ=214 nm, [A]): rt 9.80 min (99%).

Example 6

1-(1H-benzo[d]imidazol-5-yl)-5-(4-propoxyphenyl)imidazolidine-2,4-dione

The compound was synthesized starting from 5-aminobenzimidazole 0.213 g (1.6 mmol), 4-propoxyphenyl carbaldehyde 0.253 ml (1.6 mmol), n-butyl isonitrile 0.169 ml (1.6 mmol), pyridiniumchloride 0.185 g (1.6 mmol) and KOCN 0.13 g (1.6 mmol) as described in method 1.

Yield: 0.285 g (50%); MS m/z 351.2 (M+H)+; 1H NMR: (400 MHz, CD3OD) δ: 0.94-0.98 (t, 3H), 1.66-1.75 (m, 2H), 3.81-3.85 (m, 2H), 5.81 (s, 1H), 6.81-6.86 (m, 2H), 7.25-7.28 (m, 2H), 7.68-7.69 (d, 1H), 8.01 (s, 1H), 9.18 (s, 1H), HPLC (λ=214 nm, [A]): rt 10.71 min (100%).

Example 7

1-(1H-benzo[d]imidazol-5-yl)-5-(4-chloro-3-(trifluoromethyl)phenyl)imidazolidine-2,4-dione The compound was synthesized starting from 5-aminobenzimidazole 0.213 g (1.6 mmol), 4-chloro-3-(trifluoromethyl)phenyl carbaldehyde 0.23 ml (1.6 mmol), n-butyl isonitrile 0.169 ml (1.6 mmol), pyridiniumchloride 0.185 g (1.6 mmol) and KOCN 0.13 g (1.6 mmol) as described in method 1.

Yield: 0.242 g (38%); MS m/z 395.1 (M+H)+; 1H NMR: (400 MHz, CD3OD) δ: 6.09 (s, 1H), 7.56-7.78 (m, 5H), 7.51 (d, 1H), 8.06 (d, 1H), 9.107 (d, 1H), HPLC (λ=214 nm, [A]): rt 11.82 min (99%).

Example 8

1-(1H-benzo[d]imidazol-5-yl)-5-(3-fluoro-4-(trifluoromethyl)phenyl)imidazolidine-2,4-dione The compound was synthesized starting from 5-aminobenzimidazole 0.133 g (1 mmol), 3-fluoro-4-(trifluoromethyl)phenyl carbaldehyde 0.192 g (1 mmol), n-butyl isonitrile 0.083 g (1 mmol), pyridiniumchloride 0.185 g (1.6 mmol) and KOCN 0.081 g (1 mmol) as described in method 1.

Yield: 0.151 g (40%); MS m/z 379.2 (M+H)30

Example 9

1-(1H-benzo[d]imidazol-5-yl)-5-(3-hydroxy-4-methoxyphenyl)imidazolidine-2,4-dione The compound was synthesized starting from 5-aminobenzimidazole 0.213 g (1.6 mmol), 3-hydroxy-4-methoxyphenyl carbaldehyde 0.244 g (1.6 mmol), n-butyl isonitrile n-butyl isonitrile 0.169 ml (1.6 mmol), pyridiniumchloride 0.185 g (1.6 mmol) and KOCN 0.13 g (1.6 mmol) as described in method 1.

Yield: 0.107 g (19%); MS m/z 339.2 (M+H)+; 1H NMR: (CD3OD, 400 MHz) δ: 3.73-3.80 (s, 3H), 5.71-5.77 (s, 1H), 6.77-6.92 (m, 3H), 7.68-7.75 (m, 2H), 8.00-8.05 (s, 1H), 9.16-9.22 (s, 1H), HPLC (λ=214 nm, [A]): rt 6.09 min (98%).

Example 10

1-(1H-benzo[d]imidazol-5-yl)-5-(2-hydroxy-3-methoxyphenyl)imidazolidine-2,4-dione The compound was synthesized starting from 5-aminobenzimidazole 0.133 g (1 mmol), 2-hydroxy-3-methoxypheny carbaldehyde 0.153 g (1 mmol), n-butyl isonitrile 0.106 ml (1 mmol) and KOCN 0.082 g (1 mmol) as described in method 1.

Yield: 0.050 g (14%); MS m/z 339.2 (M+H)+ 1H NMR: (400 MHz, CD3OD) δ: 3.77 (s, 3H), 5.98 (s, 1H), 6.69-7.73 (m, 1H), 6.82-6.85 (m, 2H), 7.68-7.69 (m, 2H), 7.95 (s, 1H), 9.18 (s, 1H), HPLC (λ=214 nm, [A]): rt 6.60 min (98%).

Example 11

1-(1H-benzimidazol-5-yl)-5-(1,1'-biphenyl-4-yl)imidazolidine-2,4-dione

The compound was synthesized starting from 5-aminobenzimidazole 0.133 g (1 mmol), 1,1'-biphenyl-4-yl carbaldehyde 0.183 (1 mmol), n-butyl isonitrile n-butyl isonitrile 0.106 ml (1 mmol) and KOCN 0.082 g (1 mmol) as described in method 1.

Yield: 0.117 g (31%); MS m/z 369.0 (M+H)+; 1H NMR: (400 MHz, CD3OD): 5.96 (s, 1H), 7.30-7.31 (m, 0.3H), 7.31-7.32 (m, 0.3H), 7.36-7.37 (m, 0.5H), 7.38-7.39 (m, 1H), 7.39-7.41 (m, 0.5H), 7.45-7.48 (m, 2H), 7.51-7.54 (m, 2H), 7.58-7.62 (m, 2H), 7.71-7.76 (m, 2.4H), 8.07-8.08 (m, 1H), 9.14 (s, 1H), HPLC (λ=214 nm, [A]): rt 12.41 min (98%).

Example 12

1-(1H-benzo[d]imidazol-5-yl)-5-(3-chlorophenyl)imidazolidine-2,4-dione

The compound was synthesized starting from 5-aminobenzimidazole 2.13 g (16 mmol), 3-chlorobenzaldehyde 2.24 g (16 mmol), n-butyl isonitrile 1.69 ml (16 mmol), KOCN 1.3 g (16 mmol) and pyridiniumchloride 1.85 g (16 mmol) as described in method 1.

Yield: 2.0 g (38%); MS m/z 327.2 (M+H)+; 1H-NMR: (500 MHz, DMSO-D6) δ: 6.08 (s, 1H), 7.32 (m, 3H), 7.49 (s, 1H), 7.52-7.55 (m, 1H), 7.66-7.68 (m, 1H), 7.90 (s, 1H), 9.10 (s, 1H), 11.53 (s, 1H), HPLC (λ=214 nm, [A]): rt 9.76 min (100%).

Example 13

1-(1H-benzo[d]imidazol-5-yl)-5-(4-chlorophenyl)imidazolidine-2,4-dione

The compound was synthesized starting from 5-aminobenzimidazole 0.213 g (1.6 mmol), 4-chlorobenzaldehyde 0.224 g (1.6 mmol), n-butyl isonitrile 0.169 ml (1.6 mmol) pyridiniumchloride 0.185 g (1.6 mmol) and KOCN 0.130 g (1.6 mmol) as described in method 1.

Yield: 0.327 g (62%); MS m/z 327.2 (M+H)$^+$; $^1$H NMR: $^1$H-NMR (400 MHz, CD$_3$OD) δ: 5.93 (s, 1H), 7.32-7.39 (m, 4H), 7.67-7.73 (m, 2H), 8.04 (s, 1H), 9.21 (s, 1H), HPLC (λ=214 nm, [A]): rt 8.43 min (99%).

Example 14

1-(1H-benzo[d]imidazol-5-yl)-5-(2-chlorophenyl)imidazolidine-2,4-dione

The compound was synthesized starting from 5-aminobenzimidazole 0.213 g (1.6 mmol), 2-chlorobenzaldehyde 0.225 mg (1.6 mmol), n-butyl isonitrile 0.169 ml (1.6 mmol) pyridiniumchloride 0.185 g (1.6 mmol) and KOCN 0.130 g (1.6 mmol) as described in method 1.

Yield: 0.260 g (50%); MS m/z 327.2 (M+H)$^+$; $^1$H NMR: (400 MHz, CD$_3$OD): 5.93 (s, 1H), 7.32-7.40 (m, 4H), 7.67-7.73 (m, 2H), 8.04-8.05 (m, 1H), 9.20 (s, 1H), HPLC (λ=214 nm, [A]): rt 9.33 min (97%).

Example 15

1-(1H-benzo[d]imidazol-5-yl)-5-(4-fluorophenyl)imidazolidine-2,4-dione

The compound was synthesized starting from 5-aminobenzimidazole 0.134 g (1 mmol), 4-fluorobenzaldehyde 0.125 g (1 mmol), n-butyl isonitrile 0.106 ml (1 mmol), pyridiniumchloride 0.116 g (1 mmol) and KOCN 0.082 g (1 mmol) as described in method 1.

Yield: 0.332 g (100%); MS m/z 311.1 (M+H)$^+$; $^1$H NMR: (400 MHz, CD$_3$OD) δ: 5.91 (s, 1H, CH—N), 7.02-7.08 (m, 2H), 7.38-7.43 (m, 2H), 7.67-7.72 (m, 2H), 8.04 (s, 1H), 9.22 (s, 1H), HPLC (λ=214 nm, [A]): rt 9.20 min (97%).

Example 16

1-(1H-benzo[d]imidazol-5-yl)-5-(2,3-dihydrobenzo[b][1,4]dioxin-7-yl)imidazolidine-2,4-dione The compound was synthesized starting from 5-aminobenzimidazole 0.134 g (1 mmol), 2,3-dihydrobenzo[b][1,4]dioxin-7-yl carbaldehyde 0.165 g (1 mmol), n-butyl isonitrile 0.106 ml (1 mmol), pyridiniumchloride 0.116 g (1 mmol) and KOCN 0.082 g (1 mmol) as described in method 1.

Yield: 0.185 g (52%); MS m/z 351.0 (M+H)$^+$; $^1$H NMR: (400 MHz, CD$_3$OD) δ: 4.16 (s, 4H), 5.76 (s, 1H), 6.77-6.84 (m, 3H), 7.71 (m, 2H), 8.03 (s, 1H), 9.19 (s, 1H), HPLC (λ=214 nm, [A]): rt 8.37 min (100%).

Example 17

1-(3-(1H-imidazol-1-yl)propyl)-5-phenylimidazolidine-2,4-dione

The compound was synthesized starting from 3-(1H-imidazol-1-yl)propylamine 1.0 g (7.98 mmol), benzaldehyde 0.807 ml (7.98 mmol), benzylisonitrile 0.972 ml (7.98 mmol), pyidiniumchloride 0.920 and KOCN 0.648 g (7.98 mmol) as described in method 1.

Yield: 0.557 g (25%); MS m/z 285.4 (M+H)$^+$; $^1$H NMR: (400 MHz, CD$_3$OD) δ: 1.84-2.08 (m, 2H), 2.90-3.01 (m, 1H), 3.45-3.54 (m, 1H), 4.15-4.28 (m, 2H), 5.14 (s, 1H), 7.29-7.37 (m, 2H), 7.39-7.45 (m, 3H), 7.51 (s, 1H), 7.58 (s, 1H), 8.85 (s, 1H); HPLC (λ=214 nm, [A]): rt 6.64 min (100%).

Example 18

1-(3-(1H-imidazol-1-yl)propyl)-5-(2-bromo-4-fluorophenyl)imidazolidine-2,4-dione The compound was synthesized starting from 3-(1H-imidazol-1-yl)propylamine 0.358 ml (3 mmol), 2-bromo 4-fluorobenzaldehyde 0.610 g (3 mmol), benzylisonitrile 0.365 ml (3 mmol), pyridiniumchloride 0.347 g (3 mmol) and KOCN 0.243 g (3 mmol) as described in method 1.

Yield: 0.057 g (4.9%); MS m/z 381.2 (M+H)$^+$; $^1$H NMR: (400 MHz, CD$_3$OD) δ: 1.84-2.08 (m, 2H), 2.90-3.01 (m, 1H), 3.45-3.54 (m, 1H), 4.15-4.28 (m, 2H), 6.89-7.37 (m, 2H), 7.51 (s, 1H), 7.69 (s, 1H), 7.58 (s, 1H), 8.85 (s, 1H), HPLC (λ=214 nm, [A]): rt 8.08 min (99%).

Example 19

1-(3-(1H-imidazol-1-yl)propyl)-5-(4-propoxyphenyl)imidazolidine-2,4-dione

The compound was synthesized starting from 3-(1H-imidazol-1-yl)propylamine 0.358 ml (3 mmol), 4-propoxyphenyl carbaldehyde 0.492 g (3 mmol), n-butyl isonitrile 0.315 ml (3 mmol), pyridiniumchloride 0.347 g (3 mmol) and KOCN 0.243 g (3 mmol) as described in method 1.

Yield: 0.065 g (6.3%); MS m/z 342.9 (M+H)$^+$; $^1$H NMR: (400 MHz, CD$_3$OD) δ: 0.99-1.03 (m, 3H), 1.74-1.79 (m, 2H), 1.84-2.08 (m, 2H), 2.90-3.01 (m, 1H), 3.45-3.54 (m, 1H), 3.90-3.93 (m, 2H), 4.15-4.28 (m, 2H), 5.06 (s, 1H), 6.94-6.96 (m, 2H), 7.18-7.20 (m, 2H), 7.51 (s, 1H), 7.58 (s, 1H), 8.85 (s, 1H), HPLC (λ=214 nm, [A]): rt 10.35 min (98%).

Example 20

1-(3-(1H-imidazol-1-yl)propyl)-5-(3-fluoro-4-(trifluoromethyl)phenyl)imidazolidine-2,4-dione The compound was synthesized starting from 3-(1H-imidazol-1-yl)propylamine 0.358 ml (3 mmol), 3-fluoro-4-(trifluoromethyl)phenyl carbaldehyde 0.576 g (3 mmol), n-butyl isonitrile 0.315 ml (3 mmol), pyridiniumchloride 0.347 g (3 mmol) and KOCN 0.243 g (3 mmol) as described in method 1.

Yield: 0.017 g (1.5%); MS m/z 371.1 (M+H)$^+$; $^1$H NMR: (400 MHz, CD$_3$OD) δ: 1.84-2.08 (m, 2H), 2.90-3.01 (m, 1H), 3.45-3.54 (m, 1H), 4.15-4.28 (m, 2H), 5.31 (s, 1H), 7.34-7.40 (m, 2H), 7.51 (s, 1H), 7.58 (s, 1H), 7.66-7.67 (m, 1H), 8.85 (s, 1H), HPLC (λ=214 nm, [A]): rt 10.96 min (95%).

Example 21

1-[3-(1H-imidazol-1-yl)propyl]-5-(4-biphenyl)imidazolidine-2,4-dione

The compound was synthesized starting from 3-(1H-imidazol-1-yl)propylamine 0.358 ml (3 mmol), 4-phenylbenzaldehyde 0.546 g (3 mmol), n-butyl isonitrile 0.315 ml (3 mmol), pyridiniumchloride 0.347 g (3 mmol) and KOCN 0.243 g (3 mmol) as described in method 1.

Yield: 0.23 g (21%); MS m/z 361.2 (M+H)⁺; ¹H NMR: (400 MHz, CD₃OD) δ: 1.84-2.08 (m, 2H), 2.90-3.01 (m, 1H), 3.45-3.54 (m, 1H), 4.15-4.28 (m, 2H), 5.31 (s, 1H), 7.31-7.44 (m, 5H), 7.53 (s, 1H), 7.59-7.61 (m, 3H), 7.67-7.69 (m, 2H), 8.85 (s, 1H), HPLC (λ=214 nm, [A]): rt 11.65 min (100%).

Example 22

1-(3-(1H-imidazol-1-yl)propyl)-5-(3-chlorophenyl)imidazolidine-2,4-dione

The compound was synthesized starting from 3-(1H-imidazol-1-yl)propylamine 0.358 ml (3 mmol), 3-chlorophenyl carbaldehyde 0.42 g (3 mmol), n-butyl isonitrile 0.315 ml (3 mmol), pyridiniumchloride 0.347 g (3 mmol) and KOCN 0.243 g (3 mmol) as described in method 1.

Yield: 0.220 g (23%); MS m/z 319.1 (M+H)⁺; ¹H NMR: (400 MHz, CD₃OD) δ: 1.84-2.08 (m, 2H), 2.90-3.01 (m, 1H), 3.45-3.54 (m, 1H), 4.15-4.28 (m, 2H), 5.16 (s, 1H), 7.23-7.26 (m, 1H), 7.35 (s, 1H), 7.41-7.42 (m, 2H) 7.54 (s, 1H), 7.62-7.63 (m, 1H), 8.90 (s, 1H), HPLC (λ=214 nm, [A]): rt 8.53 min (99%).

Example 23

1-(3-(1H-imidazol-1-yl)propyl)-5-(2-chlorophenyl)imidazolidine-2,4-dione

The compound was synthesized starting from 3-(1H-imidazol-1-y)propylamine 0.358 ml (3 mmol), 2-chlorobenzaldehyde 0.420 g (3 mmol), n-butyl isonitrile 0.315 ml (3 mmol) pyridiniumchloride 0.347 g (3 mmol) and KOCN 0.243 g (3 mmol) as described in method 1.

Yield: 0.15 g (15%); MS m/z 351.0 (M+H)⁺; ¹H NMR: (400 MHz, CD₃OD) δ: 1.84-2.08 (m, 2H), 2.90-3.01 (m, 1H), 3.45-3.54 (m, 1H), 4.15-4.28 (m, 2H), 5.31 (s, 1H), 7.39-7.49 (m, 4H), 7.53 (s, 1H) 7.60 (s, 1H), 8.89 (s, 1H) HPLC (λ=214 nm, [A]): rt 7.31 min (94%).

Example 24

1-(3-(5-methyl-1H-imidazol-1-yl)propyl)-5-phenylimidazolidine-2,4-dione

The compound was synthesized starting from (3-(5-methyl-1H-imidazol-1-yl)propyl)amine 0.278 g (2 mmol), benzaldehyde 0.202 ml (2 mmol), benzylisonitrile 0.245 ml (2 mmol) pyridiniumchloride 0.231 g (2 mmol) and KOCN 0.165 g (2 mmol) as described in method 1.

Yield: 0.095 g (15%); MS m/z 299.3 (M+H)⁺; ¹H NMR: (400 MHz, CD₃OD) δ: 1.87-1.99 (m, 2H), 2.29 (s, 3H), 3.02-3.09 (m, 1H), 3.50-3.57 (m, 1H), 4.08-4.18 (m, 2H), 5.15 (s, 1H), 7.28 (s, 1H), 7.31-7.33 (m, 2H), 7.39-7.44 (m, 3H), 8.82 (s, 1H) HPLC (λ=214 nm, [A]): rt 7.20 min (98%).

Example 25

5-(2-bromo-5-fluorophenyl)-1-(3-(5-methyl-1H-imidazol-1-yl)propyl)imidazolidine-2,4-dione The compound was synthesized starting from (3-(5-methyl-1H-imidazol-1-yl)propyl)amine 0.278 g (2 mmol), 2-bromo-5-fluorophenyl carbaldehyde 0.406 g (2 mmol), benzylisonitrile 0.245 ml (2 mmol) pyridiniumchloride 0.231 g (2 mmol) and KOCN 0.165 g (2 mmol) as described in method 1.

Yield: 0.015 g (1.8%); MS m/z 395.2 (M+H)⁺; 397.2 (M+H, isotope)⁺ ¹H NMR: (400 MHz, CD₃OD) δ: 1.87-1.99 (m, 2H), 2.29 (s, 3H), 3.02-3.09 (m, 1H), 3.50-3.57 (m, 1H), 4.08-4.18 (m, 2H), 5.31 (s, 0.5H), 5.76 (s, 0.5H), 7.01-7.16 (m, 1H), 7.29 (s, 1H), 7.43 (s, 1H), 7.71 (m, 1H), 8.86 (s, 1H) HPLC (λ=214 nm, [A]): rt 8.80 min (100%).

Example 26

1-(3-(5-methyl-1H-imidazol-1-yl)propyl)-5-(4-propoxyphenyl)imidazolidine-2,4-dione The compound was synthesized starting from (3-(5-methyl-1H-imidazol-1-yl)propyl)amine 0.278 g (2 mmol), 4-propoxyphenyl carbaldehyde 0.316 ml (2 mmol), benzylisonitrile 0.245 ml (2 mmol), pyridiniumchloride 0.231 g (2 mmol) and KOCN 0.165 g (2 mmol) as described in method 1.

Yield: 0.08 g (11%); MS m/z 357.3 (M+H)⁺; ¹H NMR: (400 MHz, CD₃OD) δ: 1.01-1.05 (m, 3H), 1.77-1.81 (m, 2H), 1.86-1.96 (m, 2H), 2.29 (s, 3H), 3.02-3.09 (m, 1H), 3.45-3.51 (m, 1H), 3.92-3.95 (m, 2H), 4.10-4.15 (m, 2H), 5.08 (s, 1H), 6.96-6.98 (m, 2H), 7.21-7.32 (m, 2H), 7.28 (s, 1H), 8.83 (s, 1H), HPLC (λ=214 nm, [A]): rt 10.85 min (96%).

Example 27

1-[3-(5-methyl-1H-imidazol-1-yl)propyl]-5-(4-phenylphenyl)imidazolidine-2,4-dione The compound was synthesized starting from (3-(5-methyl-1H-imidazol-1-yl)propyl)amine 0.278 g (2 mmol), 4-phenylbenzaldehyde 0.364 g (2 mmol), benzylisonitrile 0.245 ml (2 mmol) pyridiniumchloride 0.231 g (2 mmol) and KOCN 0.165 g (2 mmol) as described in method 1.

Yield: 0.115 g (15%); MS m/z 375.2 (M+H)⁺; ¹H NMR: (400 MHz, CD₃OD) δ: 1.87-1.99 (m, 2H), 2.29 (s, 3H), 3.02-3.09 (m, 1H), 3.50-3.57 (m, 1H), 4.08-4.18 (m, 2H), 5.15 (s, 1H), 7.28 (s, 1H), 7.33-7.46 (m, 5H), 7.60-7.63 (m, 2H), 7.69-7.72 (m, 2H), 8.85 (s, 1H), HPLC (λ=214 nm, [A]): rt 12.11 min (97%).

Example 28

5-(3-chlorophenyl)-1-(3-(5-methyl-1H-imidazol-1-yl)propyl)imidazolidine-2,4-dione The compound was synthesized starting from (3-(5-methyl-1H-imidazol-1-yl)propyl)amine 0.278 g (2 mmol), 3-chlorophenyl carbaldehyde 0.226 ml (2 mmol), benzylisonitrile 0.245 ml (2 mmol) pyridiniumchloride 0.231 g (2 mmol) and KOCN 0.165 g (2 mmol) as described in method 1.

Yield: 0.113 g (17.2%); MS m/z 333.0 (M+H)⁺; ¹H NMR: (400 MHz, CD₃OD) δ: 1.87-1.99 (m, 2H), 2.29 (s, 3H), 3.02-3.09 (m, 1H), 3.50-3.57 (m, 1H), 4.08-4.18 (m, 2H), 5.15 (s, 1H), 7.28-7.29 (m, 1H), 7.38 (s, 1H), 7.42-7.46 (m, 2H), 8.84 (s, 1H), HPLC (λ=214 nm, [A]): rt 8.96 min (96%).

Example 29

1-(3-(4-methyl-1H-imidazol-1-yl)propyl)-5-phenylimidazolidine-2,4-dione

The compound was synthesized starting from 3-(4-methyl-1H-imidazol-1-yl)propyl amine 0.250 g (1.8 mmol), benzaldehyde 0.182 ml (1.8 mmol), benzylisonitrile 0.220 ml (1.8 mmol) pyridiniumchloride 0.210 g (1.8 mmol) and KOCN 0.150 g (1.8 mmol) as described in method 1.

Yield: 0.065 g (12%); MS m/z 299.2 (M+H)$^+$; $^1$H NMR: (400 MHz, CD$_3$OD) δ: 1.84-1.91 (m, 1H), 1.97-2.04 (m, 1H), 2.30 (s, 3H), 2.93-2.99 (m, 1H), 3.47-3.59 (m, 1H), 4.09-4.18 (m, 2H), 5.15 (s, 1H), 7.27 (s, 1H), 7.27-7.38 (m, 3H), 7.40-7.45 (m, 2H), 8.71 (s, 1H), HPLC (λ=214 nm, [A]): rt 6.93 min (99%).

Example 30

1-[3-(4-methyl-1H-imidazol-1-yl)propyl]-5-(4-biphenyl)imidazolidine-2,4-dione

The compound was synthesized starting from 3-(4-methyl-1H-imidazol-1-yl)propyl amine 0.250 g (1.8 mmol), 4-phenyl-benzaldehyde 0.220 g (1.8 mmol), benzylisonitrile 0.220 ml (1.8 mmol), pyridiniumchloride 0.210 g (1.8 mmol) and KOCN 0.150 g (1.8 mmol) as described in method 1.

Yield: 0.135 g (19.9%); MS m/z 375.1 (M+H)$^+$; $^1$H NMR: (400 MHz, CD$_3$OD) δ: 1.84-1.91 (m, 1H), 1.97-2.04 (m, 1H), 2.30 (s, 3H), 2.93-2.99 (m, 1H), 3.47-3.59 (m, 1H), 4.09-4.18 (m, 2H), 5.15 (s, 1H), 7.27 (s, 1H), 7.33-7.46 (m, 5H), 7.61-7.63 (m 2H), 7.69-7.71 (m 2H), 8.75 (s, 1H), HPLC (λ=214 nm, [A]): rt 11.55 min (98%).

Example 31

5-(3-chlorophenyl)-1-(3-(4-methyl-1H-imidazol-1-yl)propyl)imidazolidine-2,4-dione The compound was synthesized starting from 3-(4-methyl-1H-imidazol-1-yl)propyl amine 0.250 g (1.8 mmol), 3-chlorophenyl carbaldehyde 0.204 ml (1.8 mmol), benzylisonitrile 0.220 ml (1.8 mmol) pyridiniumchloride 0.210 g (1.8 mmol) and KOCN 0.150 g (1.8 mmol) as described in method 1.

Yield: 0.10 g (17%); MS m/z 333.0 (M+H)$^+$; $^1$H NMR: (400 MHz, CD$_3$OD) δ: 1.84-1.91 (m, 1H), 1.97-2.04 (m, 1H), 2.30 (s, 3H), 2.93-2.99 (m, 1H), 3.47-3.59 (m, 1H), 4.09-4.18 (m, 2H), 5.15 (s, 1H), 7.24-7.28 (m, 1H), 7.31 (s, 1H), 7.37 (s, 1H), 7.42-7.46 (m, 2H), 8.75 (s, 1H), HPLC (λ=214 nm, [A]): rt 8.64 min (92%).

Example 32

3-(1H-benzimidazol-5-yl)-1',3'-dihydro-2H,5H-spiro[imidazolidine-4,2'-indene]-2,5-dione The compound was synthesized starting from 5-aminobenzimidazole 0.4 g (3 mmol), indan-2-one 0.4 g (3 mmol), n-butyl isonitrile 0.316 ml (3 mmol), pyridiniumchloride 0.347 g (3 mmol) and KOCN 0.244 g (3 mmol) as described in method 1.

Yield: 0.044 g (4.6%); MS m/z 319.3 (M+H)$^+$; $^1$H NMR: (400 MHz, CD$_3$OD): 3.46-3.50 (d, 2H, $J_1$=17.2 Hz), 3.63-3.68 (d, 2H, 17.22), 6.97-7.02 (m, 4H), 7.47-7.59 (d, 1H, $J_1$=7.2 Hz), 7.59-7.63 (d, 1H, 7.2 Hz), 7.71 (s, 1H), 9.2 (s, 1H), HPLC (λ=214 nm, [A]): rt 9.20 min (97%).

Example 33

5-(benzo[c][1,2,5]thiadiazol-6-yl)-1-(1H-benzo[d]imidazol-5-yl)-2-thioxoimidazolidin-4-one The compound was synthesized starting from 5-aminobenzimidazole 0.013 g (0.1 mmol), benzo[c][1,2,5]thiadiazol-6-yl carbaldehyde 0.016 g (0.1 mmol), n-butyl isonitrile 0.010 ml (0.1 mmol), pyridiniumchloride 0.012 g (0.1 mmol) and KSCN 0.01 g (0.1 mmol) as described in Method 2.

Yield: 0.0045 g (12%); MS m/z 367.2 (M+H)$^+$; HPLC (λ=220 nm, [B]): rt 1.91 min (94%).

Example 34

1-(1H-benzo[d]imidazol-5-yl)-5-phenyl-2-thioxoimidazolidin-4-one

The compound was synthesized starting from 5-aminobenzimidazole 0.013 g (0.1 mmol) benzaldehyde 0.01 ml (0.1 mmol), n-butyl isonitrile 0.010 ml (0.1 mmol), pyridiniumchloride 0.012 g (0.1 mmol) and KSCN 0.01 g (0.1 mmol) as described in method 2.

Yield: 0.0069 g (22%); MS m/z 309.3 (M+H)$^+$; HPLC (λ=220 nm, [B]): rt 1.52 min (96%).

Example 35

1-(1H-benzimidazol-5-yl)-5-(1,1'-biphenyl-4-yl)-2-thioxoimidazolidin-4-one

The compound was synthesized starting from 5-aminobenzimidazole 0.013 g (0.1 mmol), 4-phenyl benzaldehyde 0.018 g (0.1 mmol), n-butyl isonitrile 0.010 ml (0.1 mmol), pyridiniumchloride 0.012 g (0.1 mmol) and KSCN 0.01 g (0.1 mmol) as described in method 2.

Yield: 0.00346 g (8.9%); MS m/z 385.5 (M+H)$^+$; HPLC (λ=220 nm, [B]): rt 2.93 min (96%).

Example 36

1-(1H-benzo[d]imidazol-5-yl)-5-(3-hydroxy-4-methoxyphenyl)-2-thioxoimidazolidin-4-one The compound was synthesized starting from 5-aminobenzimidazole 0.013 g (0.1 mmol), 3-hydroxy-4-methoxyphenyl carbaldehyde 0.015 g (0.1 mmol), n-butyl isonitrile 0.010 ml (0.1 mmol), pyridiniumchloride 0.012 g (0.1 mmol) and KSCN 0.01 g (0.1 mmol) as described in method 2.

Yield: 0.00162 g (3.5%); MS m/z 355.3 (M+H)$^+$; HPLC (λ=220 nm, [B]): rt 0.81 min (92%).

Example 37

1-(1H-benzo[d]imidazol-5-yl)-5-phenyl-4-thioxoimidazolidin-2-one

The compound was synthesized starting from 1-(1H-benzo[d]imidazol-5-yl)-4-(methylimino)-5-phenylimidazolidin-2-one 0.076 g (0.25 mmol), and Na$_2$S 0.029 g (0.375 mmol) as described in method 3.

Yield: 0.0092 g (12%); MS m/z 309.5 (M+H)$^+$; HPLC (λ=220 nm, [B]): rt 2.61 min (64%).

Example 38

1-(1H-benzimidazol-5-yl)-5-(1,1'-biphenyl-4-yl)-4-thioxoimidazolidin-2-one

The compound was synthesized starting from 1-(1H-benzo[d]imidazol-5-yl)-4-(methylimino)-5-(1,1'-biphenyl-4-yl)imidazolidin-2-one 0.095 g (0.25 mmol) Na$_2$S 0.029 g (0.375 mmol) as described in method 3.

Yield: 0.00036 g (0.37%); MS m/z 385.4 (M+H)+; HPLC (λ=220 nm, [B]): rt 3.02 min (97%).

Example 39

3-(1H-benzimidazol-5-yl)-5-thioxo-1',3'-dihydro-2H-spiro[imidazolidine-4,2'-inden]-2-one The compound was synthesized starting from 3-(1H-benzimidazol-5-yl)-4-(methylimino)-1',3'-dihydro-2H-spiro[imidazolidine-4,2'-inden]-2-one 0.082 g (0.25 mmol) and Na$_2$S 0.029 g (0.375 mmol) as described in method 3.

Yield: 0.0016 g (1.9%); MS m/z 335.2 (M+H)+; HPLC (λ=220 nm, [D]): rt 2.81 min (84%).

Example 40

1-(1H-benzo[d]imidazol-5-yl)-5-(4-chlorophenyl)-4-thioxoimidazolidin-2-one

The compound was synthesized starting from 1-(1H-benzo[d]imidazol-5-yl)-5-(4-chlorophenyl)-4-(methylimino)imidazolidin-2-one 0.084 g (0.25 mmol) and Na$_2$S 0.029 g (0.375 mmol) as described in method 3.

Yield: 0.00088 g (1.0%); MS m/z 343.8 (M+H)+; HPLC (λ=220 nm, [D]): rt 2.73 min (99%).

Example 41

1-(1H-benzo[d]imidazol-5-yl)-5-(2,3,4-trifluorophenyl)-4-thioxoimidazolidin-2-one The compound was synthesized starting from 1-(1H-benzo[d]imidazol-5-yl)-5-(2,3,4-trifluorophenyl)-4-(methylimino)imidazolidin-2-one 0.090 g (0.25 mmol) and Na$_2$S 0.029 g (0.375 mmol) as described in method 3.

Yield: 0.00613 g (6.7%); MS m/z 363.2 (M+H)+; HPLC (λ=220 nm, [D]): rt 2.02 min (97%).

Example 42

1-(1H-benzo[d]imidazol-6-yl)-5-(4-bromo-2-fluorophenyl)-4-thioxoimidazolidin-2-one The compound was synthesized starting from 1-(1H-benzo[d]imidazol-5-yl)-5-(4-bromo-2-fluorophenyl)-4-(methylimino)imidazolidin-2-one 0.100 g (0.25 mmol) and Na$_2$S 0.029 g (0.375 mmol) as described in method 3.

Yield: 0.00071 g (0.6%); MS m/z 406.2 (M+H)+; HPLC (λ=220 nm, [D]): rt 2.94 min (90%).

Example 43

1-(1H-benzo[d]imidazol-5-yl)-5-(2,3-difluoro-4-methylphenyl)-4-thioxoimidazolidin-2-one The compound was synthesized starting from 1-(1H-benzo[d]imidazol-5-yl)-5-(2,3-difluoro-4-methylphenyl)-4-(methylimino)imidazolidin-2-one 0.088 g (0.25 mmol) and Na$_2$S 0.029 g (0.375 mmol) as described in method 3.

Yield: 0.0055 g (6.1%); MS m/z 359.2 (M+H)+; HPLC (λ=220 nm, [D]): rt 3.12 min (97%).

Example 44

1-(1H-benzo[d]imidazol-5-yl)-5-(4-chloro-3-methylphenyl)-4-thioxoimidazolidin-2-one The compound was synthesized starting from 1-(1H-benzo[d]imidazol-5-yl)-5-(4-chloro-3-methylphenyl)-4-(methylimino)imidazolidin-2-one 0.088 g (0.25 mmol) and Na$_2$S 0.029 g (0.375 mmol) as described in method 3.

Yield: 0.00221 g (2.4%); MS m/z 357.2 (M+H)+; HPLC (λ=220 nm, [D]): rt 3.21 min (80%).

Example 45

1-(1H-benzo[d]imidazol-5-yl)-3-methyl-5-phenylimida4zolidine-2,4-dione

The compound was synthesized starting from 5-aminobenzimidazole 0.266 g (2 mmol), di-(1H-imidazol-1-yl) methanone 0.324 g (2 mmol), methylaminehydrochloride 0.135 g (2 mmol) TEA 0.255 ml (2 mmol) and phenylglyoxal hydrate 0.102 g (0.67 mmol) according to method 4.

Yield: 0.045 g (7.5%); MS m/z 307.4 (M+H)+; $^1$H NMR (DMSO, 400 MHz): δ 3.00 (s, 3H); 6.05 (s, H); 7.23-7.32 (m, 3H); 7.36-7.39 (m, 2H); 7.54-7.56 (dd, H, $^3$J=8.9 Hz $^4$J=1.9 Hz); 7.65-7.68 (d, H, $^3$J=8.9 Hz); 7.91 (d, H, $^4$J=1.9 Hz); 9.05 (s, H), HPLC (λ=214 nm, [A]): rt 8.45 min (99%).

Example 46

1-(H-imidazo[1,2-a]pyridin-7-yl)-5-phenylimidazolidine-2,4-dione

The compound was synthesized starting from 1-(H-imidazo[1,2-a]pyridin-7-yl)urea 0.03 g (0.170 mmol) and phenylglyoxal hydrate 0.028 g (0.20 mmol) according to method 4.

Yield: 0.021 g (42%); MS m/z 293.2 (M+H)+; $^1$H NMR (DMSO, 400 MHz): δ 6.05 (s, 1H), 7.31-7.51 (m, 5H), 7.58-7.67 (m, 1H), 7.89-7.94 (m, 1H), 7.97-8.00 (m, 1H), 8.09-8.13 (m, 1H), 8.69-8.76 (m, 1H), 11.92 (s, 1H), HPLC (λ=214 nm, [A]): rt 8.36 min (95%).

In particular, a suitable compound is example 6 (1-(1H-benzo[d]imidazol-5-yl)-5-(4-propoxyphenyl)imidazolidine-2,4-dione) (isoQC-I) of the formula

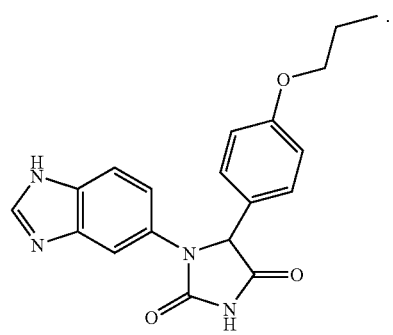 [SMILES: CCCOc1ccc(C2C(=O)NC(=O)N2c2ccc3[nH]cnc3c2)cc1]

Separation of Enantiomers

The enantiomers of example compound 6 were separated by Reversed-Phase HPLC (RP-HPLC) eluting with water containing solvent mixture.

Column: Nucleocel Alpha RP-S, 250*4.6 mm (5 μm)
Eluent:
A: water
B: acetonitrile
30-70% B in 40 min
Flow: 0.3 ml/min, 30° C.
Detection: 220 nm
Retention:
E1: 26.99 min
E2: 28.67 min The inhibitory potency of the separate enantiomers was determined as follows:

| | K$_i$ racemate | | K$_i$ enantiomers [nM] | | | |
|---|---|---|---|---|---|---|
| | [nM] | | E2 | | E1 | |
| | hQC (pH 8) | IsoQC (pH 8) | hQC (pH 8) | hQC (pH 6) | hQC (pH 8) | hQC (pH 6) |
| Example 6 | 38 | 4 | 4.87 | 15.9 | 537 | n.d. |

The inhibitory potencies were obtained using the inhibitor assay method set out in the biological examples below.

In a preferred embodiment, the present invention provides a composition, preferably a pharmaceutical composition, comprising at least one isoQC inhibitor optionally in combination with at least one other agent selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

More specifically, the aforementioned other agent is selected from the group consisting of anti-inflammatory agents, beta-amyloid antibodies, cysteine protease inhibitors, PEP-inhibitors, LiCl, acetylcholinesterase (AChE) inhibitors, PIMT enhancers, inhibitors of beta secretases, inhibitors of gamma secretases, inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents, MCP-1 antagonists or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

Further, the present invention provides pharmaceutical compositions e.g. for parenteral, enteral or oral administration, comprising at least one isoQC inhibitor, optionally in combination with at least one of the other aforementioned agents.

These combinations provide a particularly beneficial effect. Such combinations are therefore shown to be effective and useful for the treatment of the aforementioned diseases. Accordingly, the invention provides a method for the treatment of these conditions.

The method comprises either co-administration of at least one isoQC inhibitor and at least one of the other agents or the sequential administration thereof.

Co-administration includes administration of a formulation, which comprises at least one isoQC inhibitor and at least one of the other agents or the essentially simultaneous administration of separate formulations of each agent.

Especially useful for the purpose of the present invention are combinations isoQC inhibitors with MCP-1 antagonists. MCP-1 antagonists may, e.g. be selected from anti-MCP-1 antibodies, preferably monoclonal or humanized monoclonal antibodies, MCP-1 expression inhibitors, CCR2-antagonists, TNF-alpha inhibitors, VCAM-1 gene expression inhibitors and anti-C5a monoclonal antibodies. Such combinations of isoQC-inhibitors with MCP-1 antagonists may be useful for the treatment of inflammatory diseases in general.

In particular, the following combinations are considered to be useful for the purpose of the present invention:

an isoQC inhibitor, in particular isoQC-I, in combination with Atorvastatin for the treatment and/or prevention of artherosclerosis an isoQC inhibitor, in particular isoQC-I, in combination with immunosuppressive agents, preferably rapamycin for the prevention and/or treatment of restenosis an isoQC inhibitor, in particular isoQC-I, in combination with immunosuppressive agents, preferably paclitaxel for the prevention and/or treatment of restenosis an isoQC inhibitor, in particular isoQC-I, in combination with interferones, preferably Aronex, for the prevention and/or treatment of multiple sclerosis an isoQC inhibitor, in particular isoQC-I, in combination with interferones, preferably betaferon, for the prevention and/or treatment of multiple sclerosis an isoQC inhibitor, in particular isoQC-I, in combination with interferones, preferably Rebif, for the prevention and/or treatment of multiple sclerosis an isoQC inhibitor, in particular isoQC-I, in combination with Copaxone, for the prevention and/or treatment of multiple sclerosis an isoQC inhibitor, in particular isoQC-I, in combination with dexamethasone, for the prevention and/or treatment of restenosis an isoQC inhibitor, in particular isoQC-I, in combination with dexamethasone, for the prevention and/or treatment of atherosclerosis an isoQC inhibitor, in particular isoQC-I, in combination with dexamethasone, for the prevention and/or treatment of rheumatoid arthritis an isoQC inhibitor, in particular isoQC-I, in combination with HMG-Co-A-reductase inhibitors, for the prevention and/or treatment of restenosis, wherein the HMG-Co-A-reductase inhibitor is selected from atorvastatin, cerivastatin, fluvastatin, lovastatin, pitavastatin, pravastatin, rosuvastatin and simvastatin an isoQC inhibitor, in particular isoQC-I, in combination with HMG-Co-A reductase inhibitors, for the prevention and/or treatment of atherosclerosis wherein the HMG-Co-A-reductase inhibitor is selected from atorvastatin, cerivastatin, fluvastatin, lovastatin, pitavastatin, pravastatin, rosuvastatin and simvastatin an isoQC inhibitor, in particular isoQC-I, in combination with HMG-Co-A reductase inhibitors, for the prevention and/or treatment of rheumatoid arthritis wherein the HMG-Co-A-reductase inhibitor is selected from atorvastatin, cerivastatin, fluvastatin, lovastatin, pitavastatin, pravastatin, rosuvastatin and simvastatin an isoQC inhibitor, preferably isoQC-I, in combination with amyloid-beta antibodies for the prevention and/or treatment of mild cognitive impairment, wherein the amyloid-beta antibody is Acl-24, an isoQC inhibitor, preferably isoQC-I, in combination with amyloid-beta antibodies for the prevention and/or treatment of Alzheimer's disease, wherein the amyloid-beta antibody is Acl-24, an isoQC inhibitor, preferably isoQC-I, in combination with amyloid-beta antibodies for the prevention and/or treatment of neurodegeneration in Down Syndrome, wherein the amyloid-beta antibody is Acl-24, an isoQC inhibitor, preferably isoQC-I, in combination with beta-secretase inhibitors for the prevention and/or treatment of mild cognitive impairment, wherein the beta-secretase inhibitor is selected from WY-25105, GW-840736X and CTS-21166, an isoQC inhibitor, preferably isoQC-I, in combination with beta-secretase inhibitors for the prevention and/or treatment of Alzheimer's disease, wherein the beta-secretase inhibitor is selected from WY-25105, GW-840736X and CTS-21166, an isoQC inhibitor, preferably isoQC-I, in combination with beta-secretase inhibitors for the prevention and/or treatment of neurodegeneration in Down Syndrome, wherein the beta-secretase inhibitor is selected from WY-25105, GW-840736X and CTS-21166, an isoQC inhibitor, preferably isoQC-I, in combination with gamma-secretase inhibitors for the prevention and/or treatment of mild cognitive impairment, wherein the gamma-secretase inhibitor is selected from LY-450139, LY-411575 and AN-37124, an isoQC inhibitor, preferably isoQC-I, in combination with gamma-secretase inhibitors for the prevention and/or treatment of Alzheimer's disease, wherein the gamma-secretase inhibitor is selected from LY-450139, LY-411575 and AN-37124, an isoQC inhibitor, preferably isoQC-I, in combination with gamma-secretase inhibitors for the prevention and/or treatment of neurodegeneration in Down Syndrome, wherein the gamma-secretase inhibitor is selected from LY-450139, LY-411575 and AN-37124, an isoQC inhibitor, preferably isoQC-I, in combination with acetylcholinesterase inhibitors for the prevention and/or treatment of mild cognitive impairment, wherein the acetylcholinesterase inhibitor is selected from donezepil and dimebon, an isoQC inhibitor, preferably isoQC-I, in combination with acetylcholinesterase inhibitors for the prevention and/or treatment of Alzheimer's disease, wherein the acetylcholinesterase inhibitor is selected from donezepil and dimebon, an isoQC inhibitor, preferably isoQC-I, in combination with acetylcholinesterase inhibitors for the prevention and/or treatment of neurodegeneration in Down syndrome, wherein the acetylcholinesterase inhibitor is selected from donezepil and dimebon.

Such combination therapies are in particular useful for the treatment of inflammatory diseases like atherosclerosis, rheumatoid arthritis, restenosis, pancreatitis, osteoporosis and multiple sclerosis as well as neuroinflammation and resulting diseases thereof, like mild cognitive impairment (MCI), Alzheimer's disease, neurodegeneration in Down Syndrome, Familial British Dementia, Familial Danish Dementia.

Such combination therapies might result in a better therapeutic effect (less proliferation as well as less inflammation, a stimulus for proliferation) than would occur with either agent alone.

The compound may be administered to a patient by any conventional route of administration, including, but not limited to, intravenous, oral, subcutaneous, intramuscular, intradermal, parenteral and combinations thereof.

In a further preferred form of implementation, the invention relates to pharmaceutical compositions, that is to say, medicaments, that contain at least one compound of the invention or salts thereof, optionally in combination with one or more pharmaceutically acceptable carriers and/or solvents.

The pharmaceutical compositions may, for example, be in the form of parenteral or enteral formulations and contain appropriate carriers, or they may be in the form of oral formulations that may contain appropriate carriers suitable for oral administration. Preferably, they are in the form of oral formulations.

The inhibitors of isoQC activity administered according to the invention may be employed in pharmaceutically administrable formulations or formulation complexes as inhibitors or in combination with inhibitors, substrates, pseudosubstrates, inhibitors of isoQC expression, binding proteins or antibodies of those enzyme proteins that reduce the isoQC protein concentration in mammals. The compounds of the invention make it possible to adjust treatment individually to patients and diseases, it being possible, in particular, to avoid individual intolerances, allergies and side-effects.

The compounds also exhibit differing degrees of activity as a function of time. The physician providing treatment is thereby given the opportunity to respond differently to the individual situation of specific patients: he is able to adjust precisely, on the one hand, the speed of the onset of action and, on the other hand, the duration of action and especially the intensity of action.

The compounds may be advantageously administered, for example, in the form of pharmaceutical preparations that contain the active ingredient in combination with customary additives like diluents, excipients and/or carriers known from the prior art. For example, they can be administered parenterally (for example i.v. in physiological saline solution) or enterally (for example orally, formulated with customary carriers).

Depending on their endogenous stability and their bioavailability, one or more doses of the compounds can be given per day in order to achieve the desired reduction of MCP activity. For example, such a dosage range in humans may be in the range of from about 0.01 mg to 250 mg compound per kilogram of body weight per day, preferably in the range of about 0.01 to 100 mg of compound per kilogram of body weight per day, more preferably in the range of 0.01 to 10 mg of compound per kilogram of body weight per day.

The compounds used according to the invention can accordingly be converted in a manner known per se into conventional formulations, such as, for example, tablets, (bitable) capsules, dragées, pills, suppositories, granules, aerosols, syrups, drops, liquid, solid and cream-like emulsions and suspensions and/or also as suppositories or as nasal sprays solutions, using inert, non-toxic, pharmaceutically suitable carriers and additives or solvents. In each of those formulations, the therapeutically effective compounds are preferably present in a concentration of approximately from 0.1 to 80% by weight, more preferably from 1 to 50% by weight, of the total mixture, that is to say, in amounts sufficient for the mentioned dosage latitude to be obtained.

The formulations may be advantageously prepared, for example, by extending the active ingredient with solvents and/or carriers, optionally with the use of emulsifiers and/or dispersants, it being possible, for example, in the case where water is used as diluent, for organic solvents to be optionally used as auxiliary solvents.

Examples of excipients useful in connection with the present invention include: water, non-toxic organic solvents, such as paraffins (for example natural oil fractions), vegetable oils (for example rapeseed oil, groundnut oil, sesame oil), alcohols (for example ethyl alcohol, glycerol), glycols (for example propylene glycol, polyethylene glycol); solid carriers, such as, for example, natural powdered minerals (for example highly dispersed silica, silicates), sugars (for example raw sugar, lactose and dextrose); emulsifiers, such as non-ionic and anionic emulsifiers (for example polyoxyethylene fatty acid esters, polyoxyethylene fatty alcohol ethers, alkylsulphonates and arylsulphonates), dispersants (for example lignin, sulphite liquors, methylcellulose, starch and polyvinylpyrrolidone) and lubricants (for example magnesium stearate, talcum, stearic acid and sodium lauryl sulphate) and optionally flavourings.

Administration may be carried out in the usual manner, preferably enterally or parenterally, especially orally. In the case of enteral administration, tablets may contain in addition to the mentioned carriers further additives such as sodium citrate, calcium carbonate and calcium phosphate, together with various additives, such as starch, preferably potato starch, gelatin and the like. Furthermore, lubricants, such as magnesium stearate, sodium lauryl sulphate and talcum, can be used concomitantly for tabletting. In the case of aqueous suspensions and/or elixirs intended for oral administration, various taste correctives or colourings can be added to the active ingredients in addition to the above-mentioned excipients.

In the case of parenteral administration, solutions of the active ingredients using suitable liquid carriers can be employed. In general, it has been found advantageous to administer, in the case of intravenous administration, amounts of approximately from 0.01 to 2.0 mg/kg, preferably approximately from 0.01 to 1.0 mg/kg of body weight per day to obtain effective results and, in the case of enteral administration, the dosage is approximately from 0.01 to 2 mg/kg, preferably approximately from 0.01 to 1 mg/kg of body weight per day.

It may nevertheless be necessary in some cases to deviate from the stated amounts, depending upon the body weight of the experimental animal or the patient or upon the type of administration route, but also on the basis of the species of animal and its individual response to the medicament or the interval at which administration is carried out. Accordingly, it may be sufficient in some cases to use less than the above-mentioned minimum amount, while, in other cases, the mentioned upper limit will have to be exceeded. In cases where relatively large amounts are being administered, it may be advisable to divide those amounts into several single doses over the day. For administration in human medicine, the same dosage latitude is provided. The above remarks apply analogously in that case.

The above disclosure describes the present invention in general. A more complete understanding can be obtained by reference to the following figures and examples. These examples are described solely for purposes of illustration and are not intended to limit the scope of the invention. Although specific terms have been employed herein, such terms are intended in a descriptive sense and not for purposes of limitation.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Preparation of Human isoQC

Cell Lines and Media

African green monkey kidney cell line COS-7, human neuroblastoma cell line SH-SY5Y, human asatrocytoma cell line LN405, human keratinocytoma cell line HaCaT and human hepatocellular carcinoma cell line Hep-G2 were cultured in appropriate cell culture media (DMEM, 10% FBS for Cos-7, SH-SY5Y, LN405, HaCaT), (RPM11640, 10% FBS for Hep-G2), in a humidified atmosphere of 5% CO2 (HaCaT, Hep-G2, COS-7) or 10% CO2 (SH-SY5Y, LN405) at 37° C.

Analysis of Human isoQC Expression Using RT-PCR

Total RNA was isolated from SH-SY5Y, LN405, HaCaT and Hep-G2 cells using the RNeasy Mini Kit (Qiagen) and reversely transcribed by SuperScript II (Invitrogen). Subsequently, human isoQC was amplified on a 1:12.5 dilution of generated cDNA product in a 25 µl reaction with Herculase Enhanced DNA-Polymerase (Stratagene) using primers isoQCh-1 (sense, SEQ ID NO: 19) and isoQCh-2 (antisense, SEQ ID NO: 20). The PCR product of Hep-G2 was purified utilizing the Strataprep PCR Purification Kit (Stratagene) and confirmed by sequencing.

Results

Analysis of Human isoQC Expression Using RT-PCR

Transcripts of human isoQC were found to be present in cell lines SH-SY5Y (FIG. 2, lane 1), LN405 (FIG. 2, lane 2), HaCaT (FIG. 2, lane 3) and Hep-G2 (FIG. 2, lane 4). The PCR product of Hep-G2 was confirmed by sequencing.

Isolation of Human isoQC

Full-length cDNA of human isoQC was isolated from Hep-G2 cells using RT-PCR. Briefly, total RNA of Hep-G2 cells was reversely transcribed by SuperScript II (Invitrogen). Subsequently, human isoQC was amplified on a 1:12.5 dilution of generated cDNA product in a 25 µl reaction with Herculase Enhanced DNA-Polymerase (Stratagene) using primers isoQChu-1 (sense, SEQ ID NO: 21) and isoQChu-2 (antisense, SEQ ID NO: 22). The resulting PCR-product was subcloned into vector pPCRScript CAM SK (+) (Stratagene) and confirmed by sequencing.

Example 2

Preparation and Expression of Human isoQC in Mammalian Cell Culture

Molecular Cloning of Plasmid Vectors Encoding a Human isoQC-EGFP Fusion Protein

All cloning procedures were done applying standard molecular biology techniques. For expression of human isoQC-EGFP fusion protein in human cells, the vector pEGFP-N3 (Invitrogen) was used. The cDNA of the native human isoQC starting either at methionine I or at methionine II was fused N-terminally in frame with the plasmid encoded enhanced green fluorescent protein (EGFP). The primers isoQC EGFP-1 Met I (SEQ ID NO: 23) and isoQC EGFP-3 (SEQ ID NO: 25) were used for amplification of human isoQC starting with methionine I and primers isoQC EGFP-2 Met II (SEQ ID NO: 24) and isoQC EGFP-3 (SEQ ID NO: 25) were used for amplification of human isoQC starting with methionine II. The fragments were inserted into vector pEGFP-N3 (Invitrogen) employing the restriction sites of EcoRI and SalI and the correct insertion was confirmed by sequencing. Subsequently, the vectors were isolated for cell culture purposes using the EndoFree Maxi Kit (Qiagen).

Cloning Procedure of the N-Terminal Sequences of hisoQC

In addition, the EGFP sequence of vector pEGFP-N3 (Invitrogen) was introduced into vector pcDNA 3.1 (Invitrogen) using EGFP-1 (sense) (SEQ ID NO: 48) and EGFP-2 (antisense) (SEQ ID NO: 49) for amplification. The fragment was introduced into the XhoI site of pcDNA 3.1. The N-terminal sequences of hisoQC beginning with methionine I and II each ending at serine 53 were fused C-terminally with EGFP in vector pcDNA 3.1 using isoQC EGFP-1 Met I (sense, SEQ ID NO: 23) and hisoQC SS EGFP pcDNA as (antisense) (SEQ ID NO: 50) for the N-terminal fragment of hisoQC beginning with methionine I and isoQC EGFP-2 Met II (sense, SEQ ID NO: 24) and hisoQC SS EGFP pcDNA as (antisense) (SEQ ID NO: 50) for the N-terminal fragment of hisoQC beginning with methionine II. Fragments were inserted into EcoRI and NotI restriction sites of vector pcDNA 3.1. Subsequently, the vectors were isolated for cell culture purposes using the EndoFree Maxi Kit (Qiagen).

Cloning Procedure for Native Expression of hisoQC and hQC

Native hQC was inserted into HindIII and NotI restriction sites and native hisoQC was inserted into EcoRI and NotI restriction sites of vector pcDNA 3.1 (+) (Invitrogen) after amplification utilizing primers hQC-1 (sense) (SEQ ID NO: 45) and hQC-2 (antisense) (SEQ ID NO: 46) for hQC, isoQC EGFP-1 Met I (sense) (SEQ ID NO: 23) and hisoQC pcDNA as (antisense) (SEQ ID NO: 47) for hisoQC starting with methionine I and isoQC EGFP-2 Met II (sense) (SEQ ID NO: 24) and hisoQC pcDNA as (antisense) (SEQ ID NO: 47) for hisoQC starting with methionine II.

Cloning Procedure for FLAG-Tagged hisoQC and hQC

Human QC was cloned with a C-terminal FLAG-tag after amplification applying primers hQC-1 (sense) (SEQ ID NO: 45) and hQC C-FLAG pcDNA as (antisense) (SEQ ID NO: 51) into HindIII and NotI restriction sits of vector pcDNA 3.1. Human isoQC was inserted with a C-terminal FLAG-tag into pcDNA 3.1 after amplification using primers isoQC EGFP-1 Met I (sense) (SEQ ID NO: 23) and hisoQC C-FLAG pcDNA as (antisense) (SEQ ID NO: 52) for hisoQC starting with methionine I and primers isoQC EGFP-2 Met II (sense) (SEQ ID NO: 24) and hisoQC C-FLAG pcDNA as (antisense) (SEQ ID NO: 52) for hisoQC starting with methionine 2.

Example 3

Immunohistochemical Staining of Human isoQC in Mammalian Cells

Transfection and Histochemical Staining of COS-7 and LN405

For expression of human isoQC-EGFP fusion proteins starting either with methionine I or methionine II, COS-7 and LN405 were cultured in 6-well dishes containing a cover slip. Cells were grown until 80% confluency, transfected using Lipofectamin2000 (Invitrogen) according to manufacturer's manual and incubated in the transfection solution for 5 hours. Afterwards, the solution was replaced by appropriate growth media and cells were grown over-night.

The next day, cells were washed twice with D-PBS (Invitrogen) and fixed using ice-cold methanol for 10 min at −20° C., followed by 3 washing steps using D-PBS for 10 min at room temperature. For staining of the Golgi-zone, COS-7 and LN405 were incubated with rabbit anti-mannosidase II polyclonal antibody (Chemicon) in a 1:50 dilution of antibody in D-PBS for 3 h. For staining of mitochondria in COS-7 and LN405, cells were incubated with mouse anti-human mitochondria monoclonal antibody (Chemicon) in a 1:100 dilution of antibody in D-PBS for 3 h at room temperature. Subsequently, the cells were washed 3 times with D-PBS for 10 min. Cells stained for golgi-zone were incubated with goat anti-rabbit IgG secondary antibody conjugated with Rhodamin-RedX (Dianova) for 45 min at room temperature in the dark. Cells stained for mitochondria were incubated with goat anti-mouse IgG secondary antibody conjugated with Rhodamin-RedX (Dianova) for 45 min at room temperature in the dark. Afterwards, cells were washed 3 times with D-PBS for 5 min at room temperature and at last, the cover slips were mounted on a microscope slide with citifluor (Citifluor Ltd.). Cells were observed under a fluorescence microscope (Carl-Zeiss).

Results

1. Transfection and Histochemical Staining of LN405

The expression of human isoQC-EGFP fusion protein starting with methionine I and methionine II in cell line LN405 (green fluorescence) results in a compartmentalization of the resulting protein. Counterstaining of the Golgi-zone of LN405 using mannosidase II antibody (red fluorescence) and subsequent superimposition of human isoQC-EGFP with mannosidase II suggests a localization of human isoQC-EGFP fusion protein within the Golgi-compartment. Thereby, it is evident that human isoQC starting at methionine II is sufficient to generate a Golgi-localization of the human isoQC fusion protein.

The expression of human isoQC-EGFP fusion protein starting with methionine I and II (green fluorescence) and counterstaining for mitochondria (red fluorescence) did not reveal a localization of human isoQC-EGFP fusion protein starting with methionine I or II within the mitochondria due to the absence of a yellow coloration of the merged images after superimposition.

2. Transfection and Histochemical Staining of COS-7

In analogy to the expression of human isoQC-EGFP fusion protein starting with methionine I and methionine II in cell line LN405, the expression of human isoQC-EGFP fusion protein starting with methionine I and methionine II in COS-7 results in a compartmentalization of the resulting protein (green fluorescence). Counterstaining of the Golgi-zone of COS-7 cells using mannosidase II antibody (red fluorescence) and subsequent superimposition of human isoQC-EGFP with mannosidase II suggests a localization of human isoQC-EGFP fusion protein within the Golgi-compartment of COS-7. Again, in COS-7 cells the expression of human isoQC-EGFP fusion protein starting at methionine II is sufficient to cause a Golgi-localization.

As expected, the expression of human isoQC-EGFP fusion protein starting with methionine I and II in COS-7 (green fluorescence) and counterstaining for mitochondria (red fluorescence) did not result in a localization of human isoQC-EGFP fusion protein starting with methionine I or II within the mitochondria due to the absence of a yellow coloration of the merged images after superimposition.

Example 4

Expression and Purification of Human isoQC in *E. Coli*

Host Strains and Media

*Escherichia coli* strain DH5α was used for propagation of plasmids and *E. coli* strain BL21 was used for the expression of human isoQC. *E. coli* strains were grown, transformed and analyzed according to the manufacturer's instructions (Qiagen (DH5α), Stratagene (BL21)). The media required for *E. coli*, i.e. Luria-Bertani (LB) medium, was prepared according to the manufacturers recommendations.

Molecular Cloning of Plasmid Vectors Encoding the Human isoQC

All cloning procedures were done applying standard molecular biology techniques. For expression in *E. coli* BL21, the vector pET41a (Novagen) was used. The cDNA of the mature human isoQC starting with codon 30 (counting from methionine II) was fused in frame with the plasmid encoded GST-tag. After amplification utilizing the primers hisoQC pET41a-1 (SEQ ID NO: 26) and hisoQC pET41a-2 (SEQ ID NO: 27) (TABLE 5) an N-terminal protease cleavage site for Enterokinase and a C-terminal (His)6-tag were introduced. After subcloning, the fragment was inserted into the expression vector employing the restriction sites of Spe I and EcoR I.

Expression and Purification in *E. Coli* BL21

The construct encoding the human isoQC was transformed into BL21 cells (Stratagene) and grown on selective LB agar plates at 37° C. Protein expression was carried out in LB medium containing 1% glucose at 37° C. After reaching an OD600 of approximately 0.8, isoQC expression was induced with 20 µM IPTG for 4 h at 37° C. Cells were separated from the medium by centrifugation (4000×g, 20 min), resuspended in PBS (140 mM NaCl, 2.7 mM KCl, 10 mM Na2HPO4, 1.8 mM KH2PO4, pH 7.3) and lysed by one cycle of freezing and thawing followed by one cycle of French Press. The cell lysate was diluted to a final volume of 1.5 l using phosphate-containing buffer (50 mM Na2HPO4, 500 mM NaCl, pH 7.3) and centrifuged at 13.400×g at 4° C. for 1 h. After centrifugation, the protein concentration of the resulting supernatant was determined using the method of Bradford. If necessary, the solution was diluted again to obtain a final total protein concentration of 0.6 mg/ml. The GST-isoQC fusion protein was purified utilizing a 4-step protocol (TABLE 6). The purification is illustrated by SDS-PAGE analysis in FIG. 5.

Example 5

Assays for Glutaminyl Cyclase Activity

Fluorometric Assays

All measurements were performed with a NovoStar reader for microplates (BMG Labtechnologies) at 30° C. QC activity was evaluated fluorometrically using H-Gln-βNA. The samples consisted of 0.2 mM fluorogenic substrate, 0.25 U pyroglutamyl aminopeptidase (Qiagen, Hilden, Germany) in 0.05 M Tris/HCl, pH 8.0 and an appropriately diluted aliquot of isoQC in a final volume of 250 µl. Excitation/emission wavelengths were 320/410 nm. The assay reactions were initiated by addition of glutaminyl cyclase. isoQC activity was determined from a standard curve of β-naphthylamine under assay conditions. One unit is defined as the amount of isoQC catalyzing the formation of 1 µmol pGlu-βNA from H-Gln-βNA per minute under the described conditions.

In a second fluorometric assay, isoQC activity was determined using H-Gln-AMC as substrate. Reactions were carried out at 30° C. utilizing the NOVOStar reader for microplates (BMG Labtechnologies). The samples consisted of varying concentrations of the fluorogenic substrate, 0.1 U pyroglutamyl aminopeptidase (Qiagen) in 0.05 M Tris/HCl, pH 8.0 and an appropriately diluted aliquot of isoQC in a final volume of 250 µl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit sofware.

Spectrophotometric Assay of isoQC

This assay was used to determine the kinetic parameters for most of the isoQC substrates. isoQC activity was analyzed spectrophotometrically using a continuous method (Schilling, S. et al., 2003 Biol Chem 384, 1583-1592) utilizing glutamic dehydrogenase as auxiliary enzyme. Samples consisted of the respective isoQC substrate, 0.3 mM NADH, 14 mM α-Ketoglutaric acid and 30 U/ml glutamic dehydrogenase in a final volume of 250 µl. Reactions were started by addition of isoQC and pursued by monitoring of the decrease in absorbance at 340 nm for 8-15 min. The initial velocities were evaluated and the enzymatic activity was determined from a standard curve of ammonia under assay conditions. All samples were measured at 30° C., using the Sunrise reader for microplates. Kinetic data were evaluated using GraFit software.

Inhibitor Assay

For inhibitor testing, the sample composition was the same as described above, except of the putative inhibitory compound added. For a rapid test of isoQC-inhibition, samples contained 4 mM of the respective inhibitor and a substrate concentration at 1 KM. For detailed investigations of the inhibition and determination of Ki-values, influence of the inhibitor on the auxiliary enzymes was investigated first. In every case, there was no influence on either enzyme detected, thus enabling the reliable determination of the isoQC inhibition. The inhibitory constant was evaluated by fitting the set of progress curves to the general equation for competitive inhibition using GraFit software.

Results

A variety of different substrates was evaluated on conversion by human isoQC (TABLE 4). All analyzed substrates were converted by isoQC, indicating a relatively relaxed overall specificity similar to human QC (Schilling, S. et al. 2003 Biol Chem. 384, 1583-1592). Highest specificity constants (kcat/KM) were observed for substrates carrying large hydrophobic amino acids adjacent to the N-terminal glutaminyl residue, e.g. Gln-AMC. In contrast, negatively charged residues in that very position led to a drastic drop in specificity, as observed for Gln-Glu, indicating a negatively charged active site of isoQC. Compared to human QC, both recombinant iosQCs exerted a lower enzymatic activity (FIG. 7). The difference was up to one order of magnitude. According to the specificity of isoQC, it is reasonable to assume that the enzyme is responsible for conversion of different substrates in vivo, i.e. isoQC is involved in the generation of many different physiological substrates.

Figure 1:
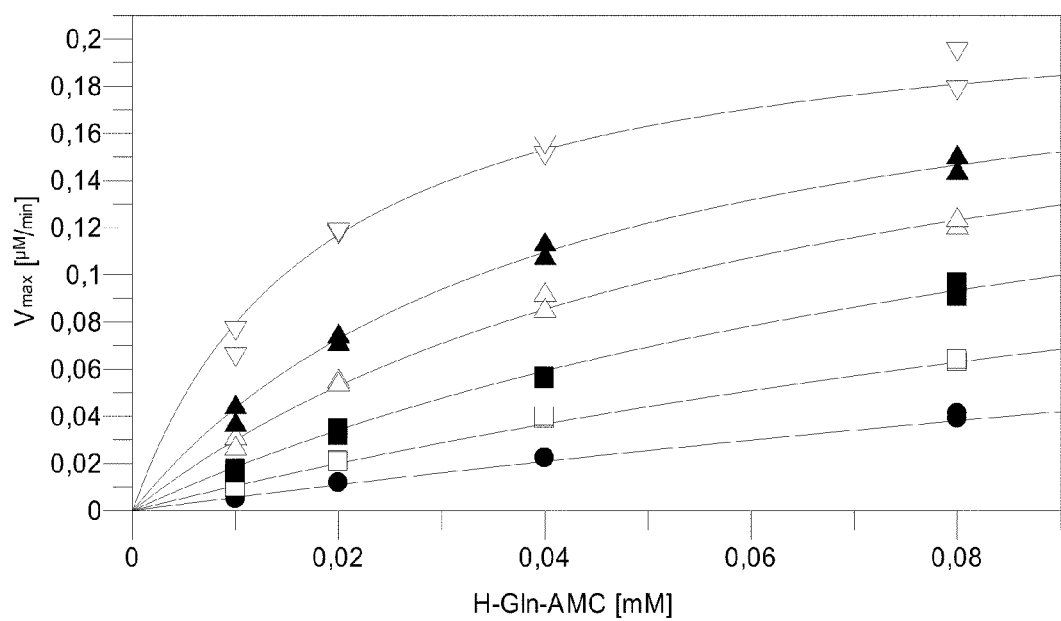
FIG. 1 shows the inhibition of human isoQC-catalyzed conversion of H-Gln-AMC into pGlu-AMC by the inhibitor 1-(3-(1H-imidazol-1-yl)propyl)-3-(3,4-dimethoxyphenyl) thiourea hydrochloride. The data were evaluated according to the Michaelis-Menten kinetic model considering linear competitive inhibition. Inhibitor concentrations were as follows.

Human isoQC activity was competitively inhibited by imidazole derivatives (TABLE 7, FIG. 1). The inhibition constants Ki for imidazole and benzimidazole were very similar to the value which was obtained for human QC previously. A 10-fold drop in Ki, however, was observed for the potent QC inhibitor 1-(3-(1H-imidazol-1-yl)propyl)-3-(3,4-dimethoxyphenyl)thiourea hydrochloride. Thus, the binding mode of the chelating part, i.e. the imidazole ring, appears to be very similar. Presumably, this results from complexation of the active site zinc ion of QC and isoQC by the imidazole basic nitrogen. The differences in the Ki-values for 1-(3-(1H-imidazol-1-yl)propyl)-3-(3,4-dimethoxyphenyl)thiourea hydrochloride clearly demonstrate that the active sites of both enzymes display subtle differences. Therefore, it is possible to generate inhibitors that exert selectivity for one enzymatic isoform. Selective inhibitors are beneficial for the treatment of the above-mentioned diseases.

Moreover, human isoQC activity was inhibited by the example compounds of formula (I) (TABLE 7A).

TABLE 4

Kinetic evaluation of peptide substrates of human QC and human isoQC. Human isoQC was expressed in E. coli BL21 (hisoQCdt) or P. pastoris (YSShisoQC). The substrates are displayed in the one-letter code of amino acids.

| Substrate | $K_M$ (mM) hisoQCdt | $K_M$ (mM) YSShisoQC | $k_{cat}$ (s$^{-1}$) hisoQCdt | $k_{cat}$ (s$^{-1}$) YSShisQC | $k_{cat}/K_M$ (mM$^{-1}$ * s$^{-1}$) hisoQCdt | $k_{cat}/K_M$ (mM$^{-1}$ * s$^{-1}$) YSShisoQC |
|---|---|---|---|---|---|---|
| Q-βNA | 0.03 ± 0.002 | 0.035 ± 0.0005 | 3.37 ± 0.12 | 8.16 ± 0.87 | 93.26 ± 6.68 | 228.70 ± 22.22 |
| Q-AMC | 0.01 ± 0.0009 | 0.03 ± 0.0064 | 1.07 ± 0.03 | 3.72 ± 0.44 | 62.57 ± 5.68 | 102.87 ± 29.22 |
| QQ | 0.11 ± 0.027 | 0.11 ± 0.007 | 2.72 ± 0.25 | 6.08 ± 0.17 | 24.50 ± 4.009 | 54.32 ± 4.61 |
| QE | 0.7 ± 0.13 | 0.61 ± 0.064 | 2.64 ± 0.21 | 5.33 ± 0.43 | 3.85 ± 0.56 | 8.75 ± 0.87 |
| QG | 0.42 ± 0.04 | 0.36 ± 0.047 | 1.65 ± 0.04 | 3.24 ± 0.18 | 3.93 ± 0.31 | 9.01 ± 1.75 |
| QGP | 0.21 ± 0.016 | 0.23 ± 0.02 | 4.01 ± 0.14 | 8.98 ± 0.07 | 18.82 ± 1.26 | 38.42 ± 3.55 |
| QYA | 0.22 ± 0.01 | 0.08 ± 0.022 | 7.7 ± 0.4 | 16.47 ± 0.72 | 66.48 ± 13.07 | 206.9 ± 57.54 |
| QFA | 0.11 ± 0.016 | 0.104 ± 0.025 | 7.49 ± 0.28 | 11.68 ± 2.39 | 33.03 ± 2.38 | 116.99 ± 34.37 |
| QEYF | 0.03 ± 0.004 | 0.04 ± 0.004 | 3.34 ± 0.15 | 5.64 ± 0.39 | 109.57 ± 21.03 | 122.56 ± 5.6 |
| QEDL | 0.63 ± 0.052 | 0.16 ± 0.01 | 6.41 ± 0.15 | 9.24 ± 0.65 | 10.2 ± 0.84 | 55.04 ± 5.14 |

TABLE 5

Utilized primers

| Primer | Sequence 5' → 3' | Application |
|---|---|---|
| IsoQCh-1 (SEQ ID NO: 19) | GGTCTACACCATTTGGAG CGGCTGGC | Cell Line Screening |
| IsoQCh-2 (SEQ ID NO: 20) | GGGTTGGAAGTACATCAC TTCCTGGGG | Cell Line Screening |
| IsoQChu-1 (SEQ ID NO: 21) | ACCATGCGTTCCGGGGGC CGCGGG | Isolation of hisoQC |
| IsoQChu-2 (SEQ ID NO: 22) | ACGCTAGAGCCCCAGGTA TTCAGCCAG | Isolation of hisoQC |
| IsoQC EGFP-1 Met I (SEQ ID NO : 23) | ATATATGAATTCATGCGT TCCGGGGGCCGC | Cloning human isoQC (Met I) into vector pEGFP-N3 |
| IsoQC EGFP-2 Met II (SEQ ID NO: 24) | ATATATGAATTCATGGAG CCACTCTTGCCGCCG | Cloning human isoQC (Met II) into vector pEGFP-N3 |
| IsoQC EGFP-3 (SEQ ID NO: 25) | ATATATGTCGACGAGCCC CAGGTATTCAGCCAG | Cloning human isoQC (Met I and Met II) into vector pEGFP-N3 |
| HisoQC pET41a-1 (SEQ ID NO: 26) | ATATACTAGTGATGACGA CGACAAGTTCTACACCAT TTGGAGCG | Cloning human isoQC into vector pET41a |
| HisoQC pET41a-2 (SEQ ID NO: 27) | TATAGAATTCCTAGTGAT GGTGATGGTGATGGAGCC CCAGGTATTCAGC | Cloning human isoQC into vector pET41a |
| hisoQC HIS C-Term pPICZAA-1 (SEQ ID NO: 28) | ATATGAATTCTTCTACAC CATTTGGAGC | Cloning human isoQC into vector PPICZαA |

TABLE 5-continued

Utilized primers

| Primer | Sequence 5' → 3' | Application |
|---|---|---|
| hisoQC HIS N-Term pPICZAA-1 (SEQ ID NO: 29) | ATATGAATTCCATCACCA TCACCATCACTTCTACAC CATTTGGAGCGGC | Cloning human isoQC into vector PPICZαA |
| hisoQC HIS N-Term pPICZAA-2 (SEQ ID NO: 30) | ATATATGCGGCCGCCTAG AGCCCCAGGTATTCAGC | Cloning human isoQC into vector PPICZαA |
| isoQCm RT s (SEQ ID NO: 31) | CCAGGATCCAGGCTATTG AG | Real-time PCR analysis of isoQC |
| hisoQC HIS C-Term pPICZAA-2 (SEQ ID NO: 32) | ATATATGCGGCCGCCTAG TGATGGTGATGGTGATGG AGCCCCAGGTATTCAGCC AG | Cloning human isoQC vector PPICZαA |
| isoQCm RT as (SEQ ID NO: 33) | TTCCACAGGGCCGGGGGG C | Real-time PCR analysis of isoQC |
| isoQCm MetI s (SEQ ID NO: 34) | ATGAGTCCCGGGAGCCGC | Cloning of murine isoQC cDNA |
| isoQCm MetI as (SEQ ID NO: 35) | CTAGAGTCCCAGGTACTC | Cloning of murine isoQC cDNA |
| isoQCm kurz s (SEQ ID NO: 36) | AGTTCCTGCCCCTGCTGC TG | Cloning of murine isoQC cDNA |
| mQC RT s (SEQ ID NO: 37) | ATCAAGAGGCACCAACCA AC | Real-time PCR analysis of mQC |
| mQC RT as (SEQ ID NO: 38) | CTGGATAATATTTCCATA G | Real-time PCR analysis of mQC |
| mQC RT N-terminal s (SEQ ID NO: 39) | ACAGCTGGGAATCTGAGT C | Real-time PCR analysis of mQC |
| mQC RT N-terminal as (SEQ ID NO: 40) | GAGCAGAATAGCTTCCGG GCG | Real-time PCR analysis of mQC |
| Iso-I55Ns (SEQ ID NO: 41) | CTGCGGGTCCCATTGAAC GGAAGCCTCCCCGAA | Site-directed mutagenesis hisoQC I55N |
| Iso-I55Nas (SEQ ID NO: 42) | TTCGGGGAGGCTTCCGTT CAATGGGACCCGCAG | Site-directed mutagenesis hisoQC I55N |
| Iso-C351As (SEQ ID NO: 43) | ACGGTACACAACTTGGCC CGCATTCTCGCTGTG | Site-directed mutagenesis hisoQC C351A |
| Iso-C351Aas (SEQ ID NO: 44) | CACAGCGAGAATGCGGGC CAAGTTGTGTACCGT | Site-directed mutagenesis hisoQC C351A |
| hQC-1 (SEQ ID NO: 45) | ATATATAAGCTTATGGCA GGCGGAAGACAC | Insertion of native hQC into pcDNA 3.1 |
| hQC-2 (SEQ ID NO: 46) | ATATGCGGCCGCTTACAA ATGAAGATATTCC | Insertion of native hQC into pcDNA 3.1 |
| hisoQC pcDNA as (SEQ ID NO: 47) | ATATATGCGGCCGCCTAG AGCCCCAGGTATTCAGC | Amplification hisoQC including the stop codon for insertion into pcDNA 3.1 |
| EGFP-1 (SEQ ID NO: 48) | ATATCTCGAGTCCATCGC CACCATGGTGAGC | Amplification EGFP |
| EGFP-2 (SEQ ID NO: 49) | ATATCTCGAGTTACTTGT ACAGCTCGTCCAT | Amplification EGFP |
| hisoQC 33 EGFP pcDNA as (SEQ ID NO: 50) | ATATGCGGCCGCATGTCG ACGCTCCAAATGGTGTAG AACGC | Amplification hisoQC N-terminal sequence |
| hQC C-FLAG pcDNA as (SEQ ID NO: 51) | ATATGCGGCCGCTTACTT GTCATCGTCATCCTTGTA ATCCAAATGAAGATATTC CAA | Amplification hQC C-FLAG |
| hisoQC C-FLAG pcDNA as (SEQ ID NO: 52) | ATATGCGGCCGCCTACTT GTCATCGTCATCCTTGTA ATCGAGCCCAGGTATTC AGC | Amplification h-isoQC C-Flag |
| Hs_QPCT_1_SG | | QuantiTect Primer Assay (200), Qiagen, Hilden qPCR hQC |
| Hs_QPCTL_1_SG | | QuantiTect Primer Assay (200), Qiagen, Hilden qPCR h-isoQC |

TABLE 6

Purification of GST-isoQC fusion protein following expression in *E. coli*. The purified fusion protein was used for determination of isoQC activity.

| | Purification Step | | | |
|---|---|---|---|---|
| | 1 | 2 | 3 | 4 |
| Method | $Ni^{2+}$-IMAC (EBA) | GST-TAG AC | GF (Desalting) | IEX (UNO S) |
| Column type (Amersham Biosciences AB, Sweden) | Chelating Sepharose Fast Flow | Glutathion Sepharose 4 Fast Flow | Sephadex G-25 Fine | "continuous bed" matrix BIO-Rad |
| Column size | d = 2.5 cm l = 42 cm CV = 206 $cm^3$ | d = 1.6 cm l = 10 cm CV = 20 $cm^3$ | d = 2.6 cm l = 10 cm CV = 53 $cm^3$ | d = 1.2 cm l = 5.3 cm CV = 6 $cm^3$ |

TABLE 6-continued

Purification of GST-isoQC fusion protein following expression in *E. coli*. The purified fusion protein was used for determination of isoQC activity.

| | Purification Step | | | |
|---|---|---|---|---|
| | 1 | 2 | 3 | 4 |
| Equilibration Buffer | PBS | PBS | 25 mM Mes | 25 mM Mes |
| pH | 7.3 | 7.3 | 6.0 | 6.0 |
| Volume | 10 CV | 10 CV | 10 CV | 10 CV |
| Intermediate (Wash) Buffer | PBS 0.5 mM Histidin | PBS | — | 25 mM Mes |
| pH | 7.3 | 7.3 | | 6.0 |
| Volume | 10. CV | 10. CV | | 10. CV |
| Elution Buffer | PBS 100 mM Histidin | 50 mM Tris 10 mM Glutathion (reduced) | 25 mM Mes | 25 mM Mes Gradient elution NaCl |
| pH | 7.3 | 8.0 | 6.0 | 6.0 |
| Volume | 1.5 CV | (reverse flow) | 1 CV | 1 CV |

TABLE 7

Ki-values for competitive inhibition of human QC and human isoQC by imidazole derivatives. Human isoQC was expressed in *E. coli* BL21 (hisoQCdt) or *P. pastoris* (YSShisoQC)

| Inhibitor | $K_i$ (μM) hisoQCdt | $K_i$ (μM) YSShisoQC | $K_i$ (μM) hQC |
|---|---|---|---|
| Imidazole | 220 ± 1 | 235 ± 13 | 103 ± 2 |
| Benzimidazole | 200 ± 8 | 250 ± 5 | 138 ± 4 |
| 1-Benzylimidazole | 7.3 ± 0.5 | 6.2 ± 0.2 | 7.1 ± 0.1 |
| 1-Methylimidazole | 80 ± 5 | 82 ± 3 | 39.7 ± 0.2 |
| 1-(3,4-Dimethoxy-phenyl)-3-(3-imidazole-1-yl-propyl)-thiourea | 0.48 ± 0.03 | 0.519 ± 0.001 | 0.0584 ± 0.0002 |

TABLE 7A

Ki-values for competitive inhibition of human QC and human isoQC by isoQC inhibitors of formula (I). Human isoQC was expressed in *P. pastoris*

| Example | $IC_{50}$ (μM) hisoQC | $K_i$ (μM) hisoQC | $IC_{50}$ (μM) hQC | $K_i$ (μM) hQC |
|---|---|---|---|---|
| 1 | 0.0033 | 0.00162 | 0.0697 | 0.00607 |
| 2 | 0.0296 | 0.0164 | 0.741 | 0.0413 |
| 3 | 0.256 | 0.0476 | 0.0349 | 0.048 |
| 4 | 0.15 | 0.0258 | 0.56 | 0.0516 |
| 5 | 0.066 | 0.00827 | 0.182 | 0.0348 |
| 6 | 0.041 | 0.00381 | 0.234 | 0.0038 |
| 7 | 1.4 | 0.0352 | 0.43 | 0.0655 |
| 9 | 0.0303 | 0.00266 | 0.00308 | 0.00324 |
| 12 | 0.058 | 0.0105 | 0.523 | 0.036 |
| 13 | 0.052 | 0.006715 | 0.298 | 0.0428 |
| 14 | 0.04 | 0.00307 | 0.173 | 0.0217 |
| 15 | 0.06 | 0.0123 | 0.54 | 0.0585 |
| 16 | 0.0576 | 0.00414 | 0.128 | 0.0136 |
| 32 | 0.166 | 0.0409 | 0.821 | 0.159 |
| 40 | 0.0583 | 0.0114 | 0.256 | 0.0459 |
| 41 | 0.163 | 0.0345 | 0.485 | 0.0853 |

Example 6

Expression and Purification of Human isoQC in *P. pastoris*

Host Strains and Media

*Escherichia coli* strain DH5α was used for propagation of plasmids and *P. pastoris* strain X-33 was used for the expression of human isoQC in yeast. *E. coli* and *P. pastoris* strains were grown, transformed and analyzed according to the manufacturer's instructions (Qiagen (DH5α), Invitrogen (X-33)). The media required for *E. coli*, i.e. Luria-Bertani (LB) medium, was prepared according to the manufacturers recommendations. The media required for *Pichia pastoris*, i.e. BMMY, BMGY, YPD, YPDS and the concentration of the antibiotics, i.e. Zeocin, were prepared as described in the *Pichia* manual (invitrogen, catalog. No. K1740-01). The manual also includes all relevant descriptions for the handling of yeast.

Molecular Cloning of Plasmid Vectors Encoding the Human isoQC

All cloning procedures were done applying standard molecular biology techniques. For expression in *Pichia pastoris* X-33, the pPiCZαA (invitrogen) was used. The cDNA of the mature human isoQC starting with codon 30 (counting from methionine II) was fused in frame with the plasmid encoded α-factor, directing the protein into the secretory pathway. After amplification utilizing the primers hisoQC HIS C-Term pPICZAA-1 (SEQ ID NO: 28) or hisoQC HIS N-Term pPICZAA-1 (SEQ ID NO: 29) as sense-primers and hisoQC HIS N-Term pPICZAA-2 (SEQ ID NO: 30) and hisoQC HIS C-Term pPICZAA-2 (SEQ ID NO: 32) (TABLE 5) as antisense primers, the fragment was inserted into the expression vector employing the restriction sites of NotI and EcoR I. Depending on the construct, mutations were introduced in codons 55 (Ile) and 351 (Cys). The mutagenesis was performed according to standard PCR techniques followed by digestion of the parent DNA using DpnI (quik-change II site-directed mutagenesis kit, Stratagene, Catalog No. 200524). The generated constructs are illustrated schematically in FIG. 3.

Transformation of *P. pastoris* and Mini-Scale Expression 1-2 µg of plasmid DNA were applied for transformation of competent *P. pastoris* cells by electroporation according to the manufacturer's instructions (BioRad). Selection was done on plates containing 100 µg/ml Zeocin. In order to test the recombinant yeast clones upon isoQC expression, recombinants were grown for 24 h in 10 ml conical tubes containing 2 ml BMGY. Afterwards, the yeast was centrifuged and resuspended in 2 ml BMMY containing 0.5% methanol. This concentration was maintained by addition of methanol every 24 h for about 72 h. Subsequently, isoQC activity in the supernatant was determined. Clones that displayed the highest activity were chosen for further experiments and fermentation. Depending on the expressed construct, the isoQC-activity in the medium differed (FIG. 4).

Expression and Purification of hisoQC in *P. pastoris*

For large scale-expression of isoQC in *Pichia pastoris*, the conditions were kept as described in the mini-scale expression, however, the total volume was 8 l. The expression was performed in shake-flasks. After expression, cells were separated from the medium by centrifugation (1500×g, 20 min), and the pellet discarded. The pH-value of the supernatant was adjusted to neutrality, centrifuged again and applied for the first purification step. The isoQC protein was purified utilizing a 3-step protocol (TABLE 8). The purification is illustrated by SDS-PAGE analysis in FIG. 5.

TABLE 8

Purification of hisoQC (YSShisoQCN55IC351A C-His) following expression in *P. pastoris*. The purified fusion protein was used for determination of isoQC activity and pH-dependance.

|  | Purification Step | | |
| --- | --- | --- | --- |
|  | 1 | 2 | 3 |
| Method | $Ni^{2+}$-IMAC | HIC | GF (Desalting) |
| Column type (Amersham Biosciences AB, Sweden) | Chelating Sepharose Fast Flow | Butyl Sepharose 4Fast Flow | Sephadex G-25 Fine |
| Column size | d = 2.5 cm<br>l = 42 cm<br>CV = 206 $cm^3$ | d = 1.6 cm<br>l = 15.5 cm<br>CV = 23 $cm^3$ | d = 2.6 cm<br>l = 10 cm<br>CV = 53 $cm^3$ |
| Equilibration Buffer | 50 mM $NaH_2PO_4$ | 30 mM $NaH_2PO_4$<br>1M $(NH_4)_2SO_4$ | 50 mM Bis-Tris<br>100 mM NaCl |
| pH | 7.0 | 7.0 | 6.8 |
| Volume | 10 CV | 10 CV | 10 CV |
| Intermediate (Wash) Buffer | 50 mM $NaH_2PO_4$<br>0.5 mM Histidin | 30 mM $NaH_2PO_4$<br>1M $(NH_4)_2SO_4$ | — |
| pH | 7.0 | 7.0 |  |
| Volume | 10 CV | 6 CV |  |
| Elution Buffer | 50 mM $NaH_2PO_4$<br>100 mM Histidin | 30 mM $NaH_2PO_4$ | 50 mM Bis-Tris<br>100 mM NaCl |
| pH | 7.0 | 7.0 | 6.8 |
| Volume | 1.5 CV | 5 CV | 1 CV |

Results

Human isoQC was expressed in the methylotrophic yeast *P. pastoris* successfully. Several different constructs were generated, in order to select the best expression conditions in yeast (FIG. 3). As illustrated in FIG. 4, the isoQC activity that is expressed and present in the medium of the expressing cells, varies depending on the expressed construct. Introduction of a glycosylation site resulted in proper secretion, as can be observed from constructs YSShisoQCN55IC351A C-His and YSShisoQCN55I C-His. Due to the highest activity in the medium, construct YSShisoQCN55IC351A C-His was expressed in large-scale and purified. The purification was carried out as described in TABLE 8, the yield of purification was 59%. The apparent homogeneous protein was glycosylated, as evidenced by a shift in migration to lower molecular mass (FIG. 5). Glycosylation did not influence the catalytic activity of the enzyme.

Example 7

The pH-Dependence of hisoQC

The fluorometric assay using H-Gln-βNA (described in example 5) was applied to investigate the pH-dependence of the catalytic specificity. The reactions were carried out at substrate concentrations of 7 µM, i.e. at [S]<<KM. Therefore, the the observed specificity constants could be directly deduced from the initial velocity of the progress curves of substrate conversion. In these studies the reaction buffer consisted of 0.075 M acetic acid, 0.075 M MES and 0.15 M TRIS, adjusted to the desired pH using HCl or NaOH. The buffer assures a constant ionic strength over a very broad pH-range. Evaluation of the acquired enzyme kinetic data was performed using the following equation:

$$k_{cat}/K_M(\text{pH}) = k_{cat}/K_M(\text{limit}) * 1/(1+[H+]/KHS+KE1/[H+]+KE1/[H+]*KE2/[H+]),$$

in which $k_{cat}/K_M(\text{PH})$ denotes the pH-dependent (observed) kinetic parameter. $k_{cat}/K_M(\text{limit})$ denotes the pH-independent ("limiting") value. KHS, KE1 and KE2 denote the dissociation constants of an dissociating group in the acidic pH-range, and two dissociating groups of the enzyme, respectively. Evaluation of all kinetic data was performed using GraFit software (version 5.0.4. for windows, ERITHACUS SOFTWARE Ltd., Horley, UK).

Results

The hisoQC displays a pH-optimum of specificity at pH 7-8. Thus, the pH-optimum of catalysis is very similar to human QC. Fitting of the data according to a model which is based on three dissociating groups resulted in a good interpretation of the pH-dependence of hisoQC and hQC (FIG. 8). Thus, the catalysis of both enzymatic reactions is influenced by similar dissociating groups, suggesting a similar catalytic mechanism in general.

It is obvious, that only one pKa differs between hisoQC and hQC significantly. In hQC, the pKa corresponds to the pKa of the dissociation constant of the substrate. Possibly, the subtle difference between hQC and hisoQC is caused by structural changes occurring in isoQC catalysis (induced fit), influencing the pH-dependence.

Example 8

Investigation of (iso)Glutamyl Cyclase Activity

It has been described for human QC, that the enzyme catalyses the cyclization of N-terminal glutamic acid into pyroglutamic acid. Therefore, QC is involved in the generation of pGlu-modified amyloid peptides.

In order to investigate the cyclization of glutamic acid, human QC and human isoQC were purified and the formation of pGlu-modified amyloid β(3-11) [pGlu-Aβ(3-11)] from Aβ(3-11) was monitored. Reactions consisted of 20 µl substrate (Aβ(3-11), 2.5 mM stock solution in 50 mM Mes buffer, pH 6.5) and 80 µl enzyme (0.62 mg/ml hQC stock solution; 0.61 mg/ml hisoQC stock solution in 50 mM Mes pH 6.5). Samples (15 μl) were removed after 0 h, 6 h, 24 h, 48 h and 72 h and boiled for 5 min in order to terminate the reaction. The analysis of substrate conversion was monitored by Maldi-Tof mass spectrometry. Substrate and product differ in their molecular mass by 18 Da, the mass of water, which is released during cyclization.

As shown in FIG. 9, human QC and human isoQC (YSShisoQCI55NC351A C-His) catalyze the conversion of Aβ(3-11) into pGlu-Aβ(3-11). However, based on equal protein concentrations in both samples, one can conclude that the conversion of N-terminal glutamic acid by hisoQC is much slower compared with hQC. Thus, the lower specificity constants for conversion of glutaminyl substrates is also observed with glutamyl substrates. No cyclization was observed under these conditions with inactivated enzyme (Schilling, S. et al. 2004 FEBS Lett. 563, 191-196).

Example 9

Preparation and Expression of Human MCP-1 in Mammalian Cell Culture

Cell Lines and Media

Human neuroblastoma cell line SH-SY5Y, human embryonic kidney cell line HEK293 and human monocyte cell line THP-1 were cultured in appropriate cell culture media (DMEM, 10% FBS for SH-SY5Y and HEK293), (RPMI1640, 10% FBS for THP-1), in a humidified atmosphere of 5% CO2 (HEK293, THP-1) or 10% CO2 (SH-SY5Y) at 37° C.

Isolation of Human MCP-1

Full-length cDNA of human MCP-1 was isolated from SH-SY5Y cells using RT-PCR. Total RNA of SH-SY5Y cells was reversely transcribed by SuperScript II (Invitrogen) and subsequently, human MCP-1 was amplified on a 1:12.5 dilution of generated cDNA product in a 25 μl reaction with Pfu-DNA-Polymerase (Promega) using primers hMCP-1-1 (sense) and hMCP-1-2 (antisense) (TABLE 9). The resulting PCR-product was cloned into vector pcDNA 3.1 using the HindIII and NotI restriction sites and the sequence was confirmed by DNA-sequencing.

Site-Directed Mutagenesis of Human MCP-1

Deletions of the first (ΔQ1) and first and second (ΔQ1P2) amino acids of the mature human MCP-1 were generated by site-directed mutagenesis using primer ΔQ1-1 and ΔQ1-2 for ΔQ1 (TABLE 9) and primers ΔQ1P2-1 and ΔQ1P2-2 for ΔQ1P2 (TABLE 9). Parental DNA was digested with Dpn I. The pcDNA 3.1 plasmids with the deletions ΔQ1 and ΔQ1P2 of the mature human MCP-1 were transformed into E. coli JM109. Ampicillin-resistant clones were confirmed by sequencing and subsequently isolated for cell culture purposes using the EndoFree Maxi Kit (Qiagen).

Expression of N-Terminal Variants of Human MCP-1 in HEK293 Cells

For expression of N-terminal variants of human MCP-1, HEK293 cells were cultured in collagen I coated 6-well dishes and grown until 80% confluency, transfected using Lipofectamin2000 (Invitrogen) according to manufacturer's manual and incubated in the transfection solution for 5 hours. Afterwards, cells were allowed to recover in normal growth media over night. The next day, cells were incubated another 24 h in growth media. For analysis of efficacy of QC-inhibition, cells were incubated for 24 h in absence or presence of the specific inhibitor. After 24 h, the media containing the human MCP-1 variants were collected and investigated in a migration assay for chemotactic potency. Furthermore, an aliquot of cell culture supernatant was stored at −80° C. for quantification of human MCP-1 concentration using a human MCP-1-ELISA (Pierce).

TransWell Chemotaxis Assay

The chemotaxis assay was performed using 24 well TransWell plates with a pore size of 5 μm (Corning). Media containing the human MCP-1 variants expressed in HEK293 were used as chemoattractant. To this avail, 600 μl of the culture media of N-terminal human MCP-1 variants was applied undiluted or in dilutions 1:3, 1:10 and 1:30 in RPMI1640 to the lower chamber of the TransWell plate. Furthermore, undiluted media of HEK293 cells transfected with vector control were applied as negative control to the lower chamber. THP-1 cells were harvested and resuspended in RPMI1640 at a concentration of 1*106 cells/100 μl and applied in 100 μl aliquots to the upper chamber. Cells were allowed to migrate towards the chemoattractant for 2 h at 37° C. Subsequently, cells from the upper chamber were discarded and the lower chamber was mixed with 50 μl 70 mM EDTA in PBS and incubated for 15 min at 37° C. to release cells attached to the membrane. Afterwards, cells migrated to the lower chamber were counted using a cell counter system (Schärfe System). The chemotactic index was calculated by dividing cells migrated to the stimulus from cells migrated to the negative control.

TABLE 9

Utilized primers

| Primer | Sequence (5'→3') | Application | SEQ ID NO |
|---|---|---|---|
| hMCP-1-1 | ATAT AAGCTT ATGAAAGTCTCTGCCGCCCTTC | Isolation of human MCP-1 | 110 |
| hMCP-1-2 | ATAT GCGGCCGC TCAAGTCTTCGGAGTTTGGG | Isolation of human MCP-1 | 111 |
| ΔQ1-1 | CATTCCCCAAGGGCTCGCTCCAGATGCAATCAATGCC | Site-directed mutagenesis ΔQ1 | 112 |
| ΔQ1-2 | GGCATTGATTGCATCTGGAGCGAGCCCTTGGGGAATG | Site-directed mutagenesis ΔQ1 | 113 |

TABLE 9-continued

Utilized primers

| Primer | Sequence (5'→3') | Application | SEQ ID NO |
|---|---|---|---|
| ΔQ1P2-1 | CATTCCCCAAGGGCTCGCTGATGCAATCAATGCCCCAG | Site-directed mutagenesis ΔQ1P2 | 114 |
| ΔQ1P2-2 | CTGGGGCATTGATTGCATCAGCGAGCCCTTGGGGAATG | Site-directed mutagenesis ΔQ1P2 | 115 |

Example 10

Subcellular Localization of Rat and Mouse isoQC

A. Cloning Procedures

For the cloning for EGFP-tagged rat and mouse isoQC, the EGFP sequence of vector pEGFP-N3 (Invitrogen) was introduced into vector pcDNA 3.1 (Invitrogen) using primers 1 (sense) (SEQ ID NO: 61) and 2 (antisense) (SEQ ID NO: 62) (see TABLE 10 below) for amplification. The fragment was introduced into the XhoI site of pcDNA 3.1. The generated vector was termed pcDNA-EGFP. The cDNA of the native mouse-isoQC starting either at MetI (SEQ ID NO: 53) or MetII (SEQ ID NO: 54) and rat-isoQC starting either at MetI (SEQ ID NO: 55) or MetII (SEQ ID NO: 56) was fused C-terminally in frame with EGFP in vector pcDNA-EGFP. The primers 3 (sense) (SEQ ID NO: 63) and 4 (antisense) (SEQ ID NO: 64) (TABLE 10) were used for amplification of mouse-isoQC starting with MetI (SEQ ID NO: 53) and primers 5 (sense) (SEQ ID NO: 65) and 4 (antisense) (SEQ ID NO: 64) (TABLE 10) were used for amplification of mouse-isoQC starting with MetII (SEQ ID NO: 54). Primers 6 (sense) (SEQ ID NO: 66), 7 (antisense) (SEQ ID NO: 67) and 5 (sense) (SEQ ID NO: 65) and 7 (antisense) (SEQ ID NO: 67) (TABLE 10) were used for amplification of rat-isoQC starting with MetI (SEQ ID NO: 55) and MetII (SEQ ID NO: 56), respectively. The fragments were inserted into vector pcDNA-EGFP employing the restriction sites of EcoRI and NotI and correct insertion of the fragments was confirmed by sequencing. The N-terminal sequences of mouse-isoQC beginning at MetI and MetII each ending at serine 55 (counting from MetI) (of both SEQ ID NOs: 57 and 58) and rat-isoQC beginning at MetI and MetII each ending at serine 55 (counting from MetI) (of both SEQ ID NOs: 59 and 60) were also fused C-terminally with EGFP in vector pcDNA-EGFP using primer 3 (sense) (SEQ ID NO: 63) and primer 8 (antisense) (SEQ ID NO: 68) (TABLE 10) for the N-terminal fragment of mouse-isoQC beginning with MetI and primer 5 (sense) (SEQ ID NO: 65) and primer 8 (antisense) (SEQ ID NO: 68) (TABLE 10) for the fragment starting with MetII. The N-terminal fragments of rat-isoQC were amplified using primer 6 (sense) (SEQ ID NO: 66) and primer 9 (antisense) (SEQ ID NO: 69) (TABLE 10) for starting with MetI, and primer 5 (sense) (SEQ ID NO: 65) and primer 9 (antisense) (SEQ ID NO: 69) (TABLE 10) for starting with MetII. Subsequently, all vectors were isolated for cell culture purposes using the EndoFree Maxi Kit (Qiagen).

TABLE 10

Oligonucleotide primers used for cloning of m-isoQC and r-isoQC into vector pcDNA 3.1

| Primer | Sequence (5'→3'), restriction sites (underlined) | Purpose | SEQ ID NO: |
|---|---|---|---|
| 1 | ATAT<u>CTCGAG</u>TCCATCGCCACCATG GTGAGC | Amplification of EGFP | 61 |
| 2 | ATAT<u>CTCGAG</u>TTACTTGTACAGCTCG TCCAT | Amplification of EGFP | 62 |
| 3 | ATAT<u>GAATTC</u>ATGAGTCCCGGGAGC CGC | Amplification of m-isoQC starting with MetI | 63 |
| 4 | ATAT<u>GCGGCCGC</u>ATGAGTCCCAGGT ACTCGGCCAG | Amplification of m-isoQC lacking the stop codon | 64 |
| 5 | ATAT<u>GAATTC</u>ATGAAACCACCCTCACT T | Amplification of m-isoQC and r-isoQC starting with MetII | 65 |
| 6 | ATAT<u>GAATTC</u>ATGAGTCCGGCCAGC CGC | Amplification r-isoQC starting with MetI | 66 |
| 7 | ATAT<u>GCGGCCGC</u>ATGAGACCCAGGT ACTCAGCCAG | Amplification of r-isoQC lacking the stop codon | 67 |
| 8 | ATAT<u>GCGGCCGC</u>ATGCTGTTCCAGA CGATATAGAAAGC | Amplification of m-isoQC N-terminal sequence | 68 |
| 9 | ATAT<u>GCGGCCGC</u>ATGCTATTCCAGA CGATATAAAAGC | Amplification of r-isoQC N-terminal sequence | 69 |

B. Cultivation and Transfection of Mammalian Cells

The human astrocytoma cell line LN405 and the human neuroblastoma cell line SH-SY5Y were cultured in appropriate cell culture media (Dulbecco's modified Eagle medium, 10% fetal bovine serum), in a humidified atmosphere of 10% $CO_2$ at 37° C. For transfection, LN405 and SH-SY5Y cells were cultured in 2-well chamber slides (BD Falcon), grown until 80% confluency and transfected by incubation in a solution containing Lipofectamin2000 (Invitrogen) and the respective plasmids (as obtained above in Step A) according to the manufacturer's manual. The solution was replaced with appropriate growth media after 5 h and cells were grown overnight.

C. Histochemical Analysis

For histochemical analysis LN405 and SH-SY5Y cells were washed twice with D-PBS (Invitrogen), one day after transfection and fixed using ice-cold methanol for 10 min at −20° C., followed by three washing steps of D-PBS for 5 min at room temperature. For the staining of the Golgi complex, LN405 and SH-SY5Y cells were incubated with anti-mannosidase II polyclonal antibody (Chemicon) in a 1:100 dilution of antibody in D-PBS for 3 h at room temperature. Subsequently, the cells were washed three times with D-PBS for 5 min. The cells were incubated with goat anti-rabbit IgG secondary antibody conjugated with Cy3 at room temperature in the dark for 45 min. Afterwards, the samples were washed three times with D-PBS for 5 min and were incubated with 1 μg/ml 4',6-Diamidin-2'-Phenylindole-(DAPI) solution (Roche) for two minutes for staining of the nucleus and washed once with D-PBS. The coverslips were mounted on the microscope slide with Citifluor (Citiflour Ltd., Leicester, UK). Cells were observed with a confocal laser scanning microscope (Carl-Zeiss).

D. Results

In order to investigate the subcellular localization of mouse-isoQC and rat-isoQC in mammalian cells and the relevance of the putative start methionines, mouse-isoQC-EGFP and rat-isoQC-EGFP fusions beginning either at methionine I (MetI) or at methionine II (MetII) were generated. Human LN405 and SH-SY5Y cells were transiently transfected and the subcellular distribution was examined using confocal laser scanning microscopy. The expression of mouse-isoQC (MetI)-EGFP and rat-isoQC-(MetI)-EGFP fusion proteins resulted in a distinct staining close to the nucleus of virtually all cells expressing the transgene (FIGS. 9a, 10a, 11a and 12a). Counterstaining of cellular mannosidase II revealed the presence of mouse-isoQC (MetI)-EGFP and rat-isoQC (MetI)-EGFP within the Golgi complex in LN405 and SH-SY5Y. Expression of mouse-isoQC (MetII)-EGFP and rat-isoQC (MetII)-EGFP fusion proteins resulted in a very similar fluorescence staining, which matched well with the localization of mannosidase II (FIGS. 9a, 10a, 11a and 12a). Thus, the subcellular distribution of mouse-isoQC and rat-isoQC is independent of the N-terminal methionine.

In order to clarify whether the predicted N-terminal signal anchor is responsible for the retention of mouse-isoQC and rat-isoQC within the Golgi complex, the signal peptides starting at MetI and MetII, including the putative signal anchor sequences, were cloned in-frame with EGFP. The resulting vectors mouse-isoQC (MetI) signal sequence (SS) EGFP, mouse-isoQC (MetII) SS EGFP, rat-isoQC (MetI) SS EGFP and rat-isoQC (MetII) SS EGFP were expressed in LN405 and SH-SY5Y cells as described before and the expression was also analyzed by confocal laser scanning microscopy. The expression of the four vectors resulted in the same Golgi complex localization that was observed for the full length fusion proteins (FIGS. 9b, 10b, 11b and 12b). Consequently, the N-terminal sequence of isoQC results in the co-translational translocation of the mouse-isoQC and rat-isoQC to the membrane of the endoplasmatic reticulum and in the retention within the Golgi complex. Furthermore, due to the expression of mouse-isoQC (MetII) SS EGFP and rat-isoQC (MetII) SS EGFP, the Golgi retention signal can be grossly mapped between residues methionine 19 and serine 55 of both, SEQ ID NO's: 58 and 60, respectively.

Example 11

Gene Expression of QC (QPCT) and isoQC (QPCTL) in RAW264.7 and THP-1 Cells

A. Characterization of RAW264.7 Cells

The murine monocyte/macrophage cell line RAW264.7 (in the following: RAW) was obtained from CLS (Eppelheim, Germany). RNA was isolated using the NucleoSpin RNA II kit (Macherey Nagel) according to the manufacturer's instructions. Constant 1000 ng of RNA were reversely transcribed to cDNA using random primers (Roche) and Superscript II (Invitrogen). Quantitative real-time PCR was performed in a Rotorgene3000 (Corbett Research) using the QuantiTect SYBR Green RT-PCR kit (Qiagen). Applied primers are depicted in TABLES 11A and 11B.

An initial 15 min activation step at 95° C. was performed, followed by 45 cycles of 15 sec denaturation at 95° C., annealing for 20 sec at 60° C. (for Qiagen primers at 55° C.), and 20 sec extension at 72° C. Gene expression was determined with the Rotorgene software version 4.6 in quantitation mode. For verification of the PCR, product melting curves were generated and amplicons were confirmed by agarose gel electrophoresis.

B. Characterization of THP-1 Cells

THP1 (human acute monocytic leukemia) cells were obtained from CLS (Eppelheim, Germany). RNA isolation, cDNA synthesis and PCR were done as described for RAW cells. Primers used for quantification of human QPCT and human QPCTL are depicted in TABLE 12.

C. Results

Using primer pairs, which are amplifying products within exon 1 of murine QPCT (mQPCT), PCR products could be obtained (FIG. 13(a), primer pairs F5/R6 (SEQ ID NO's: 70 and 73), F5/R14 (SEQ ID NO's: 70 and 74), F5/R16 (SEQ ID NO's: 70 and 75); see TABLE 11A). In contrast, primer pairs binding to the regions of exon 2 to exon 7 did not result in the detection of products with cDNA isolated from RAW cells (FIG. 13(a), primer pairs F5/R12 (SEQ ID NO's: 70 and 76), F5/R20 (SEQ ID NO's: 70 and 77), F3/R4 (SEQ ID NO's: 71 and 78), F3/R20 (SEQ ID NO's: 70 and 77), F3/R2 (SEQ ID NO's: 70 and 79), F11/R22 (SEQ ID NO's: 72 and 80), TABLE 11A, primers obtained from Qiagen). All primer pairs amplified products with cDNA isolated from B16 murine melanoma cells as well as from murine brain tissue. Consequently, RAW cells did not express full-length mQPCT mRNA. RAW cells, B16 cells as well as murine brain tissue expressed murine QPCTL (mQPCTL) (TABLE 11B, FIG. 13(a). RAW cells did not express full-length mQPCT RNA but expressed mQPCTL; therefore, this cell line is a useful tool for in vitro testing of inhibitors of the mQPCTL activity

TABLE 11A

Oligonucleotides for amplification of murine QPCT and murine QPCTL mQPCT NM_027455 Mus musculus glutaminyl-peptide cyclotransferase (glutaminyl cyclase) (Qpct), mRNA

| 5' Primer Sequence | SEQ ID NO: | 3' Primer Sequence | SEQ ID NO: |
|---|---|---|---|
| F5 GGGAGGCAGACACAATCAAT | 70 | R6 TCAGATTCCCAGCTGTCAGA | 73 |

TABLE 11A-continued

| | | | | | |
|---|---|---|---|---|---|
| F5 | GGGAGGCAGACACAA TCAAT | 70 | R14 | GCAGCGGAGACCAG ACTCA | 74 |
| F5 | GGGAGGCAGACACAA TCAAT | 70 | R16 | AGGCAGCGGAGACC AGA | 75 |
| F5 | GGGAGGCAGACACAA TCAAT | 70 | R12 | GGTTGGTGGTGGTT CTTCTC | 76 |
| F5 | GGGAGGCAGACACAA TCAAT | 70 | R20 | CTGAATTCGTTGCA TGATGTG | 77 |
| F3 | TCTGACAGCTGGGAAT CTGA | 71 | R4 | CCCACTCAGCCTGA AGTCTC | 78 |
| F3 | TGACAGCTGGGAATCT GAGT | 71 | R20 | CTGAATTCGTTGCA TGATGTG | 77 |
| F3 | TGACAGCTGGGAATCT GAGT | 71 | R2 | CTTCCGGGTTAAGA GTGCTG | 79 |
| F11 | GGCATGGATCTGTTGG TCTT | 72 | R22 | GTGCCAGACTTCAG GGAAAG | 80 |

Qiagen QT01057056 mQPCT mQPCTL NM_026111 *Mus musculus* glutaminyl-peptide cyclotransferase-like (Qpctl), mRNA

| 5' Primer Sequence | SEQ ID NO: | 3' Primer Sequence | SEQ ID NO: |
|---|---|---|---|
| QPCTL-F GCTATGGGCTTGGCTT TCTA | 81 | QPCTL-R CAATAAGGGACGCA GGAAAG | 82 |

TABLE 12

Oligonucleotides for amplification of human QPCT and human QPCTL

| Primer | Product [bp] | Amplified exons | Amplification THP-1 cells |
|---|---|---|---|
| NM_012413 *Homo sapiens* glutaminyl-peptide cyclotransferase (QPCT), mRNA | | | |
| Qiagen QT00013881 hQPCT | 108 | 3/4 | Yes |
| NM_017659 *Homo sapiens* glutaminyl-peptide cyclotransferase-like (QPCTL) mRNA | | | |
| Qiagen QT00074074 hQPCTL | 120 | 2/3 | Yes |

Example 12

Potency of Different isoQC-Inhibitors in RAW264.7 and THP-1 Cells

A. Inhibition of pGlu-MCP-1 Formation in RAW264.7

The mouse monocyte/macrophage cell line RAW264.7 was used to investigate the effect of glutaminyl cyclase (QC) inhibitors as well as isoglutaminyl cyclase (QPCTL) inhibitors on the formation of the N-terminal pyroglutamate (pGlu) of MCP-1 secreted by the cells after LPS stimulation. 40.000 cells/100 µl were seeded per well in a 96-well microplate and grown in DMEM (Invitrogen) containing 10% FBS and Gentamycin (Invitrogen). After 24 h the medium was changed to 150 µl DMEM/10% FBS/Gentamycin containing an appropriate concentration of inhibitor or control (DMSO). For inhibitor screening experiments the test compounds were used in a final concentration of 10 µM. Four replicates were performed for each compound. 30 min after inhibitor application cells were stimulated by addition of LPS (10 ng/ml, from *E. coli* strain O55:B5, Sigma). 24 h after LPS stimulation, the supernatant was harvested and stored at −20° C. until

TABLE 11B

Results of the amplification of murine QPCT and murine QPCTL

| 5' Primer | 3' Primer | Product [bp] | Found in Brain tissue | Found in B16 cells | Found in RAW cells | Amplified exons |
|---|---|---|---|---|---|---|
| mQPCT NM_027455 *Mus musculus* glutaminyl-peptide cyclotransferase (glutaminyl cyclase) (Qpct), mRNA | | | | | | |
| F5 | R6 | 211 | Yes | Yes | Yes | 1 |
| F5 | R14 | 227 | Yes | Yes | Yes | 1 |
| F5 | R16 | 229 | Yes | Yes | Yes | 1 |
| F5 | R12 | 257 | Yes | Yes | No | 1/2 |
| F5 | R20 | 410 | Yes | Yes | No | 1/3 |
| F3 | R4 | 239 | Yes | Yes | No | 1/2 |
| F3 | R20 | 218 | Yes | Yes | No | 1/3 |
| F3 | R2 | 218 | Yes | Yes | No | 1/3 |
| F11 | R22 | 273 | Yes | Yes | No | 4/7 |
| Qiagen | | 104 | Yes | Yes | No | 5/6 |
| mQPCTL NM_026111 *Mus musculus* glutaminyl-peptide cyclotransferase-like (Qpctl), mRNA | | | | | | |
| QPCTL-F | QPCTL-R | 180 | Yes | Yes | Yes | 1/2 |

In addition, human THP1 cells expressed both human QPCT (hQPCT) mRNA as well as human QPCTL (hQPCTL) mRNA. Treatment of THP1 cells with LPS (1 µg/ml) for 24 h increased hQPCT mRNA levels whereas hQPCTL RNA showed constant levels (FIG. 14). THP1 cells can be used as a human in vitro screening model for QPCT (QC) and QPCTL (isoQC) inhibitors.

analysis of MCP-1. Total MCP-1 and pGlu1-MCP-1 (mMCP-1 N1pE) were determined by specific ELISAs. (See Example 12B below)

B. ELISA for Detection of Total mMCP-1 and mMCP-1 N1pE

For determination of total mMCP-1 and mMCP-1 N1pE, specific ELISAs were developed. Briefly, 25 ng of capture antibody rabbit-anti mJE (Peprotech) were coated per well of a 96 well plate in coating buffer (PBS, pH 7.4). Plates were incubated over night at room temperature. Afterwards, each well was blocked for 2 h by addition of 200 µl blocking buffer (protein free (TBS) blocking buffer (Perbio)) and then washed 3 times using 300 µl of wash buffer (protein free T20 (TBS) blocking buffer (Perbio)). Standard peptides (Peprotech) and samples were diluted using dilution buffer (protein free T20 (TBS) blocking buffer)) and 100 µl were applied onto the test plate. The incubation of test samples and standard peptides was carried out for 2 h at room temperature and afterwards the plate was washed 3 times using wash buffer. For detection of mMCP-1 N1pE, anti-pE1-MCP-1 specific monoclonal antibody clone 4B8 (produced by Probiodrug, 0.65 mg/ml) was applied in a concentration of 0.25 µg/ml in combination with anti-mouse-HRP conjugate (KPL) in a dilution of 1:2000. For the detection of total MCP-1, rat-anti mouse MCP-1 (R&D Systems, 1 mg/ml) was applied in a concentration of 0.25 µg/ml in combination with anti-rat-HRP conjugate (Sigma) in a dilution of 1:2000. Antibodies were diluted in dilution buffer, applied in a volume of 100 µl to each well and incubated for 2 h at room temperature. Thereafter, wells were washed 5 times with 300 µl of wash buffer followed by application of the chromogen SureBlue (KPL) in a volume of 100 µl to each well. After incubation in the dark for 30 min, the reaction was abrogated using 50 µl Stop Solution (1.2 N $H_2SO_4$) and absorption was determined at 450 nm. The reference wavelength of 550 nm was subtracted from sample absorption at 450 nm.

C. Results

Using the mMCP-1 N1pE assay in RAW264.7 cells, the efficacy of QC inhibitors to suppress the formation of pGlu1-MCP-1 by the mouse-QC-negative and mouse-isoQC-positive cell line RAW264.7 could be demonstrated. A correlation of the inhibitor constants for human-isoQC with the inhibition of pGlu-MCP-1 formation was found. Only compounds, which show a strong inhibition of isoQC ($K_i$<100 nM) are capable of efficiently inhibiting the formation of pGlu-MCP-1, whereas strong QC but weak isoQC inhibitors show only weak cellular potency in inhibiting pGlu-MCP-1 formation in RAW264.7 cells.

Thus, the RAW cells provide an excellent system to investigate the inhibition of isoQC independently from potential disturbing influences of substrate conversion by QC.

Example 13

Methods for the Isolation and Characterization of isoQCs from Different Mammalian Origins Including Methods for Protein Detection by Western-Blot A. Host Strains and Media

*Escherichia coli* strain DH5α was used for propagation of plasmids and *P. pastoris* strain X-33 was used for the expression of human isoQC in yeast. *E. coli* and *P. pastoris* strains were grown, transformed and analyzed according to the manufacturer's instructions (Qiagen (DH5α), Invitrogen (X-33)). The media required for *E. coli*, i.e. Luria-Bertani (LB) medium, was prepared according to the manufacturers recommendations. The media required for *Pichia pastoris*, i.e. BMMY, BMGY, YPD, YPDS and the concentration of the antibiotics, i.e. Zeocin, were prepared as described in the *Pichia* Manual (Invitrogen, catalog. No. K1740-01). The manual also includes all relevant descriptions for the handling of yeast.

B. Molecular Cloning of Plasmid Vectors Encoding the Mouse isoQC

All cloning procedures were performed applying standard molecular biology techniques. For expression in *Pichia pastoris* X-33, the pPiCZαA vector (Invitrogen) was used. The cDNA of the mature mouse isoQC starting with codon 43 (Glu 43) of the open reading frame (counting from methionine II, i.e. the transmembrane sequence is omitted and not inserted into the yeast expression vector, as shown in FIG. 15) was fused in frame with the pPiCZαA-plasmid-encoded α-factor secretion signal, directing the protein into the secretory pathway. After amplification of mouse-isoQC utilizing the primer 10 (sense) (SEQ ID NO: 83) and primer 11 (antisense) (SEQ ID NO: 84) (TABLE 13), the fragment was inserted into the expression vector employing the restriction sites of NotI and EcoR I. For insertion of a glycosylation site, a mutation was introduced in codon 56 (Ile56Asn) of the open reading frame of isoQC (again assuming that methionine II is the first amino acid of the protein) by primers 12 (sense) (SEQ ID NO: 85) and 13 (antisense) (SEQ ID NO: 86) (TABLE 13). The mutagenesis was performed according to standard PCR techniques followed by digestion of the parent DNA using DpnI (quik-change II site-directed mutagenesis kit, Stratagene, Catalog No. 200524).

TABLE 13

Oligonucleotides used for cloning and mutation of murine isoQC

| Oligo-nucleo-tide | Sequence (5'→3'), restriction sites (underlined) | Purpose | SEQ ID NO: |
|---|---|---|---|
| 10 | ATAT<u>GAATTC</u>GAGGAGATGTCACGGAGC | Amplification of m-isoQC starting with Glu 43 | 83 |
| 11 | ATATAT<u>GCGGCCGC</u>CTAGAGTCCCAGGTACTCGGC | Amplification of m-isoQC for insertion into pPICZαA vector | 84 |
| 12 | GATCTGCGGGTCCCGCTGAACGGAAGCCTTTCAGAAGCC | Change of Ile 56 to Asn | 85 |
| 13 | GGCTTCTGAAAGGCTTCCGTTCAGCGGGACCCGCAGATC | Change of Ile 56 to Asn | 86 |

C. Transformation of *P. pastoris* and Mini-Scale Expression 1-2 µg of plasmid DNA were applied for transformation of competent *P. pastoris* cells by electroporation according to the manufacturer's instructions (BioRad). Selection was done on plates containing 100 µg/ml Zeocin. In order to test the recombinant yeast clones for mouse-isoQC expression, cells were grown for 24 h in 10 ml conical tubes containing 2 ml BMGY. Afterwards, the yeast was centrifuged and resuspended in 2 ml BMMY containing 0.5% methanol. This concentration was maintained by addition of methanol every 24 h for about 72 h. Subsequently, QC activity in the supernatant was determined. Clones that displayed the highest activity were chosen for further experiments and fermentation.

D. Expression and Purification of m-isoQC in *Pichia pastoris*

Large scale-expression of isoQCs in *Pichia pastoris* was performed in a 5 l reactor (Biostad B; Braun Biotech, Melsungen, Germany). Briefly, the fermentation was carried out in basal salt medium supplemented with trace salts at pH 5.5. Initially, the biomass was accumulated in a batch and a fed-batch phase with glycerol as the sole carbon source for about 28 h. Expression of the isoQCs was initiated by methanol-feeding according to a three-step profile recommended by Invitrogen for an entire fermentation time of approximately 65 h. After expression, the cells were separated from the medium by centrifugation (8000×g, 20 min), and the pellet was discarded. Ammonia was added to the supernatant to a final concentration of 0.8 M, subsequently again centrifuged and the resulting supernatant was further used for the first purification step. The isoQC proteins were purified utilizing a 4-step protocol (TABLE 14). Purified protein was used for determination of QC activity and analysis of metal content. The purification is illustrated in FIG. 16.

Expression and Purification of Rat-isoQC in *P. pastoris*

Large-scale expressions of isoQCs in *Pichia pastoris* were performed in a 5 l reactor (Biostad B; Braun Biotech, Melsungen, Germany). Briefly, fermentation was carried out in basal salt medium supplemented with trace salts at pH 5.5. Initially, biomass was accumulated in a batch and a fed batch phase with glycerol as the sole carbon source for about 28 h. Expression of the isoQCs was initiated by methanol feeding according to a three-step profile recommended by Invitrogen for an entire fermentation time of approximately 65 h. After expression, cells were separated from the medium by centrifugation (8000×g, 20 min), and the pellet discarded. The pH-value of the supernatant was adjusted to neutrality, centrifuged again and applied for the first purification step. The isoQC protein was purified utilizing a 3-step protocol (TABLE 16). The purification is illustrated by SDS-PAGE analysis in FIG. 17.

TABLE 14

Scheme of the purification of mouse isoQC following expression in *P. pastoris*.

| | Purification Step | | | |
|---|---|---|---|---|
| | 1 | 2 | 3 | 4 |
| Method | HIC-EBA | HIC | IEX | SEC |
| Column type (Amersham Biosciences AB, Sweden) | STREAMLINE Butyl | Butyl Sepharose 4 Fast Flow | UNO Q | Superdex 75 prep grade |
| Column size | d = 2.5 cm l = 42 cm CV = 206 cm$^3$ | d = 2.6 cm l = 10 cm CV = 53 cm$^3$ | d = 1.2 cm l = 5.3 cm CV = 6 cm$^3$ | d = 2.6 cm l = 87 cm CV = 461 cm$^3$ |
| Equilibration Buffer | 50 mM NaH$_2$PO$_4$ 0.8M (NH$_4$)$_2$SO$_4$ | 50 mM NaH$_2$PO$_4$ 0.7M (NH$_4$)$_2$SO$_4$ | 30 mM Bis-Tris | 30 mM NaH$_2$PO$_4$ |
| pH | 7.0 | 7.0 | 6.8 | 7.0 |
| Volume | 4 CV | 4 CV | 5 CV | 2 CV |
| Intermediate (Wash) Buffer | 50 mM NaH$_2$PO$_4$ 0.8M (NH$_4$)$_2$SO$_4$ | 50 mM NaH$_2$PO$_4$ 0.7M (NH$_4$)$_2$SO$_4$ | 30 mM Bis-Tris | — |
| pH | 7.0 | 7.0 | 6.8 | |
| Volume | 5 CV | 4 CV | 4 CV | |
| Elution Buffer | 50 mM NaH$_2$PO$_4$ | 50 mM NaH$_2$PO$_4$ Gradient from 0.7-0 M AS | 30 mM Bis-Tris; 3M NaCl (0-15% Gradient) | 30 mM NaH$_2$PO$_4$ 0.5M NaCl |
| pH | 7.0 | 7.0 | 6.8 | 7.0 |
| Volume | 1.5 CV | 5 CV | 10 CV | 1.5 CV |

E. Fluorometric Assays and Spectrophotomeric Assay for the Determination of QC Activity These assays were performed as described in Example 5.

F. Expression and Purification of Rat-isoQC in *Pichia pastoris*

Molecular Cloning of Plasmid Vectors Encoding the Rat isoQC

All cloning procedures were done applying standard molecular biology techniques. For expression in *Pichia pastoris* X-33, the pPiCZαA (Invitrogen) was used. The cDNA of the mature rat-isoQC starting with codon 43 (counting from methionine II, FIG. 15) was fused in frame with the plasmid encoded α-factor, directing the protein into the secretory pathway. After amplification utilizing the primer 14 (SEQ ID NO: 87) as sense and primer 15 (SEQ ID NO: 88) as antisense (TABLE 15), the fragment was inserted into the expression vector employing the restriction sites of NotI and EcoRI. A mutation was introduced in codon 56 (Ile56Asn) using primer 16 (sense) (SEQ ID NO: 89) and primer 17 (antisense) (SEQ ID NO: 90). The mutagenesis was performed according to standard PCR techniques followed by digestion of the parent DNA using DpnI (quik-change II site-directed mutagenesis kit, Stratagene, Catalog No. 200524).

TABLE 15

Oligonucleotides used for cloning and mutation of rat isoQC

| Oligo-nucleo-tide | Sequence (5'→3'), restriction sites (underlined) | Purpose | SEQ ID NO |
|---|---|---|---|
| 14 | ATAT<u>GAATTC</u>CATCACCATCACCAT CACGAGGAGGTATCACGGAGC | Amplification of r-isoQC starting with Glu 43 and N-terminal His-Tag | 87 |
| 15 | ATATAT<u>GCGGCCGC</u>CTAGAGACCC AGGTACTCAGC | Amplification of r-isoQC for insertion into pPICZαA vector | 88 |
| 16 | GATCTGCGGGTCCCGCTGAACGGA AGCCTTTCAGAAGCC | Mutation of Ile 56 into | 89 |

TABLE 15-continued

Oligonucleotides used for cloning and mutation of rat isoQC

| Oligo-nucleo-tide | Sequence (5'→3'), restriction sites (underlined) | Purpose | SEQ ID NO |
|---|---|---|---|
| 17 | GGCTTCTGAAAGGCTTCCGTTCAGC GGGACCCGCAGATC | Mutation of Ile 56 into Asn | 90 |

TABLE 16

Purification of rat-isoQC following expression in *P. pastoris*. The purified fusion protein was used for determination of QC activity and generation of a polyclonal antibody.

| | Purification Step | | |
|---|---|---|---|
| | 1 | 2 | 3 |
| Method | $Ni^{2+}$-IMAC | HIC | GF (Desalting) |
| Column type (Amersham Biosciences AB, Sweden) | Chelating Sepharose Fast Flow | Butyl Sepharose 4Fast Flow | Sephadex G-25 Fine |
| Column size | d = 2.5 cm l = 42 cm CV = 206 $cm^3$ | d = 1.6 cm l = 15.5 cm CV = 23 $cm^3$ | d = 2.6 cm l = 10 cm CV = 53 $cm^3$ |
| Equilibration Buffer | 50 mM $NaH_2PO_4$ | 30 mM $NaH_2PO_4$ 1M $(NH_4)_2SO_4$ | 50 mM Bis-Tris 100 mM NaCl |
| pH | 7.0 | 7.0 | 6.8 |
| Volume | 10 CV | 10 CV | 10 CV |
| Intermediate (Wash) Buffer | 50 mM $NaH_2PO_4$ 0.5 mM Histidin | 30 mM $NaH_2PO_4$ 1M $(NH_4)_2SO_4$ | — |
| pH | 7.0 | 7.0 | |
| Volume | 10 CV | 6 CV | |
| Elution Buffer | 50 mM $NaH_2PO_4$ 100 mM Histidin | 30 mM $NaH_2PO_4$ | 50 mM Bis-Tris 100 mM NaCl |
| pH | 7.0 | 7.0 | 6.8 |
| Volume | 1.5 CV | 5 CV | 1 CV |

G. Generation of isoQC-Specific Antibodies and Detection of isoQCs by Western Blot Analysis The purified recombinant proteins human-isoQC and rat-isoQC protein, together with an adjuvant were used to immunize rabbits. Following five injections, rabbits were sacrificed and the antibodies purified by lectin affinity chromatography. Two rabbits were immunized using human isoQC (h-isoQC), two further animals received rat isoQC (r-isoQC) injections.

For the detection of native isoQCs, specific polyclonal antibodies against human-isoQC (pAb 3284) and rat-isoQC (pAb 3286, both developed and produced by Probiodrug AG, were obtained. To characterize the specificity of the antibodies, HEK293 cells were transfected with human-isoQC, human QC, rat-isoQC and rat QC. Cells ($2*10^6$) and media were analyzed for QC and isoQC expression. Furthermore, untransfected cells ($3*10^6$) from different mammalian species (HEK293 cells, SH-SY5Y cells, U343 cells, RAW264.7 cells, N2a cells and PC12 cells) were analyzed for basal isoQC expression. For immunoblotting, the cells were disrupted using 200 μl RIPA buffer (Pierce) and sonicated for 10 s. Protein was loaded onto a Tris-Glycine, 4-20% gradient, SDS-PAGE gel (Serva) and separated. Proteins were transferred onto a nitrocellulose membrane (Roth) using semi-dry conditions. Subsequently, the membrane was blocked for 2 h using 5% (w/v) dry milk in TBS-T [20 mM Tris/HCl (pH 7.5), 500 mM NaCl, 0,05% (v/v) Tween 20]. For the detection of isoQCs the antibodies were diluted 1:1000 in 5% dry milk in TBS-T and incubated over night at 4° C. Blots were developed by applying horseradish peroxidase-conjugated secondary antibodies (anti-rabbit, Cell Signaling) and the SuperSignal West Pico System (Pierce) according to the manufacturer's guidelines.

H. Results (1) Expression and Purification of Mouse-isoQC

Mouse-isoQC was successfully expressed in the methylotrophic yeast *P. pastoris*. The protein starting with glutamate 43 including a glycosylation site at position 56 was expressed in large scale by fermentation in a 5 l bioreactor. The purification was carried out as described in TABLE 14. The purification procedure resulted in isolation of homogeneous recombinant protein (FIG. 16).

(2) Expression and Purification of Rat-isoQC

Rat-isoQC was expressed in the methylotrophic yeast *P. pastoris* successfully. The protein starting with glutamate 43 including a glycosylation site at position 56 (according to h-isoQC expression in *P. pastoris*) could be expressed in large scale by fermentation. The purification was carried out as described in TABLE 16. The purification procedure resulted in isolation of homogeneous recombinant protein (FIG. 17).

(3) Characterization of Mouse-isoQC and Rat-isoQC

Several different peptide substrates were analyzed (TABLE 17). All substrates were converted by mouse-isoQC and rat-isoQC, suggesting a broad substrate specificity similar to human isoQC. Highest specificity constants ($k_{cat}/K_M$) were observed for substrates carrying large hydrophobic amino acids adjacent to the N-terminal glutaminyl residue, e.g. Gln-Phe-Ala (QFA). In contrast, negatively charged residues in that position led to a drastic drop in specificity, as observed for Gln-Glu (QE), indicating a negatively charged active site of mouse-isoQC. Compared to human isoQC, mouse-isoQC exerted a two to three times higher enzymatic activity (FIG. 18). The broad specificity supports conversion of many different physiological substrates by all isoQCs described in this invention.

TABLE 17

Kinetic parameters of conversion of peptide substrates by murine and rat isoQC

| Substrate | $K_M$ (mM) m-isoQC | $k_{cat}$ ($s^{-1}$) m-isoQC | $k_{cat}/K_M$ ($mM^{-1} * s^{-1}$) m-isoQC | $k_{cat}/K_M$ ($mM^{-1} * s^{-1}$) r-isoQC |
|---|---|---|---|---|
| Q-βNA | 0.032 ± 0.003 | 17.48 ± 0.97 | 554.36 ± 47.02 | 475.77 ± 23.25 |
| Q-AMC | 0.022 ± 0.001 | 6.98 ± 0.35 | 311.31 ± 27.16 | 224.71 ± 36.12 |
| QQ | 0 092 ± 0.005 | 8.66 ± 0.37 | 95.08 ± 6.06 | 67.49 ± 4.65 |
| QE | 0.47 ± 0.04 | 7.79 ± 0.44 | 16.88 ± 2.32 | 9.74 ± 0.16 |
| QG | 0.16 ± 0.01 | 4.57 ± 0.12 | 28.58 ± 1.77 | 18.78 ± 0.68 |

TABLE 17-continued

Kinetic parameters of conversion of peptide substrates by murine and rat isoQC

| Substrate | $K_M$ (mM) m-isoQC | $k_{cat}$ (s$^{-1}$) m-isoQC | $k_{cat}/K_M$ (mM$^{-1}$ * s$^{-1}$) m-isoQC | $k_{cat}/K_M$ (mM$^{-1}$ * s$^{-1}$) r-isoQC |
|---|---|---|---|---|
| QGP | 0.102 ± 0.006 | 11.4 ± 0.4 | 111.44 ± 6.81 | 84.39 ± 3.38 |
| QYA | 0.058 ± 0.004 | 22.88 ± 0.86 | 394.23 ± 21.36 | 298.1 ± 20.6 |
| QFA | 0.060 ± 0.006 | 24.1 ± 0.5 | 403.47 ± 48.83 | 325.4 ± 58.1 |
| QEYF | 0.029 ± 0.003 | 11.78 ± 0.61 | 413.05 ± 46.04 | 477.59 ± 24.15 |
| QEDL | 0.132 ± 0.011 | 13.7 ± 0.8 | 104.33 ± 4.59 | 79.31 ± 3.79 |

(4) Western Blot Analysis

In order to investigate the specificity of the polyclonal isoQC antibodies, (as generated in G. above) HEK293 cells were transfected with human isoQC, rat-isoQC, human QC and rat QC and the expression was analyzed using western blot (FIG. 19). By application of human isoQC antibody pAb 8695 a band at 37 kDa in the cells transfected with human isoQC, human QC, rat-isoQC and ratQC was detected. The most intense signal was visible in the HEK293 cells which where transfected with human isoQC (FIG. 16a). The isoQCs are enzymes, which are located in the Golgi complex. Accordingly, the signal from the human isoQC transfected cells was expected. The difference in the signal intensity points to a detection of basally expressed human isoQC. After washing the western blot membrane using Restore™ Western Blot Stripping Buffer (Thermo Scientific) and incubation with human QC antibody pAb 8695 a signal in the media of hQC transfected cells appeared (FIG. 19b). Thus, the generated polyclonal h-isoQC antibody displays no cross-reactivity between isoQC and QC.

In order to analyze, whether the basal expression of human isoQC and rat-isoQC can be detected applying the novel antibodies pAb 3284 and pAb 3286, several different, untransfected cell lines were analyzed (FIG. 20). Applying the antibody pAb 3284 (which has been isolated from h-isoQC immunized rabbits) and cell extracts from the human cell lines HEK293, SH-SY5Y and U343, a signal of h-isoQC at 37 kDa was detected. A signal was not detected in the mouse cell lines RAW and N2a as well as in the rat cell line PC12. The Western-blot with rat-isoQC antibody (pAb 3286) visualizes a protein of 37 kDa in the mouse and rat but not in the human cell lines. Therefore, this antibody is able to detect the rat and the mouse isoQC. Accordingly, both antibodies are specific either for human isoQC or rodent (rat and mouse) isoQC. Thus, a detection of basally expressed isoQC is feasible using the polyclonal antibodies as described in G. above in western blot analysis. Moreover, the antibodies can be applied for deciphering, which of the two potential start methionines (FIG. 15) is used in different organisms as human and rat. Because of a difference in the molecular mass between the proteins starting at Met I and Met II, the WesternBlot analysis as described in this invention can be used to discriminate between the proteins.

The presented data prove an expression of isoQC in all cell lines of investigation. An immunodetection applying the antibodies described in this invention for isoQC might for the first time be useful for the development of novel analytic procedures for the characterization and detection of certain kinds of inflammation and in particular, neuroinflammation.

Example 14

Human isoQC-Catalyzed pGlu-Formation at the N-Terminus of MCP-1 (CCL2), MCP-2 (CCL8), MCP-3 (CCL7) and MCP-4 (CCL13)

A. Matrix-Assisted Laser Desorption/Ionization Time-of-Flight Mass Spectrometry

Matrix-assisted laser desorption/ionization mass spectrometry was carried out using the Voyager De-Pro (Applied Biosystems, Darmstadt) with a linear time of flight analyzer. The instrument was equipped with a 337 nm nitrogen laser, a potential acceleration source and a 1.4 m flight tube. Detector operation was in the positive-ion mode. Samples (5 µl) were mixed with equal volumes of the matrix solution. As matrix solution sinapinic acid was used, prepared by dissolving 20 mg sinapinic acid (Sigma-Aldrich) in 1 ml acetonitrile/0.1% TFA in water (1/1, v/v). A small volume (≈1 µl) of the matrix-analyte mixture was transferred to a probe tip.

B. N-Terminal Degradation by Recombinant Human DP4

In separate experiments, each one of the full length recombinant chemokines $CCL2_{1(Q)-76}$ (MCP-1), $CCL7_{1(Q)-76}$ (MCP-3), $CCL8_{1(Q)-76}$ (MCP-2) and $CCL13_{1(Q)-75}$ (MCP-4), starting with an N-terminal glutamine (Peprotech) was dissolved separately in 25 mM Tris/HCl pH 7.6 at a concentration of 20 µg/ml for CCL2 and 10 µg/ml for CCL7,8 and 13. The respective CCL was either pre-incubated with recombinant human isoQC for 2 h at 37° C. and subsequently incubated with recombinant human DP4 (Probiodrug) at 37° C. or incubated with DP4 without prior isoQC application. Resulting DP4 cleavage products were analyzed at indicated time points for up to 4 h. Cleavage products were analyzed using Maldi-TOF mass spectrometry.

C. Results

The application of human DP4 to human MCPs leads to an N-terminal degradation of the first 2 amino acids, since the N-terminal sequence of human recombinant MCPs (Gln-Pro) resembles a DP4 cleavage site (FIGS. 21a, 22a, 23a, 24a). In contrast, the pre-incubation of MCP-1, MCP-2, MCP-3 and MCP-4 with recombinant human isoQC leads to the formation of an N-terminal pGlu-residue, which protects the human MCPs against further truncation by human DP4 (FIGS. 21b, 22b, 23b, 24b). Therefore, all human MCPs, MCP-1 (CCL2), MCP-2 (CCL8), MCP-3 (CCL7) and MCP-4 (CCL13) are substrates of human isoQC in vitro.

Example 15

Thioglycollate-Induced Peritonitis in C57/Bl6J Wild Type Mice

A. Experimental Procedures

C57/Bl6J mice were purchased from Charles River Laboratories (Kisslegg, Germany). For each experiment, the mice were age- and sex-matched. An intraperitoneal injection of 25 ml/kg body weight of sterile 8% (w/v) thioglycollate (Sigma-Aldrich) was used to induce peritonitis. 30 min before the thioglycollate-stimulus, animals were injected with different doses of isoQC-inhibitor isoQC-I. For lavage of the peritoneum, the animals were anesthetized using 2% isofluran. The peritoneal exudates were collected by washing the peritoneum with 8 ml of sterile PBS 4 h after thioglycollate injection. Cells of 1 ml lavage fluid were collected by centrifugation (300 g, 10 min) and stained according to the manufacturer's instructions for BD Trucount tubes (BD Trucount tubes; catalog no. 340334; BD Biosciences, Heidelberg, Germany). Cells were blocked with CD16/32 (Caltag) at 4° C. for 15 min. and stained with 7/4-FITC (Serotec, Dusseldorf, Germany)/Ly6G-PE (Miltenyi, Bergisch Gladbach, Germany) as well as IgG1-PE (BD)/IgG2a-FITC (Miltenyi) as isotype controls at room temperature for 15 min. After staining, erythrocytes were lysed with BD FACSLyse (BD) in the dark at room temperature for 15 min. After washing with PBS, flow cytometric analysis was performed on a BD FACSCalibur (BD) based on 5000 beads per sample as reference standard.

B. Results

After injection of thioglycollate into the peritoneum of C57/Bl6J mice an infiltration of monocytes to this compartment was detected using FACS analysis. The application of the QC/isoQC-specific inhibitor isoQC-I in this model provokes a dose-dependent reduction of the infiltrating monocytes. A reduction could already be observed using 6 mg/kg isoQC-I. 18 mg/kg reduced the infiltration of monocytes down to baseline values, detected when saline alone was injected (FIG. 25a). In analogy, the determination of pGlu-MCP-1 in respective lavage-fluids shows a reduction of pGlu-content, suggesting a treatment effect due to action of the inhibitor at the target enzyme (FIG. 25b).

Example 16

Thioglycollate-Induced Peritonitis in isoQC (QPCTL) Knock Out Mice

QPCTL knock-out mice were generated on the basis of a genomic mutagenesis approach.

The application of thioglycollate in QPCTL knock out animals does not stimulate monocyte infiltration to the peritoneum. However, in QPCTL wild type littermates an infiltration of monocytes was detected (FIG. 26a), since the activity of isoQC is present there, resulting in proper maturation of MCPs. Granulocyte infiltration was not affected by the isoQC (QPCTL) knock out (FIG. 26b). The impaired infiltration of monocytes correlated with a reduced concentration of pGlu-MCP-1 in QPCTL knock out mice, whereas the total MCP-1 level remained normal (FIG. 27). Therefore, mouse-isoQC knock out has an impact of pGlu-MCP-1 formation and the reduction of pGlu-MCP-1 has an impact on monocyte recruitment to the peritoneum in this animal model. In addition, the genetic proof of principle substantiates the specificity of isoQC-inhibitor application in the thioglycollate-induced peritonitis. By that experiment is proven, that an inhibition of isoQC results in deactivation of pGlu-MCPs and is therefore a novel treatment strategy for inflammatory diseases.

Example 17

LPS-Stimulation of PBMCs Isolated from isoQC (QPCTL) Knock Out Mice

A. Isolation of Plasma and PBMCs

For isolation of peripheral blood mononuclear cells (PBMCs), QPCTL knock out animals and wild type littermates were anesthetized using 2% isofluran and herparinized blood was collected by cardiac puncture. Afterwards, blood was pooled from animals having the same genetic background (isoQC homozygous knock out and wild type animals, respectively) and plasma was collected obtained by centrifugation of the heparinized blood for 10 min at 1000×g. The plasma was divided in aliquots and stored at −80° C. The sedimented blood cells were resuspended in cell culture medium (RPMI1640, 10% FBS, 100 µg/ml Gentamicin).

For isolation of PBMCs, a density gradient was used: 15 ml of LSM 1077 (Lymphocyte Separation Medium, PAA) were filled in a 50 ml Leucosep tube (Greiner). The medium was centrifuged for 1 min at 1000×g. Thereafter, the blood cells were filled into the Leucosep tube (Greiner). The solution was centrifuged for 10 min at 1000×g without activated deceleration to avoid swirling. The liquid covering 1 cm of the upper phase was discarded to avoid a thrombocyte contamination of the sample. Afterward, the medium was completely removed, whereby a circular ring within the Leucosep tube prevented contamination of the PBMC fraction with pelleted erythrocytes. PBMCs were washed 2 times using 10 ml sterile PBS followed by centrifugation. Finally, the cells were resuspended in culture medium (RPMI 1640, 10% FBS, 50 µg/ml Gentamicin), plated in a 25 cm$^2$ tissue culture flask and grown over night at 37° C. and 5% $CO_2$. The next day, PBMCs adhered to the plastic. Therefore, the supernatant containing lymphocytes was removed, cells were washed once with PBS and subsequently dislodged using Accutase (PAA). After centrifugation, cells were counted using a Neubauer counting chamber and transferred to a 96-well plate in culture medium (RPMI 1640, 10% FBS, 50 µg/ml Gentamicin). The final cell density was about 1*10$^5$ cells per well. Cells were stimulated using 10 µg/ml LPS from *E. coli* strain O55:B5 (Sigma) for 24 h. Afterwards, medium was collected and analyzed using total-MCP-1 and pGlu-MCP-1 specific ELISA.

B. Results

Stimulation of PBMCs isolated from QPCTL knock out mice and wild type littermates leads to an increased total MCP-1 concentration in the culture supernatant. Unstimulated PBMCs secrete only low amounts of total MCP-1 (FIG. 28a). The total-MCP-1 level detected in the medium of cells from wild type animals is higher compared to the respective cells from knock out animals. MCP-1 secreted from wild-type-PBMCs possesses a pGlu-modified N-terminus, indicated by the equal amount of total- and pGlu-MCP-1 (FIGS. 28a, 28b). In contrast, the cells from QPCTL knock out mice generate only scarce amounts of the N-terminally pGlu-modified MCP-1 as indicated by a low amount of pGlu-MCP-1, detected by ELISA (FIG. 28a) and a low ratio of pGlu-MCP-1 vs. total MCP-1 of approximately 10% compared to >90% in wild type littermates (FIG. 28b).

Example 18

Determination of the Zinc Content of Murine isoQC

A. TXRF Measurements

After purification of mouse isoQC, the enzyme was desalted by size-exclusion chromatography using a Sephadex G-25 fast desalting column (1.0×10 cm), which was pre-equilibrated in 10 mM Tris-HCl, pH 7.6. The protein was concentrated to 3 mg/ml. Elemental analysis was performed using total reflection X-ray fluorescence (TXRF). The elution buffer was used as a background control. Five microliters of undiluted sample solution or control buffer were applied onto the TXRF quartz glass sample support and dried under IR radiation. Afterwards, 5 µl of diluted Se aqueous standard solution (internal standard, Aldrich; Taufkirchen, Germany) were added to each sample and dried again. The X-ray fluorescence signal was collected for 100 s. For all determinations, an Extra II TXRF module containing molybdenum and tungsten primary X-ray sources (Seifert, Ahrensburg, Germany) connected to a Link QX 2000 detector/analysis device (Oxford Instruments, High Wycombe, UK) was used. The X-ray sources were operated at 50 kV and 38 mA.

B. Inactivation/Reactivation

Mouse isoQC and mouse QC were inactivated by dialysis against 1.0 l of buffer containing 5 mM 1,10-phenantroline, 5 mM EDTA, 500 mM NaCl in 50 mM BisTris pH 6.8 over night at 4° C. The chelating agents were separated from the apoenzymes by dialysis against 1 l of 50 mM BisTris, pH 6.8, 500 mM NaCl, containing 50 g/l Chelex-100 (Bio-RAD, Munich), or 10 mM $NaH_2PO_4$, pH 6.8 containing 50 g/l Chelex-100 at 4° C. The buffer was changed 2 times, after 2 and 4 h of dialysis. The final dialysis was performed for 5 h. All buffers were prepared in metal-free polystyrene containers. Subsequently, the apoenzyme was centrifuged at 20.000×g for 1 h at 4° C., and the protein concentration was determined by UV absorbance.

The reactivation experiments were carried out by incubation of 20 µl of a transition metal solution with 20 µl of apoenzyme in Bis-Tris buffer at room temperature for 15 min. Finally, enzymatic activity was assessed as described above, except the reaction buffer contained 2 mM EDTA in order to avoid rapid reactivation of the enzymes by adventitious zinc ions present in the buffers.

C. CD-Spectroscopic Analysis

For the spectroscopic analysis the proteins were prepared in 10 mM $NaH_2PO_4$. CD-spectra of mouse QC and mouse isoQC were acquired with a Jasco J-715 spectrapolarimeter using quartz cuvettes of 1 mm pathlength. The mean of 10 scans between 190 and 260 nm was calculated and the spectra were corrected by subtraction of the buffer spectra. The percentage of secondary structure elements was calculated using the Jasco secondary structure estimation program based on the method of Yang. The apoenzymes and reactivation of the enzymes was confirmed by QC activity measurements after spectra analysis.

D. Results

For the mouse QC, a metal content of 1 mol zinc/mol of enzyme was determined, previously. The zinc binding motif of QC is also conserved in the sequence of the isoQCs. Therefore, the metal content of mouse isoQC was analyzed, using TXRF. The measurements of three independent enzyme samples determined a zinc content of 0.99±0.38 mol of zinc/mol of enzyme. Thus, the isoQC proteins represent single zinc metalloenzymes as shown here for the first time.

For human isoQC it was shown that the protein can be inactivated by heterocyclic chelators like 1,10-phenantroline, dipicolinic acid and EDTA. Dialysis against buffer containing 5 mM 1,10-phenantrolin and 5 mM EDTA resulted in inactivation of mouse-isoQC. After removal of the chelator, addition of $ZnSO_4$ resulted in complete reactivation of mouse-isoQC. To verify the results, different amounts of zinc were titrated to the apoenzymes (mouse isoQC, mouse QC and *Drosophila melanogaster* (Drome) QC) (FIG. 29). All tested enzymes are 100% reactivated by adding 1 mol of zinc/mol of enzyme as well as with 2 mol of zinc/mol of enzyme. With the ratio of 0.5 zinc/mol of enzyme an activity of at least 60% was reached.

Furthermore, a reactivation of mouse-isoQC by other metal ions was examined. By addition of 1 mol of cobalt/mol of enzyme, a reactivation was achieved. However, the final activity was only 50% compared to the reactivation with zinc ions. No reactivation was achieved using calcium or manganese ions.

To investigate the influence of zinc binding on the protein structure, the secondary structure of the apoenzyme and of the reactivated mouse-isoQC was evaluated via CD spectra from 190-260 nm. In both cases the calculation of the secondary structure revealed an a helical portion of 50%. Thus, zinc binding has no influence on the overall secondary structure. This supports that the metal ions primarily play a catalytic role.

ABBREVIATIONS

° C. degree Celsius
A alanine, ala
Aβ amyloid-β peptide
ABri amyloid peptide in familial British dementia
AC adenylyl cyclase
ADan amyloid peptide in familial Danish dementia
AMC amino methyl coumarine
as antisense
Asp aspartate
Asn asparagine
βNA beta-naphtylamine
BA butyric acid
bp base pair
BSA bovine serum albumin
BMMY buffered Methanol complex medium
BMGY buffered glycerol comlex medium
C cysteine, Cys
CAT chloramphenicol acetyl transferase
cAMP cyclic adenosine monophsphate
CCL2 MCP-1, monocyte chemoattractant protein 1
CCL7 MCP-3, monocyte chemoattractant protein 3
CCL8 MCP-2, monocyte chemoattractant protein 2
CCL13 MCP-4, monocyte chemoattractant protein 4
cDNA copy-DNA
C-His C-terminal histidine tag
CIDP Chronic inflammatory demyelinizing polyradiculoneuropathy
Cl chlorine
CSF cerebro-spinal fluid (liquor cerebrospinalis)
C-terminus carboxy-terminus
CTL cytotoxic T-lymphocyte
CV column volume
Cys cysteine, cys
d diameter
D aspartic acid, Asp
Da Dalton
DMSO dimethyl sulphoxide
DNA desoxyribonucleic acid
E Glutamic acid, Glu
EBV Epstein Barr virus
ECL enterochromaffin-like
*E. coli Escherichia coli*
EC glutamyl cyclase
ED effective dose
EGFP enhanced green fluorescent protein
ES enzyme-substrate complex F Phenylalanine, Phe
FPP fertilization promoting peptide
FTC follicular thyroid carcinoma
g relative centrifugal force
G Glycine, Gly
GBS Guillain-Barré syndrome
GF gel filtration
Gln glutamine
Glu glutamic acid
GnRH gonadotropin-releasing hormone (gonadoliberin)
GST glutathion S-transferase
H hydrogen
h human or hour
HGF hepatocyte growth factor
HIC hydrophobic interaction chromatography
HIC-EBA hydrophobic interaction chromatography, expanded bed absorption
His histidine
HPLC high performance liquid chromatography
I inhibitor or isoleucine
ID identification
IEX ion exchange chromatography
Ile Isoleucine
IMAC immobilized metal affinity chromatography
ip intraperitoneal
IPTG Isopropyl-β-D-thiogalactopyranosid
K potassium
k constant
kDA kilo-dalton
Ki inhibition constant (for inhibitor binding)
KLH Keyhole limpet hemocyanin
k.o. knock-out
l length
L Leucine, Leu
LB Luria-Bertani
LD lethal dose
LPS lipopolysaccharide
m mouse
M molar
μl micro-liter
μM micro-molar
Maldi-tof matrix assisted laser desorption/ionization time-of-flight
max maximum
MES 2-(N-morpholino)ethanesulfonic acid
Met methionine
min minutes
mM milli-molar
MS Multiple Sclerosis
mRNA messenger-RNA
N asparagine
Na sodium
NADH nicotinamide adenine dinucleotide
nm nanometer
NO number
NT Neurotensin
N-terminus amino terminus
O oxygen
OD optical density
P product or phosphor or proline, Pro
PBS phosphate-buffered saline
PCR polymerase chain reaction
pGlu pyroglutamic acid
pH pondus hydrogenii
Pro proline
PTC papillary thyroid carcinoma
Pyr pyroglutamate
Q Glutamine, Gln
QC glutaminyl cyclase (glutaminyl-peptide cyclotransferase)
QQ Dipeptide Gln-Gln
QE Dipeptide Gln-Glu
QG Dipeptide Gln-Gly
QGP Tripeptide Gln-Gly-Pro
QYA Tripeptide Gln-Tyr-Ala
QFA Tripeptide Gln-Phe-Ala
QEYF Tetrapeptide Gln-Glu-Tyr-Phe
QEDL Tetrapeptide Gln-Glu-Asp-Leu
qPCR quantitative real-time polymerase chain reaction
QPCTL glutaminyl-peptide cyclotransferase-like
RNA ribonucleic acid
RT reverse transcription; reverse transcriptase
S substrate
s sense
SAGE serial analysis of gene expression
SDS sodium dodecyl sulfate
SDS-PAGE SDS-polyacrylamid gel electrophoresis
SGAP Streptomyces griseus amino peptidase
SEC size exclusion chromatography
SEQ sequence
Ser Serine
SNP single nucleotide polymorphism
taa tumor-associated antigen
TGF-β transforming growth factor beta
TNF-α tumor necrosis factor alpha
TRH thyreotropin-realeasing hormone (thyreoliberin)
TRIS Tris(hydroxymethyl)-aminomethane,
TSH thyroidea-stimulating-hormone
U unit
UTC undifferentiated thyroid carcinoma
UV ultraviolet
V velocity
VpAP Vibrio proteolytica amino peptidase
Y Tyrosine, Tyr
YPD Yeast extract, Peptone, Dextrose-medium
YPDS Yeast extract, Peptone, Dextrose-medium containing sorbitol
YSS yeast signal sequence
Zn zinc

What is claimed is:

1. A method of treatment of an inflammatory disease or condition comprising administering a therapeutically effective amount of an isoQC inhibitor to a subject in need thereof wherein:
   (a) the inflammatory disease or condition is associated with a pyroglutamated peptide;
   (b) the inflammatory disease or condition is selected from the group consisting of rheumatoid arthritis, atherosclerosis, restenosis, pancreatitis, and osteoporosis;
   (c) the isoQC inhibitor comprises a compound of formula (I):

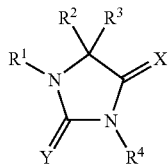

(I)

or a pharmaceutically acceptable salt, solvate or polymorph thereof, including all tautomers and stereoisomers thereof;
   (d) $R^1$ represents —$C_{3-8}$carbocyclyl-heteroaryl, —$C_{2-6}$alkenylheteroaryl, —$C_{1-6}$alkylheteroaryl, or ($CH_2$)$_a$ $CR^5R^6(CH_2)_b$ heteroaryl with (1) a and b independently representing integers 0-5 provided that a+b=0-5 and (2) $R^5$ and $R^6$ being alkylene which, together with the carbon to which they are attached, form a $C_3$-$C_5$ cycloalkyl group, or a bicyclic heteroaryl group, any of said heteroaryl groups being optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —SO$_2C_{1-4}$alkyl, $C_{1-6}$alkoxy-, —O—$C_{3-8}$cycloalkyl, $C_{3-8}$cycloalkyl, —SO$_2C_{3-8}$cycloalkyl, —SO$C_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —NH$_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)NH$_2$, —C(O)NH($C_{1-4}$alkyl) and —C(O)NH($C_{3-10}$cycloalkyl) and any of said carbocyclyl groups being optionally substituted by one or more groups selected from $C_{1-4}$alkyl, oxo, halogen and $C_{1-4}$alkoxy;
   (e) $R^2$ and $R^3$ are one of (i), (ii), (iii), (iv), or (v) defined as follows:
      (i) $R^2$ represents $C_{1-8}$alkyl, aryl, heteroaryl, carbocyclyl, heterocyclyl, —$C_{1-4}$alkylaryl, —$C_{1-4}$alkylheteroaryl, —$C_{1-4}$alkylcarbocyclyl or —$C_{1-4}$alkylheterocyclyl with (1) any of said aryl and heteroaryl groups optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl$)(C_{1-4}$alkyl$)$, —$C(O)N(C_{1-4}$alkyl$)(C_{1-4}$alkyl$)$, —$C(O)NH_2$, —$C(O)NH(C_{1-4}$alkyl$)$ and —$C(O)NH(C_{3-10}$cycloalkyl$)$; and (2) any of aforesaid carbocyclyl and heterocyclyl groups optionally substituted by one or more groups selected from $C_{1-4}$alkyl, oxo, halogen and $C_{1-4}$alkoxy; and $R^3$ represents H, —$C_{1-4}$alkyl or aryl with said aryl optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl$)(C_{1-4}$alkyl$)$, —$C(O)N(C_{1-4}$alkyl$)(C_{1-4}$alkyl$)$, —$C(O)NH_2$, —$C(O)NH(C_{1-4}$alkyl$)$ and, —$C(O)NH(C_{3-10}$cycloalkyl$)$, (ii) $R^2$ represents phenyl substituted by phenyl, phenyl substituted by a monocyclic heteroaryl group, phenyl substituted by benzyloxy, phenyl fused to carbocyclyl, phenyl fused to heterocyclyl, —$C_{1-4}$alkyl(phenyl substituted by phenyl), —$C_{1-4}$alkyl(phenyl substituted by a monocyclic heteroaryl group), —$C_{1-4}$alkyl(phenyl substituted by benzyloxy), —$C_{1-4}$alkyl (optionally substituted phenyl fused to optionally substituted carbocyclyl or —$C_{1-4}$alkyl(optionally substituted phenyl fused to optionally substituted heterocyclyl), with (1) any of said phenyl, benzyloxy and heteroaryl groups optionally substituted by one or more groups selected from $C_{1-4}$alkyl, halogen and $C_{1-4}$alkoxy and (2) any of said carbocyclyl and heterocyclyl groups optionally substituted by one or more groups selected from $C_{1-4}$alkyl, oxo, halogen and $C_{1-4}$alkoxy; and $R^3$ represents H, —$C_{1-4}$alkyl or aryl with said aryl optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl$)(C_{1-4}$alkyl$)$, —$C(O)N(C_{1-4}$alkyl$)(C_{1-4}$alkyl$)$, —$C(O)NH_2$, —$C(O)NH(C_{1-4}$alkyl$)$ and, —$C(O)NH(C_{3-10}$cycloalkyl$)$, (iii) $R^2$ and $R^3$ are joined to form a carbocyclyl ring which is optionally substituted by one or more $C_{1-2}$alkyl groups, (iv) $R^2$ and $R^3$ are joined to form a carbocyclyl ring which is fused to phenyl, with said carbocyclyl or phenyl optionally substituted by one or more groups selected from $C_{1-4}$alkyl, halogen and $C_{1-4}$alkoxy, and (v) $R^2$ and $R^3$ are joined to form a carbocyclyl ring which is fused to monocyclic heteroaryl with said carbocyclyl or heteroaryl optionally substituted by one or more groups selected from $C_{1-4}$alkyl, halogen and $C_{1-4}$alkoxy;

(f) $R^4$ represents H, —$C_{1-8}$alkyl, —$C(O)C_{1-6}$alkyl or —$NH_2$;

(g) X represents O or S; and (h) Y represents O or S.

2. The method according to claim 1 wherein the isoQC inhibitor is administered in combination with a further agent selected from the group consisting of anti-inflammatory agents, nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs, inhibitors of the angiotensin converting enzyme (ACE), angiotensin II receptor blockers, diuretics; calcium channel blockers (CCB), beta-blockers, platelet aggregation inhibitors, cholesterol absorption modulators, HMG-Co-A reductase inhibitors, high density lipoprotein (HDL) increasing compounds, renin inhibitors, IL-6 inhibitors, antiinflammatory corticosteroids, antiproliferative agents, nitric oxide donors, inhibitors of extracellular matrix synthesis, growth factor or cytokine signal transduction inhibitors, MCP-1 antagonists and tyrosine kinase inhibitors.

3. The method according to claim 1 wherein the subject is a human.

4. The method according to claim 1 wherein $R^1$ represents a bicyclic heteroaryl group.

5. The method according to claim 1 wherein $R^1$ represents a benzene or pyridine ring fused to a 5-membered ring containing one or two nitrogen atoms.

6. The method according to claim 5 wherein the point of attachment is through a benzene or pyridine ring.

7. The method according to claim 1 wherein $R^1$ is:

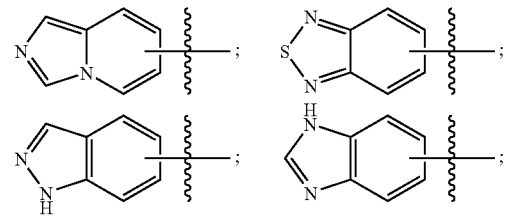

imidazo[1,2-a]pyridine; or
benzo[c][1,25]thiadiazolyl.

8. The method according to claim 7 wherein R1 represents

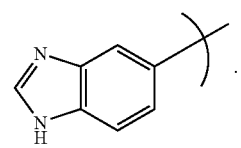

9. The method according to claim 1 wherein $R^1$ represents —$C_{1-6}$alkylheteroaryl.

10. The method according to claim 9 wherein the heteroaryl group of $R^1$ is a 5-membered ring containing 1 to 3 nitrogen atoms optionally substituted by one or more substituents selected from $C_{1-4}$ alkyl, $C_{1-4}$ alkoxy- and halogen.

11. The method according to claim 10 wherein the heteroaryl group is:

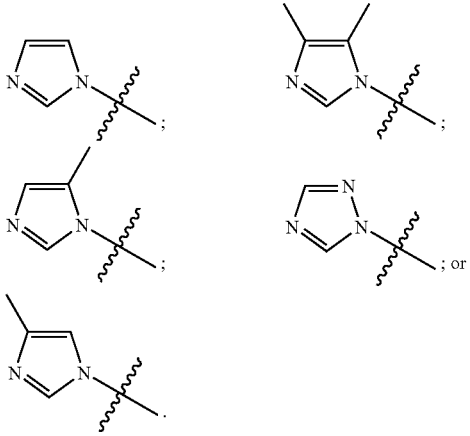

12. The method according to claim 1 wherein $R^1$ represents:

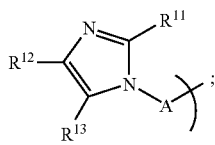

A represents
   (i) an unbranched or branched $C_{1-6}$alkylene chain;
   (ii) a branched $C_{1-6}$alkylene chain; or
   (iii) $(CH_2)_a CR^5R^6(CH_2)_b$; and
$R^{11}$, $R^{12}$ and $R^{13}$ independently represent H or $C_{1-2}$alkyl.

13. The method according to claim 12 wherein $R^1$ represents

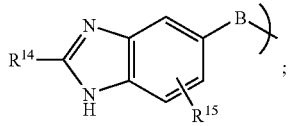

B represents a bond, —$CH_2$—, —$CH_2$—$CH_2$—, —CH(Me)—, —CH(Me)-$CH_2$— or —$CH_2$—CH(Me)-; and
$R^{14}$ and $R^{15}$ independently represent H or $C_{1-2}$alkyl.

14. The method according to claim 1 wherein $R^2$ represents:
   aryl, heteroaryl, phenyl substituted by phenyl, or phenyl fused to heterocyclyl; or
   $R^2$ and $R^3$ are joined to form a carbocyclyl ring which is fused to phenyl;
   said aryl, heteroaryl, phenyl, heterocyclyl or carbocyclyl optionally being substituted.

15. The method according to claim 14 wherein $R^2$ represents phenyl substituted by phenyl, said phenyl groups optionally being substituted by one or more substitutents independently selected from halo, OH, $C_{1-3}$alkyl, $C_{1-3}$ haloalkyl, $C_{1-3}$ alkoxy, and $C_{1-3}$ haloalkoxy.

16. The method according to claim 15 wherein $R^2$ is -biphenyl-4-yl.

17. The method according to claim 14 wherein $R^2$ represents phenyl optionally substituted by one, two or three substituents independently selected from halo, OH, $C_{1-3}$alkyl, $C_{1-3}$ haloalkyl, $C_{1-3}$ alkoxy, and $C_{1-3}$ haloalkoxy.

18. The method according to claim 17 wherein $R^2$ is phenyl substituted by n-propyloxy.

19. The method according to claim 1 wherein $R^3$ represents H.

20. The method according to claim 1 wherein $R^2$ and $R^3$ are joined to form a carbocyclyl ring which is fused to phenyl.

21. The method according to claim 1 wherein $R^4$ represents H.

22. The method according to claim 1 wherein X represents O.

23. The method according to claim 1 wherein Y represents O.

24. The method according to claim 1 wherein formula (I) is represented by:

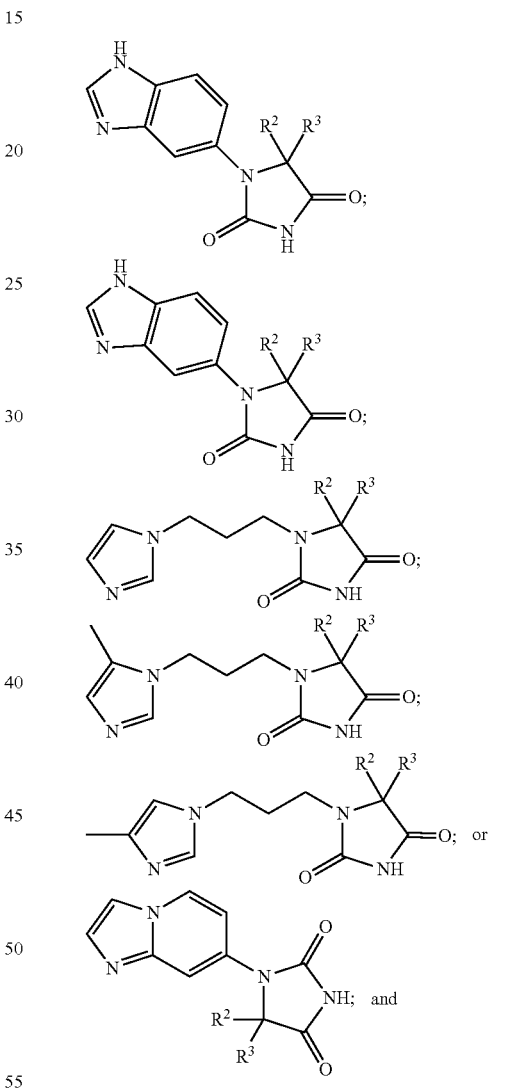

$R^2$ and $R^3$ are as defined in claim 1.

25. The method according to claim 1 wherein the compound of formula (I) is selected from the group consisting of:
   5-(benzo[c][1,2,5]thiadiazol-6-yl)-1-(1H-benzo[d]imidazol-5-yl)imidazolidine-2,4-dione;
   1-(1H-benzo[d]imidazol-5-yl)-5-phenylimidazolidine-2,4-dione;
   1-(1H-benzo[d]imidazol-5-yl)-5-(2-hydroxy-5-methylphenyl)imidazolidine-2,4-dione;
   1-(1H-benzo[d]imidazol-5-yl)-5-(2-fluoro-5-trifluoromethyl)phenyl)imidazolidine-2,4-dione;

1-(1H-benzo[d]imidazol-5-yl)-5-(2-bromo-5-fluorophenyl)imidazolidine-2,4-dione;
1-(1H-benzo[d]imidazol-5-yl)-5-(4-propoxyphenyl)imidazolidine-2,4-dione;
1-(1H-benzo[d]imidazol-5-yl)-5-(4-chloro-3-trifluoromethyl)phenyl)imidazolidine-2,4-dione;
1-(1H-benzo[d]imidazol-5-yl)-5-(3-fluoro-4(trifluoromethyl)phenyl)imidazolidine-2,4-dione;
1-(1H-benzo[d]imidazol-5-yl)-5-(3-hydroxy-4-methoxyphenyl)imidazolidine-2,4-dione;
1-(1H-benzo[d]imidazol-5-yl)-5-(2-hydroxy-3-methoxyphenyl)imidazolidine-2,4-dione;
1-(1H-benzimidazol-5-yl)-5-(1,1'-biphenyl-4-yl)imidazolidine-2,4-dione;
1-(1H-benzo[d]imidazol-5-yl)-5-(3-chlorophenyl)imidazolidine-2,4-dione;
1-(1H-benzo[d]imidazol-5-yl)-5-(4-chlorophenyl)imidazolidine-2,4-dione;
1-(1H-benzo[d]imidazol-5-yl)-5-(2-chlorophenyl)imidazolidine-2,4-dione;
1-(1H-benzo[d]imidazol-5-yl)-5-(4-fluorophenyl)imidazolidine-2,4-dione;
1-(1H-benzo[d]imidazol-5-yl)-5-(2,3-dihydrobenzo[b][1,4]dioxin-7-yl)imidazolidine-2,4-dione;
1-(3-(1H-imidazol-1-yl)propyl)-5-phenylimidazolidine-2,4-dione;
1-(3-(1H-imidazol-1-yl)propyl)-5-(2-bromo-4-fluorophenyl)imidazolidine-2,4-dione;
1-(3-(1H-imidazol-1-yl)propyl)-5-(4-propoxyphenyl)imidazolidine-2,4-dione;
1-(3-(1H-imidazol-1-yl)propyl)-5-(3-fluoro-4-trifluoromethyl)phenyl)imidazolidine-2,4-dione;
1-[3-(1H-imidazol-1-yl)propyl]-5-(4-biphenyl)imidazolidine-2,4-dione;
1-(3-(1H-imidazol-1-yl)propyl)-5-(3-chlorophenyl)imidazolidine-2,4-dione;
1-(3-(1H-imidazol-1-yl)propyl)-5-(2-chlorophenyl)imidazolidine-2,4-dione;
1-(3-(5-methyl-1H-imidazol-1-yl)propyl)-5-phenylimidazolidine-2,4-dione;
5-(2-bromo-5-fluorophenyl)-1-(3-(5-methyl-1H-imidazol-1-yl)propyl)imidazolidine-2,4-dione;
1-(3-(5-methyl-1H-imidazol-1-yl)propyl)-5-(4-propoxyphenyl)imidazolidine-2,4-dione;
1-[3-(5-methyl-1H-imidazol-1-yl)propyl]-5-(4-phenylphenyl)imidazolidine-2,4-dione;
5-(3-chlorophenyl)-1-(3-(5-methyl-1H-imidazol-1-yl)propyl)imidazolidine-2,4-dione;
1-(3-(4-methyl-1H-imidazol-1-yl)propyl)-5-phenylimidazolidine-2,4-dione;
1-[3-(4-methyl-1H-imidazol-1-yl)propyl]-5-(4-biphenyl)imidazolidine-2,4-dione;
5-(3-chlorophenyl)-1-(3-(4-methyl-1H-imidazol-1-yl)propyl)imidazolidine-2,4-dione;
3-(1H-benzimidazol-5-yl)-1',3'-dihydro-2H,5H-spiro[imidazolidine-4,2'-indene]-2,5-dione;
5-(benzo[c][1,2,5]thiadiazol-6-yl)-1-(1H-benzo[d]imidazol-5-yl)-2-thioxoimidazolidin-4-one;
1-(1H-benzo[d]imidazol-5-yl)-5-phenyl-2-thioxoimidazolidin-4-one;
1-(1H-benzimidazol-5-yl)-5-(1,1'-biphenyl-4-yl)-2-thioxoimidazolidin-4-one;
1-(1H-benzo[d]imidazol-5-yl)-5-(3-hydroxy-4-methoxyphenyl)-2-thioxoimidazolidin-4-one;
1-(1H-benzo[d]imidazol-5-yl)-5-phenyl-4-thioxoimidazolidin-2-one;
1-(1H-benzimidazol-5-yl)-5-(1,1'-biphenyl-4-yl)-4-thioxoimidazolidin-2-one;
3-(1H-benzimidazol-5-yl)-5-thioxo-1',3'-dihydro-2H-spiro[imidazolidine-4,2'-inden]-2-one;
1-(1H-benzo[d]imidazol-5-yl)-5-(4-chlorophenyl)-4-thioxoimidazolidin-2-one;
1-(1H-benzo[d]imidazol-5-yl)-5-(2,3,4-trifluorophenyl)-4-thioxoimidazolidin-2-one;
1-(1H-benzo[d]imidazol-6-yl)-5-(4-bromo-2-fluorophenyl)-4-thioxoimidazolidin-2-one;
1-(1H-benzo[d]imidazol-5-yl)-5-(2,3-difluoro-4-methylphenyl)-4-thioxoimidazolidin-2-one;
1-(1H-benzo[d]imidazol-5-yl)-5-(4-chloro-3-methylphenyl)-4-thioxoimidazolidin-2-one;
1-(1H-benzo[d]imidazol-5-yl)-3-methyl-5-phenylimida4zolidine-2,4-dione; and
1-(H-imidazo[1,2-a]pyridin-7-yl)-5-phenylimidazolidine-2,4-dione; or
a pharmaceutically acceptable salt, solvate or polymorph thereof, including all tautomers and stereoisomers thereof.

26. The method according to claim 1 wherein the compound of formula (I) is 1-(1H-benzo[d]imidazol-5-yl)-5-(4-propoxyphenyl)imidazolidine-2,4-dione, having a structure of:

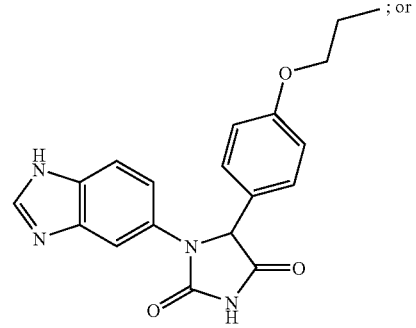 [SMILES: CCCOc1ccc(C2C(=O)NC(=O)N2c2ccc3[nH]cnc3c2)cc1]

a pharmaceutically acceptable salt, solvate or polymorph thereof, including all tautomers and stereoisomers thereof.

27. The method according to claim 1 wherein the isoQC inhibitor inhibits an activity of:
a polypeptide comprising SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 57, SEQ ID NO: 58, SEQ ID NO: 59 or SEQ ID NO: 60; or
a polypeptide encoded by a nucleic acid comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 53, SEQ ID NO: 54, SEQ ID NO: 55 or SEQ ID NO: 56.

28. The method according to claim 1 wherein the isoQC inhibitor inhibits an activity of:
a polypeptide comprising SEQ ID NO: 11 or SEQ ID NO: 12; or
a polypeptide encoded by a nucleic acid comprising SEQ ID NO: 2 or SEQ ID NO: 3.

29. The method according to claim 1 wherein the isoQC inhibitor inhibits an activity of:
a polypeptide comprising SEQ ID NO: 11; or
a polypeptide encoded by a nucleic acid comprising SEQ ID NO: 2.

30. A method according to claim 1 wherein the isoQC inhibitor inhibits an activity of:
a polypeptide comprising SEQ ID NO: 12; or
a polypeptide encoded by a nucleic acid comprising SEQ ID NO: 3.

31. The method according to claim 1 wherein the isoQC inhibitor is formulated as a pharmaceutical composition comprising one or more pharmaceutically acceptable diluents or carriers.

32. The method according to claim 1 wherein the isoQC inhibitor is formulated as a pharmaceutical composition comprising one or more pharmaceutically acceptable diluents or carriers.

33. A method of diagnosing an inflammatory disease or condition comprising:
collecting a sample from a subject suspected to be afflicted with said disease or condition;
contacting said sample with an isoQC inhibitor; and
determining whether or not said subject is afflicted by said disease or condition;
wherein,
(a) the inflammatory disease or condition is selected from the group consisting of rheumatoid arthritis, atherosclerosis, restenosis, pancreatitis, and osteoporosis;
(b) the isoQC inhibitor comprises a compound of formula (I):

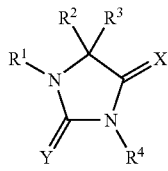

(I)

or a pharmaceutically acceptable salt, solvate or polymorph thereof, including all tautomers and stereoisomers thereof;
(d) $R^1$ represents —$C_{3-8}$carbocyclyl-heteroaryl, —$C_{2-6}$alkenylheteroaryl, —$C_{1-6}$alkylheteroaryl, or $(CH_2)_a CR^5R^6(CH_2)_b$ heteroaryl with (1) a and b independently representing integers 0-5 provided that a+b=0-5 and (2) $R^5$ and $R^6$ being alkylene which, together with the carbon to which they are attached, form a $C_3$-$C_5$cycloalkyl group, or a bicyclic heteroaryl group, any of said heteroaryl groups being optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —$C(O)N(C_{1-4}$alkyl)($C_{1-4}$alkyl), —$C(O)NH_2$, —$C(O)NH(C_{1-4}$alkyl) and —$C(O)NH(C_{3-10}$cycloalkyl) and any of said carbocyclyl groups being optionally substituted by one or more groups selected from $C_{1-4}$alkyl, oxo, halogen and $C_{1-4}$alkoxy;
(e) $R^2$ and $R^3$ are one of (i), (ii), (iii), (iv), or (v) defined as follows:
(i) $R^2$ represents $C_{1-8}$alkyl, aryl, heteroaryl, carbocyclyl, heterocyclyl, —$C_{1-4}$alkylaryl, —$C_{1-4}$alkylheteroaryl, —$C_{1-4}$alkylcarbocyclyl or —$C_{1-4}$alkylheterocyclyl with (1) any of said aryl and heteroaryl groups optionally substituted by one or more groups selected from $C_{1-6}$alkyl, $C_{2-8}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —$C(O)N(C_{1-4}$alkyl)($C_{1-4}$alkyl), —$C(O)NH_2$, —$C(O)NH(C_{1-4}$alkyl) and —$C(O)NH(C_{3-10}$cycloalkyl); and (2) any of aforesaid carbocyclyl and heterocyclyl groups optionally substituted by one or more groups selected from $C_{1-4}$alkyl, oxo, halogen an $C_{1-4}$alkoxy; and
$R^3$ represents H, —$C_{1-4}$alkyl or aryl with said aryl optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-6}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —$C(O)N(C_{1-4}$alkyl)($C_{1-4}$alkyl), —$C(O)NH_2$, —$C(O)NH(C_{1-4}$alkyl) and, —$C(O)NH(C_{3-10}$cycloalkyl),
(ii) $R^2$ represents phenyl substituted by phenyl, phenyl substituted by a monocyclic heteroaryl group, phenyl substituted by benzyloxy, phenyl fused to carbocyclyl, phenyl fused to heterocyclyl, —$C_{1-4}$alkyl(phenyl substituted by phenyl), —$C_{1-4}$alkyl(phenyl substituted by a monocyclic heteroaryl group), —$C_{1-4}$alkyl(phenyl substituted by benzyloxy), —$C_{1-4}$alkyl (optionally substituted phenyl fused to optionally substituted carbocyclyl or —$C_{1-4}$alkyl(optionally substituted phenyl fused to optionally substituted heterocyclyl), with (1) any of said phenyl, benzyloxy and heteroaryl groups optionally substituted by one or more groups selected from $C_{1-4}$alkyl, halogen and $C_{1-4}$alkoxy and (2) any of said carbocyclyl and heterocyclyl groups optionally substituted by one or more groups selected from $C_{1-4}$alkyl, oxo, halogen and $C_{1-4}$alkoxy; and
$R^3$ represents H, —$C_{1-4}$alkyl or aryl with said aryl optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —$C(O)N(C_{1-4}$alkyl)($C_{1-4}$alkyl), —$C(O)NH_2$, —$C(O)NH(C_{1-4}$alkyl) and, —$C(O)NH(C_{3-10}$cycloalkyl),
(iii) $R^2$ and $R^3$ are joined to form a carbocyclyl ring which is optionally substituted by one or more $C_{1-2}$alkyl groups,
(iv) $R^2$ and $R^3$ are joined to form a carbocyclyl ring which is fused to phenyl, with said carbocyclyl or phenyl optionally substituted by one or more groups selected from $C_{1-4}$alkyl, halogen and $C_{1-4}$alkoxy, and
(v) $R^2$ and $R^3$ are joined to form a carbocyclyl ring which is fused to monocyclic heteroaryl with said carbocyclyl or heteroaryl optionally substituted by one or more groups selected from $C_{1-4}$alkyl, halogen and $C_{1-4}$alkoxy;

(f) $R^4$ represents H, —$C_{1-8}$alkyl, —C(O)$C_{1-6}$alkyl or —$NH_2$;

(g) X represents O or S; and (h) Y represents O or S.

34. The method according to claim 33 wherein said compound of formula (I) is (1-(1H-benzo[d]imidazol-5-yl)-5-(4-propoxyphenyl)imidazolidine-2,4-dione.

35. The method according to claim 33 wherein the subject is a human.

36. A method according to claim 33 wherein said sample is a blood sample, a serum sample, a sample of cerebrospinal liquor or a urine sample.

37. A method of prevention of an inflammatory disease or condition comprising administering a therapeutically effective amount of an isoQC inhibitor to a subject in need thereof wherein:

(a) the inflammatory disease or condition is selected from the group consisting of rheumatoid arthritis, atherosclerosis, restenosis, pancreatitis, and osteoporosis;

(b) the isoQC inhibitor comprises a compound of formula (I):

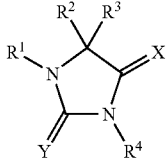

(I)

or a pharmaceutically acceptable salt, solvate or polymorph thereof, including all tautomers and stereoisomers thereof;

(d) $R^1$ represents —$C_{3-8}$carbocyclyl-heteroaryl, —$C_{2-6}$alkenylheteroaryl, —$C_{1-6}$alkylheteroaryl, or $(CH_2)_a CR^5R^6(CH_2)_b$ heteroaryl with (1) a and b independently representing integers 0-5 provided that a+b=0-5 and (2) $R^5$ and $R^6$ being alkylene which, together with the carbon to which they are attached, form a $C_3$-$C_5$ cycloalkyl group, or a bicyclic heteroaryl group, any of said heteroaryl groups being optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —SO$C_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —$NH_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)$NH_2$, —C(O)NH($C_{1-4}$alkyl) and —C(O)NH($C_{3-10}$cycloalkyl) and any of said carbocyclyl groups being optionally substituted by one or more groups selected from $C_{1-4}$alkyl, oxo, halogen and $C_{1-4}$alkoxy;

(e) $R^2$ and $R^3$ are one of (i), (ii), (iii), (iv), or (v) defined as follows:

(i) $R^2$ represents $C_{1-8}$alkyl, aryl, heteroaryl, carbocyclyl, heterocyclyl, —$C_{1-4}$alkylaryl, —$C_{1-4}$alkylheteroaryl, —$C_{1-4}$alkylcarbocyclyl or —$C_{1-4}$alkylheterocyclyl with (1) any of said aryl and heteroaryl groups optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —SO$C_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —$NH_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)$NH_2$, —C(O)NH($C_{1-4}$alkyl) and —C(O)NH($C_{3-10}$cycloalkyl); and (2) any of aforesaid carbocyclyl and heterocyclyl groups optionally substituted by one or more groups selected from $C_{1-4}$alkyl, oxo, halogen and $C_{1-4}$alkoxy; and $R^3$ represents H, —$C_{1-4}$alkyl or aryl with said aryl optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —SO$C_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —$NH_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)$NH_2$, —C(O)NH($C_{1-4}$alkyl) and, —C(O)NH($C_{3-10}$cycloalkyl), (ii) $R^2$ represents phenyl substituted by phenyl, phenyl substituted by a monocyclic heteroaryl group, phenyl substituted by benzyloxy, phenyl fused to carbocyclyl, phenyl fused to heterocyclyl, —$C_{1-4}$alkyl(phenyl substituted by phenyl), —$C_{1-4}$alkyl(phenyl substituted by a monocyclic heteroaryl group), —$C_{1-4}$alkyl(phenyl substituted by benzyloxy), —$C_{1-4}$alkyl (optionally substituted phenyl fused to optionally substituted carbocyclyl or —$C_{1-4}$alkyl(optionally substituted phenyl fused to optionally substituted heterocyclyl) with (1) any of said phenyl, benzyloxy and heteroaryl groups optionally substituted by one or more groups selected from $C_{1-4}$alkyl, halogen and $C_{1-4}$alkoxy and (2) any of said carbocyclyl and heterocyclyl groups optionally substituted by one or more groups selected from $C_{1-4}$alkyl, oxo, halogen and $C_{1-4}$alkoxy; and $R^3$ represents H, —$C_{1-4}$alkyl or aryl with said aryl optionally substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —SO$C_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —$NH_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)$NH_2$, —C(O)NH($C_{1-4}$alkyl) and, —C(O)NH($C_{3-10}$cycloalkyl), (iii) $R^2$ and $R^3$ are joined to form a carbocyclyl ring which is optionally substituted by one or more $C_{1-2}$alkyl groups, (iv) $R^2$ and $R^3$ are joined to form a carbocyclyl ring which is fused to phenyl, with said carbocyclyl or phenyl optionally substituted by one or more groups selected from $C_{1-4}$alkyl, halogen and $C_{1-4}$alkoxy, and (v) $R^2$ and $R^3$ are joined to form a carbocyclyl ring which is fused to monocyclic heteroaryl with said carbocyclyl or heteroaryl optionally substituted by one or more groups selected from $C_{1-4}$alkyl, halogen and $C_{1-4}$alkoxy;

(f) $R^4$ represents H, —$C_{1-8}$alkyl, —C(O)$C_{1-6}$alkyl or —$NH_2$;

(g) X represents O or S; and (h) Y represents O or S.

* * * * *

```
                       SEQUENCE LISTING

<160> NUMBER OF SEQ ID NOS: 115

<210> SEQ ID NO 1
<211> LENGTH: 1086
<212> TYPE: DNA
<213> ORGANISM: Homo sapiens

<400> SEQUENCE: 1
atggcaggcg gaagacaccg gcgcgtcgtg ggcaccctcc acctgctgct gctggtggcc      60
```

```
gccctgccct gggcatccag gggggtcagt ccgagtgcct cagcctggcc agaggagaag      120
aattaccacc agccagccat tttgaattca tcggctcttc ggcaaattgc agaaggcacc      180
agtatctctg aaatgtggca aaatgactta cagccattgc tgatagagcg atacccggga      240 tccctggaa gctatgctgc tcgtcagcac atcatgcagc gaattcagag gcttcaggct       300
gactgggtct tggaaataga caccttcttg agtcagacac cctatgggta ccggtctttc      360
tcaaatatca tcagcaccct caatcccact gctaaacgac atttggtcct cgcctgccac      420
tatgactcca agtattttc ccactggaac aacagagtgt tgtaggagc cactgattca       480 gccgtgccat gtgcaatgat gttggaactt gctcgtgcct tagacaagaa actcctttcc      540
ttaaagactg tttcagactc caagccagat tgtcactcc agctgatctt ctttgatggt      600
gaagaggctt ttcttcactg gtctcctcaa gattctctct atgggtctcg acacttagct      660
gcaaagatgg catcgacccc gcacccacct ggagcgagag gcaccagcca actgcatggc      720
atggatttat tggtcttatt ggatttgatt ggagctccaa acccaacgtt tcccaatttt      780
tttccaaact cagccaggtg gttcgaaaga cttcaagcaa ttgaacatga acttcatgaa      840 tgggtttgc tcaaggatca ctcttttggag gggcggtatt tccagaatta cagttatgga     900
ggtgtgattc aggatgacca tattccattt ttaagaagag gtgttccagt tctgcatctg      960
ataccgtctc ctttccctga agtctggcac accatggatg acaatgaaga aaatttggat    1020
gaatcaacca ttgacaatct aaacaaaatc ctacaagtct ttgtgttgga atatcttcat    1080
ttgtaa                                                                1086
```

<210> SEQ ID NO 2
<211> LENGTH: 1149
<212> TYPE: DNA
<213> ORGANISM: Homo sapiens

<400> SEQUENCE: 2

```
atgcgttccg ggggccgcgg gcgaccccgc ctgcggctgg gggaacgtgg cctcatggag       60
ccactcttgc cgccgaagcg ccgcctgcta ccgcgggttc ggctcttgcc tctgttgctg      120
gcgctggccg tgggctcggc gttctacacc atttggagcg gctggcaccg caggactgag      180
gagctgccgc tgggccggga gctgcgggtc ccattgatcg gaagcctccc cgaagcccgg      240
ctgcggaggg tggtgggaca actggatcca cagcgtctct ggagcactta tctgcgcccc      300
ctgctggttg tgcgaacccc gggcagcccg ggaaatctcc aagtcagaaa gttcctggag      360
gccacgctgc ggtccctgac agcaggttgg cacgtggagc tggatccctt cacagcctca      420
acacccctgg ggccagtgga ctttggcaat gtggtggcca cactgacccc aagggctgcc      480
cgtcacctca cccttgcctg ccattatgac tcgaagctct cccaccggg atcgaccccc      540 tttgtagggg ccacggattc ggctgtgccc tgtgccctgc tgctggagct ggcccaagca      600
cttgacctgg agctgagcag ggccaaaaaa caggcagccc cggtgaccct gcaactgctc      660 ttccttggatg gtgaagaggc gctgaaggag tggggaccca aggactccct ttacggttcc      720
cggcacctgg cccagctcat ggagtctata cctcacagcc ccggcccac caggatccag      780 gctattgagc tctttatgct tcttgatctc ctggagcccc caatcccac cttctacagc      840 cacttccctc gcacggtccg ctggttccat cggctgagga gcattgagaa gcgtctgcac      900
cgtttgaacc tgctgcagtc tcatcccag gaagtgatgt acttccaacc cggggagccc      960
tttggctctg tggaagacga ccacatcccc ttcctccgca gaggggtacc cgtgctccat    1020
```

| | |
|---|---:|
| ctcatctcca cgcccttccc tgctgtctgg cacacccctg cggacaccga ggtcaatctc | 1080 |
| cacccaccca cggtacacaa cttgtgccgc attctcgctg tgttcctggc tgaatacctg | 1140 |
| gggctctag | 1149 |

<210> SEQ ID NO 3
<211> LENGTH: 1145
<212> TYPE: DNA
<213> ORGANISM: Homo sapiens

<400> SEQUENCE: 3

| | |
|---|---:|
| atgcgttccg ggggccgcgg gcgacccccgc ctgcggctgg gggaacgtgg atggagccac | 60 |
| tcttgccgcc gaagcgccgc ctgctaccgc gggttcggct cttgcctctg ttgctggcgc | 120 |
| tggccgtggg ctcggcgttc tacaccattt ggagcggctg gcaccgcagg actgaggagc | 180 |
| tgccgctggg ccgggagctg cgggtcccat tgatcggaag cctccccgaa gcccggctgc | 240 |
| ggagggtggt gggacaactg gatccacagc gtctctggag cacttatctg cgcccccgc | 300 |
| tggttgtgcg aaccccgggc agcccgggaa atctccaagt cagaaagttc ctggaggcca | 360 |
| cgctgcggtc cctgacagca ggttggcacg tggagctgga tcccttcaca gcctcaacac | 420 |
| ccctggggcc agtggacttt ggcaatgtgg tggccacact ggacccaagg ctgcccgtc | 480 |
| acctcaccct tgcctgccat tatgactcga agctcttccc acccggatcg acccccttg | 540 |
| taggggccac ggattcggct gtgccctgtg ccctgctgct ggagctggcc caagcacttg | 600 |
| acctggagct gagcagggcc aaaaaacagg cagccccggt gaccctgcaa ctgctcttct | 660 |
| tggatggtga agaggcgctg aaggagtggg acccaaagga ctccctttac ggttcccggc | 720 |
| acctggccca gctcatggag tctatacctc acagccccgg cccaccagg atccaggcta | 780 |
| ttgagctctt tatgcttctt gatctcctgg agcccccaa tcccaccttc tacagccact | 840 |
| tccctcgcac ggtccgctgg ttccatcggc tgaggagcat tgagaagcgt ctgcaccgtt | 900 |
| tgaacctgct gcagtctcat ccccaggaag tgatgtactt ccaacccggg gagcccttg | 960 |
| gctctgtgga agacgaccac atcccttcc tccgcagagg ggtacccgtg ctccatctca | 1020 |
| tctccacgcc cttccctgct gtctggcaca cccctgcgga caccgaggtc aatctccacc | 1080 |
| cacccacggt acacaacttg tgccgcattc tcgctgtgtt cctggctgaa tacctggggc | 1140 |
| tctag | 1145 |

<210> SEQ ID NO 4
<211> LENGTH: 1149
<212> TYPE: DNA
<213> ORGANISM: Macaca fascicularis

<400> SEQUENCE: 4

| | |
|---|---:|
| atgcgttccg ggggccgcgg gcggcccgc ctgcggctag gggaacgtgg cgttatggag | 60 |
| ccactcttgc ccccgaagcg ccgcctgcta ccgcgggttc ggctcttgcc cctgttgctg | 120 |
| gcgctggccg tgggctcggc gttctacacc atttggagcg gctggcaccg caggactgag | 180 |
| gagctgccgc tgggccggga gctgcgggtc ccgttgatcg gaagccttcc cgaagcccgg | 240 |
| ctgcggaggg tggtgggaca actggaccca cagcgtctct ggggcactta tctgcgcccc | 300 |
| ctgctggttg tgcgaacccc aggcagcccg ggaaatctcc aagtcagaaa gttcctggag | 360 |
| gccacgctgc ggtccctgac agcaggttgg cacgtggagc tggatccctt cacagcctcg | 420 |
| acgcccctgg ggccagtgga ctttggcaat gtggtggcca cgctggaccc gggggctgcc | 480 |
| cgtcacctca cccttgcctg ccattatgac tcgaagctct tcccacccgg atcgacccg | 540 |

```
tttgtaggg ccacggactc ggctgtgccc tgtgccctgc tgctggagct ggcccaggca    600
cttgacctgg agctgagcag ggccaaagaa caggcagccc cggtgaccct gcaactgctc    660
ttcctggatg gtgaagaggc gctgaaggag tggggaccca aggactccct ttacggttcc    720
cggcacctgg cccagctcat ggagtctata cctcatagcc ccggcccac caggatccag    780 gctattgagc tctttatgct tcttgatctc ctgggagccc ccaatcccac cttctacagc    840
cacttccctc gcacggtccg ctggttccat cggctgagaa gcattgagaa cgtctgcac    900 cgtttgaacc tgctgcagtc tcatccccag gaagtgatgt acttccaacc cggggagccc    960
ttcggctctg tggaagacga ccacatcccc ttcctccgca gaggggtccc cgtgctccat    1020
ctcatctcta cgcccttccc tgctgtctgg cacacccctg cggacacaga ggccaatctc    1080
caccgcccca cggtacacaa cttaagccgc attctggccg tgttcctggc tgaataccTg    1140
gggctctag                                                            1149
```

<210> SEQ ID NO 5
<211> LENGTH: 1149
<212> TYPE: DNA
<213> ORGANISM: Macaca mulatta

<400> SEQUENCE: 5

```
atgcgttccg ggggccgcgg gcggccccgc ctgcggctag ggaacgtgg cgttatggag     60 ccactcttgc ccccgaagcg ccgcctgcta ccgcgggttc ggctcttgcc cctgttgctg    120
gcgctggccg tgggctcggc gttctacacc atttggagcg gctggcaccg caggactgag    180
gagctgccgc tgggccggga gctgcgggtc ccgttgatcg gaagccttcc cgaagcccgg    240
ctgcggaggg tggtgggaca actgacccca cagcgtctct ggggcactta tctgcgcccc    300
ctgctggttg tgcgaacccc aggcagcccg ggaaatctcc aagtcagaaa gttcctggag    360
gccacgctgc ggtccctgac agcaggttgg cacgtggagc tggatccctt cacagcctcg    420
acgcccctgg gcccagtgga cttTggcaat gtggtggcca cgctggaccc ggggctgcc    480 cgtcacctca cccttgcctg ccattatgac tcgaagctct cccaccgg atcgaccccg    540 tttgtaggg ccacagactc ggctgtgccc tgtgccctgc tgctggagct ggcccaggca    600
cttgacctgg agctgagcag ggccaaagaa caggcagccc cggtgaccct gcaactgctc    660
ttcctggatg gtgaagaggc gctgaaggag tggggaccca aggactccct ttacggttcc    720
cggcacctgg cccagctcat ggagtctata cctcatagcc ccggcccac caggatccag    780 gctattgagc tctttatgct tcttgatctc ctgggagccc ccaatcccac cttctacagc    840
cacttccctc gcacggtccg ctggttccat cggctgagaa gcattgagaa cgtctgcac    900 cgtttgaacc tgctgcagtc tcatccccag gaagtgatgt acttccaacc cggggagccc    960
tttggctctg tggaagacga ccacatcccc ttcctccgca gaggggtccc cgtgctccat    1020
ctcatctcta cgcccttccc tgctgtctgg cacacccctg cggacacaga ggccaatctc    1080
caccgcccca cggtacacaa cttaagccgc attctggccg tgttcctggc tgaataccTg    1140
gggctctag                                                             1149
```

<210> SEQ ID NO 6
<211> LENGTH: 1152
<212> TYPE: DNA
<213> ORGANISM: Canis familiaris

<400> SEQUENCE: 6

```
atgccttccg ggggccgcgg gcggtcccgg ctacggctcg gggaacgtgg cctcttggag     60
ccgccctccc cgcccaagcg ccgcctgctc ccgcgggcgc acttcttgcc tctgcttctg    120
ctggccctgg ccctggcttc ggcgacctac accatctgga gcggctggca ccaccagact    180
gaggagctgc cgcggggccg ggagctgcgg ggccgcttga tcggaagcct ctccgaagcc    240
cggctgcggc gggtggtggg gcaactggac ccacaccgtc tctggaacac ttatctgcgc    300
cccctgctgt ttgtgcggac cccgggcagc ccggcaatc tccaagtcag aaagttcctg     360
gaggctacac tacggacctt gacagcaggc tggcatgtgg aactggaccc cttcacagcc    420
ttgacacccc tggggccact ggactttggc aatgtggtgg ccacgctgga cccaggggct    480
gcccgtcacc tcaccttgc ctgccattat gactccaagc tcttcgcatc tgagtcggtt      540
cccttgtgg gggcaacaga ttcggctgta ccttgcgccc tgctgctgga gctggctcag      600
gccctcgaca gggagttgag tagggccaag gagcaggaag ccccggtgac tctgcagctg    660
ctctttttgg atggtgaaga agcactgaag gagtggggac ccacagactc cctctatggc    720
tccccggcacc tggcccagct catggagtct gcacccccaca gccggggccc caccaggatc    780
caggctatcg agctcttcat gctccttgat ctcctgggtg ccccgaatcc aaacttctac    840
agtcacttcc ctcatacagc ccgctggttc atcggctga ggagcatcga aagcgcctt      900
caccgcatga acctgctgca gtctcatccc caggaagtga tgtacttcca gcccggggag    960
cccccctggtt ctgtgaaaga tgaccacatc cccttcctcc gccagggggt ccctgtgctc   1020
cacctcatct ccatgccctt ccccctccgtc tggcacaccc ccgatgactc tgaggccaac   1080
ctgcacccac ccaccgtaca caatctgagc cgcatcctcg ccgtgttcct ggccgaatat   1140
ctggggctct ag                                                       1152
```

<210> SEQ ID NO 7
<211> LENGTH: 1152
<212> TYPE: DNA
<213> ORGANISM: Rattus norvegicus

<400> SEQUENCE: 7

```
atgagtccgg ccagccgcgg gcggtctcgg cagcggctcg gggatcgcgg cctcatgaaa     60
ccaccctcac tttccaagcg ccgtcttctg ccgcgggtgc agctcctgcc cctgctgctg    120
ctggcgctgg ccctgggctt ggcttttttat atcgtctgga atagctggca ccctggggtt    180
gaggaggtat cacggagccg ggatctgcgg gtcccgctga tcggaagcct ttcagaagcc    240
aagctgcggc ttgtgtagg gcagctggat ccacagcgtc tctggggaac ttttctgcgt     300
cccttgttga ttgtacgacc cccaggtagt cctggcaatc tccaagtgag aaagttcctg    360
gaggctacgt tgcagtccct atcgcaggc tggcacgtgg aactggaccc attcacagcc     420
tcaaccccct tggggccact ggacttcggg aacgtggtgg ccaccttga cccaggagct      480
gcccgtcacc tcaccctcgc ctgccattat gactctaagt tcttccctcc tgggttaccc    540
cccttttgtgg gggccacaga ttcagccgtg cctgtgccc tgcttctgga gttagtccag     600
gcccttgatg tcatgctgag cagaatcaag cagcaggcag caccagtgac cctgcagctg    660
ctcttcttgg acggggagga ggcactgaag gagtggggac caaaggactc cctctatggt    720
tccccggcacc tagctcagat catggagtct ataccgcaca gccctggccc caccaggatc    780
caggctattg agctcttgt ccttcttgac cttctgggag cgccagtcc aatcttcttc       840
agtcacttcc cccgcacagc ccgctggttc aacgcactgc ggagcatcga aagcgcctt     900
caccgtctga acctactgca gtctcacccc caggaagtga tgtacttcca acccggggag    960
```

```
cccccctggcc ctgtggaaga tgaccacatc cccttccttc gcagaggggt cccggtgctc    1020
cacctcattg cgatgccctt ccctgccgtg tggcacacac ctgctgacac tgaggctaac    1080
ctccacccgc ccacggtgca caacctgagc cgcatcctcg ccgtgttcct ggctgagtac    1140
ctgggtctct ag                                                        1152

<210> SEQ ID NO 8
<211> LENGTH: 1152
<212> TYPE: DNA
<213> ORGANISM: Mus musculus

<400> SEQUENCE: 8
atgagtcccg ggagccgcgg gcggccccgg cagcggctcg aggatcgtgg cctcatgaaa     60
ccaccctcac tttccaagcg ccgtcttctg ccgcgagtgc agttcctgcc cctgctgctg    120
ctggcgctgg ctatgggctt ggcttttctat atcgtctgga acagctggca ccctggggtt    180
gaggagatgt cacggagccg ggatctgcgg gtcccgctga tcggaagcct ttcagaagcc    240
aagctgcggc tggtggtagg gcagctggat ccgcagcgtc tctgggaaac tttcctgcgt    300
cccttattga ttgtgcgacc cccggggtagt tctggcaatc tccaagtgag aaagttcctg    360
gaggctacgt tgcagtccct gtcggcaggc tggcatgttg aactggaccc attcacggcc    420
tcaaccccct ggggccact ggacttcggg aacgtggtgg ccacacttga cccaggagct    480
gcccgtcacc tcaccctcgc ctgccattat gactctaagt tcttccctcc ggggttgccc    540 cccttttgtgg gggccacaga ttcagctgtg cctgtgcccc tgcttctgga gttggtccag    600
gcccttgatg ccatgctgag cagaatcaag cagcaggcag caccggtgac cctgcagctg    660
cttttcttgg atggggagga ggcactgaag gagtggggac caaaggactc cctctatggc    720
tcccggcacc tagctcagat catggagtct ataccacaca gccctggccc caccaggatc    780
caggctattg agctcttttgt cctcctcgac cttctgggag catccagtcc gatcttcttc    840
agtcacttcc ctcgcacagc ccgctggttc cagcgactga ggagcattga aagcgcctt    900 caccggctga acctactgca gtctcacccc caggaagtga tgtacttcca acccggggag    960
ccccccggcc ctgtggaaga tgaccacatc cccttccttc gcagagggt cccggtgctc   1020 cacctcattg ccacgcccctt ccctgctgtg tggcacacac ctgctgacac cgaggccaac   1080
ctccacccac ccactgtgca taacctgagc cgcatccttg ctgtgttcct ggccgagtac   1140
ctgggactct ag                                                        1152

<210> SEQ ID NO 9
<211> LENGTH: 1152
<212> TYPE: DNA
<213> ORGANISM: Bos taurus

<400> SEQUENCE: 9
atgccttccg ggggccgcgg gcggccccgg ctccaggtcg gggaacgcag ccttttggag     60
cgaccctcac cgcccaagcg ccgcctgata ccgcgggcac agctgttgcc ccagctgctg    120
ctggctctga cggtagcctc ggtgttctat accatttgga ggatctggca tagccagact    180
gaagagctac cgctggggcg ggagctgcgg ggcccttttga tcggaagcct ccccgaagct    240
cgggtgcgga gggtagtggg gcaactggac cctcaccgtc tctggaacac tttcctgcgc    300
cctctgctgg ttgtacggac tccgggcagc ccgggcaatc tccaagtgag aaagttcctg    360
gaggctacgc tgcggacact ttcagcaggc tggcatatag aactcgactc cttcactgcc    420
```

```
tccacacccg tggggccatt ggacttcagc aatgtggtgg ccacgctgga cccaggggct    480
gcccgccacc ttaccctgc ctgccattat gactccaagc tcttcccatc tgactcagcc     540
cccttgtgg gggccacgga ttcggcagtg ccttgctccc tgctactgga gctggcccaa      600
gcccttgacc aggagctggg caaagccaag gagagggcag cgccaatgac cttgcagctg    660
atcttcctgg atggtgaaga ggcactgaag cagtggggac ccaaggactc gctttatggc    720
tcccggcacc tggcccagct catggagtct acaccccacg gcctgggctc caccaggatc    780
caggctattg agctctttat gcttcttgat ctcctgggag cccccaaccc gaccttctac    840
agtcacttcc ctcgcacggc ccgctggttc catcggctca ggagcattga aagcgcctg    900
caccgtctga acctcctgca gtctcatcct tgggaagtga tgtacttcca gaccggggag    960
ccccccggct ccgtggaaga cgaccacatc ccgttcctcc gccgaggagt tcccgtgctc   1020
cacctcatcg ccacacccttt ccctctgtc tggcacacgt ccgatgactc cgaggccaac   1080
ctgcacccac ccacggtaca aacctgagc cgcatcctgg ccgtgttcct ggctgagtac   1140
ctggggctct ag                                                       1152
```

<210> SEQ ID NO 10
<211> LENGTH: 361
<212> TYPE: PRT
<213> ORGANISM: Homo sapiens

<400> SEQUENCE: 10

```
Met Ala Gly Gly Arg His Arg Arg Val Val Gly Thr Leu His Leu Leu
1               5                   10                  15

Leu Leu Val Ala Ala Leu Pro Trp Ala Ser Arg Gly Val Ser Pro Ser
            20                  25                  30

Ala Ser Ala Trp Pro Glu Glu Lys Asn Tyr His Gln Pro Ala Ile Leu
        35                  40                  45

Asn Ser Ser Ala Leu Arg Gln Ile Ala Glu Gly Thr Ser Ile Ser Glu
    50                  55                  60

Met Trp Gln Asn Asp Leu Gln Pro Leu Leu Ile Glu Arg Tyr Pro Gly
65                  70                  75                  80

Ser Pro Gly Ser Tyr Ala Ala Arg Gln His Ile Met Gln Arg Ile Gln
                85                  90                  95

Arg Leu Gln Ala Asp Trp Val Leu Glu Ile Asp Thr Phe Leu Ser Gln
            100                 105                 110

Thr Pro Tyr Gly Tyr Arg Ser Phe Ser Asn Ile Ile Ser Thr Leu Asn
        115                 120                 125

Pro Thr Ala Lys Arg His Leu Val Leu Ala Cys His Tyr Asp Ser Lys
    130                 135                 140

Tyr Phe Ser His Trp Asn Asn Arg Val Phe Val Gly Ala Thr Asp Ser
145                 150                 155                 160

Ala Val Pro Cys Ala Met Met Leu Glu Leu Ala Arg Ala Leu Asp Lys
                165                 170                 175

Lys Leu Leu Ser Leu Lys Thr Val Ser Asp Ser Lys Pro Asp Leu Ser
            180                 185                 190

Leu Gln Leu Ile Phe Phe Asp Gly Glu Glu Ala Phe Leu His Trp Ser
        195                 200                 205

Pro Gln Asp Ser Leu Tyr Gly Ser Arg His Leu Ala Ala Lys Met Ala
    210                 215                 220

Ser Thr Pro His Pro Pro Gly Ala Arg Gly Thr Ser Gln Leu His Gly
225                 230                 235                 240
```

Met Asp Leu Leu Val Leu Leu Asp Leu Ile Gly Ala Pro Asn Pro Thr
              245                 250                 255

Phe Pro Asn Phe Phe Pro Asn Ser Ala Arg Trp Phe Glu Arg Leu Gln
        260                 265                 270

Ala Ile Glu His Glu Leu His Glu Leu Gly Leu Leu Lys Asp His Ser
        275                 280                 285

Leu Glu Gly Arg Tyr Phe Gln Asn Tyr Ser Tyr Gly Gly Val Ile Gln
        290                 295                 300

Asp Asp His Ile Pro Phe Leu Arg Arg Gly Val Pro Val Leu His Leu
305                 310                 315                 320

Ile Pro Ser Pro Phe Pro Glu Val Trp His Thr Met Asp Asp Asn Glu
                325                 330                 335

Glu Asn Leu Asp Glu Ser Thr Ile Asp Asn Leu Asn Lys Ile Leu Gln
        340                 345                 350

Val Phe Val Leu Glu Tyr Leu His Leu
        355                 360

<210> SEQ ID NO 11
<211> LENGTH: 382
<212> TYPE: PRT
<213> ORGANISM: Homo sapiens

<400> SEQUENCE: 11

Met Arg Ser Gly Gly Arg Gly Arg Pro Arg Leu Arg Leu Gly Glu Arg
1               5                   10                  15

Gly Leu Met Glu Pro Leu Leu Pro Pro Lys Arg Arg Leu Leu Pro Arg
            20                  25                  30

Val Arg Leu Leu Pro Leu Leu Leu Ala Leu Ala Val Gly Ser Ala Phe
        35                  40                  45

Tyr Thr Ile Trp Ser Gly Trp His Arg Arg Thr Glu Glu Leu Pro Leu
        50                  55                  60

Gly Arg Glu Leu Arg Val Pro Leu Ile Gly Ser Leu Pro Glu Ala Arg
65                  70                  75                  80

Leu Arg Arg Val Val Gly Gln Leu Asp Pro Gln Arg Leu Trp Ser Thr
                85                  90                  95

Tyr Leu Arg Pro Leu Leu Val Val Arg Thr Pro Gly Ser Pro Gly Asn
            100                 105                 110

Leu Gln Val Arg Lys Phe Leu Glu Ala Thr Leu Arg Ser Leu Thr Ala
        115                 120                 125

Gly Trp His Val Glu Leu Asp Pro Phe Thr Ala Ser Thr Pro Leu Gly
        130                 135                 140

Pro Val Asp Phe Gly Asn Val Val Ala Thr Leu Asp Pro Arg Ala Ala
145                 150                 155                 160

Arg His Leu Thr Leu Ala Cys His Tyr Asp Ser Lys Leu Phe Pro Pro
                165                 170                 175

Gly Ser Thr Pro Phe Val Gly Ala Thr Asp Ser Ala Val Pro Cys Ala
            180                 185                 190

Leu Leu Leu Glu Leu Ala Gln Ala Leu Asp Leu Glu Leu Ser Arg Ala
        195                 200                 205

Lys Lys Gln Ala Ala Pro Val Thr Leu Gln Leu Leu Phe Leu Asp Gly
        210                 215                 220

Glu Glu Ala Leu Lys Glu Trp Gly Pro Lys Asp Ser Leu Tyr Gly Ser
225                 230                 235                 240

Arg His Leu Ala Gln Leu Met Glu Ser Ile Pro His Ser Pro Gly Pro
                245                 250                 255

```
Thr Arg Ile Gln Ala Ile Glu Leu Phe Met Leu Leu Asp Leu Leu Gly
            260                 265                 270

Ala Pro Asn Pro Thr Phe Tyr Ser His Phe Pro Arg Thr Val Arg Trp
            275                 280                 285

Phe His Arg Leu Arg Ser Ile Glu Lys Arg Leu His Arg Leu Asn Leu
            290                 295                 300

Leu Gln Ser His Pro Gln Glu Val Met Tyr Phe Gln Pro Gly Glu Pro
305                 310                 315                 320

Phe Gly Ser Val Glu Asp Asp His Ile Pro Phe Leu Arg Arg Gly Val
                325                 330                 335

Pro Val Leu His Leu Ile Ser Thr Pro Phe Pro Ala Val Trp His Thr
            340                 345                 350

Pro Ala Asp Thr Glu Val Asn Leu His Pro Pro Thr Val His Asn Leu
            355                 360                 365

Cys Arg Ile Leu Ala Val Phe Leu Ala Glu Tyr Leu Gly Leu
            370                 375                 380

<210> SEQ ID NO 12
<211> LENGTH: 364
<212> TYPE: PRT
<213> ORGANISM: Homo sapiens

<400> SEQUENCE: 12

Met Glu Pro Leu Leu Pro Pro Lys Arg Arg Leu Leu Pro Arg Val Arg
1               5                   10                  15

Leu Leu Pro Leu Leu Ala Leu Ala Val Gly Ser Ala Phe Tyr Thr
            20                  25                  30

Ile Trp Ser Gly Trp His Arg Arg Thr Glu Glu Leu Pro Leu Gly Arg
            35                  40                  45

Glu Leu Arg Val Pro Leu Ile Gly Ser Leu Pro Glu Ala Arg Leu Arg
50                  55                  60

Arg Val Val Gly Gln Leu Asp Pro Gln Arg Leu Trp Ser Thr Tyr Leu
65                  70                  75                  80

Arg Pro Leu Leu Val Val Arg Thr Pro Gly Ser Pro Gly Asn Leu Gln
            85                  90                  95

Val Arg Lys Phe Leu Glu Ala Thr Leu Arg Ser Leu Thr Ala Gly Trp
            100                 105                 110

His Val Glu Leu Asp Pro Phe Thr Ala Ser Thr Pro Leu Gly Pro Val
            115                 120                 125

Asp Phe Gly Asn Val Val Ala Thr Leu Asp Pro Arg Ala Ala Arg His
130                 135                 140

Leu Thr Leu Ala Cys His Tyr Asp Ser Lys Leu Phe Pro Pro Gly Ser
145                 150                 155                 160

Thr Pro Phe Val Gly Ala Thr Asp Ser Ala Val Pro Cys Ala Leu Leu
            165                 170                 175

Leu Glu Leu Ala Gln Ala Leu Asp Leu Glu Leu Ser Arg Ala Lys Lys
            180                 185                 190

Gln Ala Ala Pro Val Thr Leu Gln Leu Leu Phe Leu Asp Gly Glu Glu
            195                 200                 205

Ala Leu Lys Glu Trp Gly Pro Lys Asp Ser Leu Tyr Gly Ser Arg His
            210                 215                 220

Leu Ala Gln Leu Met Glu Ser Ile Pro His Ser Pro Gly Pro Thr Arg
225                 230                 235                 240

Ile Gln Ala Ile Glu Leu Phe Met Leu Leu Asp Leu Leu Gly Ala Pro
```

```
                    245                 250                 255
Asn Pro Thr Phe Tyr Ser His Phe Pro Arg Thr Val Arg Trp Phe His
                260                 265                 270

Arg Leu Arg Ser Ile Glu Lys Arg Leu His Arg Leu Asn Leu Leu Gln
            275                 280                 285

Ser His Pro Gln Glu Val Met Tyr Phe Gln Pro Gly Glu Pro Phe Gly
        290                 295                 300

Ser Val Glu Asp Asp His Ile Pro Phe Leu Arg Arg Gly Val Pro Val
305                 310                 315                 320

Leu His Leu Ile Ser Thr Pro Phe Pro Ala Val Trp His Thr Pro Ala
                325                 330                 335

Asp Thr Glu Val Asn Leu His Pro Pro Thr Val His Asn Leu Cys Arg
            340                 345                 350

Ile Leu Ala Val Phe Leu Ala Glu Tyr Leu Gly Leu
        355                 360

<210> SEQ ID NO 13
<211> LENGTH: 382
<212> TYPE: PRT
<213> ORGANISM: Macaca fascicularis

<400> SEQUENCE: 13

Met Arg Ser Gly Gly Arg Gly Arg Pro Arg Leu Arg Leu Gly Glu Arg
1               5                   10                  15

Gly Val Met Glu Pro Leu Leu Pro Pro Lys Arg Arg Leu Leu Pro Arg
            20                  25                  30

Val Arg Leu Leu Pro Leu Leu Leu Ala Leu Ala Val Gly Ser Ala Phe
        35                  40                  45

Tyr Thr Ile Trp Ser Gly Trp His Arg Arg Thr Glu Glu Leu Pro Leu
    50                  55                  60

Gly Arg Glu Leu Arg Val Pro Leu Ile Gly Ser Leu Pro Glu Ala Arg
65                  70                  75                  80

Leu Arg Arg Val Val Gly Gln Leu Asp Pro Gln Arg Leu Trp Gly Thr
                85                  90                  95

Tyr Leu Arg Pro Leu Leu Val Val Arg Thr Pro Gly Ser Pro Gly Asn
            100                 105                 110

Leu Gln Val Arg Lys Phe Leu Glu Ala Thr Leu Arg Ser Leu Thr Ala
        115                 120                 125

Gly Trp His Val Glu Leu Asp Pro Phe Thr Ala Ser Thr Pro Leu Gly
    130                 135                 140

Pro Val Asp Phe Gly Asn Val Val Ala Thr Leu Asp Pro Gly Ala Ala
145                 150                 155                 160

Arg His Leu Thr Leu Ala Cys His Tyr Asp Ser Lys Leu Phe Pro Pro
                165                 170                 175

Gly Ser Thr Pro Phe Val Gly Ala Thr Asp Ser Ala Val Pro Cys Ala
            180                 185                 190

Leu Leu Leu Glu Leu Ala Gln Ala Leu Asp Leu Glu Leu Ser Arg Ala
        195                 200                 205

Lys Glu Gln Ala Ala Pro Val Thr Leu Gln Leu Leu Phe Leu Asp Gly
    210                 215                 220

Glu Glu Ala Leu Lys Glu Trp Gly Pro Lys Asp Ser Leu Tyr Gly Ser
225                 230                 235                 240

Arg His Leu Ala Gln Leu Met Glu Ser Ile Pro His Ser Pro Gly Pro
                245                 250                 255
```

```
Thr Arg Ile Gln Ala Ile Glu Leu Phe Met Leu Leu Asp Leu Leu Gly
            260                 265                 270

Ala Pro Asn Pro Thr Phe Tyr Ser His Phe Pro Arg Thr Val Arg Trp
        275                 280                 285

Phe His Arg Leu Arg Ser Ile Glu Lys Arg Leu His Arg Leu Asn Leu
    290                 295                 300

Leu Gln Ser His Pro Gln Glu Val Met Tyr Phe Gln Pro Gly Glu Pro
305                 310                 315                 320

Phe Gly Ser Val Glu Asp Asp His Ile Pro Phe Leu Arg Arg Gly Val
                325                 330                 335

Pro Val Leu His Leu Ile Ser Thr Pro Phe Pro Ala Val Trp His Thr
            340                 345                 350

Pro Ala Asp Thr Glu Ala Asn Leu His Pro Pro Thr Val His Asn Leu
        355                 360                 365

Ser Arg Ile Leu Ala Val Phe Leu Ala Glu Tyr Leu Gly Leu
    370                 375                 380

<210> SEQ ID NO 14
<211> LENGTH: 382
<212> TYPE: PRT
<213> ORGANISM: Macaca mulatta

<400> SEQUENCE: 14

Met Arg Ser Gly Gly Arg Gly Arg Pro Arg Leu Arg Leu Gly Glu Arg
1               5                   10                  15

Gly Val Met Glu Pro Leu Leu Pro Pro Lys Arg Arg Leu Leu Pro Arg
            20                  25                  30

Val Arg Leu Leu Pro Leu Leu Leu Ala Leu Ala Val Gly Ser Ala Phe
        35                  40                  45

Tyr Thr Ile Trp Ser Gly Trp His Arg Arg Thr Glu Glu Leu Pro Leu
    50                  55                  60

Gly Arg Glu Leu Arg Val Pro Leu Ile Gly Ser Leu Pro Glu Ala Arg
65                  70                  75                  80

Leu Arg Arg Val Val Gly Gln Leu Asp Pro Gln Arg Leu Trp Gly Thr
                85                  90                  95

Tyr Leu Arg Pro Leu Leu Val Val Arg Thr Pro Gly Ser Pro Gly Asn
            100                 105                 110

Leu Gln Val Arg Lys Phe Leu Glu Ala Thr Leu Arg Ser Leu Thr Ala
        115                 120                 125

Gly Trp His Val Glu Leu Asp Pro Phe Thr Ala Ser Thr Pro Leu Gly
    130                 135                 140

Pro Val Asp Phe Gly Asn Val Val Ala Thr Leu Asp Pro Gly Ala Ala
145                 150                 155                 160

Arg His Leu Thr Leu Ala Cys His Tyr Asp Ser Lys Leu Phe Pro Pro
                165                 170                 175

Gly Ser Thr Pro Phe Val Gly Ala Thr Asp Ser Ala Val Pro Cys Ala
            180                 185                 190

Leu Leu Leu Glu Leu Ala Gln Ala Leu Asp Leu Glu Leu Ser Arg Ala
        195                 200                 205

Lys Glu Gln Ala Ala Pro Val Thr Leu Gln Leu Leu Phe Leu Asp Gly
    210                 215                 220

Glu Glu Ala Leu Lys Glu Trp Gly Pro Lys Asp Ser Leu Tyr Gly Ser
225                 230                 235                 240

Arg His Leu Ala Gln Leu Met Glu Ser Ile Pro His Ser Pro Gly Pro
                245                 250                 255
```

-continued

```
Thr Arg Ile Gln Ala Ile Glu Leu Phe Met Leu Leu Asp Leu Leu Gly
            260                 265                 270

Ala Pro Asn Pro Thr Phe Tyr Ser His Phe Pro Arg Thr Val Arg Trp
        275                 280                 285

Phe His Arg Leu Arg Ser Ile Glu Lys Arg Leu His Arg Leu Asn Leu
    290                 295                 300

Leu Gln Ser His Pro Gln Glu Val Met Tyr Phe Gln Pro Gly Glu Pro
305                 310                 315                 320

Phe Gly Ser Val Glu Asp His Ile Pro Phe Leu Arg Arg Gly Val
                325                 330                 335

Pro Val Leu His Leu Ile Ser Thr Pro Phe Pro Ala Val Trp His Thr
            340                 345                 350

Pro Ala Asp Thr Glu Ala Asn Leu His Pro Pro Thr Val His Asn Leu
        355                 360                 365

Ser Arg Ile Leu Ala Val Phe Leu Ala Glu Tyr Leu Gly Leu
    370                 375                 380

<210> SEQ ID NO 15
<211> LENGTH: 383
<212> TYPE: PRT
<213> ORGANISM: Canis familiaris

<400> SEQUENCE: 15

Met Pro Ser Gly Gly Arg Gly Arg Ser Arg Leu Arg Leu Gly Glu Arg
1               5                   10                  15

Gly Leu Leu Glu Pro Pro Ser Pro Pro Lys Arg Arg Leu Leu Pro Arg
            20                  25                  30

Ala His Phe Leu Pro Leu Leu Leu Ala Leu Ala Leu Ala Ser Ala
        35                  40                  45

Thr Tyr Thr Ile Trp Ser Gly Trp His His Gln Thr Glu Glu Leu Pro
    50                  55                  60

Arg Gly Arg Glu Leu Arg Gly Arg Leu Ile Gly Ser Leu Ser Glu Ala
65                  70                  75                  80

Arg Leu Arg Arg Val Val Gly Gln Leu Asp Pro His Arg Leu Trp Asn
                85                  90                  95

Thr Tyr Leu Arg Pro Leu Leu Val Arg Thr Pro Gly Ser Pro Gly
            100                 105                 110

Asn Leu Gln Val Arg Lys Phe Leu Glu Ala Thr Leu Arg Thr Leu Thr
        115                 120                 125

Ala Gly Trp His Val Glu Leu Asp Pro Phe Thr Ala Leu Thr Pro Leu
    130                 135                 140

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Leu Phe Ala
                165                 170                 175

Ser Glu Ser Val Pro Phe Val Gly Ala Thr Asp Ser Ala Val Pro Cys
            180                 185                 190

Ala Leu Leu Leu Glu Leu Ala Gln Ala Leu Asp Arg Glu Leu Ser Arg
        195                 200                 205

Ala Lys Glu Gln Glu Ala Pro Val Thr Leu Gln Leu Phe Leu Asp
    210                 215                 220

Gly Glu Glu Ala Leu Lys Glu Trp Gly Pro Thr Asp Ser Leu Tyr Gly
225                 230                 235                 240

Ser Arg His Leu Ala Gln Leu Met Glu Ser Ala Pro His Ser Pro Gly
```

-continued

```
            245                 250                 255
Pro Thr Arg Ile Gln Ala Ile Glu Leu Phe Met Leu Leu Asp Leu Leu
            260                 265                 270

Gly Ala Pro Asn Pro Asn Phe Tyr Ser His Phe Pro His Thr Ala Arg
        275                 280                 285

Trp Phe His Arg Leu Arg Ser Ile Glu Lys Arg Leu His Arg Met Asn
    290                 295                 300

Leu Leu Gln Ser His Pro Gln Glu Val Met Tyr Phe Gln Pro Gly Glu
305                 310                 315                 320

Pro Pro Gly Ser Val Glu Asp His Ile Pro Phe Leu Arg Arg Gly
                325                 330                 335

Val Pro Val Leu His Leu Ile Ser Met Pro Phe Pro Ser Val Trp His
            340                 345                 350

Thr Pro Asp Asp Ser Glu Ala Asn Leu His Pro Pro Thr Val His Asn
            355                 360                 365

Leu Ser Arg Ile Leu Ala Val Phe Leu Ala Glu Tyr Leu Gly Leu
        370                 375                 380

<210> SEQ ID NO 16
<211> LENGTH: 383
<212> TYPE: PRT
<213> ORGANISM: Rattus norvegicus

<400> SEQUENCE: 16

Met Ser Pro Ala Ser Arg Gly Arg Ser Arg Gln Arg Leu Gly Asp Arg
1               5                   10                  15

Gly Leu Met Lys Pro Pro Ser Leu Ser Lys Arg Arg Leu Leu Pro Arg
            20                  25                  30

Val Gln Leu Leu Pro Leu Leu Leu Ala Leu Ala Leu Gly Leu Ala
        35                  40                  45

Phe Tyr Ile Val Trp Asn Ser Trp His Pro Gly Val Glu Glu Val Ser
    50                  55                  60

Arg Ser Arg Asp Leu Arg Val Pro Leu Ile Gly Ser Leu Ser Glu Ala
65                  70                  75                  80

Lys Leu Arg Leu Val Val Gly Gln Leu Asp Pro Gln Arg Leu Trp Gly
                85                  90                  95

Thr Phe Leu Arg Pro Leu Leu Ile Val Arg Pro Pro Gly Ser Pro Gly
            100                 105                 110

Asn Leu Gln Val Arg Lys Phe Leu Glu Ala Thr Leu Gln Ser Leu Ser
        115                 120                 125

Ala Gly Trp His Val Glu Leu Asp Pro Phe Thr Ala Ser Thr Pro Leu
    130                 135                 140

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Phe Phe Pro
                165                 170                 175

Pro Gly Leu Pro Pro Phe Val Gly Ala Thr Asp Ser Ala Val Pro Cys
            180                 185                 190

Ala Leu Leu Leu Glu Leu Val Gln Ala Leu Asp Val Met Leu Ser Arg
        195                 200                 205

Ile Lys Gln Gln Ala Ala Pro Val Thr Leu Gln Leu Leu Phe Leu Asp
    210                 215                 220

Gly Glu Glu Ala Leu Lys Glu Trp Gly Pro Lys Asp Ser Leu Tyr Gly
225                 230                 235                 240
```

```
Ser Arg His Leu Ala Gln Ile Met Glu Ser Ile Pro His Ser Pro Gly
                245                 250                 255

Pro Thr Arg Ile Gln Ala Ile Glu Leu Phe Val Leu Leu Asp Leu Leu
            260                 265                 270

Gly Ala Pro Ser Pro Ile Phe Phe Ser His Phe Pro Arg Thr Ala Arg
            275                 280                 285

Trp Phe Gln Arg Leu Arg Ser Ile Glu Lys Arg Leu His Arg Leu Asn
290                 295                 300

Leu Leu Gln Ser His Pro Gln Glu Val Met Tyr Phe Gln Pro Gly Glu
305                 310                 315                 320

Pro Pro Gly Pro Val Glu Asp Asp His Ile Pro Phe Leu Arg Arg Gly
                325                 330                 335

Val Pro Val Leu His Leu Ile Ala Met Pro Phe Pro Ala Val Trp His
            340                 345                 350

Thr Pro Ala Asp Thr Glu Ala Asn Leu His Pro Pro Thr Val His Asn
            355                 360                 365

Leu Ser Arg Ile Leu Ala Val Phe Leu Ala Glu Tyr Leu Gly Leu
            370                 375                 380

<210> SEQ ID NO 17
<211> LENGTH: 383
<212> TYPE: PRT
<213> ORGANISM: Mus musculus

<400> SEQUENCE: 17

Met Ser Pro Gly Ser Arg Gly Arg Pro Arg Gln Arg Leu Glu Asp Arg
1               5                   10                  15

Gly Leu Met Lys Pro Pro Ser Leu Ser Lys Arg Arg Leu Leu Pro Arg
            20                  25                  30

Val Gln Phe Leu Pro Leu Leu Leu Ala Leu Ala Met Gly Leu Ala
            35                  40                  45

Phe Tyr Ile Val Trp Asn Ser Trp His Pro Gly Val Glu Glu Met Ser
    50                  55                  60

Arg Ser Arg Asp Leu Arg Val Pro Leu Ile Gly Ser Leu Ser Glu Ala
65                  70                  75                  80

Lys Leu Arg Leu Val Val Gly Gln Leu Asp Pro Gln Arg Leu Trp Gly
                85                  90                  95

Thr Phe Leu Arg Pro Leu Leu Ile Val Arg Pro Pro Gly Ser Ser Gly
            100                 105                 110

Asn Leu Gln Val Arg Lys Phe Leu Glu Ala Thr Leu Gln Ser Leu Ser
            115                 120                 125

Ala Gly Trp His Val Glu Leu Asp Pro Phe Thr Ala Ser Thr Pro Leu
130                 135                 140

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Phe Phe Pro
                165                 170                 175

Pro Gly Leu Pro Pro Phe Val Gly Ala Thr Asp Ser Ala Val Pro Cys
            180                 185                 190

Ala Leu Leu Leu Glu Leu Val Gln Ala Leu Asp Ala Met Leu Ser Arg
            195                 200                 205

Ile Lys Gln Gln Ala Ala Pro Val Thr Leu Leu Leu Phe Leu Asp
    210                 215                 220

Gly Glu Glu Ala Leu Lys Glu Trp Gly Pro Lys Asp Ser Leu Tyr Gly
225                 230                 235                 240
```

-continued

Ser Arg His Leu Ala Gln Ile Met Glu Ser Ile Pro His Ser Pro Gly
            245                 250                 255

Pro Thr Arg Ile Gln Ala Ile Glu Leu Phe Val Leu Leu Asp Leu Leu
        260                 265                 270

Gly Ala Ser Ser Pro Ile Phe Phe Ser His Phe Pro Arg Thr Ala Arg
            275                 280                 285

Trp Phe Gln Arg Leu Arg Ser Ile Glu Lys Arg Leu His Arg Leu Asn
        290                 295                 300

Leu Leu Gln Ser His Pro Gln Glu Val Met Tyr Phe Gln Pro Gly Glu
305                 310                 315                 320

Pro Pro Gly Pro Val Glu Asp Asp His Ile Pro Phe Leu Arg Arg Gly
            325                 330                 335

Val Pro Val Leu His Leu Ile Ala Thr Pro Phe Pro Ala Val Trp His
        340                 345                 350

Thr Pro Ala Asp Thr Glu Ala Asn Leu His Pro Pro Thr Val His Asn
            355                 360                 365

Leu Ser Arg Ile Leu Ala Val Phe Leu Ala Glu Tyr Leu Gly Leu
        370                 375                 380

<210> SEQ ID NO 18
<211> LENGTH: 383
<212> TYPE: PRT
<213> ORGANISM: Bos taurus

<400> SEQUENCE: 18

Met Pro Ser Gly Gly Arg Gly Arg Pro Arg Leu Gln Val Gly Glu Arg
1               5                   10                  15

Ser Leu Leu Glu Arg Pro Ser Pro Lys Arg Arg Leu Ile Pro Arg
            20                  25                  30

Ala Gln Leu Leu Pro Gln Leu Leu Ala Leu Thr Val Ala Ser Val
        35                  40                  45

Phe Tyr Thr Ile Trp Arg Ile Trp His Ser Gln Thr Glu Glu Leu Pro
    50                  55                  60

Leu Gly Arg Glu Leu Arg Gly Pro Leu Ile Gly Ser Leu Pro Glu Ala
65                  70                  75                  80

Arg Val Arg Arg Val Val Gly Gln Leu Asp Pro His Arg Leu Trp Asn
                85                  90                  95

Thr Phe Leu Arg Pro Leu Leu Val Val Arg Thr Pro Gly Ser Pro Gly
            100                 105                 110

Asn Leu Gln Val Arg Lys Phe Leu Glu Ala Thr Leu Arg Thr Leu Ser
        115                 120                 125

Ala Gly Trp His Ile Glu Leu Asp Ser Phe Thr Ala Ser Thr Pro Val
    130                 135                 140

Gly Pro Leu Asp Phe Ser Asn Val Val Ala Thr Leu Asp Pro Gly Ala
145                 150                 155                 160

Ala Arg His Leu Thr Leu Ala Cys His Tyr Asp Ser Lys Leu Phe Pro
                165                 170                 175

Ser Asp Ser Ala Pro Phe Val Gly Ala Thr Asp Ser Ala Val Pro Cys
            180                 185                 190

Ser Leu Leu Leu Glu Leu Ala Gln Ala Leu Asp Gln Leu Gly Lys
        195                 200                 205

Ala Lys Glu Arg Ala Ala Pro Met Thr Leu Gln Leu Ile Phe Leu Asp
    210                 215                 220

Gly Glu Glu Ala Leu Lys Gln Trp Gly Pro Lys Asp Ser Leu Tyr Gly

```
                        225                 230                 235                 240
Ser Arg His Leu Ala Gln Leu Met Glu Ser Thr Pro His Gly Leu Gly
                    245                 250                 255

Ser Thr Arg Ile Gln Ala Ile Glu Leu Phe Met Leu Leu Asp Leu Leu
                260                 265                 270

Gly Ala Pro Asn Pro Thr Phe Tyr Ser His Phe Pro Arg Thr Ala Arg
            275                 280                 285

Trp Phe His Arg Leu Arg Ser Ile Glu Lys Arg Leu His Arg Leu Asn
        290                 295                 300

Leu Leu Gln Ser His Pro Trp Glu Val Met Tyr Phe Gln Thr Gly Glu
305                 310                 315                 320

Pro Pro Gly Ser Val Glu Asp Asp His Ile Pro Phe Leu Arg Arg Gly
                325                 330                 335

Val Pro Val Leu His Leu Ile Ala Thr Pro Phe Pro Ser Val Trp His
            340                 345                 350

Thr Ser Asp Asp Ser Glu Ala Asn Leu His Pro Pro Thr Val His Asn
        355                 360                 365

Leu Ser Arg Ile Leu Ala Val Phe Leu Ala Glu Tyr Leu Gly Leu
    370                 375                 380

<210> SEQ ID NO 19
<211> LENGTH: 26
<212> TYPE: DNA
<213> ORGANISM: artificial sequence
<220> FEATURE:
<223> OTHER INFORMATION: synthetic oligonucleotide

<400> SEQUENCE: 19
ggtctacacc atttggagcg gctggc                                          26

<210> SEQ ID NO 20
<211> LENGTH: 27
<212> TYPE: DNA
<213> ORGANISM: artificial sequence
<220> FEATURE:
<223> OTHER INFORMATION: synthetic oligonucleotide

<400> SEQUENCE: 20
gggttggaag tacatcactt cctgggg                                         27

<210> SEQ ID NO 21
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 21
accatgcgtt ccgggggccg cggg                                            24

<210> SEQ ID NO 22
<211> LENGTH: 27
<212> TYPE: DNA
<213> ORGANISM: artificial sequence
<220> FEATURE:
<223> OTHER INFORMATION: synthetic oligonucleotide

<400> SEQUENCE: 22
acgctagagc cccaggtatt cagccag                                         27

<210> SEQ ID NO 23
```

```
<211> LENGTH: 30
<212> TYPE: DNA
<213> ORGANISM: artificial sequence
<220> FEATURE:
<223> OTHER INFORMATION: synthetic oligonucleotide

<400> SEQUENCE: 23
atatatgaat tcatgcgttc cggggggccgc                                   30

<210> SEQ ID NO 24
<211> LENGTH: 33
<212> TYPE: DNA
<213> ORGANISM: artificial sequence
<220> FEATURE:
<223> OTHER INFORMATION: synthetic oligonucleotide

<400> SEQUENCE: 24
atatatgaat tcatggagcc actcttgccg ccg                                33

<210> SEQ ID NO 25
<211> LENGTH: 33
<212> TYPE: DNA
<213> ORGANISM: artificial sequence
<220> FEATURE:
<223> OTHER INFORMATION: synthetic oligonucleotide

<400> SEQUENCE: 25
atatatgtcg acgagcccca ggtattcagc cag                                33

<210> SEQ ID NO 26
<211> LENGTH: 44
<212> TYPE: DNA
<213> ORGANISM: artificial sequence
<220> FEATURE:
<223> OTHER INFORMATION: synthetic oligonucleotide

<400> SEQUENCE: 26
atatactagt gatgacgacg acaagttcta caccatttgg agcg                    44

<210> SEQ ID NO 27
<211> LENGTH: 49
<212> TYPE: DNA
<213> ORGANISM: artificial sequence
<220> FEATURE:
<223> OTHER INFORMATION: synthetic oligonucleotide

<400> SEQUENCE: 27
tatagaattc ctagtgatgg tgatggtgat ggagccccag gtattcagc               49

<210> SEQ ID NO 28
<211> LENGTH: 28
<212> TYPE: DNA
<213> ORGANISM: artificial sequence
<220> FEATURE:
<223> OTHER INFORMATION: PCR primer

<400> SEQUENCE: 28
atatgaattc ttctacacca tttggagc                                     28

<210> SEQ ID NO 29
<211> LENGTH: 49
<212> TYPE: DNA
<213> ORGANISM: artificial sequence
<220> FEATURE:
<223> OTHER INFORMATION: PCR primer

<400> SEQUENCE: 29
```

```
atatgaattc catcaccatc accatcactt ctacaccatt tggagcggc        49
```

<210> SEQ ID NO 30
<211> LENGTH: 35
<212> TYPE: DNA
<213> ORGANISM: artificial sequence
<220> FEATURE:
<223> OTHER INFORMATION: PCR primer

<400> SEQUENCE: 30

```
atatatgcgg ccgcctagag ccccaggtat tcagc                       35
```

<210> SEQ ID NO 31
<211> LENGTH: 20
<212> TYPE: DNA
<213> ORGANISM: artificial sequence
<220> FEATURE:
<223> OTHER INFORMATION: PCR primer

<400> SEQUENCE: 31

```
ccaggatcca ggctattgag                                        20
```

<210> SEQ ID NO 32
<211> LENGTH: 56
<212> TYPE: DNA
<213> ORGANISM: artificial sequence
<220> FEATURE:
<223> OTHER INFORMATION: PCR primer

<400> SEQUENCE: 32

```
atatatgcgg ccgcctagtg atggtgatgg tgatggagcc ccaggtattc agccag    56
```

<210> SEQ ID NO 33
<211> LENGTH: 19
<212> TYPE: DNA
<213> ORGANISM: artificial sequence
<220> FEATURE:
<223> OTHER INFORMATION: PCR primer

<400> SEQUENCE: 33

```
ttccacaggg ccgggggc                                          19
```

<210> SEQ ID NO 34
<211> LENGTH: 18
<212> TYPE: DNA
<213> ORGANISM: artificial sequence
<220> FEATURE:
<223> OTHER INFORMATION: PCR primer

<400> SEQUENCE: 34

```
atgagtcccg ggagccgc                                          18
```

<210> SEQ ID NO 35
<211> LENGTH: 18
<212> TYPE: DNA
<213> ORGANISM: artificial sequence
<220> FEATURE:
<223> OTHER INFORMATION: PCR primer

<400> SEQUENCE: 35

```
ctagagtccc aggtactc                                          18
```

<210> SEQ ID NO 36
<211> LENGTH: 20
<212> TYPE: DNA

```
<213> ORGANISM: artificial sequence
<220> FEATURE:
<223> OTHER INFORMATION: PCR primer

<400> SEQUENCE: 36
agttcctgcc cctgctgctg                                               20

<210> SEQ ID NO 37
<211> LENGTH: 20
<212> TYPE: DNA
<213> ORGANISM: artificial sequence
<220> FEATURE:
<223> OTHER INFORMATION: PCR primer

<400> SEQUENCE: 37
atcaagaggc accaaccaac                                               20

<210> SEQ ID NO 38
<211> LENGTH: 19
<212> TYPE: DNA
<213> ORGANISM: artificial sequence
<220> FEATURE:
<223> OTHER INFORMATION: PCR primer

<400> SEQUENCE: 38
ctggataata tttccatag                                                19

<210> SEQ ID NO 39
<211> LENGTH: 19
<212> TYPE: DNA
<213> ORGANISM: artificial sequence
<220> FEATURE:
<223> OTHER INFORMATION: PCR primer

<400> SEQUENCE: 39
acagctggga atctgagtc                                                19

<210> SEQ ID NO 40
<211> LENGTH: 21
<212> TYPE: DNA
<213> ORGANISM: artificial sequence
<220> FEATURE:
<223> OTHER INFORMATION: PCR primer

<400> SEQUENCE: 40
gagcagaata gcttccgggc g                                             21

<210> SEQ ID NO 41
<211> LENGTH: 33
<212> TYPE: DNA
<213> ORGANISM: artificial sequence
<220> FEATURE:
<223> OTHER INFORMATION: PCR primer

<400> SEQUENCE: 41
ctgcgggtcc cattgaacgg aagcctcccc gaa                                33

<210> SEQ ID NO 42
<211> LENGTH: 33
<212> TYPE: DNA
<213> ORGANISM: artificial sequence
<220> FEATURE:
<223> OTHER INFORMATION: PCR primer

<400> SEQUENCE: 42
ttcggggagg cttccgttca atgggacccg cag                                33
```

<210> SEQ ID NO 43
<211> LENGTH: 33
<212> TYPE: DNA
<213> ORGANISM: artificial sequence
<220> FEATURE:
<223> OTHER INFORMATION: PCR primer

<400> SEQUENCE: 43
acggtacaca acttggcccg cattctcgct gtg          33

<210> SEQ ID NO 44
<211> LENGTH: 33
<212> TYPE: DNA
<213> ORGANISM: artificial sequence
<220> FEATURE:
<223> OTHER INFORMATION: PCR primer

<400> SEQUENCE: 44
cacagcgaga atgcgggcca agttgtgtac cgt          33

<210> SEQ ID NO 45
<211> LENGTH: 30
<212> TYPE: DNA
<213> ORGANISM: Artificial sequence
<220> FEATURE:
<223> OTHER INFORMATION: Cloning primer

<400> SEQUENCE: 45
atatataagc ttatggcagg cggaagacac              30

<210> SEQ ID NO 46
<211> LENGTH: 31
<212> TYPE: DNA
<213> ORGANISM: Artificial sequence
<220> FEATURE:
<223> OTHER INFORMATION: Cloning primer

<400> SEQUENCE: 46
atatgcggcc gcttacaaat gaagatattc c            31

<210> SEQ ID NO 47
<211> LENGTH: 35
<212> TYPE: DNA
<213> ORGANISM: Artificial sequence
<220> FEATURE:
<223> OTHER INFORMATION: PCR primer

<400> SEQUENCE: 47
atatatgcgg ccgcctagag ccccaggtat tcagc        35

<210> SEQ ID NO 48
<211> LENGTH: 31
<212> TYPE: DNA
<213> ORGANISM: Artificial sequence
<220> FEATURE:
<223> OTHER INFORMATION: PCR primer

<400> SEQUENCE: 48
atatctcgag tccatcgcca ccatggtgag c            31

<210> SEQ ID NO 49
<211> LENGTH: 31
<212> TYPE: DNA
<213> ORGANISM: Artificial sequence
<220> FEATURE:

<223> OTHER INFORMATION: PCR primer

<400> SEQUENCE: 49
atatctcgag ttacttgtac agctcgtcca t                            31

<210> SEQ ID NO 50
<211> LENGTH: 41
<212> TYPE: DNA
<213> ORGANISM: artificial sequence
<220> FEATURE:
<223> OTHER INFORMATION: PCR primer

<400> SEQUENCE: 50
atatgcggcc gcatgtcgac gctccaaatg gtgtagaacg c                 41

<210> SEQ ID NO 51
<211> LENGTH: 57
<212> TYPE: DNA
<213> ORGANISM: Artificial sequence
<220> FEATURE:
<223> OTHER INFORMATION: PCR primer

<400> SEQUENCE: 51
atatgcggcc gcttacttgt catcgtcatc cttgtaatcc aaatgaagat attccaa    57

<210> SEQ ID NO 52
<211> LENGTH: 57
<212> TYPE: DNA
<213> ORGANISM: Artificial sequence
<220> FEATURE:
<223> OTHER INFORMATION: PCR primer

<400> SEQUENCE: 52
atatgcggcc gcctacttgt catcgtcatc cttgtaatcg agccccaggt attcagc    57

<210> SEQ ID NO 53
<211> LENGTH: 1149
<212> TYPE: DNA
<213> ORGANISM: Mus musculus

<400> SEQUENCE: 53
atgagtcccg ggagccgcgg gcggccccgg cagcggctcg aggatcgtgg cctcatgaaa    60
ccaccctcac tttccaagcg ccgtcttctg ccgcgagtgc agttcctgcc cctgctgctg   120
ctggcgctgg ctatgggctt ggcttttctat atcgtctgga cagctggca ccctggggtt    180
gaggagatgt cacggagccg ggatctgcgg gtcccgctga tcggaagcct ttcagaagcc   240
aagctgcggc tggtggtagg gcagctggat ccgcagcgtc tctggggaac tttcctgcgt   300
cccttattga ttgtgcgacc cccgggtagt tctggcaatc tccaagtgag aaagttcctg   360
gaggctacgt tgcagtccct gtcggcaggc tggcatgttg aactggaccc attcacggcc   420
tcaacccct tggggccact ggacttcggg aacgtggtgg ccacacttga cccaggagct    480
gccccgtcacc tcaccctcgc ctgccattat gactctaagt tcttccctcc ggggttgccc   540
cccttgtgg gggccacaga ttcagctgtg ccctgtgccc tgcttctgga gttggtccag    600
gcccttgatg ccatgctgag cagaatcaag cagcaggcag caccggtgac cctgcagctg   660
ctttcttgg gggaggaggc actgaaggag tggggaccaa aggactccct ctatggctcc    720
cggcacctag ctcagatcat ggagtctata ccacacagcc ctggccccac caggatccag    780
gctattgagc tcttttgtcct cctcgacctt ctggagcat ccagtccgat cttcttcagt    840
cacttccctc gcacagcccg ctggttccag cgactgagga gcattgagaa gcgccttcac    900

```
cggctgaacc tactgcagtc tcacccccag gaagtgatgt acttccaacc cggggagccc        960
cccggccctg tggaagatga ccacatcccc ttccttcgca gaggggtccc ggtgctccac       1020
ctcattgcca cgcccttccc tgctgtgttg cacacacctg ctgacaccga ggccaacctc       1080
cacccaccca ctgtgcataa cctgagccgc atccttgctg tgttcctggc cgagtacctg       1140
ggactctag                                                                1149
```

<210> SEQ ID NO 54
<211> LENGTH: 1095
<212> TYPE: DNA
<213> ORGANISM: Mus musculus

<400> SEQUENCE: 54

```
atgaaaccac cctcactttc caagcgccgt cttctgccgc gagtgcagtt cctgcccctg         60
ctgctgctgg cgctggctat gggcttggct ttctatatcg tctggaacag ctggcaccct        120
ggggttgagg agatgtcacg gagccggagt ctgcgggtcc cgctgatcgg aagcctttca        180
gaagccaagc tgcggctggt ggtagggcag ctggatccgc agcgtctctg ggaactttc         240 ctgcgtccct tattgattgt gcgacccccg ggtagttctg caatctcca agtgagaaag         300 ttcctggagg ctacgttgca gtccctgtcg gcaggctggc atgttgaact ggacccattc        360
acggcctcaa ccccccttggg gccactggac ttcgggaacg tggtggccac acttgaccca       420
ggagctgccc gtcacctcac cctcgcctgc cattatgact ctaagttctt ccctccgggg        480
ttgcccccct ttgtggggc cacagattca gctgtgccct gtgccctgct tctggagttg        540
gtccaggccc ttgatgccat gctgagcaga atcaagcagc aggcagcacc ggtgaccctg        600
cagctgcttt tcttggggga ggaggcactg aaggagtggg gaccaaagga ctccctctat        660 ggctccggc acctagctca gatcatggag tctataccac acagccctgg ccccaccagg         720
atccaggcta ttgagctctt tgtcctcctc gaccttctgg gagcatccag tccgatcttc       780
ttcagtcact cccctcgcac agcccgctgg ttccagcgac tgaggagcat tgagaagcgc        840
cttcaccggc tgaacctact gcagtctcac ccccaggaag tgatgtactt ccaacccggg       900 gagcccccg gccctgtgga agatgaccac atcccttcc ttcgcagagg ggtcccggtg          960
ctccacctca ttgccacgcc cttccctgct gtgttgcaca cacctgctga caccgaggcc       1020
aacctccacc cacccactgt gcataacctg agccgcatcc ttgctgtgtt cctggccgag       1080
tacctgggac tctag                                                        1095
```

<210> SEQ ID NO 55
<211> LENGTH: 1152
<212> TYPE: DNA
<213> ORGANISM: Rattus norvegicus

<400> SEQUENCE: 55

```
atgagtccgg ccagccgcgg gcggtctcgg cagcggctcg gggatcgcgg cctcatgaaa         60
ccaccctcac tttccaagcg ccgtcttctg ccgcgggtgc agctcctgcc cctgctgctg        120
ctggcgctgg ccctgggctt ggcttttttat atcgtctgga atagctggca ccctggggtt       180
gaggaggtat cacggagccg ggatctgcgg gtcccgctga tcggaagcct ttcagaagcc        240
aagctgcggc ttgtggtagg gcagctggat ccacagcgtc tctgggaac ttttctgcgt         300 cccttgttga ttgtacgacc cccaggtagt cctggcaatc tccaagtgag aaagttcctg        360
gaggctacgt tgcagtccct atcggcaggc tggcacgtgg aactggaccc attcacagcc        420
```

```
tcaaccccct tggggccact ggacttcggg aacgtggtgg ccaccccttga cccaggagct    480 gcccgtcacc tcaccctcgc ctgccattat gactctaagt tcttccctcc tgggttaccc    540 cccctttgtgg gggccacaga ttcagccgtg ccctgtgccc tgcttctgga gttagtccag    600
gcccttgatg tcatgctgag cagaatcaag cagcaggcag caccagtgac cctgcagctg    660
ctcttcttgg acggggagga ggcactgaag gagtggggac caaaggactc cctctatggt    720
tcccggcacc tagctcagat catggagtct ataccgcaca gccctggccc caccaggatc    780
caggctattg agctctttgt ccttcttgac cttctgggag cgcccagtcc aatcttcttc    840
agtcacttcc cccgcacagc ccgctggttc aacgactgc ggagcatcga aagcgcctt     900 caccgtctga acctactgca gtctcacccc caggaagtga tgtacttcca acccggggag    960 cccctggcc ctgtggaaga tgaccacatc cccttccttc gcagagggt cccgtgctc      1020 cacctcattg cgatgccctt ccctgccgtg tggcacacac ctgctgacac tgaggctaac    1080
ctccacccgc ccacggtgca aacctgagcc cgcatcctcg ccgtgttcct ggctgagtac    1140
ctgggtctct ag                                                        1152
```

<210> SEQ ID NO 56
<211> LENGTH: 1098
<212> TYPE: DNA
<213> ORGANISM: Rattus norvegicus

<400> SEQUENCE: 56

```
atgaaaccac cctcactttc caagcgccgt cttctgccgc gggtgcagct cctgcccctg     60
ctgctgctgg cgctggccct gggcttggct ttttatatcg tctggaatag ctggcaccct    120
ggggttgagg aggtatcacg gagccgggat ctgcgggtcc cgctgatcgg aagcctttca    180
gaagccaagc tgcggcttgt ggtagggcag ctggatccac agcgtctctg gggaactttt    240
ctgcgtccct tgttgattgt acgaccccca ggtagtcctg gcaatctcca agtgagaaag    300
ttcctggagc tacgttgca gtccctatcg gcaggctggc acgtggaact ggacccattc    360
acagcctcaa ccccttgggg gccactggac ttcgggaacg tggtggccac ccttgaccca    420
ggagctgccc gtcacctcac cctcgcctgc cattatgact ctaagttctt ccctcctggg    480 ttaccccct tgtggggggc cacagattca gccgtgccct gtgcctgctg tctggagtta    540
gtccaggccc ttgatgtcat gctgagcaga atcaagcagc aggcagcacc agtgaccctg    600
cagctgctct tcttggacgg ggaggaggca ctgaaggagt ggggaccaaa ggactccctc    660
tatggttccc ggcacctagc tcagatcatg gagtctatac cgcacagccc tggccccacc    720
aggatccagg ctattgagct ctttgtcctt cttgaccttc tgggagcgcc cagtccaatc    780
ttcttcagtc acttccccgg cacagcccgc tggttccaac gactgcggag catcgagaag    840
cgccttcacc gtctgaacct actgcagtct caccccagg aagtgatgta cttccaaccc    900
ggggagcccc tggccctgt ggaagatgac cacatcccct tccttcgcag aggggtcccg    960
gtgctccacc tcattgcgat gcccttccct gccgtgtggc acacacctgc tgacactgag    1020
gctaacctcc acccgcccac ggtgcacaac ctgagccgca tcctcgccgt gttcctggct    1080
gagtacctgg gtctctag                                                  1098
```

<210> SEQ ID NO 57
<211> LENGTH: 382
<212> TYPE: PRT
<213> ORGANISM: Mus musculus

<400> SEQUENCE: 57

```
Met Ser Pro Gly Ser Arg Gly Arg Pro Arg Gln Arg Leu Glu Asp Arg
1               5                   10                  15

Gly Leu Met Lys Pro Pro Ser Leu Ser Lys Arg Arg Leu Leu Pro Arg
            20                  25                  30

Val Gln Phe Leu Pro Leu Leu Leu Ala Leu Ala Met Gly Leu Ala
        35                  40                  45

Phe Tyr Ile Val Trp Asn Ser Trp His Pro Gly Val Glu Glu Met Ser
    50                  55                  60

Arg Ser Arg Asp Leu Arg Val Pro Leu Ile Gly Ser Leu Ser Glu Ala
65                  70                  75                  80

Lys Leu Arg Leu Val Val Gly Gln Leu Asp Pro Gln Arg Leu Trp Gly
                85                  90                  95

Thr Phe Leu Arg Pro Leu Leu Ile Val Arg Pro Pro Gly Ser Ser Gly
            100                 105                 110

Asn Leu Gln Val Arg Lys Phe Leu Glu Ala Thr Leu Gln Ser Leu Ser
            115                 120                 125

Ala Gly Trp His Val Glu Leu Asp Pro Phe Thr Ala Ser Thr Pro Leu
            130                 135                 140

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Phe Phe Pro
                165                 170                 175

Pro Gly Leu Pro Pro Phe Val Gly Ala Thr Asp Ser Ala Val Pro Cys
            180                 185                 190

Ala Leu Leu Leu Glu Leu Val Gln Ala Leu Asp Ala Met Leu Ser Arg
            195                 200                 205

Ile Lys Gln Gln Ala Ala Pro Val Thr Leu Gln Leu Leu Phe Leu Gly
        210                 215                 220

Glu Glu Ala Leu Lys Glu Trp Gly Pro Lys Asp Ser Leu Tyr Gly Ser
225                 230                 235                 240

Arg His Leu Ala Gln Ile Met Glu Ser Ile Pro His Ser Pro Gly Pro
                245                 250                 255

Thr Arg Ile Gln Ala Ile Glu Leu Phe Val Leu Leu Asp Leu Leu Gly
            260                 265                 270

Ala Ser Ser Pro Ile Phe Phe Ser His Phe Pro Arg Thr Ala Arg Trp
        275                 280                 285

Phe Gln Arg Leu Arg Ser Ile Glu Lys Arg Leu His Arg Leu Asn Leu
            290                 295                 300

Leu Gln Ser His Pro Gln Glu Val Met Tyr Phe Gln Pro Gly Glu Pro
305                 310                 315                 320

Pro Gly Pro Val Glu Asp Asp His Ile Pro Phe Leu Arg Arg Gly Val
                325                 330                 335

Pro Val Leu His Leu Ile Ala Thr Pro Phe Pro Ala Val Leu His Thr
            340                 345                 350

Pro Ala Asp Thr Glu Ala Asn Leu His Pro Pro Thr Val His Asn Leu
        355                 360                 365

Ser Arg Ile Leu Ala Val Phe Leu Ala Glu Tyr Leu Gly Leu
    370                 375                 380

<210> SEQ ID NO 58
<211> LENGTH: 364
<212> TYPE: PRT
<213> ORGANISM: Mus musculus
```

<400> SEQUENCE: 58

```
Met Lys Pro Pro Ser Leu Ser Lys Arg Arg Leu Leu Pro Arg Val Gln
1               5                   10                  15

Phe Leu Pro Leu Leu Leu Ala Leu Ala Met Gly Leu Ala Phe Tyr
            20                  25                  30

Ile Val Trp Asn Ser Trp His Pro Gly Val Glu Met Ser Arg Ser
        35                  40                  45

Arg Asp Leu Arg Val Pro Leu Ile Gly Ser Leu Ser Glu Ala Lys Leu
    50                  55                  60

Arg Leu Val Val Gly Gln Leu Asp Pro Gln Arg Leu Trp Gly Thr Phe
65                  70                  75                  80

Leu Arg Pro Leu Leu Ile Val Arg Pro Pro Gly Ser Ser Gly Asn Leu
                85                  90                  95

Gln Val Arg Lys Phe Leu Glu Ala Thr Leu Gln Ser Leu Ser Ala Gly
            100                 105                 110

Trp His Val Glu Leu Asp Pro Phe Thr Ala Ser Thr Pro Leu Gly Pro
        115                 120                 125

Leu Asp Phe Gly Asn Val Val Ala Thr Leu Asp Pro Gly Ala Ala Arg
    130                 135                 140

His Leu Thr Leu Ala Cys His Tyr Asp Ser Lys Phe Phe Pro Pro Gly
145                 150                 155                 160

Leu Pro Pro Phe Val Gly Ala Thr Asp Ser Ala Val Pro Cys Ala Leu
                165                 170                 175

Leu Leu Glu Leu Val Gln Ala Leu Asp Ala Met Leu Ser Arg Ile Lys
            180                 185                 190

Gln Gln Ala Ala Pro Val Thr Leu Gln Leu Leu Phe Leu Gly Glu Glu
        195                 200                 205

Ala Leu Lys Glu Trp Gly Pro Lys Asp Ser Leu Tyr Gly Ser Arg His
    210                 215                 220

Leu Ala Gln Ile Met Glu Ser Ile Pro His Ser Pro Gly Pro Thr Arg
225                 230                 235                 240

Ile Gln Ala Ile Glu Leu Phe Val Leu Leu Asp Leu Leu Gly Ala Ser
                245                 250                 255

Ser Pro Ile Phe Phe Ser His Phe Pro Arg Thr Ala Arg Trp Phe Gln
            260                 265                 270

Arg Leu Arg Ser Ile Glu Lys Arg Leu His Arg Leu Asn Leu Leu Gln
        275                 280                 285

Ser His Pro Gln Glu Val Met Tyr Phe Gln Pro Gly Glu Pro Pro Gly
    290                 295                 300

Pro Val Glu Asp Asp His Ile Pro Phe Leu Arg Arg Gly Val Pro Val
305                 310                 315                 320

Leu His Leu Ile Ala Thr Pro Phe Pro Ala Val Leu His Thr Pro Ala
                325                 330                 335

Asp Thr Glu Ala Asn Leu His Pro Pro Thr Val His Asn Leu Ser Arg
            340                 345                 350

Ile Leu Ala Val Phe Leu Ala Glu Tyr Leu Gly Leu
        355                 360
```

<210> SEQ ID NO 59
<211> LENGTH: 383
<212> TYPE: PRT
<213> ORGANISM: Rattus norvegicus

<400> SEQUENCE: 59

Met Ser Pro Ala Ser Arg Gly Arg Ser Arg Gln Arg Leu Gly Asp Arg
1               5                   10                  15

Gly Leu Met Lys Pro Pro Ser Leu Ser Lys Arg Arg Leu Leu Pro Arg
            20                  25                  30

Val Gln Leu Leu Pro Leu Leu Leu Ala Leu Ala Leu Gly Leu Ala
        35                  40                  45

Phe Tyr Ile Val Trp Asn Ser Trp His Pro Gly Val Glu Glu Val Ser
    50                  55                  60

Arg Ser Arg Asp Leu Arg Val Pro Leu Ile Gly Ser Leu Ser Glu Ala
65                  70                  75                  80

Lys Leu Arg Leu Val Val Gly Gln Leu Asp Pro Gln Arg Leu Trp Gly
                85                  90                  95

Thr Phe Leu Arg Pro Leu Leu Ile Val Arg Pro Pro Gly Ser Pro Gly
            100                 105                 110

Asn Leu Gln Val Arg Lys Phe Leu Glu Ala Thr Leu Gln Ser Leu Ser
            115                 120                 125

Ala Gly Trp His Val Glu Leu Asp Pro Phe Thr Ala Ser Thr Pro Leu
            130                 135                 140

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Phe Phe Pro
            165                 170                 175

Pro Gly Leu Pro Pro Phe Val Gly Ala Thr Asp Ser Ala Val Pro Cys
            180                 185                 190

Ala Leu Leu Leu Glu Leu Val Gln Ala Leu Asp Val Met Leu Ser Arg
            195                 200                 205

Ile Lys Gln Gln Ala Ala Pro Val Thr Leu Gln Leu Leu Phe Leu Asp
210                 215                 220

Gly Glu Glu Ala Leu Lys Glu Trp Gly Pro Lys Asp Ser Leu Tyr Gly
225                 230                 235                 240

Ser Arg His Leu Ala Gln Ile Met Glu Ser Ile Pro His Ser Pro Gly
            245                 250                 255

Pro Thr Arg Ile Gln Ala Ile Glu Leu Phe Val Leu Leu Asp Leu Leu
            260                 265                 270

Gly Ala Pro Ser Pro Ile Phe Phe Ser His Phe Pro Arg Thr Ala Arg
            275                 280                 285

Trp Phe Gln Arg Leu Arg Ser Ile Glu Lys Arg Leu His Arg Leu Asn
            290                 295                 300

Leu Leu Gln Ser His Pro Gln Glu Val Met Tyr Phe Gln Pro Gly Glu
305                 310                 315                 320

Pro Pro Gly Pro Val Glu Asp Asp His Ile Pro Phe Leu Arg Arg Gly
            325                 330                 335

Val Pro Val Leu His Leu Ile Ala Met Pro Phe Pro Ala Val Trp His
            340                 345                 350

Thr Pro Ala Asp Thr Glu Ala Asn Leu His Pro Pro Thr Val His Asn
            355                 360                 365

Leu Ser Arg Ile Leu Ala Val Phe Leu Ala Glu Tyr Leu Gly Leu
            370                 375                 380

<210> SEQ ID NO 60
<211> LENGTH: 365
<212> TYPE: PRT
<213> ORGANISM: Rattus norvegicus

<400> SEQUENCE: 60

Met Lys Pro Pro Ser Leu Ser Lys Arg Arg Leu Leu Pro Arg Val Gln
1               5                   10                  15

Leu Leu Pro Leu Leu Leu Ala Leu Ala Leu Gly Leu Ala Phe Tyr
            20                  25                  30

Ile Val Trp Asn Ser Trp His Pro Gly Val Glu Glu Val Ser Arg Ser
        35                  40                  45

Arg Asp Leu Arg Val Pro Leu Ile Gly Ser Leu Ser Glu Ala Lys Leu
    50                  55                  60

Arg Leu Val Val Gly Gln Leu Asp Pro Gln Arg Leu Trp Gly Thr Phe
65                  70                  75                  80

Leu Arg Pro Leu Leu Ile Val Arg Pro Pro Gly Ser Pro Gly Asn Leu
                85                  90                  95

Gln Val Arg Lys Phe Leu Glu Ala Thr Leu Gln Ser Leu Ser Ala Gly
                100                 105                 110

Trp His Val Glu Leu Asp Pro Phe Thr Ala Ser Thr Pro Leu Gly Pro
        115                 120                 125

Leu Asp Phe Gly Asn Val Val Ala Thr Leu Asp Pro Gly Ala Ala Arg
    130                 135                 140

His Leu Thr Leu Ala Cys His Tyr Asp Ser Lys Phe Phe Pro Pro Gly
145                 150                 155                 160

Leu Pro Pro Phe Val Gly Ala Thr Asp Ser Ala Val Pro Cys Ala Leu
                165                 170                 175

Leu Leu Glu Leu Val Gln Ala Leu Asp Val Met Leu Ser Arg Ile Lys
                180                 185                 190

Gln Gln Ala Ala Pro Val Thr Leu Gln Leu Leu Phe Leu Asp Gly Glu
                195                 200                 205

Glu Ala Leu Lys Glu Trp Gly Pro Lys Asp Ser Leu Tyr Gly Ser Arg
        210                 215                 220

His Leu Ala Gln Ile Met Glu Ser Ile Pro His Ser Pro Gly Pro Thr
225                 230                 235                 240

Arg Ile Gln Ala Ile Glu Leu Phe Val Leu Leu Asp Leu Leu Gly Ala
                245                 250                 255

Pro Ser Pro Ile Phe Phe Ser His Phe Pro Arg Thr Ala Arg Trp Phe
            260                 265                 270

Gln Arg Leu Arg Ser Ile Glu Lys Arg Leu His Arg Leu Asn Leu Leu
        275                 280                 285

Gln Ser His Pro Gln Glu Val Met Tyr Phe Gln Pro Gly Glu Pro Pro
    290                 295                 300

Gly Pro Val Glu Asp Asp His Ile Pro Phe Leu Arg Arg Gly Val Pro
305                 310                 315                 320

Val Leu His Leu Ile Ala Met Pro Phe Pro Ala Val Trp His Thr Pro
                325                 330                 335

Ala Asp Thr Glu Ala Asn Leu His Pro Pro Thr Val His Asn Leu Ser
            340                 345                 350

Arg Ile Leu Ala Val Phe Leu Ala Glu Tyr Leu Gly Leu
                355                 360                 365

<210> SEQ ID NO 61
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 61

```
atatctcgag tccatcgcca ccatggtgag c                           31

<210> SEQ ID NO 62
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 62
atatctcgag ttacttgtac agctcgtcca t                           31

<210> SEQ ID NO 63
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 63
atatgaattc atgagtcccg ggagccgc                               28

<210> SEQ ID NO 64
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 64
atatgcggcc gcatgagtcc caggtactcg gccag                       35

<210> SEQ ID NO 65
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 65
atatgaattc atgaaaccac cctcactt                               28

<210> SEQ ID NO 66
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 66
atatgaattc atgagtccgg ccagccgc                               28

<210> SEQ ID NO 67
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 67
atatgcggcc gcatgagacc caggtactca gccag                       35

<210> SEQ ID NO 68
<211> LENGTH: 38
<212> TYPE: DNA
```

```
<213> ORGANISM: Artificial sequence
<220> FEATURE:
<223> OTHER INFORMATION: Synthetic oligonucleotide

<400> SEQUENCE: 68
atatgcggcc gcatgctgtt ccagacgata tagaaagc                              38

<210> SEQ ID NO 69
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 69
atatgcggcc gcatgctatt ccagacgata taaaaagc                              38

<210> SEQ ID NO 70
<211> LENGTH: 20
<212> TYPE: DNA
<213> ORGANISM: Artificial sequence
<220> FEATURE:
<223> OTHER INFORMATION: Synthetic olignucleotide

<400> SEQUENCE: 70
gggaggcaga cacaatcaat                                                  20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
tctgacagct gggaatctga                                                  20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucloetide

<400> SEQUENCE: 72
ggcatggatc tgttggtctt                                                  20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
tcagattccc agctgtcaga                                                  20

<210> SEQ ID NO 74
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 74
gcagcggaga ccagactca                                                   19
```

<210> SEQ ID NO 75
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 75
aggcagcgga gaccaga                                                    17

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
ggttggtggt ggttcttctc                                                 20

<210> SEQ ID NO 77
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 77
ctgaattcgt tgcatgatgt g                                               21

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
cccactcagc ctgaagtctc                                                 20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
cttccgggtt aagagtgctg                                                 20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
gtgccagact tcagggaaag                                                 20

<210> SEQ ID NO 81
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 81
gctatgggct tggctttcta                                            20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
caataaggga cgcaggaaag                                            20

<210> SEQ ID NO 83
<211> LENGTH: 28
<212> TYPE: DNA
<213> ORGANISM: Artificial sequence
<220> FEATURE:
<223> OTHER INFORMATION: Synthetic olignucleotide

<400> SEQUENCE: 83
atatgaattc gaggagatgt cacggagc                                   28

<210> SEQ ID NO 84
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 84
atatatgcgg ccgcctagag tcccaggtac tcggc                           35

<210> SEQ ID NO 85
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 85
gatctgcggg tcccgctgaa cggaagcctt tcagaagcc                       39

<210> SEQ ID NO 86
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 86
ggcttctgaa aggcttccgt tcagcgggac ccgcagatc                       39

<210> SEQ ID NO 87
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 87
atatgaattc catcaccatc accatcacga ggaggtatca cggagc                46

```
<210> SEQ ID NO 88
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 88
atatatgcgg ccgcctagag acccaggtac tcagc                                35

<210> SEQ ID NO 89
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 89
gatctgcggg tcccgctgaa cggaagcctt tcagaagcc                            39

<210> SEQ ID NO 90
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 90
ggcttctgaa aggcttccgt tcagcgggac ccgcagatc                            39

<210> SEQ ID NO 91
<211> LENGTH: 38
<212> TYPE: PRT
<213> ORGANISM: Homo sapiens

<400> SEQUENCE: 91

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 92
<211> LENGTH: 40
<212> TYPE: PRT
<213> ORGANISM: Homo sapiens

<400> SEQUENCE: 92

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 93
<211> LENGTH: 30
<212> TYPE: PRT
<213> ORGANISM: Artificial sequence
<220> FEATURE:
<223> OTHER INFORMATION: Synthetic peptide

<400> SEQUENCE: 93
```

```
Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
            20                  25                  30
```

<210> SEQ ID NO 94
<211> LENGTH: 32
<212> TYPE: PRT
<213> ORGANISM: Artificial sequence
<220> FEATURE:
<223> OTHER INFORMATION: Synthetic peptide

<400> SEQUENCE: 94

```
Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val Ile Ala
            20                  25                  30
```

<210> SEQ ID NO 95
<211> LENGTH: 34
<212> TYPE: PRT
<213> ORGANISM: Artificial sequence
<220> FEATURE:
<223> OTHER INFORMATION: Synthetic peptide

<400> SEQUENCE: 95

```
Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Asn
```

<210> SEQ ID NO 96
<211> LENGTH: 34
<212> TYPE: PRT
<213> ORGANISM: Artificial sequence
<220> FEATURE:
<223> OTHER INFORMATION: Synthetic peptide

<400> SEQUENCE: 96

```
Glu Ala Ser Asn Cys Phe Ala Ile Arg His Phe Glu Asn Lys Phe Ala
1               5                   10                  15

Val Glu Thr Leu Ile Cys Phe Asn Leu Phe Leu Asn Ser Gln Glu Lys
            20                  25                  30

His Tyr
```

<210> SEQ ID NO 97
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 97

```
Gln Gly Pro Trp Leu Glu Glu Glu Glu Glu Ala Tyr Gly Trp Met Asp
1               5                   10                  15

Phe
```

<210> SEQ ID NO 98
<211> LENGTH: 13
<212> TYPE: PRT

-continued

```
<213> ORGANISM: Homo sapiens

<400> SEQUENCE: 98

Gln Leu Tyr Glu Asn Lys Pro Arg Arg Pro Tyr Ile Leu
1               5                   10

<210> SEQ ID NO 99
<211> LENGTH: 3
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: AMIDATION

<400> SEQUENCE: 99

Gln Glu Pro
1

<210> SEQ ID NO 100
<211> LENGTH: 76
<212> TYPE: PRT
<213> ORGANISM: Homo sapiens

<400> SEQUENCE: 100

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 101
<211> LENGTH: 76
<212> TYPE: PRT
<213> ORGANISM: Homo sapiens

<400> SEQUENCE: 101

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75

<210> SEQ ID NO 102
<211> LENGTH: 76
<212> TYPE: PRT
<213> ORGANISM: Homo sapiens

<400> SEQUENCE: 102

Gln Pro Asp Ser Val Ser Ile Pro Ile Thr Cys Cys Phe Asn Val Ile
1               5                   10                  15
```

```
Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
 50                  55                  60

Lys His Leu Asp Gln Ile Phe Gln Asn Leu Lys Pro
 65                  70                  75
```

<210> SEQ ID NO 103
<211> LENGTH: 98
<212> TYPE: PRT
<213> ORGANISM: Homo sapiens

<400> SEQUENCE: 103

```
Met Lys Val Ser Ala Val Leu Leu Cys Leu Leu Leu Met Thr Ala Ala
 1               5                  10                  15

Phe Asn Pro Gln Gly Leu Ala Gln Pro Asp Ala Leu Asn Val Pro Ser
            20                  25                  30

Thr Cys Cys Phe Thr Phe Ser Ser Lys Lys Ile Ser Leu Gln Arg Leu
            35                  40                  45

Lys Ser Tyr Val Ile Thr Thr Ser Arg Cys Pro Gln Lys Ala Val Ile
 50                  55                  60

Phe Arg Thr Lys Leu Gly Lys Glu Ile Cys Ala Asp Pro Lys Glu Lys
 65                  70                  75                  80

Trp Val Gln Asn Tyr Met Lys His Leu Gly Arg Lys Ala His Thr Leu
                85                  90                  95

Lys Thr
```

<210> SEQ ID NO 104
<211> LENGTH: 97
<212> TYPE: PRT
<213> ORGANISM: Homo sapiens

<400> SEQUENCE: 104

```
Gln Pro Lys Val Pro Glu Trp Val Asn Thr Pro Ser Thr Cys Cys Leu
 1               5                  10                  15

Lys Tyr Tyr Glu Lys Val Leu Pro Arg Arg Leu Val Val Gly Tyr Arg
            20                  25                  30

Lys Ala Leu Asn Cys His Leu Pro Ala Ile Ile Phe Val Thr Lys Arg
            35                  40                  45

Asn Arg Glu Val Cys Thr Asn Pro Asn Asp Asp Trp Val Gln Glu Tyr
 50                  55                  60

Ile Lys Asp Pro Asn Leu Pro Leu Leu Pro Thr Arg Asn Leu Ser Thr
 65                  70                  75                  80

Val Lys Ile Ile Thr Ala Lys Asn Gly Gln Pro Gln Leu Leu Asn Ser
                85                  90                  95

Gln
```

<210> SEQ ID NO 105
<211> LENGTH: 68
<212> TYPE: PRT
<213> ORGANISM: Homo sapiens

<400> SEQUENCE: 105

```
Gln Val Gly Thr Asn Lys Glu Leu Cys Cys Leu Val Tyr Thr Ser Trp
 1               5                  10                  15
```

```
Gln Ile Pro Gln Lys Phe Ile Val Asp Tyr Ser Glu Thr Ser Pro Gln
                20                  25                  30

Cys Pro Lys Pro Gly Val Ile Leu Leu Thr Lys Arg Gly Arg Gln Ile
            35                  40                  45

Cys Ala Asp Pro Asn Lys Lys Trp Val Gln Lys Tyr Ile Ser Asp Leu
 50                  55                  60

Lys Leu Asn Ala
 65

<210> SEQ ID NO 106
<211> LENGTH: 373
<212> TYPE: PRT
<213> ORGANISM: Homo sapiens

<400> SEQUENCE: 106

Gln His His Gly Val Thr Lys Cys Asn Ile Thr Cys Ser Lys Met Thr
 1               5                  10                  15

Ser Lys Ile Pro Val Ala Leu Leu Ile His Tyr Gln Gln Asn Gln Ala
                20                  25                  30

Ser Cys Gly Lys Arg Ala Ile Ile Leu Glu Thr Arg Gln His Arg Leu
            35                  40                  45

Phe Cys Ala Asp Pro Lys Glu Gln Trp Val Lys Asp Ala Met Gln His
 50                  55                  60

Leu Asp Arg Gln Ala Ala Ala Leu Thr Arg Asn Gly Gly Thr Phe Glu
 65                  70                  75                  80

Lys Gln Ile Gly Glu Val Lys Pro Arg Thr Thr Pro Ala Ala Gly Gly
                 85                  90                  95

Met Asp Glu Ser Val Val Leu Glu Pro Glu Ala Thr Gly Glu Ser Ser
                100                 105                 110

Ser Leu Glu Pro Thr Pro Ser Ser Gln Glu Ala Gln Arg Ala Leu Gly
            115                 120                 125

Thr Ser Pro Glu Leu Pro Thr Gly Val Thr Gly Ser Ser Gly Thr Arg
130                 135                 140

Leu Pro Pro Thr Pro Lys Ala Gln Asp Gly Gly Pro Val Gly Thr Glu
145                 150                 155                 160

Leu Phe Arg Val Pro Pro Val Ser Thr Ala Ala Thr Trp Gln Ser Ser
                165                 170                 175

Ala Pro His Gln Pro Gly Pro Ser Leu Trp Ala Glu Ala Lys Thr Ser
            180                 185                 190

Glu Ala Pro Ser Thr Gln Asp Pro Ser Thr Gln Ala Ser Thr Ala Ser
        195                 200                 205

Ser Pro Ala Pro Glu Glu Asn Ala Pro Ser Glu Gly Gln Arg Val Trp
210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                245                 250                 255

Gly Ser Met Ala His Val Ser Val Pro Val Ser Ser Glu Gly Thr
            260                 265                 270

Pro Ser Arg Glu Pro Val Ala Ser Gly Ser Trp Thr Pro Lys Ala Glu
        275                 280                 285

Glu Pro Ile His Ala Thr Met Asp Pro Gln Arg Leu Gly Val Leu Ile
    290                 295                 300

Thr Pro Val Pro Asp Ala Gln Ala Ala Thr Arg Arg Gln Ala Val Gly
305                 310                 315                 320
```

```
Leu Leu Ala Phe Leu Gly Leu Phe Cys Leu Gly Val Ala Met Phe
            325                 330                 335

Thr Tyr Gln Ser Leu Gln Gly Cys Pro Arg Lys Met Ala Gly Glu Met
            340                 345                 350

Ala Glu Gly Leu Arg Tyr Ile Pro Arg Ser Cys Gly Ser Asn Ser Tyr
            355                 360                 365

Val Leu Val Pro Val
        370

<210> SEQ ID NO 107
<211> LENGTH: 33
<212> TYPE: PRT
<213> ORGANISM: Homo sapiens

<400> SEQUENCE: 107

Gln Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu

<210> SEQ ID NO 108
<211> LENGTH: 11
<212> TYPE: PRT
<213> ORGANISM: Homo sapiens

<400> SEQUENCE: 108

Arg Pro Lys Pro Gln Gln Phe Phe Gly Leu Met
1               5                   10

<210> SEQ ID NO 109
<211> LENGTH: 5
<212> TYPE: PRT
<213> ORGANISM: Artificial sequence
<220> FEATURE:
<223> OTHER INFORMATION: Synthetic peptide

<400> SEQUENCE: 109

Gln Tyr Asn Ala Asp
1               5

<210> SEQ ID NO 110
<211> LENGTH: 32
<212> TYPE: DNA
<213> ORGANISM: Artificial sequence
<220> FEATURE:
<223> OTHER INFORMATION: DNA primer

<400> SEQUENCE: 110
atataagctt atgaaagtct ctgccgccct tc                                32

<210> SEQ ID NO 111
<211> LENGTH: 32
<212> TYPE: DNA
<213> ORGANISM: Artificial sequence
<220> FEATURE:
<223> OTHER INFORMATION: DNA primer

<400> SEQUENCE: 111
atatgcggcc gctcaagtct tcggagtttg gg                                32

<210> SEQ ID NO 112
```

```
<211> LENGTH: 37
<212> TYPE: DNA
<213> ORGANISM: Artificial sequence
<220> FEATURE:
<223> OTHER INFORMATION: DNA primer

<400> SEQUENCE: 112
cattccccaa gggctcgctc cagatgcaat caatgcc                              37

<210> SEQ ID NO 113
<211> LENGTH: 37
<212> TYPE: DNA
<213> ORGANISM: Artificial sequence
<220> FEATURE:
<223> OTHER INFORMATION: DNA primer

<400> SEQUENCE: 113
ggcattgatt gcatctggag cgagcccttg gggaatg                              37

<210> SEQ ID NO 114
<211> LENGTH: 38
<212> TYPE: DNA
<213> ORGANISM: Artificial sequence
<220> FEATURE:
<223> OTHER INFORMATION: DNA primer

<400> SEQUENCE: 114
cattccccaa gggctcgctg atgcaatcaa tgcccag                              38

<210> SEQ ID NO 115
<211> LENGTH: 38
<212> TYPE: DNA
<213> ORGANISM: Artificial sequence
<220> FEATURE:
<223> OTHER INFORMATION: DNA primer

<400> SEQUENCE: 115
ctggggcatt gattgcatca gcgagccctt ggggaatg                             38
```